United States Patent
Barsoum et al.

(10) Patent No.: US 10,530,629 B2
(45) Date of Patent: Jan. 7, 2020

(54) METHODS AND APPARATUSES FOR SIGNALING WITH GEOMETRIC CONSTELLATIONS

(71) Applicant: Constellation Designs, LLC, Anaheim, CA (US)

(72) Inventors: Maged F. Barsoum, San Jose, CA (US); Christopher R. Jones, Pacific Palisades, CA (US)

(73) Assignee: Constellation Designs, LLC, Anaheim, CA (US)

( * ) Notice: Subject to any disclaimer, the term of this patent is extended or adjusted under 35 U.S.C. 154(b) by 0 days.

(21) Appl. No.: 15/826,579

(22) Filed: Nov. 29, 2017

(65) Prior Publication Data

US 2018/0191548 A1    Jul. 5, 2018

Related U.S. Application Data

(63) Continuation of application No. 13/608,838, filed on Sep. 10, 2012, now Pat. No. 9,887,870, which is a
(Continued)

(51) Int. Cl.
*H04L 27/02*    (2006.01)
*H04L 27/34*    (2006.01)
(Continued)

(52) U.S. Cl.
CPC ........... *H04L 27/3405* (2013.01); *A61B 6/12* (2013.01); *A61B 6/527* (2013.01); *A61B 6/5264* (2013.01);
(Continued)

(58) Field of Classification Search
CPC ....... H04L 27/3405; A61B 34/20; A61B 6/12; A61B 6/5264; A61B 6/527; G06T 7/33
See application file for complete search history.

(56) References Cited

U.S. PATENT DOCUMENTS 5,289,501 A    2/1994    Seshadri et al.
5,862,179 A    1/1999    Goldstein et al.
(Continued)

FOREIGN PATENT DOCUMENTS

EP    1578021 A1    9/2005
EP    1971098 A1    9/2008
(Continued)

OTHER PUBLICATIONS

Nuno Sout et al.,"Iterative Turbo Multipath Interference Cancellation for WCDMA System with Non-Uniform Modulation," IEEE pp. 811-815, 2005.*
(Continued)

*Primary Examiner* — Tesfaldet Bocure
(74) *Attorney, Agent, or Firm* — KPPB LLP

(57) ABSTRACT

Communication systems are described that use signal constellations, which have unequally spaced (i.e. 'geometrically' shaped) points. In many embodiments, the communication systems use specific geometric constellations that are capacity optimized at a specific SNR. In addition, ranges within which the constellation points of a capacity optimized constellation can be perturbed and are still likely to achieve a given percentage of the optimal capacity increase compared to a constellation that maximizes $d_{min}$, are also described. Capacity measures that are used in the selection of the location of constellation points include, but are not limited to, parallel decode (PD) capacity and joint capacity.

27 Claims, 167 Drawing Sheets

Related U.S. Application Data continuation of application No. 12/650,532, filed on Dec. 30, 2009, now Pat. No. 8,265,175, and a continuation-in-part of application No. 12/156,989, filed on Jun. 5, 2008, now Pat. No. 7,978,777.

(60) Provisional application No. 61/141,662, filed on Dec. 30, 2008, provisional application No. 61/141,935, filed on Dec. 31, 2008, provisional application No. 60/933,319, filed on Jun. 5, 2007.

(51) Int. Cl.

| | | |
|---|---|---|
| *H04B 14/02* | (2006.01) | |
| *H04L 1/00* | (2006.01) | |
| *A61B 6/12* | (2006.01) | |
| *A61B 6/00* | (2006.01) | |
| *A61B 34/20* | (2016.01) | |
| *G06T 7/33* | (2017.01) | |
| *A61B 17/00* | (2006.01) | |
| *A61B 90/00* | (2016.01) | |

(52) U.S. Cl.
CPC ............ *A61B 34/20* (2016.02); *G06T 7/33* (2017.01); *H04B 14/023* (2013.01); *H04L 1/0003* (2013.01); *A61B 6/503* (2013.01); *A61B 6/5235* (2013.01); *A61B 2017/00703* (2013.01); *A61B 2034/2051* (2016.02); *A61B 2090/376* (2016.02); *A61B 2090/3983* (2016.02); *G06T 2207/10121* (2013.01); *G06T 2207/30021* (2013.01); *G06T 2207/30048* (2013.01); *H04L 1/0009* (2013.01)

(56) References Cited

U.S. PATENT DOCUMENTS

| | | | |
|---|---|---|---|
| 6,084,915 | A | 7/2000 | Williams et al. |
| 6,115,415 | A | 9/2000 | Goldstein et al. |
| 6,157,678 | A | 12/2000 | Wei |
| 6,603,801 | B1 | 8/2003 | Andren et al. |
| 6,606,355 | B1 | 8/2003 | Wei |
| 6,611,554 | B1 | 8/2003 | Chouly et al. |
| 6,665,831 | B1 | 12/2003 | Yoshida et al. |
| 7,212,582 | B2 | 5/2007 | Zhang |
| 7,245,666 | B1 | 7/2007 | Gardner et al. |
| 7,376,203 | B2 | 5/2008 | Brunel et al. |
| 7,620,067 | B2 | 11/2009 | Niu et al. |
| 7,978,777 | B2 | 7/2011 | Barsoum et al. |
| 8,265,175 | B2 | 9/2012 | Barsoum et al. |
| 8,270,511 | B2 | 9/2012 | Barsoum et al. |
| 8,842,761 | B2 | 9/2014 | Barsoum et al. |
| 9,191,148 | B2 | 11/2015 | Barsoum |
| 9,385,832 | B2 | 7/2016 | Barsoum et al. |
| 9,743,290 | B2 | 8/2017 | Barsoum et al. |
| 9,743,292 | B2 | 8/2017 | Barsoum et al. |
| 9,887,870 | B2 | 2/2018 | Barsoum et al. |
| 9,967,127 | B1 | 5/2018 | Sun et al. |
| 10,149,179 | B2 | 12/2018 | Barsoum et al. |
| 2002/0044597 | A1 | 4/2002 | Shively |
| 2002/0106010 | A1 | 8/2002 | Jones |
| 2003/0231715 | A1 | 12/2003 | Shoemake |
| 2004/0022179 | A1 | 2/2004 | Giannakis et al. |
| 2004/0066738 | A1 | 4/2004 | Stopler |
| 2004/0161050 | A1 | 8/2004 | Larsson et al. |
| 2004/0258177 | A1 | 12/2004 | Shen et al. |
| 2005/0180531 | A1 | 8/2005 | Wellig et al. |
| 2005/0207507 | A1 | 9/2005 | Mitsutani |
| 2005/0276343 | A1 | 12/2005 | Jones |
| 2005/0286409 | A1 | 12/2005 | Yoon et al. |
| 2006/0045169 | A1 | 3/2006 | Kim |
| 2006/0144843 | A1 | 7/2006 | Vandal et al. |
| 2006/0155843 | A1 | 7/2006 | Glass et al. |
| 2007/0022179 | A1 | 1/2007 | Kim et al. |
| 2007/0025283 | A1 | 2/2007 | Koslov et al. |
| 2007/0054614 | A1 | 3/2007 | Walker et al. |
| 2007/0116161 | A1 | 5/2007 | Tokoro et al. |
| 2007/0147530 | A1 | 6/2007 | Li |
| 2007/0280147 | A1 | 12/2007 | Catreux-erceg et al. |
| 2008/0200114 | A1 | 8/2008 | Eberlein et al. |
| 2009/0097582 | A1 | 4/2009 | Barsoum et al. |
| 2009/0161786 | A1 | 6/2009 | Nakagawa et al. |
| 2010/0195743 | A1 | 8/2010 | Barsoum et al. |
| 2010/0303174 | A1 | 12/2010 | Oh et al. |
| 2011/0090948 | A1 | 4/2011 | Zhou et al. |
| 2011/0228869 | A1 | 9/2011 | Barsoum et al. |
| 2011/0305300 | A1 | 12/2011 | Ko |
| 2012/0147983 | A1 | 6/2012 | Barsoum et al. |
| 2013/0083862 | A1 | 4/2013 | Barsoum et al. |
| 2013/0170571 | A1 | 7/2013 | Barsoum et al. |
| 2014/0314177 | A1 | 10/2014 | Choi et al. |
| 2015/0236812 | A1 | 8/2015 | Barsoum et al. |
| 2016/0204967 | A1 | 7/2016 | Choi et al. |
| 2016/0309342 | A1 | 10/2016 | Barsoum et al. |
| 2016/0316382 | A1 | 10/2016 | Barsoum et al. |
| 2017/0374564 | A1 | 12/2017 | Barsoum et al. |
| 2017/0374565 | A1 | 12/2017 | Barsoum et al. |
| 2018/0102933 | A1 | 4/2018 | Schneider et al. |

FOREIGN PATENT DOCUMENTS

| | | |
|---|---|---|
| JP | 09130438 A | 5/1997 |
| JP | 2003229835 | 8/2003 |
| JP | 2005269258 A | 9/2005 |
| JP | 2010538502 A | 12/2010 |
| JP | 5513377 B2 | 6/2014 |
| WO | 9832257 | 7/1998 |
| WO | 2007074524 A1 | 7/2007 |
| WO | 2008151308 A1 | 12/2008 |
| WO | 2010078472 A1 | 7/2010 |

OTHER PUBLICATIONS

Fei Zesong et al., "Shaping Gain by Non-Uniform QAM Constellation with Binary Turbo Coded Modulation," IEEE, pp. 1863-1867,2003.*

Magged F. Barsoum, "Constellation Design via Capacity maximization," IEEE, pp. 1821-1825, 2007.*

Frank et al., "Optimal Nonuniform Signaling for Gaussian Channels," IEEE, pp. 913-929, 1993.*

Brendan Moor, "Pairwise optimization of modulation constellations for non-uniform sources Modulation," Can. J. Elect. Computer Eng. vol. 34, pp. 167-177, 2009.*

Roalds Otnes et al.,"Adaptive Data Rate using ARQ and Nonuniform Constellations," Vehicular Technology Conference, pp. 1211-1215, 2001.*

European Supplementary Search Report for Application No. EP 08795885, International Filing Date Jun. 5, 2008, Search Completed Apr. 1, 2014, 8 pgs.

International Preliminary Report on Patentability for International Application No. PCT/US/2008/065994, Report Completed Jun. 18, 2009, dated Jun. 30, 2009, 4 pgs.

International Preliminary Report on Patentability for International Application No. PCT/US2009/069881, dated Jan. 7, 2011, dated Jan. 14, 2011, 11 pgs.

International Search Report for International Application No. PCT/US09/69881, date completed Apr. 12, 2010, dated May 3, 2010, 2 pgs.

International Search Report for International Application No. PCT/US2008/065994, Report completed Oct. 3, 2008, dated Oct. 22, 2008, 2 pgs.

Written Opinion for International Application No. PCT/US2008/065994, completed Oct. 3, 2008, dated Oct. 22, 2008, 5 pgs.

Written Opinion of the International Searching Authority for International Application No. PCT/US 09/69881, date completed Apr. 13, 2010, dated May 3, 2010, 10 pgs.

"ETSI EN 302 307 V1.1.1, European Standard (Telecommunications series), Digital Video Braodcasting (DVB); Second generation framing structure,", channel coding and modulation systems for

(56) References Cited

OTHER PUBLICATIONS

Broadcasting, Interactive Services, News Gathering and other broadband satellite applications, Mar. 2005, Retrieved from: http://www.etsi.org/deliver/etsi_en/302300_302399/302307/01.01.01_60/en_302307v010101p.pdf.

U.S. Appl. No. 13/618,630, "Notice of Allowance Received", dated May 15, 2014, 10 pgs.

Agrell et al., "Gray Coding for Multilevel Constellations in Gaussian Noise", To appear in IEEE Transactions on Information Theory, vol. 53, Issue 1, Jan. 2007, Published Dec. 26, 2006, 14 pgs.

Agrell et al., "On optimal constellations for BICM at low SNR", Information Theory Workshop, 2009. ITW 2009. IEEE, Conference: Oct. 11-16, 2009, 6 pgs.

Agrell et al., "On the BICM Capacity", ArXiv.org, Dec. 8, 2010, 53 pgs.

Agrell et al., "On the Optimality of the Binary Reflected Gray Code", IEEE Transactions on Information Theory, Dec. 2004, vol. 50, No. 12, pp. 3170-3182.

Agrell et al., "Optimal Signal Sets and Binary Labelings for BICM at low SNR", To Appear in IEEE Transactions on Information Theory, vol. 57, Issue 10, Oct. 2011, Published Oct. 6, 2011, 24 pgs.

Alvarado et al., "On the BICM Capacity—Part I: Binary Labelings, Arbitrary Input Distributions, and First-Order Asymptotics", Arxiv.org, Jan. 25, 2010, 45 pgs.

Alvarado et al., "On the capacity of BICM with QAM constellations (Invited Paper)", Retrieved from: http://publications.lib.chalmers.se/records/fulltext/local_92655.pdf, IWCMC'09, Jun. 21-24, 2009, Leipzig, Germany, 8 pgs.

Arafa et al., "Non-Uniform Signal Constellation for Iteratively Decoded Bit Interleaved Coded Modulation (BICM-ID) with Convolution and LDPC Codes", 2011 International Conference on Innovations in Information Technology, Conference: Apr. 25-27, 2011, pp. 23-28.

Batshon et al., "Iterative Polar Quantization-Based Modulation to Achieve Channel Capacity in Ultrahigh-Speed Optical Communication Systems", IEEE Photonics Journal, vol. 2, No. 4, pp. 593-599 Aug. 2010.

Betts et al., "Performance of Nonuniform Constellations on the Gaussian Channel", IEEE Transactions on Information Theory, Sep. 1994, vol. 40, No. 5, pp. 1633-1638.

Chen et al., "Increasing achievable information rates via geometric shaping", arXiv.org, e-Print Archive, Physics, arXiv:1804.08850v1, Apr. 24, 2018.

Choi et al., "Channel Capacity Enhancement Scheme for Satellite Communication System", 2007 6th International Conference on Information, Communications & Signal Processing, Conference: Dec. 10-13, 2007, 4 pgs.

Choi et al., "Satellite-DMB applied to the 8PSK hierarchical modulation", Digest of Technical Papers. International Conference on Consumer Electronics, 2007. ICCE 2007, Conference: Jan. 10-14, 2007, 2 pgs.

Conway et al., "A Fast Encoding Method for Lattice Codes and Quantizers", IEEE Transactions on Information Theory, Nov. 1983, vol. IT-29, No. 6, pp. 820-824.

De Gaudenzi et al., "APSK Coded Modulation Schemes for Nonlinear Satellite Channels with High Power and Spectral Efficiency", American Institute of Aeronautics and Astronautics Paper AIAA, 2002-1861, 2002, Retrieved from: http://www.dtic.upf.edu/~aguillen/home_upf/Publications_files/aiaa2001.pdf.

De Gaudenzi et al., "Performance Analysis of Turbo-Coded APSK Modulations over Nonlinear Satellite Channels", IEEE Transactions on Wireless Communications, vol. 5, No. 9, Sep. 6, 2006, XP002457811, ISSN: 15361276, DOI: 10.1109/TWC.2006.1687763, 12 pgs.

De Gaudenzi et al., "Turbo-Coded APSK Modulations Design for Satellite Broadband Communications", International Journal of Satellite Communications and Networking, vol. 24, No. 4, Jul. 1, 2006, pp. 261-281, XP008134566, ISSN: 1542-0973, DOIL 10.002/SAT.841.

Fabregas et al., "Bit-Interleaved Coded Modulation", Foundations and Trends® in Communications and Information Theory: vol. 5: No. 1-2, pp. 1-153. http://dx.doi.org/10.1561/0100000019, Published: Nov. 30, 2008.

Fabregas et al., "Bit-Interleaved Coded Modulation with Shaping", IEEE Information Theory Workshop (ITW), 2010, Conference: Aug. 30-Sep. 3, 2010, 6 pgs.

Fabregas et al., "Error Probability of Bit-Interleaved Coded Modulation using the Gaussian Approximation", 2004 Conference on Information Sciences and Systems, Princeton University, Mar. 17-19, 2004, 7 pgs.

Fabregas et al., "Impact of Signal Constellation Expansion on the Achievable Diversity of Pragmatic Bit-interleaved Space-Time Codes", IEEE Transactions on Wireless Communications, vol. 5, Issue 8, Aug. 2006, 15 pgs.

Farid, et al. , "Design of Non-Uniform Capacity-Approaching Signaling for Optical Wireless Intensity Channels", IEEE International Symposium on Information Theory, 2008, Conference: Jul. 6-11, 2008, pp. 2327-2331.

Farid et al., "Channel Capacity and Non-Uniform Signalling for Free-Space Optical Intensity Channels", IEEE Journal on Selected Areas in Communications, vol. 27, No. 9, Dec. 2009, 12 pgs.

Forney, et al. , "Multidimensional Constellations—Part II: Voronoi Constellations", IEEE Journal on Selected Areas in Communications, Aug. 1989, vol. 7, No. 6, pp. 941-958.

Forney, Jr. et al., "Efficient Modulation for Band-Limited Channels", IEEE Journal on Selected Areas in Communications, Sep. 1984, vol. SAC-2, No. 5, pp. 632-647.

Forney, Jr. et al., "Multidimensional Constellations—Part I: Introduction, Figures of Merit, and Generalized Cross Constellations", IEEE Journal on Selected Areas in Communication, Aug. 1989, vol. 7, No. 6, pp. 877-892.

Foschini et al., "Optimization of Two-Dimensional Signal Constellations in the Presence of Gaussian Noise", IEEE Transactions on Communications, Jan. 1974, vol. Com-22, No. 1, pp. 28-38.

Fragouli et al., "Serially Concatenated Coding for Broadcasting S-UMTS Applications", IEEE 7th Int. Symp. on Spread-Spectrum Tech. & Appl., Prague, Czech Republic, Sep. 2-5, 2002, pp. 697-701.

Fragouli et al., "Turbo Codes with Non-Uniform Constellations", IEEE Int. Conf. Commun., Jun. 2001, pp. 70-73.

Goff et al., "Channel capacity of bit-interleaved coded modulation schemes using 8-ary signal constellations", Electronics Letters, vol. 38, Issue 4, Feb. 14, 2002, pp. 187-188.

Goff et al., "Signal Constellations for Bit-Interleaved Coded Modulation", IEEE Transactions on Information Theory, vol. 49, Issue 1, Jan. 2003, pp. 307-313.

Hamkins et al., "Asymptotically Dense Spherical Codes—Part I: Wrapped Spherical Codes", IEEE Transactions on Information Theory, Nov. 1997, vol. 43, No. 6, pp. 1774-1785.

Hamkins et al., "Asymptotically Dense Spherical Codes—Part II: Laminated Spherical Codes", IEEE Transactions on Information Theory, Nov. 1997, vol. 43, No. 6, pp. 1786-1798.

Hossain et al., "BICM Transmission using Non-Uniform QAM Constellations: Performance Analysis and Design", IEEE International Conference on Communications (ICC), 2010, Conference: May 23-27, 2010, 7 pgs.

Hossain et al., "Constellation and Interleaver Design for BICM", Global Telecommunications Conference (GLOBECOM 2011), 2011 IEEE, Conference: Dec. 5-9, 2011, 7 pgs.

Hossain et al., "Towards Fully Optimized BICM Transceivers", Arxiv.org, Dec. 8, 2010, 31 pgs.

Jo et al., "An Advanced Hierarchical Modulation with Rotated Constellation", The 12th International Conference on Advanced Communication Technology (ICACT), 2010, Conference: Feb. 7-10, 2010, pp. 515-518.

Kayhan et al., "Joint Signal-Labeling Optimization for Pragmatic Capacity under Peak-Power Constraint", Global Telecommunications Conference (GLOBECOM 2010), 2010 IEEE, Conference Dec. 6-10, 2010, Miami, FL, USA, 6 pgs.

Khandani et al., "Application of Shaping Technique to Multi-level Turbo-coded Modulation", University of Waterloo, Department of

(56) References Cited

OTHER PUBLICATIONS

Electrical and Computer Engineering, Waterloo, Ontario, Canada, Technical Report UW-E&CE#02-07, May 30, 2002, 24 pgs.
Khoo et al., "Bit Interleaved Coded Modulation with Iterative Decoding Using Constellation Shaping", IEEE Transactions on Communications, Oct. 2006, 5 pgs.
Lee et al., "Hierarchical Constellation Based Adaptive Relay Scheme in Multi-Hop Networks", IEEE Communication Letters, vol. 11, No. 3, Mar. 2007, pp. 225-227.
Liolis et al., "Amplitude Phase Shift Keying Constellation Design and its Applications to Satellite Digital Video Broadcasting", Retrieved from: http://www.dtic.upf.edu/~aguillen/home_upf/Publications_files/apsk_chapter.pdf, Jun. 1, 2009, 28 pgs.
Liu et al., "APSK Constellation with Gray Mapping", IEEE Communications Letters, vol. 15, Issue 12, Dec. 2011, pp. 127-1273, Date of Publication Oct. 31, 2011.
Loghin et al., "Non-Uniform Constellations for ATSC 3.0", IEEE Transactions on Broadcasting, vol. 62, No. 1, Mar. 2016, pp. 197-203.
Long Duan et al., "Approaching the AWGN Channel Capacity without Active Shaping", Proceedings of the International Symposium on Information Theory, pp. 374, 1997.
Ma et al., "Coded Modulation Using Superimposed Binary Codes", IEEE Transactions of Information Theory, vol. 50, No. 12, Dec. 2004, pp. 3331-3343.
Makowski, "On the Optimality of Uniform Pulse Amplitude Modulation", IEEE Transactions on information Theory, Dec. 2006, vol. 52, No. 12, pp. 5546-5549.
Martinez et al., "Bit-Interleaved Coded Modulation in the Wideband Regime", Retrieved from: https://arxiv.org/pdf/0710.4046.pdf, Draft, Oct. 22, 2007, 23 pgs.
Martinez et al., "Coding and Modulation for the Additive Exponential Noise Channel", IEEE International Symposium on Information Theory, 2008. ISIT 2008, Conference: Jul. 6-11, 2008, 5 pgs.
Meric et al., "Generic Approach for Hierarchical Modulation Performance Analysis: Application to DVB-SH and DVB-S2", Retrieved from: https://arxiv.org/abs/1103.1742, Submitted Mar. 9, 2011, Draft Mar. 10, 2011, 17 pgs.
Mheich et al., "Constellation Shaping for Broadcast Channels in Practical Situations", 19th European Signal Processing Conference (EUSIPCO 2011), Barcelona, Spain, Aug. 29-Sep. 2, 2011, pp. 96-100.
Milovanovic et al., "Simple Optimization Method of One-Dimensional M-PAM Constellations for the AWGN Channels", 4th International Conference on Telecommunications in Modern Satellite, Cable and Broadcasting Services, Oct. 13-15, 1999, 4 pgs.
Muhammad, Nabil Sven, "Coding and Modulation for Spectral Efficient Transmission", University of Stuttgart. Aug. 25, 2010 (http://dx.doi.org/10.18419/opus-2676).
Muhammad et al., "Joint Optimization of Signal Constellation and Bit Labeling for Bit-Interleaved Coded Modulation with Iterative Decoding", IEEE Communications Letters, Sep. 2005, vol. 9, No. 9, pp. 775-777.
Ngo et al., "A New Iterative Decoder for Turbo Codes on the Nonlinear Channel with Non-uniform 16QAM Modulation", Turbo Coding 2006, Apr. 3-7, 2006, Munich, 7 pgs.
Ngo et al., "Performance of non-uniform 16QAM modulation over linear and nonlinear channels", Electronics Letters, vol. 42, Issue 9, Apr. 27, 2006, 2 pgs.
Raphaeli et al., "An Improved Pragmatic Turbo Encoding Scheme for High Spectral Efficiency Using Constellation Shaping", IEEE International Conference on Communications, ICC 2003, Conference May 11-15, 2003, Anchorage, AK, USA, 6 pgs.
Raphaeli et al., "Constellation Shaping for Pragmatic Turbo-Coded Modulation with High Spectral Efficiency", IEEE Transactions on Communications, Mar. 2004, vol. 52, No. 3, pp. 341-345.
Ruotsalainen et al., "On the construction of the higher dimensional constellations", ISIT 2000, Lausanne, Switzerland, Jun. 30-Jul. 5, 2002, p. 490.

Schreckenach et al., "Signal Shaping Using Non-Unique Symbol Mappings", Proceedings of the 43rd Annual Allerton Conference on Communication, Control and Computing, Sep. 2005, 10 pgs.
Shannon et al., "A Mathematical Theory of Communication", The Bell System Technical Journal, vol. 27, Jul., Oct. 1948, 379-423, 623-656.
Shen et al., "On the Design of Modern Multilevel Coded Modulation for Unequal Error Protection", IEEE International Conference on Communications, 2008. ICC '08, Conference: May 19-23, 2008, 6 pgs.
Sommer et al., "Signal Shaping by Non-Uniform QAM for AWGN Channels and Applications Using Turbo Coding", ITG Conference on Source and Channel Coding, Jan. 2000, pp. 81-86.
Souto et al., "Iterative Detection and Channel Estimation for WCDMA Systems Employing Non-Uniform QAM Constellations", IST Mobile and Wireless Communications Summit, Jun. 2006, 6 pgs.
Souto et al., "Non-Uniform Constellations for Broadcasting and Multicasting Services in WCDMA Systems", Retrieved from: http://www.eurasip.org/Proceedings/Ext/IST05/papers/424.pdf, Jun. 19-23, 2005, 5 pgs.
Stierstorfer et al., "Asymptotically Optimal Mappings for BICM with M-PAM and M¬¬2QAM", Retrieved from: http://www.lit.lnt.de/papers/elet_set_part_cst_2009.pdf, Draft, Jul. 13, 2009, 6 pgs.
Stierstorfer et al., "Optimizing BICM with convolutional codes for transmission over the AWGN channel", Int. Zurich Seminar on Communications (IZS), Mar. 3-5, 2010, 5 pgs.
Sun et al., "Approaching Capacity by Equiprobable Signaling on the Gaussian Channel", IEEE Transactions on Information Theory, Sep. 1993, vol. 39, No. 5, pp. 1714-1716.
Theodorakopoulos et al., "Comparison of Uniform and Non-uniform M-QAM Schemes for Mobile Video Applications", Proceedings of the 2005 Systems Communications, 2005, Conference: Aug. 14-17, 2005, 6 pgs.
Ungerboeck et al., "Channel Coding with Multilevel/Phase Signals", IEEE Transactions on Information Theory, Jan. 1982, vol. IT-28, No. 1, pp. 55-67.
Valles et al., "Constellation Design for Improved Iterative LDPC Decoding", Aerospace Conference, 2008 IEEE, Conference: Mar. 1-8, 2008, Big Sky, MT, USA, DOI: 10.1109/AERO.2008.4526371, 7 pgs.
Vitthaladevuni et al., "A Recursive Algorithm for the Exact BER Computation of Generalized Hierarchical QAM Constellations", IEEE Transactions on Information Theory, vol. 49, No. 1, Jan. 14, 2003, pp. 297-307.
Von Deetzen et al., "On Code Design for Unequal Error Protection Multilevel Coding", 7th International ITG Conference on Source and Channel Coding (SCC), 2008, Conference: Jan. 14-16, 2008, 4 pgs.
Wang et al, "Shaping Gain for AWGN Channel by Non-Uniform Constellation in LDPC-Coded System", 11th IEEE Singapore International Conference on Communication Systems, 2008, ICCS 2008, Conference: Nov. 19-21, 2008, pp. 1302-1306.
Wu et al., "Non-uniform and Large Distance Constellation Design for Hierarchical Modulation", 2010 IEEE International Conference on Communications (ICC), Conference: May 23-27, 2010, 5 pgs.
Xie et al., "Bit-Interleaved LDPC-Coded Modulation with Iterative Demapping and Decoding", IEEE 69th Vehicular Technology Conference, Barcelona, Spain, Date of Conference Apr. 26-29, 2009, 5 pgs.
Xie et al., "On the Channel Capacity and Iterative Demapping of Generalized 4PAM over AWGN Channel", 11th IEEE Singapore International Conference on Communication Systems, 2008. ICCS 2008. Dec. 2008, pp. 860-863.
Yang et al., "A Novel BICM-ID System Approaching Shannon-Limit at High Spectrum Efficiency", IEICE Trans. Commun., vol. E94-B, No. 3, Mar. 2011, pp. 793-795.
Yuan et al., "Robust Hierarchical Broadcasting for AWGN and Flat Rayleigh Fading Channels using Multilevel Codes", Proceedings of IEEE Fifth International Symposium on Communication Theory & Applications, ISCTA'99, Ambleside, UK, 1999, S. 3 pgs.

(56) References Cited

OTHER PUBLICATIONS

Zhang et al., "A New Constellation Shaping Method and Its Performance Evaluation in BICM-ID", IEEE 70th Vehicular Technology Conference Fall (VTC 2009-Fall). Conference: Sep. 20-23, 2009, 5 pgs.
Zheng et al., "Shaping Gain of LDPC Coded-QAM Transmitting Systems with Non-Uniform Constellation", IEEE, pp. 6-9, 2007.
Khandani et al., Application of Shaping Technique to Multi-level Turbo-coded Modulation, 2002, 5 pgs.
Barsoum, "On Constellation Design and Iterative Codes", University of California, Los Angeles, Dissertation, 2008, 119 pgs.
Tran et al., "Signal Mappings of 8-Ary Constellations for BICM-ID Systems Over a Rayleigh Fading Channel", Canadian Conference on Electrical and Computer Engineering, 2004, pp. 1809-1813.
Extended European Search Report for European Application No. 18212572.4, Search completed May 27, 2019, dated Jun. 6, 2019, 13 Pgs.
Isaka et al., "Error performance analysis of multilevel coded asymmetric 8-PSK modulation with multistage decoding and unequal error protection", 1998 IEEE International Symposium on Cambridge, MA, USA 16-21, Aug. 16, 1998, p. 210.
Sawaya, "Performance optimization for capacity-approaching channel coding schemes", XP055604929 Ph.D. report, ENST Paris, France Mar. 31, 2002, 164 pgs.
Sawaya et al., "Multilevel coded modulations based on asymmetric constellations", Proceedings of the 2001 IEEE International Symposium on Information Theory, Washington, D.C., US, Jun. 24, 2001, p. 281.

\* cited by examiner

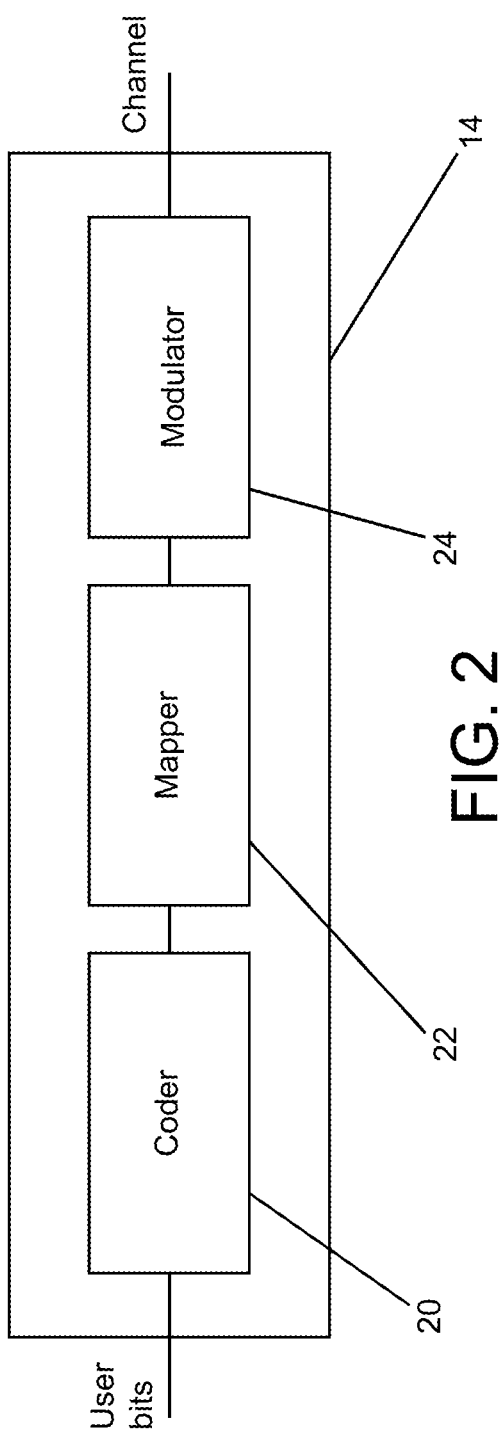
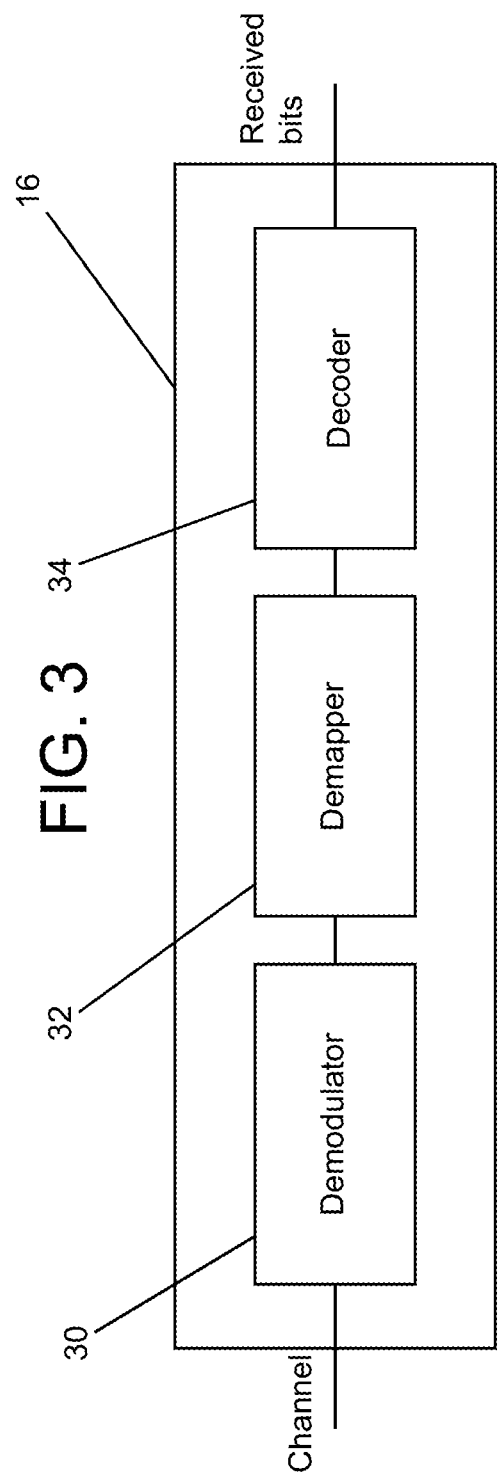
FIG. 2
FIG. 3

PAM-4 constellations optimized for joint capacity at different rates

| (bps) | 0.50 | 0.75 | 1.00 | 1.25 | 1.50 |
|---|---|---|---|---|---|
| (SNR) | 0.03 | 2.71 | 5.00 | 7.15 | 9.24 |
| $x_0$ | -1.41 | -1.41 | -1.40 | -1.37 | -1.36 |
| $x_1$ | 0.00 | 0.00 | -0.20 | -0.33 | -0.39 |
| $x_2$ | 0.00 | 0.00 | 0.20 | 0.33 | 0.39 |
| $x_3$ | 1.41 | 1.41 | 1.40 | 1.37 | 1.36 |

FIG. 11a

PAM-4 constellations optimized for parallel decoding capacity at different

| (bps) | 0.50 | 0.75 | 1.00 | 1.25 | 1.50 |
|---|---|---|---|---|---|
| (SNR) | 0.19 | 3.11 | 5.26 | 7.22 | 9.25 |
| $x_0$ | -1.00 | -1.30 | -1.36 | -1.37 | -1.36 |
| $x_1$ | -1.00 | -0.56 | -0.39 | -0.33 | -0.39 |
| $x_2$ | 1.00 | 1.30 | 1.36 | 0.33 | 1.36 |
| $x_3$ | 1.00 | 0.56 | 0.39 | 1.37 | 0.39 |

FIG. 11b

PAM-8 constellations optimized for joint capacity at different rates

| (bps) | 0.5 | 1.0 | 1.5 | 2.0 | 2.5 |
|---|---|---|---|---|---|
| (SNR) | 0.00 | 4.82 | 8.66 | 12.26 | 15.93 |
| $x_0$ | -1.81 | -1.76 | -1.70 | -1.66 | -1.60 |
| $x_1$ | -0.50 | -0.55 | -0.84 | -0.97 | -1.03 |
| $x_2$ | -0.50 | -0.55 | -0.63 | -0.53 | -0.58 |
| $x_3$ | -0.50 | -0.55 | -0.00 | -0.17 | -0.19 |
| $x_4$ | 0.50 | 0.55 | 0.00 | 0.17 | 0.19 |
| $x_5$ | 0.50 | 0.55 | 0.63 | 0.53 | 0.58 |
| $x_6$ | 0.50 | 0.55 | 0.84 | 0.97 | 1.03 |
| $x_7$ | 1.81 | 1.76 | 1.70 | 1.66 | 1.60 |

FIG. 13a

PAM-8 constellations optimized for parallel decoding capacity at different

| (bps) | 0.5 | 1.0 | 1.5 | 2.0 | 2.5 |
|---|---|---|---|---|---|
| (SNR) | 0.19 | 5.27 | 9.00 | 12.42 | 15.93 |
| $x_0$ | -1.00 | -1.36 | -1.72 | -1.64 | -1.60 |
| $x_1$ | -1.00 | -1.36 | -0.81 | -0.97 | -1.03 |
| $x_2$ | -1.00 | -0.39 | 1.72 | 1.64 | -0.19 |
| $x_3$ | -1.00 | -0.39 | -0.62 | -0.58 | -0.58 |
| $x_4$ | 1.00 | 1.36 | 0.62 | 0.58 | 1.60 |
| $x_5$ | 1.00 | 1.36 | 0.02 | 0.15 | 1.03 |
| $x_6$ | 1.00 | 0.39 | 0.81 | 0.97 | 0.19 |
| $x_7$ | 1.00 | 0.39 | -0.02 | -0.15 | 0.58 |

FIG. 13b

PAM-16 constellations optimized for joint capacity at different rates

| (bps) | 1.5 | 2.0 | 2.5 | 3.0 | 3.5 |
|---|---|---|---|---|---|
| (SNR) | 8.52 | 11.94 | 15.25 | 18.60 | 22.12 |
| $x_0$ | -2.02 | -1.96 | -1.91 | -1.85 | -1.76 |
| $x_1$ | -1.16 | -1.33 | -1.40 | -1.42 | -1.42 |
| $x_2$ | -1.16 | -1.10 | -1.05 | -1.10 | -1.15 |
| $x_3$ | -0.90 | -0.69 | -0.82 | -0.84 | -0.90 |
| $x_4$ | -0.34 | -0.69 | -0.60 | -0.62 | -0.68 |
| $x_5$ | -0.34 | -0.40 | -0.43 | -0.43 | -0.47 |
| $x_6$ | -0.34 | -0.17 | -0.24 | -0.26 | -0.28 |
| $x_7$ | -0.34 | -0.17 | -0.09 | -0.08 | -0.09 |
| $x_8$ | 0.34 | 0.17 | 0.09 | 0.08 | 0.09 |
| $x_9$ | 0.34 | 0.17 | 0.24 | 0.26 | 0.28 |
| $x_{10}$ | 0.34 | 0.40 | 0.43 | 0.43 | 0.47 |
| $x_{11}$ | 0.34 | 0.69 | 0.60 | 0.62 | 0.68 |
| $x_{12}$ | 0.90 | 0.69 | 0.82 | 0.84 | 0.90 |
| $x_{13}$ | 1.16 | 1.10 | 1.05 | 1.10 | 1.15 |
| $x_{14}$ | 1.16 | 1.33 | 1.40 | 1.42 | 1.42 |
| $x_{15}$ | 2.02 | 1.96 | 1.91 | 1.85 | 1.76 |

FIG. 15a

PAM-16 constellations optimized for parallel decoding capacity at different

| (bps) | 1.5 | 2.0 | 2.5 | 3.0 | 3.5 |
|---|---|---|---|---|---|
| (SNR) | 9.00 | 12.25 | 15.42 | 18.72 | 22.13 |
| $x_0$ | -1.72 | -1.98 | -1.89 | -1.84 | -1.75 |
| $x_1$ | -1.72 | -1.29 | -1.36 | -1.42 | -1.42 |
| $x_2$ | -0.81 | 1.94 | 1.89 | 1.84 | 1.75 |
| $x_3$ | -0.81 | -1.17 | -1.14 | -1.11 | -1.15 |
| $x_4$ | 1.72 | -0.38 | -0.35 | -0.40 | -0.47 |
| $x_5$ | 1.72 | -0.65 | -0.70 | -0.65 | -0.68 |
| $x_6$ | -0.62 | -0.38 | -0.34 | -0.29 | -0.28 |
| $x_7$ | -0.62 | -0.68 | -0.76 | -0.83 | -0.90 |
| $x_8$ | 0.62 | 1.09 | 1.13 | 1.11 | 1.15 |
| $x_9$ | 0.62 | 0.76 | 0.76 | 0.84 | 0.90 |
| $x_{10}$ | 0.02 | 1.26 | 1.35 | 1.42 | 1.42 |
| $x_{11}$ | 0.02 | 0.76 | 0.70 | 0.65 | 0.68 |
| $x_{12}$ | 0.81 | 0.06 | 0.00 | 0.05 | 0.09 |
| $x_{13}$ | 0.81 | 0.29 | 0.34 | 0.29 | 0.28 |
| $x_{14}$ | -0.02 | 0.06 | 0.00 | -0.05 | -0.09 |
| $x_{15}$ | -0.02 | 0.29 | 0.35 | 0.40 | 0.47 |

FIG. 15b

PAM-32 constellations optimized for joint capacity at different rates

| (bps) | 2.0 | 2.5 | 3.0 | 3.5 | 4.0 | 4.5 |
|---|---|---|---|---|---|---|
| (SNR) | 11.83 | 15.05 | 18.23 | 21.42 | 24.69 | 28.19 |
| $x_0$ | -2.25 | -2.19 | -2.14 | -2.07 | -1.97 | -1.85 |
| $x_1$ | -1.58 | -1.71 | -1.74 | -1.74 | -1.72 | -1.66 |
| $x_2$ | -1.58 | -1.46 | -1.46 | -1.49 | -1.51 | -1.50 |
| $x_3$ | -1.10 | -1.23 | -1.27 | -1.29 | -1.33 | -1.35 |
| $x_4$ | -1.10 | -1.13 | -1.11 | -1.13 | -1.17 | -1.21 |
| $x_5$ | -1.10 | -0.90 | -0.98 | -0.99 | -1.02 | -1.08 |
| $x_6$ | -0.83 | -0.90 | -0.85 | -0.87 | -0.90 | -0.95 |
| $x_7$ | -0.60 | -0.75 | -0.75 | -0.76 | -0.78 | -0.84 |
| $x_8$ | -0.60 | -0.58 | -0.63 | -0.65 | -0.67 | -0.73 |
| $x_9$ | -0.60 | -0.58 | -0.57 | -0.56 | -0.57 | -0.62 |
| $x_{10}$ | -0.60 | -0.49 | -0.42 | -0.46 | -0.48 | -0.52 |
| $x_{11}$ | -0.24 | -0.29 | -0.40 | -0.38 | -0.39 | -0.42 |
| $x_{12}$ | -0.21 | -0.28 | -0.24 | -0.29 | -0.30 | -0.32 |
| $x_{13}$ | -0.20 | -0.28 | -0.24 | -0.21 | -0.21 | -0.23 |
| $x_{14}$ | -0.20 | -0.09 | -0.09 | -0.12 | -0.13 | -0.14 |
| $x_{15}$ | -0.16 | -0.00 | -0.07 | -0.04 | -0.04 | -0.05 |
| $x_{16}$ | 0.16 | 0.00 | 0.07 | 0.04 | 0.04 | 0.05 |
| $x_{17}$ | 0.19 | 0.09 | 0.09 | 0.12 | 0.13 | 0.14 |
| $x_{18}$ | 0.21 | 0.28 | 0.24 | 0.21 | 0.21 | 0.23 |
| $x_{19}$ | 0.22 | 0.28 | 0.24 | 0.29 | 0.30 | 0.32 |
| $x_{20}$ | 0.23 | 0.28 | 0.41 | 0.38 | 0.39 | 0.42 |
| $x_{21}$ | 0.60 | 0.49 | 0.42 | 0.46 | 0.48 | 0.52 |
| $x_{22}$ | 0.60 | 0.58 | 0.57 | 0.56 | 0.57 | 0.62 |
| $x_{23}$ | 0.60 | 0.58 | 0.62 | 0.65 | 0.67 | 0.73 |
| $x_{24}$ | 0.60 | 0.75 | 0.75 | 0.76 | 0.78 | 0.84 |
| $x_{25}$ | 0.83 | 0.90 | 0.85 | 0.87 | 0.90 | 0.95 |
| $x_{26}$ | 1.10 | 0.90 | 0.98 | 0.99 | 1.02 | 1.08 |
| $x_{27}$ | 1.10 | 1.13 | 1.11 | 1.13 | 1.17 | 1.21 |
| $x_{28}$ | 1.10 | 1.23 | 1.27 | 1.29 | 1.33 | 1.35 |
| $x_{29}$ | 1.58 | 1.46 | 1.46 | 1.49 | 1.51 | 1.50 |
| $x_{30}$ | 1.58 | 1.71 | 1.74 | 1.74 | 1.72 | 1.66 |
| $x_{31}$ | 2.25 | 2.19 | 2.14 | 2.07 | 1.97 | 1.85 |

FIG. 17a

PAM-32 constellations optimized for parallel decoding capacity at different

| (bps) | 2.0 | 2.5 | 3.0 | 3.5 | 4.0 | 4.5 |
|---|---|---|---|---|---|---|
| (SNR) | 12.21 | 15.27 | 18.42 | 21.52 | 24.79 | 28.20 |
| $x_0$ | -2.25 | -2.16 | -2.14 | -2.05 | -1.97 | -1.85 |
| $x_1$ | -1.52 | -1.64 | -1.75 | -1.74 | -1.72 | -1.66 |
| $x_2$ | 2.30 | 2.19 | -1.31 | 2.05 | 1.97 | -1.35 |
| $x_3$ | -1.39 | -1.48 | -1.43 | -1.49 | -1.51 | -1.49 |
| $x_4$ | 1.56 | 1.54 | 2.14 | -0.96 | -1.03 | 1.85 |
| $x_5$ | -1.31 | -1.23 | 1.75 | -1.15 | -1.17 | 1.66 |
| $x_6$ | 1.67 | 1.65 | -1.07 | -0.91 | -0.90 | -1.21 |
| $x_7$ | -1.31 | -1.24 | -1.04 | -1.28 | -1.33 | -1.08 |
| $x_8$ | -0.48 | -0.43 | -0.36 | -0.17 | -0.17 | -0.42 |
| $x_9$ | -0.72 | -0.76 | -0.36 | -0.34 | -0.31 | -0.52 |
| $x_{10}$ | -0.48 | -0.43 | -0.62 | -0.17 | -0.15 | -0.73 |
| $x_{11}$ | -0.73 | -0.76 | -0.62 | -0.34 | -0.35 | -0.62 |
| $x_{12}$ | -0.48 | -0.42 | -0.29 | -0.71 | -0.67 | -0.33 |
| $x_{13}$ | -0.76 | -0.86 | -0.29 | -0.52 | -0.55 | -0.23 |
| $x_{14}$ | -0.48 | -0.42 | -0.77 | -0.72 | -0.77 | -0.84 |
| $x_{15}$ | -0.76 | -0.86 | -0.77 | -0.52 | -0.48 | -0.96 |
| $x_{16}$ | 0.87 | 0.98 | 1.07 | 1.49 | 1.51 | 1.21 |
| $x_{17}$ | 0.66 | 0.63 | 1.04 | 1.28 | 1.33 | 1.08 |
| $x_{18}$ | 0.87 | 0.98 | 0.77 | 1.74 | 1.72 | 0.84 |
| $x_{19}$ | 0.66 | 0.63 | 0.77 | 1.15 | 1.17 | 0.96 |
| $x_{20}$ | 1.07 | 1.13 | 1.31 | 0.72 | 0.77 | 1.35 |
| $x_{21}$ | 0.66 | 0.59 | 1.43 | 0.91 | 0.90 | 1.49 |
| $x_{22}$ | 1.05 | 1.10 | 0.62 | 0.71 | 0.67 | 0.73 |
| $x_{23}$ | 0.66 | 0.60 | 0.62 | 0.96 | 1.03 | 0.62 |
| $x_{24}$ | -0.01 | -0.08 | 0.02 | 0.00 | 0.01 | 0.05 |
| $x_{25}$ | 0.17 | 0.25 | 0.02 | 0.17 | 0.15 | 0.14 |
| $x_{26}$ | -0.01 | -0.08 | 0.29 | 0.00 | -0.01 | 0.33 |
| $x_{27}$ | 0.17 | 0.25 | 0.29 | 0.17 | 0.17 | 0.23 |
| $x_{28}$ | -0.01 | -0.08 | -0.02 | 0.52 | 0.48 | -0.05 |
| $x_{29}$ | 0.17 | 0.25 | -0.02 | 0.34 | 0.35 | -0.14 |
| $x_{30}$ | -0.01 | -0.08 | 0.36 | 0.52 | 0.55 | 0.42 |
| $x_{31}$ | 0.17 | 0.25 | 0.36 | 0.34 | 0.31 | 0.52 |

FIG. 17b

|  | SNR | Opt. Cap | Std. Cap | Gain [bits] | Gain % |
|---|---|---|---|---|---|
| Design # | | | | | |
| 1 | -5.0000 | 0.1982 | 0.1980 | 0.0002 | 0.0833 |
| 2 | -4.8000 | 0.2063 | 0.2061 | 0.0002 | 0.0924 |
| 3 | -4.6000 | 0.2147 | 0.2145 | 0.0002 | 0.1024 |
| 4 | -4.4000 | 0.2234 | 0.2232 | 0.0003 | 0.1133 |
| 5 | -4.2000 | 0.2324 | 0.2321 | 0.0003 | 0.1252 |
| 6 | -4.0000 | 0.2417 | 0.2414 | 0.0003 | 0.1382 |
| 7 | -3.8000 | 0.2513 | 0.2510 | 0.0004 | 0.1523 |
| 8 | -3.6000 | 0.2613 | 0.2608 | 0.0004 | 0.1677 |
| 9 | -3.4000 | 0.2715 | 0.2710 | 0.0005 | 0.1845 |
| 10 | -3.2000 | 0.2821 | 0.2815 | 0.0006 | 0.2026 |
| 11 | -3.0000 | 0.2930 | 0.2924 | 0.0006 | 0.2222 |
| 12 | -2.8000 | 0.3043 | 0.3035 | 0.0007 | 0.2433 |
| 13 | -2.6000 | 0.3159 | 0.3150 | 0.0008 | 0.2662 |
| 14 | -2.4000 | 0.3278 | 0.3269 | 0.0010 | 0.2907 |
| 15 | -2.2000 | 0.3401 | 0.3390 | 0.0011 | 0.3171 |
| 16 | -2.0000 | 0.3528 | 0.3516 | 0.0012 | 0.3453 |
| 17 | -1.8000 | 0.3658 | 0.3644 | 0.0014 | 0.3755 |
| 18 | -1.6000 | 0.3792 | 0.3776 | 0.0015 | 0.4078 |
| 19 | -1.4000 | 0.3929 | 0.3912 | 0.0017 | 0.4422 |
| 20 | -1.2000 | 0.4070 | 0.4051 | 0.0019 | 0.4788 |
| 21 | -1.0000 | 0.4215 | 0.4194 | 0.0022 | 0.5176 |
| 22 | -0.8000 | 0.4364 | 0.4340 | 0.0024 | 0.5587 |
| 23 | -0.6000 | 0.4516 | 0.4489 | 0.0027 | 0.6021 |
| 24 | -0.4000 | 0.4672 | 0.4642 | 0.0030 | 0.6479 |
| 25 | -0.2000 | 0.4832 | 0.4799 | 0.0033 | 0.6961 |
| 26 | 0.0000 | 0.4996 | 0.4959 | 0.0037 | 0.7468 |
| 27 | 0.0050 | 0.5000 | 0.4963 | 0.0037 | 0.7481 |
| 28 | 0.2000 | 0.5163 | 0.5122 | 0.0041 | 0.7999 |
| 29 | 0.4000 | 0.5334 | 0.5289 | 0.0045 | 0.8554 |
| 30 | 0.6000 | 0.5509 | 0.5459 | 0.0050 | 0.9133 |
| 31 | 0.8000 | 0.5688 | 0.5633 | 0.0055 | 0.9736 |
| 32 | 1.0000 | 0.5870 | 0.5810 | 0.0060 | 1.0363 |
| 33 | 1.2000 | 0.6056 | 0.5990 | 0.0066 | 1.1012 |
| 34 | 1.4000 | 0.6245 | 0.6173 | 0.0072 | 1.1684 |
| 35 | 1.6000 | 0.6439 | 0.6360 | 0.0079 | 1.2377 |
| 36 | 1.8000 | 0.6635 | 0.6550 | 0.0086 | 1.3090 |
| 37 | 2.0000 | 0.6835 | 0.6742 | 0.0093 | 1.3822 |
| 38 | 2.2000 | 0.7039 | 0.6938 | 0.0101 | 1.4572 |
| 39 | 2.4000 | 0.7246 | 0.7137 | 0.0109 | 1.5338 |
| 40 | 2.6000 | 0.7457 | 0.7338 | 0.0118 | 1.6117 |

Table 1

FIG. 25

| Design # | SNR | Opt. Cap | Std. Cap | Gain [bits] | Gain % |
|---|---|---|---|---|---|
| 41 | 2.8000 | 0.7670 | 0.7543 | 0.0128 | 1.6909 |
| 42 | 3.0000 | 0.7887 | 0.7750 | 0.0137 | 1.7709 |
| 43 | 3.2000 | 0.8107 | 0.7960 | 0.0147 | 1.8516 |
| 44 | 3.4000 | 0.8331 | 0.8173 | 0.0158 | 1.9326 |
| 45 | 3.6000 | 0.8557 | 0.8388 | 0.0169 | 2.0134 |
| 46 | 3.8000 | 0.8786 | 0.8606 | 0.0180 | 2.0938 |
| 47 | 4.0000 | 0.9018 | 0.8826 | 0.0192 | 2.1731 |
| 48 | 4.2000 | 0.9252 | 0.9049 | 0.0204 | 2.2508 |
| 49 | 4.4000 | 0.9490 | 0.9274 | 0.0216 | 2.3263 |
| 50 | 4.6000 | 0.9729 | 0.9501 | 0.0228 | 2.3989 |
| 51 | 4.8000 | 0.9971 | 0.9731 | 0.0240 | 2.4677 |
| 52 | 4.8237 | 1.0000 | 0.9758 | 0.0242 | 2.4755 |
| 53 | 5.0000 | 1.0215 | 0.9963 | 0.0252 | 2.5318 |
| 54 | 5.2000 | 1.0461 | 1.0197 | 0.0264 | 2.5905 |
| 55 | 5.4000 | 1.0710 | 1.0433 | 0.0276 | 2.6491 |
| 56 | 5.6000 | 1.0960 | 1.0672 | 0.0289 | 2.7048 |
| 57 | 5.8000 | 1.1213 | 1.0912 | 0.0301 | 2.7584 |
| 58 | 6.0000 | 1.1468 | 1.1154 | 0.0313 | 2.8099 |
| 59 | 6.2000 | 1.1724 | 1.1398 | 0.0326 | 2.8593 |
| 60 | 6.4000 | 1.1983 | 1.1644 | 0.0338 | 2.9064 |
| 61 | 6.6000 | 1.2243 | 1.1892 | 0.0351 | 2.9511 |
| 62 | 6.8000 | 1.2505 | 1.2142 | 0.0363 | 2.9934 |
| 63 | 7.0000 | 1.2769 | 1.2393 | 0.0376 | 3.0322 |
| 64 | 7.2000 | 1.3034 | 1.2646 | 0.0388 | 3.0663 |
| 65 | 7.4000 | 1.3300 | 1.2901 | 0.0399 | 3.0952 |
| 66 | 7.6000 | 1.3567 | 1.3157 | 0.0410 | 3.1187 |
| 67 | 7.8000 | 1.3836 | 1.3415 | 0.0421 | 3.1367 |
| 68 | 8.0000 | 1.4105 | 1.3674 | 0.0431 | 3.1506 |
| 69 | 8.2000 | 1.4376 | 1.3935 | 0.0440 | 3.1605 |
| 70 | 8.4000 | 1.4647 | 1.4197 | 0.0450 | 3.1665 |
| 71 | 8.6000 | 1.4919 | 1.4461 | 0.0458 | 3.1682 |
| 72 | 8.6592 | 1.5000 | 1.4539 | 0.0461 | 3.1678 |
| 73 | 8.8000 | 1.5192 | 1.4726 | 0.0466 | 3.1655 |
| 74 | 9.0000 | 1.5466 | 1.4992 | 0.0474 | 3.1584 |
| 75 | 9.2000 | 1.5740 | 1.5260 | 0.0480 | 3.1466 |
| 76 | 9.4000 | 1.6015 | 1.5529 | 0.0486 | 3.1299 |
| 77 | 9.6000 | 1.6290 | 1.5799 | 0.0491 | 3.1084 |
| 78 | 9.8000 | 1.6566 | 1.6070 | 0.0496 | 3.0839 |
| 79 | 10.0000 | 1.6843 | 1.6343 | 0.0500 | 3.0574 |
| 80 | 10.2000 | 1.7120 | 1.6616 | 0.0503 | 3.0290 |

Table 2

FIG. 26

| Design # | SNR | Opt. Cap | Std. Cap | Gain [bits] | Gain % |
|---|---|---|---|---|---|
| 81 | 10.4000 | 1.7398 | 1.6891 | 0.0506 | 2.9986 |
| 82 | 10.6000 | 1.7676 | 1.7167 | 0.0509 | 2.9662 |
| 83 | 10.8000 | 1.7955 | 1.7443 | 0.0511 | 2.9317 |
| 84 | 11.0000 | 1.8234 | 1.7721 | 0.0513 | 2.8951 |
| 85 | 11.2000 | 1.8514 | 1.8000 | 0.0514 | 2.8562 |
| 86 | 11.4000 | 1.8794 | 1.8279 | 0.0515 | 2.8149 |
| 87 | 11.6000 | 1.9074 | 1.8560 | 0.0514 | 2.7710 |
| 88 | 11.8000 | 1.9354 | 1.8841 | 0.0513 | 2.7244 |
| 89 | 12.0000 | 1.9634 | 1.9123 | 0.0512 | 2.6750 |
| 90 | 12.2000 | 1.9915 | 1.9406 | 0.0509 | 2.6226 |
| 91 | 12.2611 | 2.0000 | 1.9492 | 0.0508 | 2.6059 |
| 92 | 12.4000 | 2.0195 | 1.9689 | 0.0505 | 2.5670 |
| 93 | 12.6000 | 2.0474 | 1.9973 | 0.0501 | 2.5084 |
| 94 | 12.8000 | 2.0754 | 2.0258 | 0.0496 | 2.4466 |
| 95 | 13.0000 | 2.1033 | 2.0544 | 0.0489 | 2.3816 |
| 96 | 13.2000 | 2.1311 | 2.0829 | 0.0482 | 2.3135 |
| 97 | 13.4000 | 2.1589 | 2.1116 | 0.0473 | 2.2424 |
| 98 | 13.6000 | 2.1867 | 2.1402 | 0.0464 | 2.1683 |
| 99 | 13.8000 | 2.2143 | 2.1689 | 0.0454 | 2.0915 |
| 100 | 14.0000 | 2.2419 | 2.1976 | 0.0442 | 2.0121 |
| 101 | 14.2000 | 2.2693 | 2.2263 | 0.0430 | 1.9306 |
| 102 | 14.4000 | 2.2967 | 2.2550 | 0.0417 | 1.8471 |
| 103 | 14.6000 | 2.3239 | 2.2837 | 0.0402 | 1.7622 |
| 104 | 14.8000 | 2.3510 | 2.3122 | 0.0388 | 1.6762 |
| 105 | 15.0000 | 2.3779 | 2.3407 | 0.0372 | 1.5896 |
| 106 | 15.2000 | 2.4047 | 2.3691 | 0.0356 | 1.5030 |
| 107 | 15.4000 | 2.4313 | 2.3973 | 0.0340 | 1.4168 |
| 108 | 15.6000 | 2.4576 | 2.4253 | 0.0323 | 1.3317 |
| 109 | 15.8000 | 2.4837 | 2.4531 | 0.0306 | 1.2481 |
| 110 | 15.9256 | 2.5000 | 2.4704 | 0.0296 | 1.1965 |
| 111 | 16.0000 | 2.5096 | 2.4806 | 0.0289 | 1.1664 |
| 112 | 16.2000 | 2.5351 | 2.5078 | 0.0273 | 1.0871 |
| 113 | 16.4000 | 2.5603 | 2.5347 | 0.0256 | 1.0105 |
| 114 | 16.6000 | 2.5851 | 2.5611 | 0.0240 | 0.9369 |
| 115 | 16.8000 | 2.6095 | 2.5871 | 0.0224 | 0.8664 |
| 116 | 17.0000 | 2.6334 | 2.6125 | 0.0209 | 0.7992 |
| 117 | 17.2000 | 2.6568 | 2.6374 | 0.0194 | 0.7354 |
| 118 | 17.4000 | 2.6796 | 2.6616 | 0.0180 | 0.6750 |
| 119 | 17.6000 | 2.7017 | 2.6851 | 0.0166 | 0.6179 |
| 120 | 17.8000 | 2.7233 | 2.7080 | 0.0153 | 0.5642 |

Table 3

FIG. 27

| Design # | SNR | Opt. Cap | Std. Cap | Gain [bits] | Gain % |
|---|---|---|---|---|---|
| 121 | 18.0000 | 2.7441 | 2.7300 | 0.0140 | 0.5137 |
| 122 | 18.2000 | 2.7641 | 2.7513 | 0.0128 | 0.4664 |
| 123 | 18.4000 | 2.7834 | 2.7717 | 0.0117 | 0.4222 |
| 124 | 18.6000 | 2.8018 | 2.7912 | 0.0106 | 0.3811 |
| 125 | 18.8000 | 2.8194 | 2.8097 | 0.0096 | 0.3428 |
| 126 | 19.0000 | 2.8360 | 2.8274 | 0.0087 | 0.3072 |
| 127 | 19.2000 | 2.8518 | 2.8440 | 0.0078 | 0.2744 |
| 128 | 19.4000 | 2.8667 | 2.8597 | 0.0070 | 0.2442 |
| 129 | 19.6000 | 2.8806 | 2.8743 | 0.0062 | 0.2164 |
| 130 | 19.8000 | 2.8936 | 2.8880 | 0.0055 | 0.1910 |
| 131 | 20.0000 | 2.9056 | 2.9007 | 0.0049 | 0.1678 |
| 132 | 20.2000 | 2.9167 | 2.9125 | 0.0043 | 0.1468 |
| 133 | 20.4000 | 2.9269 | 2.9232 | 0.0037 | 0.1277 |
| 134 | 20.6000 | 2.9363 | 2.9330 | 0.0032 | 0.1104 |
| 135 | 20.8000 | 2.9448 | 2.9420 | 0.0028 | 0.0951 |
| 136 | 21.0000 | 2.9524 | 2.9500 | 0.0024 | 0.0813 |
| 137 | 21.2000 | 2.9593 | 2.9572 | 0.0020 | 0.0692 |
| 138 | 21.4000 | 2.9654 | 2.9636 | 0.0017 | 0.0584 |
| 139 | 21.6000 | 2.9708 | 2.9693 | 0.0015 | 0.0491 |
| 140 | 21.8000 | 2.9755 | 2.9743 | 0.0012 | 0.0409 |
| 141 | 22.0000 | 2.9797 | 2.9786 | 0.0010 | 0.0338 |
| 142 | 22.2000 | 2.9832 | 2.9824 | 0.0008 | 0.0278 |
| 143 | 22.4000 | 2.9863 | 2.9856 | 0.0007 | 0.0226 |
| 144 | 22.6000 | 2.9889 | 2.9884 | 0.0005 | 0.0183 |
| 145 | 22.8000 | 2.9911 | 2.9907 | 0.0004 | 0.0145 |
| 146 | 23.0000 | 2.9929 | 2.9926 | 0.0003 | 0.0115 |
| 147 | 23.2000 | 2.9944 | 2.9942 | 0.0003 | 0.0092 |
| 148 | 23.4000 | 2.9957 | 2.9955 | 0.0002 | 0.0071 |

Table 4

FIG. 28

|  | Label | | | | | | | |
|---|---|---|---|---|---|---|---|---|
|  | 0 | 1 | 2 | 3 | 4 | 5 | 6 | 7 |
| Design # | | | | | | | | |
| 1 | -8.450 | -2.051 | -2.051 | -2.048 | 2.035 | 2.057 | 2.057 | 8.450 |
| 2 | -8.446 | -2.061 | -2.059 | -2.046 | 2.055 | 2.055 | 2.055 | 8.446 |
| 3 | -8.441 | -2.064 | -2.064 | -2.057 | 2.061 | 2.061 | 2.062 | 8.441 |
| 4 | -8.436 | -2.067 | -2.069 | -2.068 | 2.067 | 2.067 | 2.069 | 8.436 |
| 5 | -8.432 | -2.075 | -2.076 | -2.072 | 2.074 | 2.075 | 2.074 | 8.432 |
| 6 | -8.426 | -2.082 | -2.081 | -2.081 | 2.081 | 2.081 | 2.081 | 8.426 |
| 7 | -8.421 | -2.089 | -2.089 | -2.089 | 2.089 | 2.089 | 2.089 | 8.421 |
| 8 | -8.416 | -2.097 | -2.097 | -2.095 | 2.096 | 2.096 | 2.097 | 8.416 |
| 9 | -8.410 | -2.104 | -2.104 | -2.104 | 2.102 | 2.105 | 2.105 | 8.410 |
| 10 | -8.404 | -2.112 | -2.112 | -2.112 | 2.111 | 2.112 | 2.112 | 8.404 |
| 11 | -8.397 | -2.120 | -2.120 | -2.120 | 2.120 | 2.120 | 2.120 | 8.397 |
| 12 | -8.391 | -2.129 | -2.129 | -2.129 | 2.129 | 2.129 | 2.129 | 8.391 |
| 13 | -8.384 | -2.138 | -2.138 | -2.138 | 2.138 | 2.138 | 2.138 | 8.384 |
| 14 | -8.377 | -2.147 | -2.147 | -2.147 | 2.147 | 2.147 | 2.147 | 8.377 |
| 15 | -8.370 | -2.156 | -2.156 | -2.156 | 2.156 | 2.156 | 2.156 | 8.370 |
| 16 | -8.362 | -2.166 | -2.166 | -2.166 | 2.166 | 2.166 | 2.166 | 8.362 |
| 17 | -8.354 | -2.176 | -2.176 | -2.176 | 2.176 | 2.176 | 2.176 | 8.354 |
| 18 | -8.347 | -2.186 | -2.186 | -2.186 | 2.186 | 2.186 | 2.186 | 8.347 |
| 19 | -8.338 | -2.196 | -2.196 | -2.196 | 2.196 | 2.196 | 2.196 | 8.338 |
| 20 | -8.330 | -2.207 | -2.207 | -2.207 | 2.207 | 2.207 | 2.207 | 8.330 |
| 21 | -8.322 | -2.218 | -2.218 | -2.218 | 2.217 | 2.218 | 2.218 | 8.322 |
| 22 | -8.313 | -2.228 | -2.228 | -2.228 | 2.228 | 2.228 | 2.228 | 8.313 |
| 23 | -8.304 | -2.239 | -2.239 | -2.239 | 2.239 | 2.239 | 2.239 | 8.304 |
| 24 | -8.295 | -2.250 | -2.250 | -2.250 | 2.250 | 2.250 | 2.250 | 8.295 |
| 25 | -8.286 | -2.261 | -2.261 | -2.261 | 2.261 | 2.261 | 2.261 | 8.286 |
| 26 | -8.277 | -2.273 | -2.273 | -2.272 | 2.273 | 2.273 | 2.273 | 8.277 |
| 27 | -8.277 | -2.273 | -2.273 | -2.273 | 2.273 | 2.273 | 2.272 | 8.277 |
| 28 | -8.268 | -2.284 | -2.284 | -2.284 | 2.284 | 2.284 | 2.284 | 8.268 |
| 29 | -8.258 | -2.295 | -2.295 | -2.295 | 2.295 | 2.295 | 2.295 | 8.258 |
| 30 | -8.249 | -2.306 | -2.306 | -2.306 | 2.306 | 2.306 | 2.306 | 8.249 |
| 31 | -8.240 | -2.317 | -2.317 | -2.317 | 2.317 | 2.317 | 2.317 | 8.240 |
| 32 | -8.230 | -2.328 | -2.328 | -2.328 | 2.328 | 2.328 | 2.328 | 8.230 |
| 33 | -8.221 | -2.339 | -2.339 | -2.339 | 2.339 | 2.339 | 2.339 | 8.221 |
| 34 | -8.212 | -2.350 | -2.350 | -2.350 | 2.350 | 2.350 | 2.350 | 8.212 |
| 35 | -8.202 | -2.361 | -2.361 | -2.361 | 2.361 | 2.361 | 2.361 | 8.202 |
| 36 | -8.193 | -2.372 | -2.372 | -2.372 | 2.372 | 2.372 | 2.372 | 8.193 |
| 37 | -8.184 | -2.382 | -2.382 | -2.382 | 2.382 | 2.382 | 2.382 | 8.184 |
| 38 | -8.175 | -2.392 | -2.392 | -2.392 | 2.392 | 2.392 | 2.392 | 8.175 |
| 39 | -8.166 | -2.402 | -2.402 | -2.402 | 2.402 | 2.402 | 2.402 | 8.166 |
| 40 | -8.157 | -2.412 | -2.412 | -2.412 | 2.412 | 2.412 | 2.412 | 8.157 |

Table 5

FIG. 29

| Design # | Label | | | | | | | |
|---|---|---|---|---|---|---|---|---|
| | 0 | 1 | 2 | 3 | 4 | 5 | 6 | 7 |
| 41 | -8.149 | -2.422 | -2.422 | -2.422 | 2.422 | 2.422 | 2.422 | 8.149 |
| 42 | -8.141 | -2.431 | -2.431 | -2.431 | 2.431 | 2.431 | 2.431 | 8.141 |
| 43 | -8.132 | -2.440 | -2.440 | -2.440 | 2.440 | 2.440 | 2.440 | 8.132 |
| 44 | -8.124 | -2.449 | -2.449 | -2.449 | 2.449 | 2.449 | 2.449 | 8.124 |
| 45 | -8.117 | -2.458 | -2.458 | -2.458 | 2.458 | 2.458 | 2.458 | 8.117 |
| 46 | -8.109 | -2.466 | -2.466 | -2.466 | 2.466 | 2.466 | 2.466 | 8.109 |
| 47 | -8.102 | -2.474 | -2.474 | -2.474 | 2.474 | 2.474 | 2.474 | 8.102 |
| 48 | -8.095 | -2.481 | -2.481 | -2.481 | 2.481 | 2.481 | 2.481 | 8.095 |
| 49 | -8.088 | -2.489 | -2.489 | -2.489 | 2.489 | 2.489 | 2.489 | 8.088 |
| 50 | -8.082 | -2.496 | -2.496 | -2.496 | 2.496 | 2.496 | 2.496 | 8.082 |
| 51 | -8.075 | -2.503 | -2.503 | -2.503 | 2.503 | 2.503 | 2.503 | 8.075 |
| 52 | -8.075 | -2.503 | -2.503 | -2.503 | 2.503 | 2.503 | 2.503 | 8.075 |
| 53 | -8.069 | -2.509 | -2.509 | -2.509 | 2.509 | 2.509 | 2.509 | 8.069 |
| 54 | -8.063 | -2.513 | -2.513 | -2.513 | 2.391 | 2.391 | 2.761 | 8.061 |
| 55 | -8.031 | -2.900 | -2.900 | -1.639 | 1.639 | 2.900 | 2.900 | 8.031 |
| 56 | -8.012 | -2.987 | -2.987 | -1.403 | 1.403 | 2.987 | 2.987 | 8.012 |
| 57 | -7.993 | -3.055 | -3.055 | -1.199 | 1.199 | 3.055 | 3.055 | 7.993 |
| 58 | -7.976 | -3.111 | -3.111 | -1.012 | 1.012 | 3.111 | 3.111 | 7.976 |
| 59 | -7.960 | -3.158 | -3.158 | -0.832 | 0.832 | 3.158 | 3.158 | 7.960 |
| 60 | -7.945 | -3.199 | -3.199 | -0.649 | 0.649 | 3.199 | 3.199 | 7.945 |
| 61 | -7.930 | -3.234 | -3.234 | -0.445 | 0.445 | 3.234 | 3.234 | 7.930 |
| 62 | -7.916 | -3.265 | -3.265 | -0.123 | 0.123 | 3.265 | 3.265 | 7.916 |
| 63 | -7.906 | -3.279 | -3.279 | 0.000 | 0.000 | 3.279 | 3.279 | 7.906 |
| 64 | -7.896 | -3.291 | -3.291 | 0.000 | 0.000 | 3.291 | 3.291 | 7.896 |
| 65 | -7.885 | -3.303 | -3.303 | 0.000 | 0.000 | 3.303 | 3.303 | 7.885 |
| 66 | -7.875 | -3.316 | -3.316 | 0.000 | 0.000 | 3.316 | 3.316 | 7.875 |
| 67 | -7.862 | -3.486 | -3.168 | 0.000 | 0.000 | 3.168 | 3.486 | 7.862 |
| 68 | -7.847 | -3.621 | -3.052 | 0.000 | 0.000 | 3.052 | 3.621 | 7.847 |
| 69 | -7.833 | -3.711 | -2.979 | 0.000 | 0.000 | 2.979 | 3.711 | 7.833 |
| 70 | -7.819 | -3.782 | -2.925 | 0.000 | 0.000 | 2.925 | 3.782 | 7.819 |
| 71 | -7.806 | -3.843 | -2.881 | 0.000 | 0.000 | 2.881 | 3.843 | 7.806 |
| 72 | -7.802 | -3.860 | -2.870 | 0.000 | 0.000 | 2.870 | 3.860 | 7.802 |
| 73 | -7.793 | -3.897 | -2.844 | 0.000 | 0.000 | 2.844 | 3.897 | 7.793 |
| 74 | -7.780 | -3.945 | -2.812 | 0.000 | 0.000 | 2.812 | 3.945 | 7.780 |
| 75 | -7.768 | -3.990 | -2.783 | 0.000 | 0.000 | 2.783 | 3.990 | 7.768 |
| 76 | -7.756 | -4.031 | -2.756 | 0.000 | 0.000 | 2.756 | 4.031 | 7.756 |
| 77 | -7.744 | -4.075 | -2.720 | -0.164 | 0.164 | 2.720 | 4.075 | 7.744 |
| 78 | -7.730 | -4.131 | -2.656 | -0.362 | 0.362 | 2.656 | 4.131 | 7.730 |
| 79 | -7.717 | -4.178 | -2.603 | -0.471 | 0.471 | 2.603 | 4.178 | 7.717 |
| 80 | -7.704 | -4.219 | -2.560 | -0.549 | 0.549 | 2.560 | 4.219 | 7.704 |

Table 6

FIG. 30

| Design # | \multicolumn{8}{c}{Label} |
| | 0 | 1 | 2 | 3 | 4 | 5 | 6 | 7 |
|---|---|---|---|---|---|---|---|---|
| 81 | -7.692 | -4.255 | -2.524 | -0.608 | 0.608 | 2.524 | 4.255 | 7.692 |
| 82 | -7.680 | -4.286 | -2.494 | -0.654 | 0.654 | 2.494 | 4.286 | 7.680 |
| 83 | -7.669 | -4.314 | -2.471 | -0.690 | 0.690 | 2.471 | 4.314 | 7.669 |
| 84 | -7.657 | -4.340 | -2.452 | -0.718 | 0.718 | 2.452 | 4.340 | 7.657 |
| 85 | -7.647 | -4.363 | -2.438 | -0.740 | 0.740 | 2.438 | 4.363 | 7.647 |
| 86 | -7.636 | -4.385 | -2.428 | -0.757 | 0.757 | 2.428 | 4.385 | 7.636 |
| 87 | -7.625 | -4.405 | -2.422 | -0.770 | 0.770 | 2.422 | 4.405 | 7.625 |
| 88 | -7.614 | -4.424 | -2.418 | -0.780 | 0.780 | 2.418 | 4.424 | 7.614 |
| 89 | -7.603 | -4.441 | -2.417 | -0.787 | 0.787 | 2.417 | 4.441 | 7.603 |
| 90 | -7.592 | -4.458 | -2.419 | -0.792 | 0.792 | 2.419 | 4.458 | 7.592 |
| 91 | -7.589 | -4.464 | -2.420 | -0.793 | 0.793 | 2.420 | 4.464 | 7.589 |
| 92 | -7.581 | -4.475 | -2.423 | -0.795 | 0.795 | 2.423 | 4.475 | 7.581 |
| 93 | -7.570 | -4.491 | -2.428 | -0.797 | 0.797 | 2.428 | 4.491 | 7.570 |
| 94 | -7.558 | -4.507 | -2.435 | -0.799 | 0.799 | 2.435 | 4.507 | 7.558 |
| 95 | -7.546 | -4.522 | -2.444 | -0.800 | 0.800 | 2.444 | 4.522 | 7.546 |
| 96 | -7.533 | -4.538 | -2.453 | -0.800 | 0.800 | 2.453 | 4.538 | 7.533 |
| 97 | -7.521 | -4.553 | -2.464 | -0.801 | 0.801 | 2.464 | 4.553 | 7.521 |
| 98 | -7.508 | -4.568 | -2.475 | -0.802 | 0.802 | 2.475 | 4.568 | 7.508 |
| 99 | -7.494 | -4.583 | -2.488 | -0.804 | 0.804 | 2.488 | 4.583 | 7.494 |
| 100 | -7.481 | -4.597 | -2.501 | -0.805 | 0.805 | 2.501 | 4.597 | 7.481 |
| 101 | -7.467 | -4.612 | -2.514 | -0.808 | 0.808 | 2.514 | 4.612 | 7.467 |
| 102 | -7.453 | -4.626 | -2.529 | -0.811 | 0.811 | 2.529 | 4.626 | 7.453 |
| 103 | -7.439 | -4.641 | -2.543 | -0.815 | 0.815 | 2.543 | 4.641 | 7.439 |
| 104 | -7.424 | -4.655 | -2.559 | -0.819 | 0.819 | 2.559 | 4.655 | 7.424 |
| 105 | -7.409 | -4.669 | -2.574 | -0.824 | 0.824 | 2.574 | 4.669 | 7.409 |
| 106 | -7.395 | -4.682 | -2.590 | -0.830 | 0.830 | 2.590 | 4.682 | 7.395 |
| 107 | -7.380 | -4.695 | -2.607 | -0.836 | 0.836 | 2.607 | 4.695 | 7.380 |
| 108 | -7.365 | -4.708 | -2.623 | -0.842 | 0.842 | 2.623 | 4.708 | 7.365 |
| 109 | -7.350 | -4.721 | -2.640 | -0.849 | 0.849 | 2.640 | 4.721 | 7.350 |
| 110 | -7.340 | -4.729 | -2.651 | -0.853 | 0.853 | 2.651 | 4.729 | 7.340 |
| 111 | -7.336 | -4.733 | -2.656 | -0.855 | 0.855 | 2.656 | 4.733 | 7.336 |
| 112 | -7.322 | -4.745 | -2.672 | -0.862 | 0.862 | 2.672 | 4.745 | 7.322 |
| 113 | -7.308 | -4.756 | -2.687 | -0.869 | 0.869 | 2.687 | 4.756 | 7.308 |
| 114 | -7.294 | -4.767 | -2.703 | -0.875 | 0.875 | 2.703 | 4.767 | 7.294 |
| 115 | -7.281 | -4.778 | -2.717 | -0.882 | 0.882 | 2.717 | 4.778 | 7.281 |
| 116 | -7.269 | -4.788 | -2.731 | -0.888 | 0.888 | 2.731 | 4.788 | 7.269 |
| 117 | -7.256 | -4.798 | -2.744 | -0.893 | 0.893 | 2.744 | 4.798 | 7.256 |
| 118 | -7.245 | -4.807 | -2.757 | -0.899 | 0.899 | 2.757 | 4.807 | 7.245 |
| 119 | -7.233 | -4.816 | -2.769 | -0.904 | 0.904 | 2.769 | 4.816 | 7.233 |
| 120 | -7.223 | -4.824 | -2.781 | -0.909 | 0.909 | 2.781 | 4.824 | 7.223 |

Table 7

FIG. 31

|  | Label | | | | | | | |
|---|---|---|---|---|---|---|---|---|
|  | 0 | 1 | 2 | 3 | 4 | 5 | 6 | 7 |
| Design # | | | | | | | | |
| 121 | -7.213 | -4.832 | -2.792 | -0.914 | 0.914 | 2.792 | 4.832 | 7.213 |
| 122 | -7.203 | -4.840 | -2.802 | -0.918 | 0.918 | 2.802 | 4.840 | 7.203 |
| 123 | -7.194 | -4.847 | -2.812 | -0.922 | 0.922 | 2.812 | 4.847 | 7.194 |
| 124 | -7.185 | -4.854 | -2.821 | -0.926 | 0.926 | 2.821 | 4.854 | 7.185 |
| 125 | -7.176 | -4.861 | -2.830 | -0.930 | 0.930 | 2.830 | 4.861 | 7.176 |
| 126 | -7.168 | -4.867 | -2.838 | -0.933 | 0.933 | 2.838 | 4.867 | 7.168 |
| 127 | -7.161 | -4.873 | -2.846 | -0.937 | 0.937 | 2.846 | 4.873 | 7.161 |
| 128 | -7.154 | -4.879 | -2.853 | -0.940 | 0.940 | 2.853 | 4.879 | 7.154 |
| 129 | -7.147 | -4.885 | -2.860 | -0.943 | 0.943 | 2.860 | 4.885 | 7.147 |
| 130 | -7.140 | -4.890 | -2.867 | -0.945 | 0.945 | 2.867 | 4.890 | 7.140 |
| 131 | -7.134 | -4.895 | -2.873 | -0.948 | 0.948 | 2.873 | 4.895 | 7.134 |
| 132 | -7.128 | -4.900 | -2.879 | -0.950 | 0.950 | 2.879 | 4.900 | 7.128 |
| 133 | -7.122 | -4.904 | -2.885 | -0.953 | 0.953 | 2.885 | 4.904 | 7.122 |
| 134 | -7.116 | -4.909 | -2.890 | -0.955 | 0.955 | 2.890 | 4.909 | 7.116 |
| 135 | -7.111 | -4.913 | -2.895 | -0.957 | 0.957 | 2.895 | 4.913 | 7.111 |
| 136 | -7.106 | -4.917 | -2.900 | -0.959 | 0.959 | 2.900 | 4.917 | 7.106 |
| 137 | -7.102 | -4.920 | -2.904 | -0.961 | 0.961 | 2.904 | 4.920 | 7.102 |
| 138 | -7.097 | -4.924 | -2.909 | -0.963 | 0.963 | 2.909 | 4.924 | 7.097 |
| 139 | -7.093 | -4.927 | -2.913 | -0.965 | 0.965 | 2.913 | 4.927 | 7.093 |
| 140 | -7.089 | -4.931 | -2.917 | -0.966 | 0.966 | 2.917 | 4.931 | 7.089 |
| 141 | -7.084 | -4.934 | -2.921 | -0.968 | 0.968 | 2.921 | 4.934 | 7.084 |
| 142 | -7.081 | -4.937 | -2.924 | -0.969 | 0.969 | 2.924 | 4.937 | 7.081 |
| 143 | -7.077 | -4.940 | -2.928 | -0.971 | 0.971 | 2.928 | 4.940 | 7.077 |
| 144 | -7.074 | -4.942 | -2.931 | -0.972 | 0.972 | 2.931 | 4.942 | 7.074 |
| 145 | -7.071 | -4.945 | -2.934 | -0.973 | 0.973 | 2.934 | 4.945 | 7.071 |
| 146 | -7.068 | -4.947 | -2.937 | -0.974 | 0.974 | 2.937 | 4.947 | 7.068 |
| 147 | -7.064 | -4.950 | -2.941 | -0.976 | 0.976 | 2.941 | 4.950 | 7.064 |
| 148 | -7.062 | -4.952 | -2.942 | -0.977 | 0.977 | 2.942 | 4.952 | 7.062 |

Table 8

FIG. 32

| Design # | SNRs | 5.00% | 15.00% | 30.00% | 45.00% | 60.00% | 100.00% |
|---|---|---|---|---|---|---|---|
| 1 | -5 | 0.12 | 0.11 | 0.1 | 0.09 | 0.06 | 0 |
| 2 | -4.8 | 0.12 | 0.11 | 0.1 | 0.09 | 0.06 | 0 |
| 3 | -4.6 | 0.13 | 0.12 | 0.11 | 0.09 | 0.08 | 0 |
| 4 | -4.4 | 0.13 | 0.12 | 0.1 | 0.09 | 0.07 | 0 |
| 5 | -4.2 | 0.14 | 0.13 | 0.11 | 0.1 | 0.07 | 0 |
| 6 | -4 | 0.15 | 0.14 | 0.12 | 0.11 | 0.08 | 0 |
| 7 | -3.8 | 0.15 | 0.14 | 0.12 | 0.11 | 0.08 | 0 |
| 8 | -3.6 | 0.17 | 0.15 | 0.14 | 0.12 | 0.09 | 0 |
| 9 | -3.4 | 0.18 | 0.16 | 0.15 | 0.13 | 0.09 | 0 |
| 10 | -3.2 | 0.18 | 0.16 | 0.15 | 0.13 | 0.1 | 0 |
| 11 | -3 | 0.2 | 0.18 | 0.16 | 0.14 | 0.1 | 0 |
| 12 | -2.8 | 0.19 | 0.17 | 0.16 | 0.14 | 0.1 | 0 |
| 13 | -2.6 | 0.21 | 0.19 | 0.17 | 0.15 | 0.11 | 0 |
| 14 | -2.4 | 0.23 | 0.21 | 0.19 | 0.17 | 0.12 | 0 |
| 15 | -2.2 | 0.23 | 0.2 | 0.18 | 0.17 | 0.12 | 0 |
| 16 | -2 | 0.25 | 0.22 | 0.2 | 0.18 | 0.13 | 0 |
| 17 | -1.8 | 0.27 | 0.24 | 0.22 | 0.2 | 0.13 | 0 |
| 18 | -1.6 | 0.26 | 0.24 | 0.21 | 0.19 | 0.14 | 0 |
| 19 | -1.4 | 0.29 | 0.26 | 0.23 | 0.21 | 0.15 | 0 |
| 20 | -1.2 | 0.28 | 0.25 | 0.23 | 0.2 | 0.15 | 0 |
| 21 | -1 | 0.3 | 0.27 | 0.25 | 0.22 | 0.16 | 0 |
| 22 | -0.8 | 0.33 | 0.3 | 0.27 | 0.24 | 0.18 | 0 |
| 23 | -0.6 | 0.32 | 0.29 | 0.26 | 0.23 | 0.17 | 0 |
| 24 | -0.4 | 0.35 | 0.31 | 0.28 | 0.25 | 0.18 | 0 |
| 25 | -0.2 | 0.34 | 0.3 | 0.27 | 0.25 | 0.2 | 0 |
| 26 | 0 | 0.33 | 0.3 | 0.27 | 0.24 | 0.19 | 0 |
| 27 | 0.01 | 0.33 | 0.3 | 0.27 | 0.24 | 0.19 | 0 |
| 28 | 0.2 | 0.32 | 0.29 | 0.26 | 0.23 | 0.21 | 0 |
| 29 | 0.4 | 0.31 | 0.28 | 0.25 | 0.23 | 0.2 | 0 |
| 30 | 0.6 | 0.3 | 0.27 | 0.24 | 0.22 | 0.2 | 0 |
| 31 | 0.8 | 0.29 | 0.26 | 0.23 | 0.21 | 0.19 | 0 |
| 32 | 1 | 0.28 | 0.25 | 0.23 | 0.2 | 0.18 | 0 |
| 33 | 1.2 | 0.27 | 0.24 | 0.22 | 0.2 | 0.18 | 0 |
| 34 | 1.4 | 0.26 | 0.24 | 0.21 | 0.19 | 0.17 | 0 |
| 35 | 1.6 | 0.25 | 0.23 | 0.2 | 0.18 | 0.17 | 0 |
| 36 | 1.8 | 0.24 | 0.22 | 0.2 | 0.18 | 0.16 | 0 |
| 37 | 2 | 0.23 | 0.21 | 0.19 | 0.17 | 0.15 | 0 |
| 38 | 2.2 | 0.22 | 0.2 | 0.18 | 0.16 | 0.15 | 0 |
| 39 | 2.4 | 0.22 | 0.19 | 0.17 | 0.16 | 0.14 | 0 |
| 40 | 2.6 | 0.21 | 0.19 | 0.17 | 0.15 | 0.14 | 0 |

Table 9

FIG. 33

| Design # | SNRs | 5.00% | 15.00% | 30.00% | 45.00% | 60.00% | 100.00% |
|---|---|---|---|---|---|---|---|
| 41 | 2.8 | 0.2 | 0.18 | 0.16 | 0.14 | 0.13 | 0 |
| 42 | 3 | 0.19 | 0.17 | 0.15 | 0.14 | 0.13 | 0 |
| 43 | 3.2 | 0.18 | 0.16 | 0.15 | 0.13 | 0.12 | 0 |
| 44 | 3.4 | 0.17 | 0.16 | 0.14 | 0.13 | 0.11 | 0 |
| 45 | 3.6 | 0.17 | 0.15 | 0.14 | 0.12 | 0.11 | 0 |
| 46 | 3.8 | 0.16 | 0.14 | 0.13 | 0.12 | 0.11 | 0 |
| 47 | 4 | 0.15 | 0.14 | 0.12 | 0.11 | 0.1 | 0 |
| 48 | 4.2 | 0.15 | 0.13 | 0.12 | 0.11 | 0.1 | 0 |
| 49 | 4.4 | 0.14 | 0.13 | 0.11 | 0.1 | 0.09 | 0 |
| 50 | 4.6 | 0.13 | 0.12 | 0.11 | 0.1 | 0.09 | 0 |
| 51 | 4.8 | 0.13 | 0.11 | 0.1 | 0.09 | 0.08 | 0 |
| 52 | 4.82 | 0.13 | 0.11 | 0.1 | 0.09 | 0.08 | 0 |
| 53 | 5 | 0.12 | 0.11 | 0.1 | 0.09 | 0.08 | 0 |
| 54 | 5.2 | 0.2 | 0.18 | 0.16 | 0.15 | 0.13 | 0 |
| 55 | 5.4 | 0.57 | 0.51 | 0.46 | 0.41 | 0.27 | 0 |
| 56 | 5.6 | 0.56 | 0.51 | 0.45 | 0.41 | 0.3 | 0 |
| 57 | 5.8 | 0.53 | 0.47 | 0.43 | 0.38 | 0.28 | 0 |
| 58 | 6 | 0.56 | 0.51 | 0.46 | 0.41 | 0.3 | 0 |
| 59 | 6.2 | 0.54 | 0.49 | 0.44 | 0.39 | 0.29 | 0 |
| 60 | 6.4 | 0.55 | 0.49 | 0.44 | 0.4 | 0.29 | 0 |
| 61 | 6.6 | 0.55 | 0.43 | 0.39 | 0.35 | 0.31 | 0 |
| 62 | 6.8 | 0.56 | 0.34 | 0.31 | 0.28 | 0.25 | 0 |
| 63 | 7 | 0.56 | 0.3 | 0.27 | 0.25 | 0.22 | 0 |
| 64 | 7.2 | 0.56 | 0.3 | 0.27 | 0.24 | 0.22 | 0 |
| 65 | 7.4 | 0.56 | 0.29 | 0.26 | 0.23 | 0.21 | 0 |
| 66 | 7.6 | 0.57 | 0.28 | 0.25 | 0.23 | 0.2 | 0 |
| 67 | 7.8 | 0.53 | 0.27 | 0.24 | 0.22 | 0.2 | 0 |
| 68 | 8 | 0.54 | 0.26 | 0.24 | 0.21 | 0.19 | 0 |
| 69 | 8.2 | 0.53 | 0.26 | 0.23 | 0.21 | 0.19 | 0 |
| 70 | 8.4 | 0.53 | 0.25 | 0.23 | 0.2 | 0.18 | 0 |
| 71 | 8.6 | 0.53 | 0.24 | 0.22 | 0.2 | 0.18 | 0 |
| 72 | 8.66 | 0.53 | 0.24 | 0.22 | 0.2 | 0.18 | 0 |
| 73 | 8.8 | 0.48 | 0.24 | 0.21 | 0.19 | 0.17 | 0 |
| 74 | 9 | 0.47 | 0.23 | 0.21 | 0.19 | 0.17 | 0 |
| 75 | 9.2 | 0.47 | 0.22 | 0.2 | 0.18 | 0.16 | 0 |
| 76 | 9.4 | 0.47 | 0.22 | 0.2 | 0.18 | 0.16 | 0 |
| 77 | 9.6 | 0.46 | 0.25 | 0.23 | 0.2 | 0.18 | 0 |
| 78 | 9.8 | 0.35 | 0.29 | 0.26 | 0.24 | 0.21 | 0 |
| 79 | 10 | 0.26 | 0.23 | 0.21 | 0.19 | 0.17 | 0 |
| 80 | 10.2 | 0.2 | 0.18 | 0.16 | 0.14 | 0.13 | 0 |

Table 10

FIG. 34

| Design # | SNRs | 5.00% | 15.00% | 30.00% | 45.00% | 60.00% | 100.00% |
|---|---|---|---|---|---|---|---|
| 81 | 10.4 | 0.15 | 0.13 | 0.12 | 0.11 | 0.1 | 0 |
| 82 | 10.6 | 0.11 | 0.1 | 0.09 | 0.08 | 0.07 | 0 |
| 83 | 10.8 | 0.08 | 0.07 | 0.06 | 0.06 | 0.05 | 0 |
| 84 | 11 | 0.05 | 0.05 | 0.04 | 0.04 | 0.04 | 0 |
| 85 | 11.2 | 0.04 | 0.03 | 0.03 | 0.03 | 0.02 | 0 |
| 86 | 11.4 | 0.02 | 0.02 | 0.02 | 0.02 | 0.01 | 0 |
| 87 | 11.6 | 0.01 | 0.01 | 0.01 | 0.01 | 0.01 | 0 |
| 88 | 11.8 | 0.01 | 0.01 | 0 | 0 | 0 | 0 |
| 89 | 12 | 0.03 | 0.02 | 0.01 | 0.01 | 0.01 | 0 |
| 90 | 12.2 | 0.04 | 0.03 | 0.02 | 0.02 | 0.02 | 0 |
| 91 | 12.26 | 0.04 | 0.04 | 0.03 | 0.02 | 0.02 | 0 |
| 92 | 12.4 | 0.05 | 0.05 | 0.03 | 0.03 | 0.02 | 0 |
| 93 | 12.6 | 0.06 | 0.06 | 0.04 | 0.03 | 0.03 | 0 |
| 94 | 12.8 | 0.08 | 0.07 | 0.05 | 0.04 | 0.04 | 0 |
| 95 | 13 | 0.09 | 0.08 | 0.05 | 0.05 | 0.04 | 0 |
| 96 | 13.2 | 0.1 | 0.09 | 0.06 | 0.05 | 0.05 | 0 |
| 97 | 13.4 | 0.12 | 0.1 | 0.07 | 0.06 | 0.06 | 0 |
| 98 | 13.6 | 0.13 | 0.12 | 0.08 | 0.07 | 0.07 | 0 |
| 99 | 13.8 | 0.14 | 0.13 | 0.09 | 0.08 | 0.08 | 0 |
| 100 | 14 | 0.15 | 0.14 | 0.1 | 0.09 | 0.08 | 0 |
| 101 | 14.2 | 0.17 | 0.15 | 0.11 | 0.1 | 0.09 | 0 |
| 102 | 14.4 | 0.18 | 0.16 | 0.13 | 0.11 | 0.1 | 0 |
| 103 | 14.6 | 0.19 | 0.17 | 0.14 | 0.13 | 0.11 | 0 |
| 104 | 14.8 | 0.21 | 0.19 | 0.15 | 0.14 | 0.11 | 0 |
| 105 | 15 | 0.2 | 0.18 | 0.16 | 0.14 | 0.1 | 0 |
| 106 | 15.2 | 0.21 | 0.19 | 0.17 | 0.14 | 0.1 | 0 |
| 107 | 15.4 | 0.18 | 0.16 | 0.14 | 0.13 | 0.09 | 0 |
| 108 | 15.6 | 0.17 | 0.15 | 0.14 | 0.12 | 0.09 | 0 |
| 109 | 15.8 | 0.16 | 0.14 | 0.13 | 0.12 | 0.08 | 0 |
| 110 | 15.93 | 0.16 | 0.15 | 0.13 | 0.12 | 0.09 | 0 |
| 111 | 16 | 0.15 | 0.13 | 0.12 | 0.11 | 0.08 | 0 |
| 112 | 16.2 | 0.14 | 0.13 | 0.11 | 0.1 | 0.07 | 0 |
| 113 | 16.4 | 0.13 | 0.12 | 0.11 | 0.1 | 0.07 | 0 |
| 114 | 16.6 | 0.13 | 0.11 | 0.1 | 0.09 | 0.07 | 0 |
| 115 | 16.8 | 0.12 | 0.11 | 0.1 | 0.09 | 0.06 | 0 |
| 116 | 17 | 0.12 | 0.1 | 0.09 | 0.08 | 0.06 | 0 |
| 117 | 17.2 | 0.11 | 0.1 | 0.09 | 0.08 | 0.06 | 0 |
| 118 | 17.4 | 0.1 | 0.09 | 0.08 | 0.08 | 0.06 | 0 |
| 119 | 17.6 | 0.1 | 0.09 | 0.08 | 0.07 | 0.05 | 0 |
| 120 | 17.8 | 0.09 | 0.09 | 0.08 | 0.07 | 0.05 | 0 |

Table 11

FIG. 35

| Design # | SNRs | 5.00% | 15.00% | 30.00% | 45.00% | 60.00% | 100.00% |
|---|---|---|---|---|---|---|---|
| 121 | 18 | 0.09 | 0.08 | 0.07 | 0.07 | 0.05 | 0 |
| 122 | 18.2 | 0.09 | 0.08 | 0.07 | 0.06 | 0.05 | 0 |
| 123 | 18.4 | 0.08 | 0.07 | 0.07 | 0.06 | 0.04 | 0 |
| 124 | 18.6 | 0.08 | 0.07 | 0.06 | 0.06 | 0.04 | 0 |
| 125 | 18.8 | 0.07 | 0.07 | 0.06 | 0.05 | 0.04 | 0 |
| 126 | 19 | 0.07 | 0.06 | 0.06 | 0.05 | 0.04 | 0 |
| 127 | 19.2 | 0.07 | 0.06 | 0.05 | 0.05 | 0.04 | 0 |
| 128 | 19.4 | 0.06 | 0.06 | 0.05 | 0.05 | 0.03 | 0 |
| 129 | 19.6 | 0.06 | 0.06 | 0.05 | 0.04 | 0.03 | 0 |
| 130 | 19.8 | 0.06 | 0.05 | 0.05 | 0.04 | 0.03 | 0 |
| 131 | 20 | 0.06 | 0.05 | 0.05 | 0.04 | 0.03 | 0 |
| 132 | 20.2 | 0.05 | 0.05 | 0.04 | 0.04 | 0.03 | 0 |
| 133 | 20.4 | 0.05 | 0.05 | 0.04 | 0.04 | 0.02 | 0 |
| 134 | 20.6 | 0.05 | 0.04 | 0.04 | 0.04 | 0.02 | 0 |
| 135 | 20.8 | 0.04 | 0.04 | 0.03 | 0.03 | 0.02 | 0 |
| 136 | 21 | 0.04 | 0.04 | 0.04 | 0.03 | 0.02 | 0 |
| 137 | 21.2 | 0.04 | 0.04 | 0.03 | 0.03 | 0.02 | 0 |
| 138 | 21.4 | 0.04 | 0.03 | 0.03 | 0.03 | 0.02 | 0 |
| 139 | 21.6 | 0.03 | 0.03 | 0.03 | 0.03 | 0.02 | 0 |
| 140 | 21.8 | 0.03 | 0.03 | 0.03 | 0.02 | 0.02 | 0 |
| 141 | 22 | 0.03 | 0.03 | 0.03 | 0.02 | 0.02 | 0 |
| 142 | 22.2 | 0.03 | 0.03 | 0.02 | 0.02 | 0.02 | 0 |
| 143 | 22.4 | 0.03 | 0.03 | 0.02 | 0.02 | 0.02 | 0 |
| 144 | 22.6 | 0.03 | 0.02 | 0.02 | 0.02 | 0.01 | 0 |
| 145 | 22.8 | 0.03 | 0.02 | 0.02 | 0.02 | 0.01 | 0 |
| 146 | 23 | 0.02 | 0.02 | 0.02 | 0.02 | 0.01 | 0 |
| 147 | 23.2 | 0.02 | 0.02 | 0.02 | 0.02 | 0.01 | 0 |
| 148 | 23.4 | 0.02 | 0.02 | 0.02 | 0.02 | 0.01 | 0 |

Table 12

FIG. 36

| Design # | SNR | Opt. Cap | Std. Cap | Gain [bits] | Gain % |
|---|---|---|---|---|---|
| 1 | -5.0000 | 0.1977 | 0.1598 | 0.0379 | 23.7349 |
| 2 | -4.8000 | 0.2058 | 0.1666 | 0.0391 | 23.4911 |
| 3 | -4.6000 | 0.2141 | 0.1737 | 0.0404 | 23.2414 |
| 4 | -4.4000 | 0.2227 | 0.1811 | 0.0416 | 22.9855 |
| 5 | -4.2000 | 0.2316 | 0.1887 | 0.0429 | 22.7233 |
| 6 | -4.0000 | 0.2407 | 0.1966 | 0.0441 | 22.4546 |
| 7 | -3.8000 | 0.2502 | 0.2048 | 0.0454 | 22.1792 |
| 8 | -3.6000 | 0.2600 | 0.2133 | 0.0467 | 21.8969 |
| 9 | -3.4000 | 0.2700 | 0.2220 | 0.0480 | 21.6075 |
| 10 | -3.2000 | 0.2804 | 0.2311 | 0.0493 | 21.3107 |
| 11 | -3.0000 | 0.2910 | 0.2405 | 0.0505 | 21.0063 |
| 12 | -2.8000 | 0.3020 | 0.2502 | 0.0518 | 20.6939 |
| 13 | -2.6000 | 0.3133 | 0.2602 | 0.0530 | 20.3732 |
| 14 | -2.4000 | 0.3248 | 0.2706 | 0.0542 | 20.0439 |
| 15 | -2.2000 | 0.3367 | 0.2813 | 0.0554 | 19.7054 |
| 16 | -2.0000 | 0.3489 | 0.2923 | 0.0566 | 19.3575 |
| 17 | -1.8000 | 0.3613 | 0.3037 | 0.0577 | 18.9996 |
| 18 | -1.6000 | 0.3741 | 0.3154 | 0.0588 | 18.6313 |
| 19 | -1.4000 | 0.3872 | 0.3274 | 0.0598 | 18.2519 |
| 20 | -1.2000 | 0.4005 | 0.3398 | 0.0607 | 17.8609 |
| 21 | -1.0000 | 0.4141 | 0.3526 | 0.0615 | 17.4577 |
| 22 | -0.8000 | 0.4280 | 0.3657 | 0.0623 | 17.0415 |
| 23 | -0.6000 | 0.4421 | 0.3791 | 0.0630 | 16.6117 |
| 24 | -0.4000 | 0.4565 | 0.3930 | 0.0635 | 16.1675 |
| 25 | -0.2000 | 0.4711 | 0.4072 | 0.0640 | 15.7080 |
| 26 | 0.0000 | 0.4859 | 0.4217 | 0.0642 | 15.2325 |
| 27 | 0.1871 | 0.5000 | 0.4356 | 0.0644 | 14.7724 |
| 28 | 0.2000 | 0.5010 | 0.4366 | 0.0644 | 14.7399 |
| 29 | 0.4000 | 0.5162 | 0.4519 | 0.0643 | 14.2295 |
| 30 | 0.6000 | 0.5316 | 0.4675 | 0.0641 | 13.7002 |
| 31 | 0.8000 | 0.5471 | 0.4835 | 0.0636 | 13.1510 |
| 32 | 1.0000 | 0.5628 | 0.4999 | 0.0629 | 12.5809 |
| 33 | 1.2000 | 0.5786 | 0.5166 | 0.0619 | 11.9887 |
| 34 | 1.4000 | 0.5944 | 0.5337 | 0.0607 | 11.3736 |
| 35 | 1.6000 | 0.6104 | 0.5511 | 0.0593 | 10.7597 |
| 36 | 1.8000 | 0.6270 | 0.5689 | 0.0581 | 10.2106 |
| 37 | 2.0000 | 0.6442 | 0.5871 | 0.0571 | 9.7259 |
| 38 | 2.2000 | 0.6619 | 0.6056 | 0.0563 | 9.3017 |
| 39 | 2.4000 | 0.6802 | 0.6244 | 0.0558 | 8.9342 |
| 40 | 2.6000 | 0.6991 | 0.6437 | 0.0555 | 8.6193 |

Table 13

FIG. 37

| Design # | SNR | Opt. Cap | Std. Cap | Gain [bits] | Gain % |
|---|---|---|---|---|---|
| 41 | 2.8000 | 0.7186 | 0.6632 | 0.0554 | 8.3527 |
| 42 | 3.0000 | 0.7386 | 0.6831 | 0.0555 | 8.1300 |
| 43 | 3.2000 | 0.7593 | 0.7034 | 0.0559 | 7.9468 |
| 44 | 3.4000 | 0.7804 | 0.7240 | 0.0565 | 7.7983 |
| 45 | 3.6000 | 0.8021 | 0.7449 | 0.0572 | 7.6801 |
| 46 | 3.8000 | 0.8243 | 0.7662 | 0.0581 | 7.5872 |
| 47 | 4.0000 | 0.8470 | 0.7878 | 0.0592 | 7.5148 |
| 48 | 4.2000 | 0.8702 | 0.8098 | 0.0604 | 7.4581 |
| 49 | 4.4000 | 0.8938 | 0.8321 | 0.0617 | 7.4120 |
| 50 | 4.6000 | 0.9178 | 0.8548 | 0.0630 | 7.3718 |
| 51 | 4.8000 | 0.9421 | 0.8778 | 0.0644 | 7.3328 |
| 52 | 5.0000 | 0.9668 | 0.9011 | 0.0657 | 7.2903 |
| 53 | 5.2000 | 0.9917 | 0.9248 | 0.0670 | 7.2406 |
| 54 | 5.2657 | 1.0000 | 0.9326 | 0.0674 | 7.2219 |
| 55 | 5.4000 | 1.0169 | 0.9488 | 0.0681 | 7.1793 |
| 56 | 5.6000 | 1.0423 | 0.9732 | 0.0691 | 7.1031 |
| 57 | 5.8000 | 1.0678 | 0.9979 | 0.0699 | 7.0087 |
| 58 | 6.0000 | 1.0934 | 1.0229 | 0.0705 | 6.8934 |
| 59 | 6.2000 | 1.1191 | 1.0483 | 0.0708 | 6.7550 |
| 60 | 6.4000 | 1.1448 | 1.0740 | 0.0708 | 6.5919 |
| 61 | 6.6000 | 1.1704 | 1.1000 | 0.0704 | 6.4032 |
| 62 | 6.8000 | 1.1960 | 1.1263 | 0.0697 | 6.1889 |
| 63 | 7.0000 | 1.2216 | 1.1530 | 0.0686 | 5.9490 |
| 64 | 7.2000 | 1.2470 | 1.1799 | 0.0671 | 5.6843 |
| 65 | 7.4000 | 1.2724 | 1.2072 | 0.0652 | 5.4035 |
| 66 | 7.6000 | 1.2980 | 1.2348 | 0.0632 | 5.1173 |
| 67 | 7.8000 | 1.3238 | 1.2626 | 0.0612 | 4.8477 |
| 68 | 8.0000 | 1.3500 | 1.2907 | 0.0593 | 4.5905 |
| 69 | 8.2000 | 1.3780 | 1.3191 | 0.0589 | 4.4669 |
| 70 | 8.4000 | 1.4086 | 1.3477 | 0.0609 | 4.5190 |
| 71 | 8.6000 | 1.4392 | 1.3766 | 0.0626 | 4.5447 |
| 72 | 8.8000 | 1.4696 | 1.4057 | 0.0639 | 4.5449 |
| 73 | 9.0000 | 1.4999 | 1.4350 | 0.0649 | 4.5208 |
| 74 | 9.0008 | 1.5000 | 1.4351 | 0.0649 | 4.5207 |
| 75 | 9.2000 | 1.5300 | 1.4645 | 0.0655 | 4.4740 |
| 76 | 9.4000 | 1.5600 | 1.4942 | 0.0658 | 4.4056 |
| 77 | 9.6000 | 1.5899 | 1.5241 | 0.0658 | 4.3170 |
| 78 | 9.8000 | 1.6195 | 1.5541 | 0.0654 | 4.2101 |
| 79 | 10.0000 | 1.6490 | 1.5843 | 0.0647 | 4.0864 |
| 80 | 10.2000 | 1.6783 | 1.6145 | 0.0637 | 3.9475 |

Table 14

FIG. 38

| Design # | SNR | Opt. Cap | Std. Cap | Gain [bits] | Gain % |
|---|---|---|---|---|---|
| 81 | 10.4000 | 1.7074 | 1.6449 | 0.0624 | 3.7953 |
| 82 | 10.6000 | 1.7363 | 1.6754 | 0.0609 | 3.6327 |
| 83 | 10.8000 | 1.7650 | 1.7060 | 0.0591 | 3.4625 |
| 84 | 11.0000 | 1.7937 | 1.7366 | 0.0571 | 3.2884 |
| 85 | 11.2000 | 1.8223 | 1.7672 | 0.0551 | 3.1155 |
| 86 | 11.4000 | 1.8509 | 1.7979 | 0.0530 | 2.9491 |
| 87 | 11.6000 | 1.8797 | 1.8286 | 0.0511 | 2.7943 |
| 88 | 11.8000 | 1.9086 | 1.8593 | 0.0494 | 2.6548 |
| 89 | 12.0000 | 1.9378 | 1.8899 | 0.0478 | 2.5317 |
| 90 | 12.2000 | 1.9671 | 1.9206 | 0.0466 | 2.4250 |
| 91 | 12.4000 | 1.9966 | 1.9511 | 0.0455 | 2.3327 |
| 92 | 12.4227 | 2.0000 | 1.9546 | 0.0454 | 2.3230 |
| 93 | 12.6000 | 2.0263 | 1.9816 | 0.0446 | 2.2522 |
| 94 | 12.8000 | 2.0559 | 2.0121 | 0.0439 | 2.1810 |
| 95 | 13.0000 | 2.0856 | 2.0424 | 0.0432 | 2.1167 |
| 96 | 13.2000 | 2.1153 | 2.0726 | 0.0426 | 2.0569 |
| 97 | 13.4000 | 2.1448 | 2.1028 | 0.0421 | 1.9998 |
| 98 | 13.6000 | 2.1742 | 2.1328 | 0.0415 | 1.9437 |
| 99 | 13.8000 | 2.2035 | 2.1627 | 0.0408 | 1.8875 |
| 100 | 14.0000 | 2.2326 | 2.1925 | 0.0401 | 1.8301 |
| 101 | 14.2000 | 2.2614 | 2.2221 | 0.0394 | 1.7711 |
| 102 | 14.4000 | 2.2901 | 2.2516 | 0.0385 | 1.7096 |
| 103 | 14.6000 | 2.3184 | 2.2809 | 0.0375 | 1.6457 |
| 104 | 14.8000 | 2.3465 | 2.3100 | 0.0365 | 1.5792 |
| 105 | 15.0000 | 2.3743 | 2.3390 | 0.0353 | 1.5104 |
| 106 | 15.2000 | 2.4018 | 2.3678 | 0.0341 | 1.4395 |
| 107 | 15.4000 | 2.4290 | 2.3963 | 0.0328 | 1.3670 |
| 108 | 15.6000 | 2.4559 | 2.4246 | 0.0314 | 1.2934 |
| 109 | 15.8000 | 2.4825 | 2.4526 | 0.0299 | 1.2192 |
| 110 | 15.9336 | 2.5000 | 2.4711 | 0.0289 | 1.1703 |
| 111 | 16.0000 | 2.5087 | 2.4802 | 0.0284 | 1.1457 |
| 112 | 16.2000 | 2.5344 | 2.5076 | 0.0269 | 1.0722 |
| 113 | 16.4000 | 2.5598 | 2.5345 | 0.0253 | 1.0000 |
| 114 | 16.6000 | 2.5848 | 2.5610 | 0.0238 | 0.9296 |
| 115 | 16.8000 | 2.6093 | 2.5870 | 0.0223 | 0.8615 |
| 116 | 17.0000 | 2.6332 | 2.6124 | 0.0208 | 0.7960 |
| 117 | 17.2000 | 2.6567 | 2.6373 | 0.0193 | 0.7333 |
| 118 | 17.4000 | 2.6795 | 2.6616 | 0.0179 | 0.6737 |
| 119 | 17.6000 | 2.7017 | 2.6851 | 0.0166 | 0.6171 |
| 120 | 17.8000 | 2.7232 | 2.7080 | 0.0153 | 0.5637 |

Table 15

FIG. 39

|  | SNR | Opt. Cap | Std. Cap | Gain [bits] | Gain % |
|---|---|---|---|---|---|
| Design # | | | | | |
| 121 | 18.0000 | 2.7440 | 2.7300 | 0.0140 | 0.5134 |
| 122 | 18.2000 | 2.7641 | 2.7513 | 0.0128 | 0.4663 |
| 123 | 18.4000 | 2.7834 | 2.7717 | 0.0117 | 0.4222 |
| 124 | 18.6000 | 2.8018 | 2.7912 | 0.0106 | 0.3810 |

Table 16

FIG. 40

|  | Label | | | | | | | |
|---|---|---|---|---|---|---|---|---|
|  | 0 | 1 | 2 | 3 | 4 | 5 | 6 | 7 |
| Design # | | | | | | | | |
| 1 | -4.583 | -4.583 | -4.582 | -4.583 | 4.583 | 4.583 | 4.583 | 4.583 |
| 2 | -4.584 | -4.584 | -4.581 | -4.582 | 4.584 | 4.582 | 4.582 | 4.582 |
| 3 | -4.584 | -4.582 | -4.582 | -4.582 | 4.584 | 4.584 | 4.579 | 4.584 |
| 4 | -4.584 | -4.582 | -4.582 | -4.582 | 4.583 | 4.583 | 4.582 | 4.583 |
| 5 | -4.583 | -4.583 | -4.583 | -4.583 | 4.586 | 4.586 | 4.579 | 4.579 |
| 6 | -4.585 | -4.582 | -4.582 | -4.582 | 4.584 | 4.584 | 4.580 | 4.583 |
| 7 | -4.587 | -4.587 | -4.578 | -4.578 | 4.583 | 4.583 | 4.582 | 4.583 |
| 8 | -4.585 | -4.585 | -4.580 | -4.580 | 4.583 | 4.583 | 4.583 | 4.583 |
| 9 | -4.583 | -4.583 | -4.582 | -4.582 | 4.583 | 4.583 | 4.582 | 4.583 |
| 10 | -4.585 | -4.584 | -4.581 | -4.581 | 4.583 | 4.583 | 4.583 | 4.583 |
| 11 | -4.583 | -4.583 | -4.583 | -4.583 | 4.584 | 4.584 | 4.581 | 4.581 |
| 12 | -4.583 | -4.583 | -4.582 | -4.582 | 4.585 | 4.582 | 4.582 | 4.582 |
| 13 | -4.587 | -4.581 | -4.581 | -4.581 | 4.587 | 4.582 | 4.581 | 4.581 |
| 14 | -4.583 | -4.583 | -4.582 | -4.583 | 4.583 | 4.583 | 4.582 | 4.583 |
| 15 | -4.583 | -4.583 | -4.582 | -4.582 | 4.583 | 4.583 | 4.582 | 4.583 |
| 16 | -4.583 | -4.583 | -4.582 | -4.583 | 4.583 | 4.583 | 4.583 | 4.583 |
| 17 | -4.587 | -4.582 | -4.580 | -4.581 | 4.587 | 4.582 | 4.581 | 4.582 |
| 18 | -4.583 | -4.583 | -4.582 | -4.583 | 4.584 | 4.584 | 4.581 | 4.581 |
| 19 | -4.583 | -4.583 | -4.582 | -4.582 | 4.584 | 4.584 | 4.581 | 4.582 |
| 20 | -4.583 | -4.583 | -4.582 | -4.582 | 4.583 | 4.583 | 4.582 | 4.582 |
| 21 | -4.583 | -4.583 | -4.582 | -4.583 | 4.583 | 4.584 | 4.582 | 4.582 |
| 22 | -4.584 | -4.584 | -4.580 | -4.583 | 4.587 | 4.588 | 4.576 | 4.579 |
| 23 | -4.589 | -4.586 | -4.578 | -4.578 | 4.588 | 4.581 | 4.581 | 4.581 |
| 24 | -4.584 | -4.584 | -4.581 | -4.581 | 4.583 | 4.583 | 4.582 | 4.583 |
| 25 | -4.585 | -4.582 | -4.582 | -4.582 | 4.584 | 4.583 | 4.582 | 4.582 |
| 26 | -4.583 | -4.583 | -4.583 | -4.583 | 4.583 | 4.583 | 4.582 | 4.583 |
| 27 | -4.584 | -4.583 | -4.582 | -4.582 | 4.583 | 4.583 | 4.582 | 4.582 |
| 28 | -4.583 | -4.583 | -4.583 | -4.583 | 4.583 | 4.583 | 4.582 | 4.582 |
| 29 | -4.583 | -4.582 | -4.582 | -4.582 | 4.583 | 4.583 | 4.583 | 4.583 |
| 30 | -4.587 | -4.587 | -4.578 | -4.579 | 4.587 | 4.587 | 4.579 | 4.579 |
| 31 | -4.584 | -4.583 | -4.582 | -4.582 | 4.584 | 4.584 | 4.581 | 4.582 |
| 32 | -4.583 | -4.583 | -4.582 | -4.582 | 4.583 | 4.583 | 4.582 | 4.582 |
| 33 | -4.584 | -4.584 | -4.578 | -4.584 | 4.584 | 4.584 | 4.580 | 4.582 |
| 34 | -4.584 | -4.584 | -4.578 | -4.584 | 4.584 | 4.584 | 4.578 | 4.584 |
| 35 | -5.110 | -5.110 | -3.986 | -3.986 | 5.110 | 5.110 | 3.986 | 3.986 |
| 36 | -5.355 | -5.354 | -3.651 | -3.651 | 5.355 | 5.355 | 3.650 | 3.650 |
| 37 | -5.515 | -5.514 | -3.404 | -3.404 | 5.515 | 5.515 | 3.404 | 3.404 |
| 38 | -5.638 | -5.638 | -3.196 | -3.196 | 5.640 | 5.637 | 3.196 | 3.196 |
| 39 | -5.729 | -5.729 | -3.029 | -3.029 | 5.729 | 5.729 | 3.029 | 3.029 |
| 40 | -5.808 | -5.807 | -2.876 | -2.876 | 5.808 | 5.808 | 2.876 | 2.876 |

Table 17

FIG. 41

|  | Label | | | | | | | |
|---|---|---|---|---|---|---|---|---|
|  | 0 | 1 | 2 | 3 | 4 | 5 | 6 | 7 |
| Design # | | | | | | | | |
| 41 | -5.874 | -5.874 | -2.739 | -2.739 | 5.874 | 5.872 | 2.740 | 2.740 |
| 42 | -5.929 | -5.929 | -2.617 | -2.617 | 5.929 | 5.929 | 2.617 | 2.617 |
| 43 | -5.978 | -5.975 | -2.506 | -2.506 | 5.978 | 5.976 | 2.505 | 2.505 |
| 44 | -6.018 | -6.018 | -2.405 | -2.405 | 6.018 | 6.018 | 2.405 | 2.405 |
| 45 | -6.055 | -6.054 | -2.312 | -2.312 | 6.054 | 6.054 | 2.312 | 2.312 |
| 46 | -6.087 | -6.085 | -2.227 | -2.227 | 6.087 | 6.086 | 2.227 | 2.227 |
| 47 | -6.113 | -6.113 | -2.151 | -2.151 | 6.113 | 6.113 | 2.151 | 2.151 |
| 48 | -6.138 | -6.138 | -2.081 | -2.081 | 6.138 | 6.137 | 2.081 | 2.081 |
| 49 | -6.159 | -6.159 | -2.017 | -2.017 | 6.159 | 6.159 | 2.017 | 2.017 |
| 50 | -6.179 | -6.176 | -1.960 | -1.960 | 6.178 | 6.178 | 1.959 | 1.959 |
| 51 | -6.194 | -6.193 | -1.907 | -1.907 | 6.194 | 6.194 | 1.907 | 1.907 |
| 52 | -6.208 | -6.208 | -1.860 | -1.860 | 6.208 | 6.208 | 1.860 | 1.860 |
| 53 | -6.221 | -6.220 | -1.819 | -1.819 | 6.221 | 6.219 | 1.819 | 1.820 |
| 54 | -6.224 | -6.224 | -1.807 | -1.807 | 6.224 | 6.224 | 1.807 | 1.807 |
| 55 | -6.231 | -6.230 | -1.783 | -1.783 | 6.231 | 6.231 | 1.783 | 1.783 |
| 56 | -6.240 | -6.240 | -1.752 | -1.752 | 6.242 | 6.237 | 1.752 | 1.752 |
| 57 | -6.247 | -6.247 | -1.725 | -1.725 | 6.247 | 6.247 | 1.725 | 1.725 |
| 58 | -6.254 | -6.253 | -1.703 | -1.703 | 6.253 | 6.253 | 1.703 | 1.703 |
| 59 | -6.260 | -6.256 | -1.686 | -1.686 | 6.260 | 6.256 | 1.686 | 1.686 |
| 60 | -6.261 | -6.261 | -1.673 | -1.673 | 6.261 | 6.261 | 1.673 | 1.673 |
| 61 | -6.263 | -6.263 | -1.665 | -1.665 | 6.263 | 6.263 | 1.665 | 1.665 |
| 62 | -6.264 | -6.264 | -1.661 | -1.661 | 6.264 | 6.264 | 1.661 | 1.661 |
| 63 | -6.265 | -6.265 | -1.660 | -1.660 | 6.265 | 6.264 | 1.660 | 1.660 |
| 64 | -6.264 | -6.264 | -1.663 | -1.663 | 6.291 | 6.237 | 1.658 | 1.667 |
| 65 | -6.734 | -5.796 | -1.570 | -1.737 | 6.244 | 6.244 | 1.674 | 1.674 |
| 66 | -6.781 | -5.697 | -1.582 | -1.750 | 6.781 | 5.697 | 1.582 | 1.750 |
| 67 | -6.914 | -5.533 | -1.550 | -1.781 | 6.915 | 5.533 | 1.549 | 1.781 |
| 68 | -7.016 | -5.403 | -1.517 | -1.809 | 7.017 | 5.403 | 1.517 | 1.809 |
| 69 | -7.923 | -3.658 | 7.923 | -2.800 | 2.800 | 0.035 | 3.659 | -0.035 |
| 70 | -7.913 | -3.668 | 7.913 | -2.816 | 2.816 | 0.052 | 3.668 | -0.052 |
| 71 | -7.902 | -3.680 | 7.902 | -2.831 | 2.831 | 0.068 | 3.680 | -0.068 |
| 72 | -7.890 | -3.694 | 7.890 | -2.845 | 2.845 | 0.084 | 3.694 | -0.084 |
| 73 | -7.878 | -3.710 | 7.878 | -2.859 | 2.859 | 0.099 | 3.710 | -0.099 |
| 74 | -7.878 | -3.710 | 7.878 | -2.859 | 2.859 | 0.099 | 3.710 | -0.099 |
| 75 | -7.864 | -3.728 | 7.864 | -2.872 | 2.872 | 0.115 | 3.728 | -0.115 |
| 76 | -7.850 | -3.749 | 7.850 | -2.883 | 2.883 | 0.131 | 3.749 | -0.131 |
| 77 | -7.835 | -3.772 | 7.835 | -2.893 | 2.893 | 0.148 | 3.772 | -0.148 |
| 78 | -7.819 | -3.798 | 7.819 | -2.902 | 2.902 | 0.166 | 3.798 | -0.166 |
| 79 | -7.802 | -3.827 | 7.802 | -2.908 | 2.908 | 0.185 | 3.827 | -0.185 |
| 80 | -7.784 | -3.859 | 7.784 | -2.911 | 2.911 | 0.206 | 3.859 | -0.206 |

Table 18

FIG. 42

|  | Label | | | | | | | |
|---|---|---|---|---|---|---|---|---|
|  | 0 | 1 | 2 | 3 | 4 | 5 | 6 | 7 |
| Design # | | | | | | | | |
| 81 | -7.765 | -3.896 | 7.765 | -2.911 | 2.911 | 0.230 | 3.896 | -0.230 |
| 82 | -7.745 | -3.937 | 7.745 | -2.907 | 2.907 | 0.257 | 3.937 | -0.257 |
| 83 | -7.724 | -3.983 | 7.724 | -2.897 | 2.897 | 0.290 | 3.983 | -0.290 |
| 84 | -7.701 | -4.036 | 7.701 | -2.880 | 2.880 | 0.328 | 4.036 | -0.328 |
| 85 | -7.677 | -4.095 | 7.677 | -2.857 | 2.857 | 0.374 | 4.095 | -0.374 |
| 86 | -7.651 | -4.157 | 7.651 | -2.828 | 2.829 | 0.425 | 4.157 | -0.425 |
| 87 | -7.625 | -4.220 | 7.625 | -2.797 | 2.797 | 0.479 | 4.220 | -0.479 |
| 88 | -7.600 | -4.280 | 7.600 | -2.765 | 2.765 | 0.533 | 4.280 | -0.533 |
| 89 | -7.576 | -4.334 | 7.576 | -2.734 | 2.734 | 0.585 | 4.334 | -0.585 |
| 90 | -7.555 | -4.382 | 7.555 | -2.707 | 2.707 | 0.632 | 4.382 | -0.632 |
| 91 | -7.536 | -4.423 | 7.536 | -2.682 | 2.682 | 0.672 | 4.423 | -0.672 |
| 92 | -7.534 | -4.428 | 7.534 | -2.680 | 2.680 | 0.677 | 4.428 | -0.677 |
| 93 | -7.519 | -4.459 | 7.519 | -2.662 | 2.662 | 0.707 | 4.459 | -0.707 |
| 94 | -7.504 | -4.489 | 7.504 | -2.644 | 2.644 | 0.736 | 4.489 | -0.736 |
| 95 | -7.491 | -4.515 | 7.491 | -2.630 | 2.630 | 0.761 | 4.515 | -0.761 |
| 96 | -7.479 | -4.538 | 7.479 | -2.618 | 2.618 | 0.780 | 4.538 | -0.780 |
| 97 | -7.469 | -4.558 | 7.469 | -2.609 | 2.609 | 0.796 | 4.558 | -0.796 |
| 98 | -7.459 | -4.576 | 7.459 | -2.603 | 2.603 | 0.808 | 4.576 | -0.808 |
| 99 | -7.449 | -4.593 | 7.449 | -2.598 | 2.599 | 0.818 | 4.593 | -0.817 |
| 100 | -7.439 | -4.608 | 7.439 | -2.597 | 2.597 | 0.825 | 4.608 | -0.825 |
| 101 | -7.430 | -4.623 | 7.430 | -2.597 | 2.597 | 0.831 | 4.623 | -0.830 |
| 102 | -7.420 | -4.636 | 7.420 | -2.599 | 2.599 | 0.835 | 4.636 | -0.835 |
| 103 | -7.410 | -4.650 | 7.410 | -2.603 | 2.603 | 0.838 | 4.650 | -0.838 |
| 104 | -7.399 | -4.663 | 7.399 | -2.608 | 2.608 | 0.841 | 4.663 | -0.841 |
| 105 | -7.389 | -4.675 | 7.388 | -2.615 | 2.615 | 0.844 | 4.675 | -0.844 |
| 106 | -7.377 | -4.688 | 7.377 | -2.624 | 2.624 | 0.847 | 4.688 | -0.847 |
| 107 | -7.366 | -4.700 | 7.366 | -2.634 | 2.633 | 0.850 | 4.700 | -0.850 |
| 108 | -7.354 | -4.712 | 7.354 | -2.644 | 2.644 | 0.854 | 4.712 | -0.854 |
| 109 | -7.342 | -4.724 | 7.342 | -2.656 | 2.656 | 0.858 | 4.724 | -0.858 |
| 110 | -7.334 | -4.732 | -0.862 | -2.661 | 7.334 | 4.732 | 0.862 | 2.661 |
| 111 | -7.330 | -4.736 | -0.863 | -2.666 | 7.329 | 4.736 | 0.863 | 2.666 |
| 112 | -7.317 | -4.747 | -0.868 | -2.679 | 7.317 | 4.747 | 0.868 | 2.679 |
| 113 | -7.304 | -4.758 | -0.873 | -2.693 | 7.304 | 4.758 | 0.873 | 2.693 |
| 114 | -7.292 | -4.768 | -0.878 | -2.707 | 7.292 | 4.768 | 0.878 | 2.707 |
| 115 | -7.279 | -4.778 | -0.884 | -2.720 | 7.279 | 4.778 | 0.884 | 2.720 |
| 116 | -7.267 | -4.788 | -0.889 | -2.733 | 7.267 | 4.788 | 0.889 | 2.733 |
| 117 | -7.255 | -4.798 | -0.894 | -2.746 | 7.256 | 4.798 | 0.894 | 2.746 |
| 118 | -7.244 | -4.807 | -0.899 | -2.758 | 7.244 | 4.807 | 0.899 | 2.758 |
| 119 | -7.233 | -4.816 | -0.904 | -2.770 | 7.233 | 4.816 | 0.904 | 2.770 |
| 120 | -7.223 | -4.824 | -0.909 | -2.781 | 7.223 | 4.824 | 0.909 | 2.781 |

Table 19

FIG. 43

|  | Label | | | | | | | |
|---|---|---|---|---|---|---|---|---|
|  | 0 | 1 | 2 | 3 | 4 | 5 | 6 | 7 |
| Design # | | | | | | | | |
| 121 | -7.212 | -4.832 | -0.914 | -2.792 | 7.212 | 4.832 | 0.914 | 2.792 |
| 122 | -7.203 | -4.840 | -0.918 | -2.802 | 7.203 | 4.840 | 0.918 | 2.802 |
| 123 | -7.194 | -4.847 | -0.922 | -2.812 | 7.194 | 4.847 | 0.922 | 2.812 |
| 124 | -7.185 | -4.854 | -0.926 | -2.821 | 7.185 | 4.854 | 0.926 | 2.821 |

Table 20

FIG. 44

| Design # | SNRs | 5.00% | 40.00% | 50.00% | 60.00% | 70.00% | 100.00% |
|---|---|---|---|---|---|---|---|
| 65 | 7.4 | 0.62 | 0.22 | 0.2 | 0.18 | 0.16 | 0 |
| 66 | 7.6 | 0.55 | 0.21 | 0.19 | 0.17 | 0.15 | 0 |
| 67 | 7.8 | 0.57 | 0.26 | 0.23 | 0.21 | 0.19 | 0 |
| 68 | 8 | 0.5 | 0.3 | 0.27 | 0.24 | 0.22 | 0 |
| 69 | 8.2 | 0.46 | 0.34 | 0.3 | 0.27 | 0.25 | 0 |
| 70 | 8.4 | 0.45 | 0.33 | 0.3 | 0.27 | 0.24 | 0 |
| 71 | 8.6 | 0.44 | 0.33 | 0.3 | 0.27 | 0.24 | 0 |
| 72 | 8.8 | 0.48 | 0.32 | 0.29 | 0.26 | 0.24 | 0 |
| 73 | 9 | 0.47 | 0.32 | 0.29 | 0.26 | 0.23 | 0 |
| 74 | 9 | 0.47 | 0.32 | 0.29 | 0.26 | 0.23 | 0 |
| 75 | 9.2 | 0.46 | 0.31 | 0.28 | 0.25 | 0.23 | 0 |
| 76 | 9.4 | 0.45 | 0.3 | 0.27 | 0.25 | 0.22 | 0 |
| 77 | 9.6 | 0.43 | 0.3 | 0.27 | 0.24 | 0.22 | 0 |
| 78 | 9.8 | 0.42 | 0.29 | 0.26 | 0.23 | 0.21 | 0 |
| 79 | 10 | 0.41 | 0.28 | 0.25 | 0.23 | 0.21 | 0 |
| 80 | 10.2 | 0.4 | 0.27 | 0.25 | 0.22 | 0.2 | 0 |
| 81 | 10.4 | 0.39 | 0.27 | 0.24 | 0.22 | 0.19 | 0 |
| 82 | 10.6 | 0.42 | 0.26 | 0.23 | 0.21 | 0.19 | 0 |
| 83 | 10.8 | 0.39 | 0.26 | 0.23 | 0.21 | 0.19 | 0 |
| 84 | 11 | 0.37 | 0.25 | 0.23 | 0.2 | 0.18 | 0 |
| 85 | 11.2 | 0.37 | 0.25 | 0.22 | 0.2 | 0.18 | 0 |
| 86 | 11.4 | 0.33 | 0.25 | 0.22 | 0.2 | 0.18 | 0 |
| 87 | 11.6 | 0.29 | 0.24 | 0.22 | 0.2 | 0.18 | 0 |
| 88 | 11.8 | 0.24 | 0.22 | 0.2 | 0.18 | 0.16 | 0 |
| 89 | 12 | 0.22 | 0.2 | 0.18 | 0.16 | 0.14 | 0 |
| 90 | 12.2 | 0.2 | 0.18 | 0.17 | 0.15 | 0.13 | 0 |
| 91 | 12.4 | 0.19 | 0.17 | 0.15 | 0.13 | 0.12 | 0 |
| 92 | 12.42 | 0.19 | 0.17 | 0.15 | 0.13 | 0.12 | 0 |
| 93 | 12.6 | 0.18 | 0.16 | 0.14 | 0.12 | 0.11 | 0 |
| 94 | 12.8 | 0.17 | 0.16 | 0.14 | 0.13 | 0.11 | 0 |
| 95 | 13 | 0.17 | 0.15 | 0.13 | 0.12 | 0.11 | 0 |
| 96 | 13.2 | 0.16 | 0.14 | 0.13 | 0.12 | 0.11 | 0 |
| 97 | 13.4 | 0.16 | 0.14 | 0.13 | 0.11 | 0.1 | 0 |
| 98 | 13.6 | 0.15 | 0.14 | 0.13 | 0.11 | 0.1 | 0 |
| 99 | 13.8 | 0.16 | 0.15 | 0.13 | 0.12 | 0.11 | 0 |
| 100 | 14 | 0.17 | 0.16 | 0.14 | 0.13 | 0.11 | 0 |
| 101 | 14.2 | 0.19 | 0.17 | 0.15 | 0.14 | 0.12 | 0 |
| 102 | 14.4 | 0.2 | 0.18 | 0.16 | 0.14 | 0.12 | 0 |
| 103 | 14.6 | 0.21 | 0.19 | 0.17 | 0.15 | 0.11 | 0 |
| 104 | 14.8 | 0.2 | 0.18 | 0.16 | 0.14 | 0.1 | 0 |

Table 21

FIG. 45

| Design # | SNRs | 5.00% | 40.00% | 50.00% | 60.00% | 70.00% | 100.00% |
| --- | --- | --- | --- | --- | --- | --- | --- |
| 105 | 15 | 0.19 | 0.17 | 0.15 | 0.14 | 0.1 | 0 |
| 106 | 15.2 | 0.19 | 0.18 | 0.16 | 0.14 | 0.1 | 0 |
| 107 | 15.4 | 0.18 | 0.16 | 0.15 | 0.13 | 0.1 | 0 |
| 108 | 15.6 | 0.17 | 0.15 | 0.14 | 0.13 | 0.09 | 0 |
| 109 | 15.8 | 0.16 | 0.14 | 0.13 | 0.12 | 0.09 | 0 |
| 110 | 15.93 | 0.15 | 0.13 | 0.12 | 0.11 | 0.08 | 0 |
| 111 | 16 | 0.15 | 0.14 | 0.12 | 0.11 | 0.08 | 0 |
| 112 | 16.2 | 0.14 | 0.12 | 0.11 | 0.1 | 0.07 | 0 |
| 113 | 16.4 | 0.13 | 0.12 | 0.11 | 0.1 | 0.07 | 0 |
| 114 | 16.6 | 0.13 | 0.11 | 0.1 | 0.09 | 0.07 | 0 |
| 115 | 16.8 | 0.12 | 0.11 | 0.1 | 0.09 | 0.06 | 0 |
| 116 | 17 | 0.11 | 0.1 | 0.09 | 0.08 | 0.06 | 0 |
| 117 | 17.2 | 0.11 | 0.1 | 0.09 | 0.08 | 0.06 | 0 |
| 118 | 17.4 | 0.1 | 0.09 | 0.08 | 0.08 | 0.06 | 0 |
| 119 | 17.6 | 0.1 | 0.09 | 0.08 | 0.07 | 0.05 | 0 |
| 120 | 17.8 | 0.09 | 0.09 | 0.08 | 0.07 | 0.05 | 0 |
| 121 | 18 | 0.09 | 0.08 | 0.07 | 0.07 | 0.05 | 0 |
| 122 | 18.2 | 0.09 | 0.08 | 0.07 | 0.06 | 0.05 | 0 |
| 123 | 18.4 | 0.08 | 0.07 | 0.07 | 0.06 | 0.04 | 0 |
| 124 | 18.6 | 0.08 | 0.07 | 0.06 | 0.06 | 0.04 | 0 |

Table 22

FIG. 46

| Design # | SNR | Opt. Cap | Std. Cap | Gain [bits] | Gain % |
|---|---|---|---|---|---|
| 1 | -5.0000 | 0.1982 | 0.1980 | 0.0002 | 0.0812 |
| 2 | -4.8000 | 0.2063 | 0.2061 | 0.0002 | 0.0902 |
| 3 | -4.6000 | 0.2147 | 0.2145 | 0.0002 | 0.1001 |
| 4 | -4.4000 | 0.2234 | 0.2232 | 0.0002 | 0.1110 |
| 5 | -4.2000 | 0.2324 | 0.2321 | 0.0003 | 0.1229 |
| 6 | -4.0000 | 0.2417 | 0.2414 | 0.0003 | 0.1359 |
| 7 | -3.8000 | 0.2514 | 0.2510 | 0.0004 | 0.1501 |
| 8 | -3.6000 | 0.2613 | 0.2609 | 0.0004 | 0.1656 |
| 9 | -3.4000 | 0.2715 | 0.2710 | 0.0005 | 0.1825 |
| 10 | -3.2000 | 0.2821 | 0.2816 | 0.0006 | 0.2009 |
| 11 | -3.0000 | 0.2930 | 0.2924 | 0.0006 | 0.2209 |
| 12 | -2.8000 | 0.3043 | 0.3036 | 0.0007 | 0.2425 |
| 13 | -2.6000 | 0.3159 | 0.3151 | 0.0008 | 0.2659 |
| 14 | -2.4000 | 0.3279 | 0.3269 | 0.0010 | 0.2911 |
| 15 | -2.2000 | 0.3402 | 0.3391 | 0.0011 | 0.3183 |
| 16 | -2.0000 | 0.3529 | 0.3516 | 0.0012 | 0.3476 |
| 17 | -1.8000 | 0.3659 | 0.3645 | 0.0014 | 0.3791 |
| 18 | -1.6000 | 0.3793 | 0.3777 | 0.0016 | 0.4128 |
| 19 | -1.4000 | 0.3930 | 0.3913 | 0.0018 | 0.4488 |
| 20 | -1.2000 | 0.4072 | 0.4052 | 0.0020 | 0.4872 |
| 21 | -1.0000 | 0.4217 | 0.4195 | 0.0022 | 0.5281 |
| 22 | -0.8000 | 0.4366 | 0.4341 | 0.0025 | 0.5715 |
| 23 | -0.6000 | 0.4519 | 0.4491 | 0.0028 | 0.6175 |
| 24 | -0.4000 | 0.4675 | 0.4644 | 0.0031 | 0.6663 |
| 25 | -0.2000 | 0.4835 | 0.4801 | 0.0034 | 0.7177 |
| 26 | 0.0000 | 0.4999 | 0.4961 | 0.0038 | 0.7719 |
| 27 | 0.0008 | 0.5000 | 0.4962 | 0.0038 | 0.7658 |
| 28 | 0.2000 | 0.5167 | 0.5125 | 0.0042 | 0.8289 |
| 29 | 0.4000 | 0.5339 | 0.5292 | 0.0047 | 0.8886 |
| 30 | 0.6000 | 0.5514 | 0.5462 | 0.0052 | 0.9511 |
| 31 | 0.8000 | 0.5694 | 0.5636 | 0.0057 | 1.0164 |
| 32 | 1.0000 | 0.5877 | 0.5814 | 0.0063 | 1.0844 |
| 33 | 1.2000 | 0.6063 | 0.5994 | 0.0069 | 1.1552 |
| 34 | 1.4000 | 0.6254 | 0.6178 | 0.0076 | 1.2283 |
| 35 | 1.6000 | 0.6448 | 0.6365 | 0.0083 | 1.3040 |
| 36 | 1.8000 | 0.6646 | 0.6555 | 0.0091 | 1.3820 |
| 37 | 2.0000 | 0.6847 | 0.6748 | 0.0099 | 1.4625 |
| 38 | 2.2000 | 0.7052 | 0.6945 | 0.0107 | 1.5451 |
| 39 | 2.4000 | 0.7260 | 0.7144 | 0.0116 | 1.6297 |
| 40 | 2.6000 | 0.7472 | 0.7346 | 0.0126 | 1.7162 |

Table 23

FIG. 47

| Design # | SNR | Opt. Cap | Std. Cap | Gain [bits] | Gain % |
|---|---|---|---|---|---|
| 41 | 2.8000 | 0.7688 | 0.7551 | 0.0136 | 1.8045 |
| 42 | 3.0000 | 0.7906 | 0.7759 | 0.0147 | 1.8944 |
| 43 | 3.2000 | 0.8128 | 0.7970 | 0.0158 | 1.9858 |
| 44 | 3.4000 | 0.8354 | 0.8184 | 0.0170 | 2.0783 |
| 45 | 3.6000 | 0.8582 | 0.8400 | 0.0182 | 2.1719 |
| 46 | 3.8000 | 0.8814 | 0.8619 | 0.0195 | 2.2663 |
| 47 | 4.0000 | 0.9049 | 0.8840 | 0.0209 | 2.3612 |
| 48 | 4.2000 | 0.9286 | 0.9064 | 0.0223 | 2.4564 |
| 49 | 4.4000 | 0.9527 | 0.9290 | 0.0237 | 2.5516 |
| 50 | 4.6000 | 0.9771 | 0.9519 | 0.0252 | 2.6465 |
| 51 | 4.7864 | 1.0000 | 0.9734 | 0.0266 | 2.7327 |
| 52 | 4.8000 | 1.0017 | 0.9750 | 0.0267 | 2.7407 |
| 53 | 5.0000 | 1.0266 | 0.9983 | 0.0283 | 2.8339 |
| 54 | 5.2000 | 1.0517 | 1.0218 | 0.0299 | 2.9256 |
| 55 | 5.4000 | 1.0771 | 1.0456 | 0.0315 | 3.0153 |
| 56 | 5.6000 | 1.1028 | 1.0696 | 0.0332 | 3.1025 |
| 57 | 5.8000 | 1.1286 | 1.0938 | 0.0349 | 3.1868 |
| 58 | 6.0000 | 1.1547 | 1.1182 | 0.0366 | 3.2699 |
| 59 | 6.2000 | 1.1810 | 1.1427 | 0.0383 | 3.3517 |
| 60 | 6.4000 | 1.2076 | 1.1675 | 0.0401 | 3.4318 |
| 61 | 6.6000 | 1.2343 | 1.1925 | 0.0419 | 3.5103 |
| 62 | 6.8000 | 1.2613 | 1.2176 | 0.0437 | 3.5868 |
| 63 | 7.0000 | 1.2885 | 1.2430 | 0.0455 | 3.6606 |
| 64 | 7.2000 | 1.3158 | 1.2685 | 0.0473 | 3.7311 |
| 65 | 7.4000 | 1.3433 | 1.2941 | 0.0491 | 3.7978 |
| 66 | 7.6000 | 1.3710 | 1.3200 | 0.0510 | 3.8609 |
| 67 | 7.8000 | 1.3988 | 1.3460 | 0.0528 | 3.9211 |
| 68 | 8.0000 | 1.4268 | 1.3722 | 0.0546 | 3.9785 |
| 69 | 8.2000 | 1.4549 | 1.3985 | 0.0564 | 4.0328 |
| 70 | 8.4000 | 1.4832 | 1.4250 | 0.0582 | 4.0837 |
| 71 | 8.5186 | 1.5000 | 1.4408 | 0.0592 | 4.1088 |
| 72 | 8.6000 | 1.5116 | 1.4516 | 0.0600 | 4.1311 |
| 73 | 8.8000 | 1.5401 | 1.4784 | 0.0617 | 4.1748 |
| 74 | 9.0000 | 1.5688 | 1.5053 | 0.0635 | 4.2162 |
| 75 | 9.2000 | 1.5976 | 1.5324 | 0.0652 | 4.2547 |
| 76 | 9.4000 | 1.6265 | 1.5596 | 0.0669 | 4.2906 |
| 77 | 9.6000 | 1.6555 | 1.5869 | 0.0686 | 4.3237 |
| 78 | 9.8000 | 1.6846 | 1.6143 | 0.0703 | 4.3538 |
| 79 | 10.0000 | 1.7138 | 1.6419 | 0.0719 | 4.3805 |
| 80 | 10.2000 | 1.7431 | 1.6696 | 0.0735 | 4.4034 |

Table 24

FIG. 48

| Design # | SNR | Opt. Cap | Std. Cap | Gain [bits] | Gain % |
|---|---|---|---|---|---|
| 81 | 10.4000 | 1.7725 | 1.6974 | 0.0751 | 4.4223 |
| 82 | 10.6000 | 1.8019 | 1.7254 | 0.0765 | 4.4366 |
| 83 | 10.8000 | 1.8314 | 1.7534 | 0.0780 | 4.4462 |
| 84 | 11.0000 | 1.8609 | 1.7816 | 0.0793 | 4.4514 |
| 85 | 11.2000 | 1.8905 | 1.8099 | 0.0806 | 4.4542 |
| 86 | 11.4000 | 1.9202 | 1.8383 | 0.0819 | 4.4549 |
| 87 | 11.6000 | 1.9499 | 1.8667 | 0.0831 | 4.4534 |
| 88 | 11.8000 | 1.9797 | 1.8953 | 0.0843 | 4.4497 |
| 89 | 11.9363 | 2.0000 | 1.9149 | 0.0851 | 4.4441 |
| 90 | 12.0000 | 2.0095 | 1.9240 | 0.0855 | 4.4438 |
| 91 | 12.2000 | 2.0394 | 1.9528 | 0.0866 | 4.4355 |
| 92 | 12.4000 | 2.0694 | 1.9817 | 0.0877 | 4.4249 |
| 93 | 12.6000 | 2.0994 | 2.0107 | 0.0887 | 4.4121 |
| 94 | 12.8000 | 2.1294 | 2.0397 | 0.0897 | 4.3969 |
| 95 | 13.0000 | 2.1595 | 2.0689 | 0.0906 | 4.3798 |
| 96 | 13.2000 | 2.1896 | 2.0981 | 0.0915 | 4.3610 |
| 97 | 13.4000 | 2.2197 | 2.1274 | 0.0923 | 4.3403 |
| 98 | 13.6000 | 2.2499 | 2.1568 | 0.0931 | 4.3178 |
| 99 | 13.8000 | 2.2801 | 2.1863 | 0.0939 | 4.2934 |
| 100 | 14.0000 | 2.3104 | 2.2158 | 0.0946 | 4.2671 |
| 101 | 14.2000 | 2.3406 | 2.2454 | 0.0952 | 4.2389 |
| 102 | 14.4000 | 2.3709 | 2.2751 | 0.0958 | 4.2085 |
| 103 | 14.6000 | 2.4012 | 2.3049 | 0.0963 | 4.1761 |
| 104 | 14.8000 | 2.4314 | 2.3347 | 0.0967 | 4.1414 |
| 105 | 15.0000 | 2.4617 | 2.3646 | 0.0971 | 4.1045 |
| 106 | 15.2000 | 2.4920 | 2.3946 | 0.0974 | 4.0654 |
| 107 | 15.2531 | 2.5000 | 2.4026 | 0.0974 | 4.0539 |
| 108 | 15.4000 | 2.5222 | 2.4247 | 0.0976 | 4.0241 |
| 109 | 15.6000 | 2.5525 | 2.4547 | 0.0977 | 3.9805 |
| 110 | 15.8000 | 2.5827 | 2.4849 | 0.0978 | 3.9347 |
| 111 | 16.0000 | 2.6129 | 2.5151 | 0.0978 | 3.8868 |
| 112 | 16.2000 | 2.6430 | 2.5454 | 0.0977 | 3.8366 |
| 113 | 16.4000 | 2.6732 | 2.5757 | 0.0975 | 3.7842 |
| 114 | 16.6000 | 2.7033 | 2.6061 | 0.0972 | 3.7296 |
| 115 | 16.8000 | 2.7333 | 2.6365 | 0.0968 | 3.6729 |
| 116 | 17.0000 | 2.7634 | 2.6670 | 0.0964 | 3.6139 |
| 117 | 17.2000 | 2.7933 | 2.6975 | 0.0958 | 3.5527 |
| 118 | 17.4000 | 2.8233 | 2.7281 | 0.0952 | 3.4893 |
| 119 | 17.6000 | 2.8531 | 2.7587 | 0.0944 | 3.4237 |
| 120 | 17.8000 | 2.8829 | 2.7893 | 0.0936 | 3.3558 |

Table 25

FIG. 49

| Design # | SNR | Opt. Cap | Std. Cap | Gain [bits] | Gain % |
|---|---|---|---|---|---|
| 121 | 18.0000 | 2.9127 | 2.8200 | 0.0927 | 3.2856 |
| 122 | 18.2000 | 2.9424 | 2.8508 | 0.0916 | 3.2130 |
| 123 | 18.4000 | 2.9720 | 2.8815 | 0.0904 | 3.1382 |
| 124 | 18.5898 | 3.0000 | 2.9108 | 0.0892 | 3.0644 |
| 125 | 18.6000 | 3.0015 | 2.9123 | 0.0891 | 3.0610 |
| 126 | 18.8000 | 3.0309 | 2.9432 | 0.0877 | 2.9814 |
| 127 | 19.0000 | 3.0603 | 2.9740 | 0.0862 | 2.8995 |
| 128 | 19.2000 | 3.0895 | 3.0049 | 0.0846 | 2.8153 |
| 129 | 19.4000 | 3.1187 | 3.0358 | 0.0828 | 2.7288 |
| 130 | 19.6000 | 3.1477 | 3.0667 | 0.0810 | 2.6400 |
| 131 | 19.8000 | 3.1766 | 3.0977 | 0.0790 | 2.5491 |
| 132 | 20.0000 | 3.2054 | 3.1286 | 0.0768 | 2.4563 |
| 133 | 20.2000 | 3.2341 | 3.1594 | 0.0746 | 2.3616 |
| 134 | 20.4000 | 3.2626 | 3.1903 | 0.0723 | 2.2653 |
| 135 | 20.6000 | 3.2909 | 3.2211 | 0.0698 | 2.1677 |
| 136 | 20.8000 | 3.3191 | 3.2518 | 0.0673 | 2.0691 |
| 137 | 21.0000 | 3.3471 | 3.2824 | 0.0647 | 1.9700 |
| 138 | 21.2000 | 3.3749 | 3.3129 | 0.0620 | 1.8706 |
| 139 | 21.4000 | 3.4025 | 3.3433 | 0.0592 | 1.7714 |
| 140 | 21.6000 | 3.4298 | 3.3734 | 0.0564 | 1.6730 |
| 141 | 21.8000 | 3.4569 | 3.4033 | 0.0536 | 1.5758 |
| 142 | 22.0000 | 3.4837 | 3.4329 | 0.0508 | 1.4802 |
| 143 | 22.1229 | 3.5000 | 3.4510 | 0.0490 | 1.4199 |
| 144 | 22.2000 | 3.5102 | 3.4622 | 0.0480 | 1.3867 |
| 145 | 22.4000 | 3.5364 | 3.4911 | 0.0452 | 1.2956 |
| 146 | 22.6000 | 3.5621 | 3.5196 | 0.0425 | 1.2074 |
| 147 | 22.8000 | 3.5874 | 3.5476 | 0.0398 | 1.1222 |
| 148 | 23.0000 | 3.6123 | 3.5751 | 0.0372 | 1.0403 |
| 149 | 23.2000 | 3.6366 | 3.6019 | 0.0346 | 0.9619 |
| 150 | 23.4000 | 3.6603 | 3.6281 | 0.0322 | 0.8870 |
| 151 | 23.6000 | 3.6835 | 3.6537 | 0.0298 | 0.8158 |
| 152 | 23.8000 | 3.7059 | 3.6784 | 0.0275 | 0.7482 |
| 153 | 24.0000 | 3.7277 | 3.7023 | 0.0253 | 0.6842 |
| 154 | 24.2000 | 3.7487 | 3.7254 | 0.0232 | 0.6239 |
| 155 | 24.4000 | 3.7689 | 3.7476 | 0.0213 | 0.5672 |
| 156 | 24.6000 | 3.7882 | 3.7688 | 0.0194 | 0.5139 |
| 157 | 24.8000 | 3.8067 | 3.7891 | 0.0176 | 0.4641 |
| 158 | 25.0000 | 3.8242 | 3.8083 | 0.0159 | 0.4176 |
| 159 | 25.2000 | 3.8409 | 3.8266 | 0.0143 | 0.3744 |
| 160 | 25.4000 | 3.8566 | 3.8437 | 0.0129 | 0.3344 |

Table 26

FIG. 50

|  | SNR | Opt. Cap | Std. Cap | Gain [bits] | Gain % |
|---|---|---|---|---|---|
| Design # |  |  |  |  |  |
| 161 | 25.6000 | 3.8713 | 3.8598 | 0.0115 | 0.2974 |
| 162 | 25.8000 | 3.8851 | 3.8749 | 0.0102 | 0.2634 |
| 163 | 26.0000 | 3.8979 | 3.8889 | 0.0090 | 0.2323 |
| 164 | 26.2000 | 3.9097 | 3.9018 | 0.0079 | 0.2037 |
| 165 | 26.4000 | 3.9207 | 3.9137 | 0.0070 | 0.1779 |
| 166 | 26.6000 | 3.9306 | 3.9246 | 0.0061 | 0.1545 |
| 167 | 26.8000 | 3.9397 | 3.9345 | 0.0052 | 0.1334 |
| 168 | 27.0000 | 3.9479 | 3.9434 | 0.0045 | 0.1145 |
| 169 | 27.2000 | 3.9553 | 3.9515 | 0.0039 | 0.0977 |
| 170 | 27.4000 | 3.9619 | 3.9587 | 0.0033 | 0.0829 |
| 171 | 27.6000 | 3.9678 | 3.9650 | 0.0028 | 0.0698 |
| 172 | 27.8000 | 3.9729 | 3.9706 | 0.0023 | 0.0584 |
| 173 | 28.0000 | 3.9775 | 3.9755 | 0.0019 | 0.0485 |
| 174 | 28.2000 | 3.9814 | 3.9798 | 0.0016 | 0.0399 |
| 175 | 28.4000 | 3.9847 | 3.9834 | 0.0013 | 0.0326 |
| 176 | 28.6000 | 3.9876 | 3.9865 | 0.0011 | 0.0264 |
| 177 | 28.8000 | 3.9900 | 3.9892 | 0.0008 | 0.0212 |
| 178 | 29.0000 | 3.9920 | 3.9914 | 0.0007 | 0.0169 |
| 179 | 29.2000 | 3.9937 | 3.9932 | 0.0005 | 0.0134 |
| 180 | 29.4000 | 3.9951 | 3.9947 | 0.0004 | 0.0103 |

Table 27

FIG. 51

| Design # | \multicolumn{8}{c}{Label} |
| | 0 | 1 | 2 | 3 | 4 | 5 | 6 | 7 |
|---|---|---|---|---|---|---|---|---|
| 1 | -20.036 | -6.369 | -6.322 | -6.315 | -6.314 | -6.302 | -6.294 | -6.240 |
| 2 | -20.035 | -6.309 | -6.309 | -6.309 | -6.309 | -6.309 | -6.309 | -6.309 |
| 3 | -20.032 | -6.337 | -6.280 | -6.271 | -6.346 | -6.289 | -6.366 | -6.282 |
| 4 | -20.029 | -6.320 | -6.311 | -6.311 | -6.311 | -6.311 | -6.307 | -6.307 |
| 5 | -20.026 | -6.323 | -6.323 | -6.323 | -6.305 | -6.305 | -6.305 | -6.305 |
| 6 | -20.024 | -6.335 | -6.335 | -6.335 | -6.335 | -6.335 | -6.260 | -6.260 |
| 7 | -20.021 | -6.315 | -6.316 | -6.316 | -6.315 | -6.317 | -6.317 | -6.313 |
| 8 | -20.017 | -6.320 | -6.320 | -6.320 | -6.320 | -6.320 | -6.320 | -6.300 |
| 9 | -20.014 | -6.341 | -6.329 | -6.329 | -6.329 | -6.300 | -6.300 | -6.300 |
| 10 | -20.011 | -6.308 | -6.320 | -6.316 | -6.307 | -6.343 | -6.326 | -6.318 |
| 11 | -20.008 | -6.363 | -6.326 | -6.318 | -6.318 | -6.318 | -6.306 | -6.300 |
| 12 | -20.004 | -6.333 | -6.325 | -6.325 | -6.323 | -6.323 | -6.323 | -6.310 |
| 13 | -20.001 | -6.336 | -6.333 | -6.320 | -6.326 | -6.317 | -6.316 | -6.323 |
| 14 | -19.997 | -6.323 | -6.331 | -6.323 | -6.331 | -6.327 | -6.322 | -6.325 |
| 15 | -19.993 | -6.328 | -6.328 | -6.328 | -6.328 | -6.328 | -6.328 | -6.328 |
| 16 | -19.990 | -6.332 | -6.331 | -6.331 | -6.332 | -6.324 | -6.328 | -6.326 |
| 17 | -19.986 | -6.331 | -6.331 | -6.331 | -6.331 | -6.331 | -6.331 | -6.331 |
| 18 | -19.983 | -6.332 | -6.332 | -6.332 | -6.332 | -6.332 | -6.332 | -6.332 |
| 19 | -19.979 | -6.339 | -6.339 | -6.336 | -6.336 | -6.330 | -6.330 | -6.330 |
| 20 | -19.976 | -6.332 | -6.330 | -6.336 | -6.336 | -6.346 | -6.332 | -6.339 |
| 21 | -19.972 | -6.362 | -6.362 | -6.362 | -6.333 | -6.315 | -6.315 | -6.312 |
| 22 | -19.950 | -6.582 | -6.589 | -6.596 | -6.580 | -6.574 | -6.584 | -4.681 |
| 23 | -19.919 | -6.734 | -6.725 | -6.725 | -6.725 | -6.724 | -6.730 | -3.421 |
| 24 | -19.889 | -6.822 | -6.823 | -6.821 | -6.829 | -6.826 | -6.831 | -2.221 |
| 25 | -19.862 | -6.899 | -6.898 | -6.901 | -6.903 | -6.894 | -6.895 | -0.058 |
| 26 | -19.850 | -6.922 | -6.913 | -6.913 | -6.913 | -6.911 | -6.911 | 0.144 |
| 27 | -19.840 | -7.180 | -7.160 | -7.150 | -7.140 | -7.140 | -5.430 | -0.150 |
| 28 | -19.823 | -6.964 | -6.962 | -6.967 | -6.955 | -6.965 | -6.961 | 0.939 |
| 29 | -19.796 | -7.238 | -7.238 | -7.238 | -7.238 | -7.233 | -5.505 | 1.455 |
| 30 | -19.756 | -7.424 | -7.426 | -7.426 | -7.426 | -7.425 | -4.126 | 1.219 |
| 31 | -19.713 | -7.576 | -7.574 | -7.574 | -7.574 | -7.574 | -0.998 | -0.906 |
| 32 | -19.683 | -7.631 | -7.628 | -7.630 | -7.626 | -7.627 | -0.542 | -0.543 |
| 33 | -19.663 | -7.660 | -7.660 | -7.660 | -7.659 | -7.659 | 0.000 | 0.000 |
| 34 | -19.654 | -7.668 | -7.668 | -7.668 | -7.664 | -7.655 | -0.001 | 0.000 |
| 35 | -19.597 | -8.155 | -8.155 | -8.154 | -8.154 | -5.289 | -0.161 | -0.159 |
| 36 | -19.601 | -7.739 | -7.739 | -7.737 | -7.737 | -7.734 | 0.324 | 0.324 |
| 37 | -19.507 | -8.421 | -8.421 | -8.421 | -8.421 | -3.082 | -0.540 | -0.540 |
| 38 | -19.551 | -7.804 | -7.804 | -7.804 | -7.804 | -7.804 | 1.020 | 1.020 |
| 39 | -19.445 | -8.528 | -8.528 | -8.528 | -8.528 | -0.978 | -0.977 | -0.977 |
| 40 | -19.418 | -8.562 | -8.562 | -8.562 | -8.562 | -0.916 | -0.916 | -0.916 |

Table 28

FIG. 52

|  | Label | | | | | | | |
|---|---|---|---|---|---|---|---|---|
|  | 8 | 9 | 10 | 11 | 12 | 13 | 14 | 15 |
| Design # | | | | | | | | |
| 1 | 6.314 | 6.351 | 6.351 | 6.315 | 6.320 | 6.236 | 6.269 | 20.036 |
| 2 | 6.159 | 6.287 | 6.287 | 6.287 | 6.381 | 6.381 | 6.381 | 20.034 |
| 3 | 6.316 | 6.262 | 6.286 | 6.298 | 6.298 | 6.296 | 6.414 | 20.032 |
| 4 | 6.248 | 6.309 | 6.309 | 6.328 | 6.328 | 6.328 | 6.328 | 20.029 |
| 5 | 6.303 | 6.303 | 6.303 | 6.303 | 6.326 | 6.326 | 6.326 | 20.026 |
| 6 | 6.200 | 6.267 | 6.267 | 6.267 | 6.398 | 6.398 | 6.398 | 20.023 |
| 7 | 6.309 | 6.312 | 6.318 | 6.316 | 6.320 | 6.320 | 6.313 | 20.020 |
| 8 | 6.273 | 6.321 | 6.321 | 6.321 | 6.321 | 6.330 | 6.330 | 20.017 |
| 9 | 6.302 | 6.302 | 6.308 | 6.329 | 6.329 | 6.329 | 6.329 | 20.014 |
| 10 | 6.312 | 6.312 | 6.326 | 6.311 | 6.325 | 6.325 | 6.328 | 20.011 |
| 11 | 6.321 | 6.321 | 6.321 | 6.321 | 6.321 | 6.321 | 6.321 | 20.007 |
| 12 | 6.320 | 6.320 | 6.320 | 6.324 | 6.326 | 6.326 | 6.326 | 20.004 |
| 13 | 6.317 | 6.322 | 6.322 | 6.323 | 6.327 | 6.323 | 6.335 | 20.001 |
| 14 | 6.323 | 6.329 | 6.328 | 6.324 | 6.323 | 6.324 | 6.332 | 19.997 |
| 15 | 6.324 | 6.324 | 6.324 | 6.324 | 6.326 | 6.333 | 6.337 | 19.993 |
| 16 | 6.324 | 6.323 | 6.328 | 6.325 | 6.327 | 6.336 | 6.341 | 19.990 |
| 17 | 6.328 | 6.328 | 6.330 | 6.332 | 6.332 | 6.332 | 6.334 | 19.986 |
| 18 | 6.331 | 6.331 | 6.331 | 6.331 | 6.333 | 6.333 | 6.338 | 19.983 |
| 19 | 6.330 | 6.331 | 6.333 | 6.333 | 6.337 | 6.337 | 6.337 | 19.979 |
| 20 | 6.333 | 6.336 | 6.339 | 6.339 | 6.334 | 6.328 | 6.340 | 19.975 |
| 21 | 6.313 | 6.313 | 6.313 | 6.355 | 6.355 | 6.355 | 6.355 | 19.972 |
| 22 | 4.681 | 6.578 | 6.571 | 6.582 | 6.587 | 6.603 | 6.582 | 19.950 |
| 23 | 3.421 | 6.716 | 6.716 | 6.722 | 6.737 | 6.738 | 6.734 | 19.919 |
| 24 | 2.221 | 6.820 | 6.831 | 6.822 | 6.830 | 6.826 | 6.822 | 19.889 |
| 25 | 0.059 | 6.893 | 6.894 | 6.902 | 6.901 | 6.901 | 6.899 | 19.862 |
| 26 | 0.144 | 5.429 | 7.147 | 7.147 | 7.154 | 7.154 | 7.169 | 19.843 |
| 27 | -0.140 | 6.900 | 6.900 | 6.900 | 6.910 | 6.920 | 6.950 | 19.850 |
| 28 | 0.895 | 2.960 | 7.406 | 7.403 | 7.400 | 7.399 | 7.399 | 19.796 |
| 29 | 1.467 | 1.467 | 7.466 | 7.466 | 7.466 | 7.466 | 7.466 | 19.770 |
| 30 | 1.219 | 1.225 | 7.521 | 7.521 | 7.521 | 7.521 | 7.521 | 19.741 |
| 31 | -0.906 | 2.985 | 7.536 | 7.537 | 7.537 | 7.537 | 7.545 | 19.719 |
| 32 | -0.546 | 1.662 | 7.624 | 7.621 | 7.621 | 7.624 | 7.620 | 19.685 |
| 33 | 0.000 | 0.000 | 7.659 | 7.660 | 7.660 | 7.660 | 7.660 | 19.663 |
| 34 | 0.000 | 0.000 | 7.663 | 7.663 | 7.663 | 7.665 | 7.668 | 19.654 |
| 35 | -0.159 | -0.159 | 7.703 | 7.703 | 7.703 | 7.703 | 7.703 | 19.627 |
| 36 | 0.324 | 0.327 | 4.201 | 8.309 | 8.309 | 8.309 | 8.309 | 19.551 |
| 37 | -0.540 | -0.540 | 7.771 | 7.771 | 7.771 | 7.771 | 7.771 | 19.576 |
| 38 | 1.020 | 1.020 | 1.021 | 8.501 | 8.501 | 8.501 | 8.501 | 19.468 |
| 39 | -0.977 | -0.977 | 6.441 | 8.121 | 8.121 | 8.121 | 8.121 | 19.517 |
| 40 | -0.915 | -0.915 | 5.622 | 8.286 | 8.286 | 8.286 | 8.287 | 19.476 |

Table 29

FIG. 53

|        | Label |  |  |  |  |  |  |  |
|--------|---------|---------|---------|---------|---------|---------|---------|---------|
|        | 0 | 1 | 2 | 3 | 4 | 5 | 6 | 7 |
| Design # |  |  |  |  |  |  |  |  |
| 41 | -19.438 | -8.393 | -8.393 | -8.393 | -8.393 | -5.030 | 0.855 | 0.855 |
| 42 | -19.365 | -8.624 | -8.624 | -8.624 | -8.624 | -0.796 | -0.796 | -0.795 |
| 43 | -19.369 | -8.542 | -8.542 | -8.542 | -8.542 | -4.089 | 0.735 | 0.735 |
| 44 | -19.315 | -8.681 | -8.681 | -8.681 | -8.681 | -0.676 | -0.676 | -0.675 |
| 45 | -19.290 | -8.706 | -8.707 | -8.707 | -8.707 | -0.617 | -0.617 | -0.617 |
| 46 | -19.267 | -8.731 | -8.731 | -8.731 | -8.731 | -0.559 | -0.559 | -0.558 |
| 47 | -19.252 | -8.724 | -8.724 | -8.724 | -8.724 | -2.617 | 0.500 | 0.500 |
| 48 | -19.221 | -8.776 | -8.776 | -8.776 | -8.776 | -0.444 | -0.444 | -0.444 |
| 49 | -19.199 | -8.796 | -8.796 | -8.796 | -8.795 | -0.388 | -0.388 | -0.388 |
| 50 | -19.181 | -8.805 | -8.805 | -8.805 | -8.805 | -1.696 | 0.329 | 0.329 |
| 51 | -19.160 | -8.820 | -8.820 | -8.820 | -8.820 | -1.430 | 0.280 | 0.280 |
| 52 | -19.158 | -8.831 | -8.831 | -8.831 | -8.831 | -0.285 | -0.278 | -0.278 |
| 53 | -19.138 | -8.846 | -8.847 | -8.846 | -8.846 | -0.241 | -0.227 | -0.241 |
| 54 | -19.119 | -8.860 | -8.860 | -8.860 | -8.860 | -0.702 | -0.066 | -0.066 |
| 55 | -19.100 | -8.873 | -8.873 | -8.873 | -8.873 | -0.232 | -0.232 | -0.212 |
| 56 | -19.081 | -8.884 | -8.884 | -8.884 | -8.884 | -0.360 | -0.342 | 0.100 |
| 57 | -19.043 | -9.266 | -9.266 | -9.265 | -7.601 | -1.129 | -1.129 | 0.534 |
| 58 | -18.995 | -9.478 | -9.478 | -9.478 | -6.660 | -1.335 | -1.335 | -1.335 |
| 59 | -18.952 | -9.606 | -9.606 | -9.606 | -5.932 | -1.717 | -1.717 | -1.715 |
| 60 | -18.914 | -9.697 | -9.697 | -9.697 | -5.244 | -2.057 | -2.057 | -2.056 |
| 61 | -18.879 | -9.767 | -9.767 | -9.767 | -4.469 | -2.412 | -2.412 | -2.412 |
| 62 | -18.848 | -9.816 | -9.816 | -9.816 | -2.987 | -2.987 | -2.987 | -2.987 |
| 63 | -18.824 | -9.832 | -9.832 | -9.832 | -2.985 | -2.985 | -2.985 | -2.985 |
| 64 | -18.800 | -9.848 | -9.848 | -9.848 | -2.986 | -2.986 | -2.986 | -2.986 |
| 65 | -18.775 | -9.862 | -9.862 | -9.862 | -2.988 | -2.988 | -2.988 | -2.988 |
| 66 | -18.742 | -10.161 | -10.161 | -9.278 | -3.006 | -3.006 | -3.006 | -3.006 |
| 67 | -18.705 | -10.362 | -10.362 | -8.862 | -3.036 | -3.036 | -3.036 | -3.036 |
| 68 | -18.671 | -10.482 | -10.482 | -8.612 | -3.061 | -3.061 | -3.061 | -3.061 |
| 69 | -18.638 | -10.573 | -10.573 | -8.428 | -3.083 | -3.083 | -3.083 | -3.083 |
| 70 | -18.608 | -10.645 | -10.645 | -8.285 | -3.102 | -3.102 | -3.102 | -3.102 |
| 71 | -18.600 | -10.660 | -10.660 | -8.250 | -3.110 | -3.110 | -3.110 | -3.110 |
| 72 | -18.579 | -10.705 | -10.705 | -8.170 | -3.118 | -3.118 | -3.118 | -3.118 |
| 73 | -18.545 | -10.797 | -10.797 | -7.881 | -3.559 | -3.559 | -3.559 | -1.674 |
| 74 | -18.512 | -10.880 | -10.880 | -7.584 | -3.788 | -3.788 | -3.788 | 0.000 |
| 75 | -18.481 | -10.932 | -10.932 | -7.425 | -3.867 | -3.867 | -3.867 | 0.259 |
| 76 | -18.450 | -11.005 | -11.005 | -6.996 | -4.647 | -4.647 | -2.290 | 0.000 |
| 77 | -18.421 | -11.052 | -11.052 | -6.725 | -4.860 | -4.861 | -1.978 | 0.000 |
| 78 | -18.394 | -11.089 | -11.089 | -6.487 | -5.027 | -5.027 | -1.764 | 0.000 |
| 79 | -18.366 | -11.120 | -11.120 | -6.261 | -5.182 | -5.181 | -1.146 | -1.075 |
| 80 | -18.339 | -11.146 | -11.146 | -5.849 | -5.849 | -4.951 | -1.079 | -1.078 |

Table 30

FIG. 54

|  | Label | | | | | | | |
|---|---|---|---|---|---|---|---|---|
|  | 8 | 9 | 10 | 11 | 12 | 13 | 14 | 15 |
| Design # | | | | | | | | |
| 41 | 0.855 | 0.855 | 0.856 | 8.594 | 8.594 | 8.594 | 8.594 | 19.391 |
| 42 | -0.795 | -0.792 | 4.532 | 8.475 | 8.475 | 8.475 | 8.476 | 19.403 |
| 43 | 0.735 | 0.735 | 0.737 | 8.653 | 8.653 | 8.653 | 8.653 | 19.340 |
| 44 | -0.675 | -0.675 | 3.684 | 8.599 | 8.599 | 8.599 | 8.599 | 19.338 |
| 45 | -0.617 | -0.617 | 3.307 | 8.646 | 8.646 | 8.646 | 8.647 | 19.308 |
| 46 | -0.558 | -0.558 | 2.953 | 8.688 | 8.688 | 8.688 | 8.688 | 19.279 |
| 47 | 0.500 | 0.501 | 0.502 | 8.754 | 8.754 | 8.754 | 8.754 | 19.243 |
| 48 | -0.443 | -0.443 | 2.296 | 8.755 | 8.755 | 8.755 | 8.755 | 19.227 |
| 49 | -0.387 | -0.387 | 1.989 | 8.782 | 8.782 | 8.782 | 8.782 | 19.203 |
| 50 | 0.335 | 0.335 | 0.336 | 8.814 | 8.814 | 8.814 | 8.814 | 19.178 |
| 51 | 0.280 | 0.290 | 0.290 | 8.830 | 8.830 | 8.830 | 8.830 | 19.160 |
| 52 | -0.278 | -0.278 | 1.416 | 8.826 | 8.826 | 8.826 | 8.826 | 19.159 |
| 53 | -0.208 | -0.224 | 1.152 | 8.843 | 8.844 | 8.844 | 8.844 | 19.139 |
| 54 | 0.002 | 0.148 | 0.683 | 8.860 | 8.860 | 8.860 | 8.860 | 19.119 |
| 55 | -0.212 | 0.445 | 0.445 | 8.873 | 8.873 | 8.873 | 8.873 | 19.100 |
| 56 | 0.181 | 0.181 | 0.241 | 8.884 | 8.884 | 8.885 | 8.885 | 19.081 |
| 57 | 0.534 | 0.543 | 0.619 | 7.675 | 9.250 | 9.250 | 9.250 | 19.044 |
| 58 | 1.335 | 1.335 | 1.335 | 6.660 | 9.478 | 9.478 | 9.478 | 18.995 |
| 59 | 1.716 | 1.716 | 1.717 | 5.932 | 9.606 | 9.606 | 9.606 | 18.952 |
| 60 | 2.056 | 2.056 | 2.056 | 5.244 | 9.697 | 9.697 | 9.697 | 18.914 |
| 61 | 2.411 | 2.412 | 2.412 | 4.469 | 9.767 | 9.767 | 9.767 | 18.879 |
| 62 | 2.987 | 2.987 | 2.987 | 2.987 | 9.816 | 9.816 | 9.816 | 18.848 |
| 63 | 2.985 | 2.985 | 2.985 | 2.985 | 9.832 | 9.832 | 9.832 | 18.824 |
| 64 | 2.986 | 2.986 | 2.986 | 2.986 | 9.848 | 9.848 | 9.848 | 18.800 |
| 65 | 2.988 | 2.988 | 2.988 | 2.988 | 9.862 | 9.862 | 9.862 | 18.775 |
| 66 | 3.006 | 3.006 | 3.006 | 3.006 | 9.278 | 10.161 | 10.161 | 18.742 |
| 67 | 3.036 | 3.036 | 3.036 | 3.036 | 8.862 | 10.362 | 10.362 | 18.705 |
| 68 | 3.061 | 3.061 | 3.061 | 3.061 | 8.612 | 10.482 | 10.482 | 18.671 |
| 69 | 3.083 | 3.083 | 3.083 | 3.083 | 8.428 | 10.573 | 10.573 | 18.638 |
| 70 | 3.102 | 3.102 | 3.102 | 3.102 | 8.285 | 10.645 | 10.645 | 18.608 |
| 71 | 3.110 | 3.110 | 3.110 | 3.110 | 8.250 | 10.660 | 10.660 | 18.600 |
| 72 | 3.118 | 3.118 | 3.118 | 3.118 | 8.170 | 10.705 | 10.705 | 18.579 |
| 73 | 1.674 | 3.559 | 3.559 | 3.559 | 7.881 | 10.797 | 10.797 | 18.545 |
| 74 | 0.000 | 3.788 | 3.788 | 3.788 | 7.584 | 10.880 | 10.880 | 18.512 |
| 75 | 0.259 | 2.208 | 4.527 | 4.527 | 7.200 | 10.956 | 10.956 | 18.481 |
| 76 | 0.000 | 2.290 | 4.647 | 4.647 | 6.997 | 11.005 | 11.005 | 18.450 |
| 77 | 0.001 | 1.977 | 4.861 | 4.861 | 6.724 | 11.052 | 11.052 | 18.421 |
| 78 | 0.000 | 1.764 | 5.027 | 5.027 | 6.487 | 11.089 | 11.089 | 18.394 |
| 79 | 1.111 | 1.111 | 5.182 | 5.182 | 6.261 | 11.120 | 11.120 | 18.366 |
| 80 | 1.078 | 1.078 | 4.951 | 5.848 | 5.849 | 11.146 | 11.146 | 18.339 |

Table 31

FIG. 55

|          | Label   |         |         |        |        |        |        |        |
|----------|---------|---------|---------|--------|--------|--------|--------|--------|
|          | 0       | 1       | 2       | 3      | 4      | 5      | 6      | 7      |
| Design # |         |         |         |        |        |        |        |        |
| 81       | -18.310 | -11.166 | -11.166 | -5.820 | -5.820 | -5.038 | -1.059 | -1.059 |
| 82       | -18.281 | -11.184 | -11.184 | -5.829 | -5.829 | -5.042 | -1.064 | -1.064 |
| 83       | -18.250 | -11.200 | -11.200 | -5.869 | -5.869 | -4.977 | -1.088 | -1.088 |
| 84       | -18.216 | -11.625 | -10.769 | -6.029 | -6.028 | -4.637 | -1.196 | -1.196 |
| 85       | -18.183 | -11.856 | -10.518 | -6.167 | -6.167 | -4.318 | -1.321 | -1.321 |
| 86       | -18.151 | -12.003 | -10.359 | -6.260 | -6.260 | -4.096 | -1.419 | -1.419 |
| 87       | -18.121 | -12.114 | -10.244 | -6.327 | -6.327 | -3.928 | -1.497 | -1.497 |
| 88       | -18.092 | -12.202 | -10.156 | -6.378 | -6.378 | -3.800 | -1.559 | -1.559 |
| 89       | -18.070 | -12.250 | -10.110 | -6.410 | -6.410 | -3.730 | -1.590 | -1.590 |
| 90       | -18.064 | -12.276 | -10.088 | -6.417 | -6.417 | -3.703 | -1.607 | -1.607 |
| 91       | -18.037 | -12.339 | -10.034 | -6.448 | -6.448 | -3.630 | -1.644 | -1.643 |
| 92       | -18.011 | -12.397 | -9.985  | -6.483 | -6.483 | -3.412 | -2.368 | -0.967 |
| 93       | -17.985 | -12.447 | -9.947  | -6.510 | -6.510 | -2.960 | -2.960 | -0.633 |
| 94       | -17.960 | -12.496 | -9.905  | -6.787 | -6.251 | -2.977 | -2.977 | -0.578 |
| 95       | -17.935 | -12.548 | -9.844  | -7.024 | -6.017 | -3.029 | -3.029 | -0.316 |
| 96       | -17.911 | -12.592 | -9.800  | -7.137 | -5.915 | -3.056 | -3.056 | 0.000  |
| 97       | -17.887 | -12.632 | -9.760  | -7.242 | -5.805 | -3.365 | -2.785 | 0.000  |
| 98       | -17.863 | -12.668 | -9.730  | -7.318 | -5.727 | -3.481 | -2.701 | 0.000  |
| 99       | -17.839 | -12.702 | -9.704  | -7.391 | -5.629 | -3.688 | -2.476 | -0.486 |
| 100      | -17.814 | -12.732 | -9.684  | -7.450 | -5.545 | -3.844 | -2.283 | -0.732 |
| 101      | -17.789 | -12.759 | -9.675  | -7.487 | -5.497 | -3.924 | -2.181 | -0.851 |
| 102      | -17.763 | -12.784 | -9.674  | -7.511 | -5.476 | -3.962 | -2.136 | -0.902 |
| 103      | -17.736 | -12.807 | -9.678  | -7.526 | -5.473 | -3.975 | -2.128 | -0.914 |
| 104      | -17.708 | -12.829 | -9.687  | -7.535 | -5.482 | -3.975 | -2.140 | -0.903 |
| 105      | -17.679 | -12.849 | -9.700  | -7.541 | -5.496 | -3.966 | -2.162 | -0.882 |
| 106      | -17.650 | -12.869 | -9.716  | -7.544 | -5.514 | -3.955 | -2.187 | -0.858 |
| 107      | -17.640 | -12.870 | -9.720  | -7.550 | -5.520 | -3.950 | -2.190 | -0.850 |
| 108      | -17.619 | -12.888 | -9.734  | -7.547 | -5.533 | -3.944 | -2.212 | -0.835 |
| 109      | -17.588 | -12.906 | -9.753  | -7.550 | -5.552 | -3.934 | -2.234 | -0.815 |
| 110      | -17.556 | -12.925 | -9.774  | -7.554 | -5.571 | -3.926 | -2.253 | -0.799 |
| 111      | -17.523 | -12.942 | -9.795  | -7.558 | -5.588 | -3.921 | -2.269 | -0.787 |
| 112      | -17.490 | -12.960 | -9.818  | -7.563 | -5.604 | -3.918 | -2.282 | -0.777 |
| 113      | -17.456 | -12.977 | -9.841  | -7.570 | -5.619 | -3.917 | -2.293 | -0.771 |
| 114      | -17.421 | -12.993 | -9.864  | -7.578 | -5.633 | -3.919 | -2.301 | -0.767 |
| 115      | -17.385 | -13.009 | -9.888  | -7.587 | -5.646 | -3.922 | -2.308 | -0.765 |
| 116      | -17.349 | -13.025 | -9.913  | -7.598 | -5.659 | -3.927 | -2.314 | -0.765 |
| 117      | -17.312 | -13.040 | -9.938  | -7.611 | -5.671 | -3.933 | -2.320 | -0.765 |
| 118      | -17.274 | -13.054 | -9.963  | -7.625 | -5.683 | -3.940 | -2.325 | -0.766 |
| 119      | -17.235 | -13.067 | -9.989  | -7.641 | -5.695 | -3.948 | -2.329 | -0.768 |
| 120      | -17.196 | -13.080 | -10.015 | -7.658 | -5.708 | -3.956 | -2.334 | -0.770 |

Table 32

FIG. 56

|  | Label | | | | | | | |
|---|---|---|---|---|---|---|---|---|
|  | 8 | 9 | 10 | 11 | 12 | 13 | 14 | 15 |
| Design # | | | | | | | | |
| 81 | 1.059 | 1.059 | 5.038 | 5.820 | 5.820 | 11.166 | 11.166 | 18.310 |
| 82 | 1.064 | 1.064 | 5.042 | 5.829 | 5.829 | 11.184 | 11.184 | 18.281 |
| 83 | 1.088 | 1.088 | 4.977 | 5.869 | 5.869 | 11.200 | 11.200 | 18.250 |
| 84 | 1.196 | 1.196 | 4.637 | 6.028 | 6.028 | 10.769 | 11.625 | 18.216 |
| 85 | 1.321 | 1.321 | 4.318 | 6.167 | 6.167 | 10.518 | 11.856 | 18.183 |
| 86 | 1.419 | 1.419 | 4.096 | 6.260 | 6.260 | 10.359 | 12.003 | 18.151 |
| 87 | 1.497 | 1.497 | 3.928 | 6.327 | 6.327 | 10.244 | 12.114 | 18.121 |
| 88 | 1.559 | 1.559 | 3.800 | 6.378 | 6.378 | 10.156 | 12.202 | 18.092 |
| 89 | 1.590 | 1.590 | 3.730 | 6.410 | 6.410 | 10.110 | 12.250 | 18.070 |
| 90 | 1.607 | 1.607 | 3.703 | 6.417 | 6.417 | 10.088 | 12.276 | 18.064 |
| 91 | 1.644 | 1.644 | 3.630 | 6.448 | 6.448 | 10.034 | 12.339 | 18.037 |
| 92 | 0.967 | 2.369 | 3.412 | 6.483 | 6.483 | 9.985 | 12.397 | 18.011 |
| 93 | 0.633 | 2.960 | 2.960 | 6.510 | 6.510 | 9.947 | 12.447 | 17.985 |
| 94 | 0.578 | 2.977 | 2.977 | 6.251 | 6.787 | 9.905 | 12.496 | 17.960 |
| 95 | 0.316 | 3.029 | 3.029 | 6.017 | 7.024 | 9.844 | 12.548 | 17.935 |
| 96 | 0.000 | 3.056 | 3.056 | 5.915 | 7.137 | 9.800 | 12.592 | 17.911 |
| 97 | 0.000 | 2.785 | 3.365 | 5.805 | 7.242 | 9.760 | 12.632 | 17.887 |
| 98 | 0.000 | 2.701 | 3.481 | 5.727 | 7.318 | 9.730 | 12.668 | 17.863 |
| 99 | 0.486 | 2.476 | 3.688 | 5.629 | 7.391 | 9.704 | 12.702 | 17.839 |
| 100 | 0.732 | 2.283 | 3.844 | 5.545 | 7.450 | 9.684 | 12.732 | 17.814 |
| 101 | 0.851 | 2.181 | 3.924 | 5.497 | 7.487 | 9.675 | 12.759 | 17.789 |
| 102 | 0.902 | 2.136 | 3.962 | 5.476 | 7.511 | 9.674 | 12.784 | 17.763 |
| 103 | 0.914 | 2.128 | 3.975 | 5.473 | 7.526 | 9.678 | 12.807 | 17.736 |
| 104 | 0.903 | 2.140 | 3.975 | 5.482 | 7.535 | 9.687 | 12.829 | 17.708 |
| 105 | 0.882 | 2.162 | 3.966 | 5.496 | 7.541 | 9.700 | 12.849 | 17.679 |
| 106 | 0.858 | 2.187 | 3.955 | 5.514 | 7.544 | 9.716 | 12.869 | 17.650 |
| 107 | 0.850 | 2.190 | 3.950 | 5.520 | 7.550 | 9.720 | 12.870 | 17.640 |
| 108 | 0.835 | 2.212 | 3.944 | 5.533 | 7.547 | 9.734 | 12.888 | 17.619 |
| 109 | 0.815 | 2.234 | 3.934 | 5.552 | 7.550 | 9.753 | 12.906 | 17.588 |
| 110 | 0.799 | 2.253 | 3.926 | 5.571 | 7.554 | 9.774 | 12.925 | 17.556 |
| 111 | 0.787 | 2.269 | 3.921 | 5.588 | 7.558 | 9.795 | 12.942 | 17.523 |
| 112 | 0.777 | 2.282 | 3.918 | 5.604 | 7.563 | 9.818 | 12.960 | 17.490 |
| 113 | 0.771 | 2.293 | 3.917 | 5.619 | 7.570 | 9.841 | 12.977 | 17.456 |
| 114 | 0.767 | 2.301 | 3.919 | 5.633 | 7.578 | 9.864 | 12.993 | 17.421 |
| 115 | 0.765 | 2.308 | 3.922 | 5.646 | 7.587 | 9.888 | 13.009 | 17.385 |
| 116 | 0.765 | 2.314 | 3.927 | 5.659 | 7.598 | 9.913 | 13.025 | 17.349 |
| 117 | 0.765 | 2.320 | 3.933 | 5.671 | 7.611 | 9.938 | 13.040 | 17.312 |
| 118 | 0.766 | 2.325 | 3.940 | 5.683 | 7.625 | 9.963 | 13.054 | 17.274 |
| 119 | 0.768 | 2.329 | 3.948 | 5.695 | 7.641 | 9.989 | 13.067 | 17.235 |
| 120 | 0.770 | 2.334 | 3.956 | 5.708 | 7.658 | 10.015 | 13.080 | 17.196 |

Table 33

FIG. 57

|  | Label | | | | | | | |
|---|---|---|---|---|---|---|---|---|
|  | 0 | 1 | 2 | 3 | 4 | 5 | 6 | 7 |
| Design # | | | | | | | | |
| 121 | -17.156 | -13.092 | -10.041 | -7.676 | -5.720 | -3.966 | -2.339 | -0.772 |
| 122 | -17.115 | -13.104 | -10.068 | -7.696 | -5.734 | -3.975 | -2.344 | -0.774 |
| 123 | -17.074 | -13.114 | -10.095 | -7.718 | -5.748 | -3.986 | -2.349 | -0.776 |
| 124 | -17.030 | -13.120 | -10.120 | -7.740 | -5.760 | -4.000 | -2.350 | -0.780 |
| 125 | -17.031 | -13.124 | -10.122 | -7.741 | -5.762 | -3.997 | -2.355 | -0.778 |
| 126 | -16.988 | -13.132 | -10.150 | -7.765 | -5.778 | -4.008 | -2.362 | -0.780 |
| 127 | -16.944 | -13.140 | -10.177 | -7.791 | -5.795 | -4.020 | -2.368 | -0.783 |
| 128 | -16.900 | -13.147 | -10.205 | -7.817 | -5.814 | -4.032 | -2.376 | -0.785 |
| 129 | -16.854 | -13.152 | -10.232 | -7.845 | -5.833 | -4.046 | -2.383 | -0.788 |
| 130 | -16.809 | -13.157 | -10.259 | -7.875 | -5.855 | -4.060 | -2.392 | -0.790 |
| 131 | -16.762 | -13.161 | -10.286 | -7.905 | -5.877 | -4.075 | -2.401 | -0.793 |
| 132 | -16.715 | -13.163 | -10.313 | -7.936 | -5.901 | -4.091 | -2.410 | -0.796 |
| 133 | -16.667 | -13.165 | -10.339 | -7.967 | -5.927 | -4.109 | -2.420 | -0.800 |
| 134 | -16.619 | -13.166 | -10.365 | -8.000 | -5.955 | -4.128 | -2.431 | -0.803 |
| 135 | -16.570 | -13.165 | -10.390 | -8.033 | -5.983 | -4.148 | -2.443 | -0.807 |
| 136 | -16.521 | -13.164 | -10.415 | -8.066 | -6.014 | -4.170 | -2.456 | -0.811 |
| 137 | -16.471 | -13.162 | -10.439 | -8.100 | -6.045 | -4.193 | -2.470 | -0.816 |
| 138 | -16.422 | -13.159 | -10.462 | -8.134 | -6.077 | -4.217 | -2.484 | -0.821 |
| 139 | -16.372 | -13.155 | -10.484 | -8.167 | -6.111 | -4.243 | -2.500 | -0.826 |
| 140 | -16.323 | -13.151 | -10.506 | -8.201 | -6.144 | -4.270 | -2.517 | -0.832 |
| 141 | -16.273 | -13.146 | -10.527 | -8.234 | -6.179 | -4.297 | -2.534 | -0.838 |
| 142 | -16.225 | -13.140 | -10.547 | -8.266 | -6.213 | -4.326 | -2.552 | -0.844 |
| 143 | -16.190 | -13.140 | -10.560 | -8.290 | -6.230 | -4.340 | -2.560 | -0.850 |
| 144 | -16.176 | -13.134 | -10.566 | -8.298 | -6.247 | -4.354 | -2.571 | -0.850 |
| 145 | -16.129 | -13.128 | -10.585 | -8.329 | -6.281 | -4.383 | -2.589 | -0.857 |
| 146 | -16.083 | -13.122 | -10.603 | -8.359 | -6.313 | -4.411 | -2.608 | -0.863 |
| 147 | -16.038 | -13.116 | -10.620 | -8.388 | -6.345 | -4.439 | -2.627 | -0.870 |
| 148 | -15.994 | -13.110 | -10.636 | -8.416 | -6.376 | -4.466 | -2.645 | -0.876 |
| 149 | -15.952 | -13.104 | -10.652 | -8.443 | -6.406 | -4.492 | -2.662 | -0.882 |
| 150 | -15.911 | -13.098 | -10.667 | -8.469 | -6.435 | -4.517 | -2.679 | -0.888 |
| 151 | -15.872 | -13.093 | -10.681 | -8.494 | -6.462 | -4.541 | -2.695 | -0.894 |
| 152 | -15.834 | -13.087 | -10.695 | -8.517 | -6.488 | -4.564 | -2.710 | -0.899 |
| 153 | -15.798 | -13.083 | -10.708 | -8.540 | -6.513 | -4.585 | -2.725 | -0.904 |
| 154 | -15.763 | -13.078 | -10.721 | -8.561 | -6.536 | -4.606 | -2.739 | -0.909 |
| 155 | -15.730 | -13.074 | -10.733 | -8.582 | -6.558 | -4.625 | -2.752 | -0.913 |
| 156 | -15.698 | -13.070 | -10.745 | -8.601 | -6.579 | -4.643 | -2.764 | -0.918 |
| 157 | -15.668 | -13.066 | -10.756 | -8.619 | -6.599 | -4.660 | -2.776 | -0.922 |
| 158 | -15.639 | -13.062 | -10.767 | -8.637 | -6.618 | -4.677 | -2.787 | -0.926 |
| 159 | -15.611 | -13.059 | -10.777 | -8.654 | -6.636 | -4.692 | -2.797 | -0.929 |
| 160 | -15.584 | -13.056 | -10.787 | -8.669 | -6.653 | -4.707 | -2.807 | -0.933 |

Table 34

FIG. 58

|  | Label | | | | | | | |
|---|---|---|---|---|---|---|---|---|
|  | 8 | 9 | 10 | 11 | 12 | 13 | 14 | 15 |
| Design # | | | | | | | | |
| 121 | 0.772 | 2.339 | 3.966 | 5.720 | 7.676 | 10.041 | 13.092 | 17.156 |
| 122 | 0.774 | 2.344 | 3.975 | 5.734 | 7.696 | 10.068 | 13.104 | 17.115 |
| 123 | 0.776 | 2.349 | 3.986 | 5.748 | 7.718 | 10.095 | 13.114 | 17.074 |
| 124 | 0.780 | 2.350 | 4.000 | 5.760 | 7.740 | 10.120 | 13.120 | 17.030 |
| 125 | 0.778 | 2.355 | 3.997 | 5.762 | 7.741 | 10.122 | 13.124 | 17.031 |
| 126 | 0.780 | 2.362 | 4.008 | 5.778 | 7.765 | 10.150 | 13.132 | 16.988 |
| 127 | 0.783 | 2.368 | 4.020 | 5.795 | 7.791 | 10.177 | 13.140 | 16.944 |
| 128 | 0.785 | 2.376 | 4.032 | 5.814 | 7.817 | 10.205 | 13.147 | 16.900 |
| 129 | 0.788 | 2.383 | 4.046 | 5.833 | 7.845 | 10.232 | 13.152 | 16.854 |
| 130 | 0.790 | 2.392 | 4.060 | 5.855 | 7.875 | 10.259 | 13.157 | 16.809 |
| 131 | 0.793 | 2.401 | 4.075 | 5.877 | 7.905 | 10.286 | 13.161 | 16.762 |
| 132 | 0.796 | 2.410 | 4.091 | 5.901 | 7.936 | 10.313 | 13.163 | 16.715 |
| 133 | 0.800 | 2.420 | 4.109 | 5.927 | 7.967 | 10.339 | 13.165 | 16.667 |
| 134 | 0.803 | 2.431 | 4.128 | 5.955 | 8.000 | 10.365 | 13.166 | 16.619 |
| 135 | 0.807 | 2.443 | 4.148 | 5.983 | 8.033 | 10.390 | 13.165 | 16.570 |
| 136 | 0.811 | 2.456 | 4.170 | 6.014 | 8.066 | 10.415 | 13.164 | 16.521 |
| 137 | 0.816 | 2.470 | 4.193 | 6.045 | 8.100 | 10.439 | 13.162 | 16.471 |
| 138 | 0.821 | 2.484 | 4.217 | 6.077 | 8.134 | 10.462 | 13.159 | 16.422 |
| 139 | 0.826 | 2.500 | 4.243 | 6.111 | 8.167 | 10.484 | 13.155 | 16.372 |
| 140 | 0.832 | 2.517 | 4.270 | 6.144 | 8.201 | 10.506 | 13.151 | 16.323 |
| 141 | 0.838 | 2.534 | 4.297 | 6.179 | 8.234 | 10.527 | 13.146 | 16.273 |
| 142 | 0.844 | 2.552 | 4.326 | 6.213 | 8.266 | 10.547 | 13.140 | 16.225 |
| 143 | 0.850 | 2.560 | 4.340 | 6.230 | 8.290 | 10.560 | 13.140 | 16.190 |
| 144 | 0.850 | 2.571 | 4.354 | 6.247 | 8.298 | 10.566 | 13.134 | 16.176 |
| 145 | 0.857 | 2.589 | 4.383 | 6.281 | 8.329 | 10.585 | 13.128 | 16.129 |
| 146 | 0.863 | 2.608 | 4.411 | 6.313 | 8.359 | 10.603 | 13.122 | 16.083 |
| 147 | 0.870 | 2.627 | 4.439 | 6.345 | 8.388 | 10.620 | 13.116 | 16.038 |
| 148 | 0.876 | 2.645 | 4.466 | 6.376 | 8.416 | 10.636 | 13.110 | 15.994 |
| 149 | 0.882 | 2.662 | 4.492 | 6.406 | 8.443 | 10.652 | 13.104 | 15.952 |
| 150 | 0.888 | 2.679 | 4.517 | 6.435 | 8.469 | 10.667 | 13.098 | 15.911 |
| 151 | 0.894 | 2.695 | 4.541 | 6.462 | 8.494 | 10.681 | 13.093 | 15.872 |
| 152 | 0.899 | 2.710 | 4.564 | 6.488 | 8.517 | 10.695 | 13.087 | 15.834 |
| 153 | 0.904 | 2.725 | 4.585 | 6.513 | 8.540 | 10.708 | 13.083 | 15.798 |
| 154 | 0.909 | 2.739 | 4.606 | 6.536 | 8.561 | 10.721 | 13.078 | 15.763 |
| 155 | 0.913 | 2.752 | 4.625 | 6.558 | 8.582 | 10.733 | 13.074 | 15.730 |
| 156 | 0.918 | 2.764 | 4.643 | 6.579 | 8.601 | 10.745 | 13.070 | 15.698 |
| 157 | 0.922 | 2.776 | 4.660 | 6.599 | 8.619 | 10.756 | 13.066 | 15.668 |
| 158 | 0.926 | 2.787 | 4.677 | 6.618 | 8.637 | 10.767 | 13.062 | 15.639 |
| 159 | 0.929 | 2.797 | 4.692 | 6.636 | 8.654 | 10.777 | 13.059 | 15.611 |
| 160 | 0.933 | 2.807 | 4.707 | 6.653 | 8.669 | 10.787 | 13.056 | 15.584 |

Table 35

FIG. 59

|  | Label | | | | | | | |
|---|---|---|---|---|---|---|---|---|
|  | 0 | 1 | 2 | 3 | 4 | 5 | 6 | 7 |
| Design # | | | | | | | | |
| 161 | -15.559 | -13.053 | -10.796 | -8.684 | -6.670 | -4.721 | -2.816 | -0.936 |
| 162 | -15.534 | -13.050 | -10.805 | -8.699 | -6.685 | -4.734 | -2.825 | -0.939 |
| 163 | -15.512 | -13.047 | -10.813 | -8.712 | -6.699 | -4.747 | -2.833 | -0.942 |
| 164 | -15.489 | -13.045 | -10.822 | -8.726 | -6.714 | -4.758 | -2.841 | -0.945 |
| 165 | -15.468 | -13.042 | -10.829 | -8.738 | -6.727 | -4.770 | -2.848 | -0.947 |
| 166 | -15.447 | -13.040 | -10.837 | -8.750 | -6.739 | -4.781 | -2.856 | -0.950 |
| 167 | -15.428 | -13.038 | -10.844 | -8.761 | -6.751 | -4.791 | -2.862 | -0.952 |
| 168 | -15.409 | -13.036 | -10.851 | -8.772 | -6.763 | -4.801 | -2.869 | -0.954 |
| 169 | -15.392 | -13.035 | -10.857 | -8.782 | -6.773 | -4.809 | -2.874 | -0.956 |
| 170 | -15.374 | -13.033 | -10.864 | -8.792 | -6.784 | -4.818 | -2.880 | -0.958 |
| 171 | -15.359 | -13.032 | -10.870 | -8.801 | -6.793 | -4.826 | -2.886 | -0.960 |
| 172 | -15.344 | -13.030 | -10.875 | -8.810 | -6.802 | -4.834 | -2.891 | -0.962 |
| 173 | -15.328 | -13.028 | -10.881 | -8.819 | -6.812 | -4.842 | -2.896 | -0.964 |
| 174 | -15.312 | -13.027 | -10.887 | -8.827 | -6.821 | -4.850 | -2.901 | -0.966 |
| 175 | -15.300 | -13.025 | -10.891 | -8.835 | -6.829 | -4.856 | -2.906 | -0.967 |
| 176 | -15.287 | -13.024 | -10.896 | -8.842 | -6.836 | -4.862 | -2.910 | -0.969 |
| 177 | -15.275 | -13.023 | -10.900 | -8.849 | -6.843 | -4.868 | -2.913 | -0.970 |
| 178 | -15.261 | -13.022 | -10.905 | -8.856 | -6.851 | -4.875 | -2.918 | -0.971 |
| 179 | -15.252 | -13.022 | -10.909 | -8.861 | -6.856 | -4.879 | -2.921 | -0.973 |
| 180 | -15.240 | -13.020 | -10.913 | -8.869 | -6.865 | -4.887 | -2.926 | -0.974 |

Table 36

FIG. 60

|  | Label | | | | | | | |
|---|---|---|---|---|---|---|---|---|
|  | 8 | 9 | 10 | 11 | 12 | 13 | 14 | 15 |
| Design # | | | | | | | | |
| 161 | 0.936 | 2.816 | 4.721 | 6.670 | 8.684 | 10.796 | 13.053 | 15.559 |
| 162 | 0.939 | 2.825 | 4.734 | 6.685 | 8.699 | 10.805 | 13.050 | 15.534 |
| 163 | 0.942 | 2.833 | 4.747 | 6.699 | 8.712 | 10.813 | 13.047 | 15.512 |
| 164 | 0.945 | 2.841 | 4.758 | 6.714 | 8.726 | 10.822 | 13.045 | 15.489 |
| 165 | 0.947 | 2.848 | 4.770 | 6.727 | 8.738 | 10.829 | 13.042 | 15.468 |
| 166 | 0.950 | 2.856 | 4.781 | 6.739 | 8.750 | 10.837 | 13.040 | 15.447 |
| 167 | 0.952 | 2.862 | 4.791 | 6.751 | 8.761 | 10.844 | 13.038 | 15.428 |
| 168 | 0.954 | 2.869 | 4.801 | 6.763 | 8.772 | 10.851 | 13.036 | 15.409 |
| 169 | 0.956 | 2.874 | 4.809 | 6.773 | 8.782 | 10.857 | 13.035 | 15.392 |
| 170 | 0.958 | 2.880 | 4.818 | 6.784 | 8.792 | 10.864 | 13.033 | 15.374 |
| 171 | 0.960 | 2.886 | 4.826 | 6.793 | 8.801 | 10.870 | 13.032 | 15.359 |
| 172 | 0.962 | 2.891 | 4.834 | 6.802 | 8.810 | 10.875 | 13.030 | 15.344 |
| 173 | 0.964 | 2.896 | 4.842 | 6.812 | 8.819 | 10.881 | 13.028 | 15.328 |
| 174 | 0.966 | 2.901 | 4.850 | 6.821 | 8.827 | 10.887 | 13.027 | 15.312 |
| 175 | 0.967 | 2.906 | 4.856 | 6.829 | 8.835 | 10.891 | 13.025 | 15.300 |
| 176 | 0.969 | 2.909 | 4.862 | 6.836 | 8.842 | 10.896 | 13.024 | 15.287 |
| 177 | 0.970 | 2.913 | 4.868 | 6.843 | 8.849 | 10.900 | 13.023 | 15.275 |
| 178 | 0.971 | 2.918 | 4.875 | 6.851 | 8.856 | 10.905 | 13.022 | 15.261 |
| 179 | 0.973 | 2.921 | 4.879 | 6.856 | 8.861 | 10.909 | 13.022 | 15.252 |
| 180 | 0.974 | 2.926 | 4.887 | 6.865 | 8.869 | 10.913 | 13.019 | 15.240 |

Table 37

FIG. 61

| Design # | SNRs | 5.00% | 15.00% | 30.00% | 45.00% | 60.00% | 100.00% |
|---|---|---|---|---|---|---|---|
| 1 | -5 | 0.27 | 0.23 | 0.2 | 0.17 | 0.14 | 0 |
| 2 | -4.8 | 0.31 | 0.26 | 0.22 | 0.19 | 0.16 | 0 |
| 3 | -4.6 | 0.38 | 0.32 | 0.27 | 0.23 | 0.18 | 0 |
| 4 | -4.4 | 0.34 | 0.29 | 0.25 | 0.21 | 0.16 | 0 |
| 5 | -4.2 | 0.34 | 0.29 | 0.25 | 0.21 | 0.18 | 0 |
| 6 | -4 | 0.38 | 0.32 | 0.27 | 0.23 | 0.2 | 0 |
| 7 | -3.8 | 0.38 | 0.32 | 0.27 | 0.23 | 0.2 | 0 |
| 8 | -3.6 | 0.42 | 0.36 | 0.3 | 0.26 | 0.22 | 0 |
| 9 | -3.4 | 0.38 | 0.32 | 0.27 | 0.23 | 0.2 | 0 |
| 10 | -3.2 | 0.47 | 0.4 | 0.34 | 0.29 | 0.24 | 0 |
| 11 | -3 | 0.52 | 0.4 | 0.34 | 0.26 | 0.22 | 0 |
| 12 | -2.8 | 0.52 | 0.44 | 0.38 | 0.32 | 0.27 | 0 |
| 13 | -2.6 | 0.47 | 0.4 | 0.34 | 0.29 | 0.24 | 0 |
| 14 | -2.4 | 0.52 | 0.44 | 0.38 | 0.32 | 0.27 | 0 |
| 15 | -2.2 | 0.58 | 0.49 | 0.42 | 0.36 | 0.3 | 0 |
| 16 | -2 | 0.58 | 0.49 | 0.42 | 0.36 | 0.27 | 0 |
| 17 | -1.8 | 0.65 | 0.55 | 0.47 | 0.4 | 0.34 | 0 |
| 18 | -1.6 | 0.65 | 0.55 | 0.47 | 0.4 | 0.34 | 0 |
| 19 | -1.4 | 0.72 | 0.61 | 0.52 | 0.44 | 0.37 | 0 |
| 20 | -1.2 | 0.65 | 0.55 | 0.47 | 0.4 | 0.34 | 0 |
| 21 | -1 | 0.71 | 0.61 | 0.52 | 0.44 | 0.37 | 0 |
| 22 | -0.8 | 0.8 | 0.68 | 0.58 | 0.49 | 0.42 | 0 |
| 23 | -0.6 | 0.74 | 0.63 | 0.53 | 0.45 | 0.38 | 0 |
| 24 | -0.4 | 0.83 | 0.7 | 0.6 | 0.51 | 0.43 | 0 |
| 25 | -0.2 | 0.93 | 0.79 | 0.67 | 0.57 | 0.44 | 0 |
| 26 | 0 | 0.93 | 0.79 | 0.67 | 0.57 | 0.49 | 0 |
| 27 | 0 | 0.93 | 0.79 | 0.67 | 0.57 | 0.44 | 0 |
| 28 | 0.2 | 1.04 | 0.89 | 0.75 | 0.64 | 0.49 | 0 |
| 29 | 0.4 | 0.97 | 0.82 | 0.7 | 0.59 | 0.45 | 0 |
| 30 | 0.6 | 0.97 | 0.82 | 0.7 | 0.59 | 0.5 | 0 |
| 31 | 0.8 | 0.97 | 0.82 | 0.7 | 0.6 | 0.51 | 0 |
| 32 | 1 | 0.97 | 0.83 | 0.7 | 0.6 | 0.51 | 0 |
| 33 | 1.2 | 0.98 | 0.83 | 0.71 | 0.6 | 0.51 | 0 |
| 34 | 1.4 | 1.09 | 0.92 | 0.79 | 0.67 | 0.57 | 0 |
| 35 | 1.6 | 1.09 | 0.93 | 0.79 | 0.67 | 0.57 | 0 |
| 36 | 1.8 | 1.22 | 1.04 | 0.88 | 0.75 | 0.64 | 0 |
| 37 | 2 | 1.23 | 1.04 | 0.89 | 0.75 | 0.64 | 0 |
| 38 | 2.2 | 1.23 | 1.05 | 0.89 | 0.76 | 0.64 | 0 |
| 39 | 2.4 | 1.26 | 1.07 | 0.91 | 0.77 | 0.66 | 0 |

Table 38

FIG. 62

| Design # | SNRs | 5.00% | 15.00% | 30.00% | 45.00% | 60.00% | 100.00% |
|---|---|---|---|---|---|---|---|
| 40 | 2.6 | 1.25 | 1.06 | 0.9 | 0.77 | 0.65 | 0 |
| 41 | 2.8 | 1.25 | 1.06 | 0.9 | 0.77 | 0.65 | 0 |
| 42 | 3 | 1.38 | 1.18 | 1 | 0.85 | 0.65 | 0 |
| 43 | 3.2 | 1.38 | 1.18 | 1 | 0.85 | 0.65 | 0 |
| 44 | 3.4 | 1.38 | 1.18 | 1 | 0.85 | 0.72 | 0 |
| 45 | 3.6 | 1.34 | 1.14 | 0.97 | 0.83 | 0.7 | 0 |
| 46 | 3.8 | 1.2 | 1.02 | 0.87 | 0.74 | 0.63 | 0 |
| 47 | 4 | 1.46 | 1.24 | 1.05 | 0.9 | 0.69 | 0 |
| 48 | 4.2 | 1.42 | 1.21 | 1.03 | 0.87 | 0.74 | 0 |
| 49 | 4.4 | 1.52 | 1.29 | 1.1 | 0.93 | 0.71 | 0 |
| 50 | 4.6 | 1.44 | 1.23 | 1.04 | 0.89 | 0.68 | 0 |
| 51 | 4.79 | 1.22 | 1.04 | 0.88 | 0.75 | 0.64 | 0 |
| 52 | 4.8 | 1.2 | 1.02 | 0.87 | 0.74 | 0.63 | 0 |
| 53 | 5 | 0.98 | 0.83 | 0.71 | 0.6 | 0.51 | 0 |
| 54 | 5.2 | 0.6 | 0.51 | 0.43 | 0.37 | 0.31 | 0 |
| 55 | 5.4 | 0.38 | 0.33 | 0.28 | 0.24 | 0.2 | 0 |
| 56 | 5.6 | 0.37 | 0.32 | 0.27 | 0.23 | 0.19 | 0 |
| 57 | 5.8 | 1.09 | 0.93 | 0.79 | 0.67 | 0.57 | 0 |
| 58 | 6 | 1.45 | 1.23 | 1.05 | 0.89 | 0.76 | 0 |
| 59 | 6.2 | 1.46 | 1.24 | 1.06 | 0.9 | 0.69 | 0 |
| 60 | 6.4 | 1.4 | 1.19 | 1.01 | 0.86 | 0.73 | 0 |
| 61 | 6.6 | 1.41 | 1.2 | 1.02 | 0.86 | 0.74 | 0 |
| 62 | 6.8 | 1.42 | 1.2 | 1.02 | 0.87 | 0.67 | 0 |
| 63 | 7 | 1.42 | 1.21 | 1.02 | 0.87 | 0.67 | 0 |
| 64 | 7.2 | 1.42 | 1.21 | 1.03 | 0.87 | 0.67 | 0 |
| 65 | 7.4 | 1.28 | 1.09 | 0.92 | 0.79 | 0.67 | 0 |
| 66 | 7.6 | 1.42 | 1.21 | 1.02 | 0.87 | 0.67 | 0 |
| 67 | 7.8 | 1.29 | 1.1 | 0.93 | 0.79 | 0.67 | 0 |
| 68 | 8 | 1.3 | 1.11 | 0.94 | 0.8 | 0.68 | 0 |
| 69 | 8.2 | 1.31 | 1.11 | 0.95 | 0.8 | 0.68 | 0 |
| 70 | 8.4 | 1.32 | 1.12 | 0.95 | 0.81 | 0.69 | 0 |
| 71 | 8.52 | 1.32 | 1.12 | 0.95 | 0.81 | 0.62 | 0 |
| 72 | 8.6 | 1.32 | 1.13 | 0.96 | 0.81 | 0.69 | 0 |
| 73 | 8.8 | 1.29 | 1.09 | 0.93 | 0.79 | 0.67 | 0 |
| 74 | 9 | 1.35 | 1.15 | 0.97 | 0.83 | 0.7 | 0 |
| 75 | 9.2 | 1.38 | 1.17 | 0.99 | 0.85 | 0.65 | 0 |
| 76 | 9.4 | 1.24 | 1.05 | 0.89 | 0.76 | 0.65 | 0 |
| 77 | 9.6 | 1.24 | 1.06 | 0.89 | 0.76 | 0.65 | 0 |
| 78 | 9.8 | 1.25 | 1.06 | 0.89 | 0.76 | 0.64 | 0 |
| 79 | 10 | 1.25 | 1.06 | 0.89 | 0.76 | 0.64 | 0 |
| 80 | 10.2 | 1.18 | 1 | 0.85 | 0.72 | 0.61 | 0 |

Table 39

FIG. 63

| Design # | SNRs  | 5.00% | 15.00% | 30.00% | 45.00% | 60.00% | 100.00% |
|----------|-------|-------|--------|--------|--------|--------|---------|
| 81       | 10.4  | 1.2   | 1.02   | 0.86   | 0.73   | 0.62   | 0       |
| 82       | 10.6  | 1.2   | 1.02   | 0.87   | 0.74   | 0.63   | 0       |
| 83       | 10.8  | 1.19  | 1.01   | 0.86   | 0.73   | 0.56   | 0       |
| 84       | 11    | 1.08  | 0.92   | 0.6    | 0.51   | 0.43   | 0       |
| 85       | 11.2  | 0.92  | 0.78   | 0.44   | 0.37   | 0.32   | 0       |
| 86       | 11.4  | 0.82  | 0.7    | 0.36   | 0.31   | 0.26   | 0       |
| 87       | 11.6  | 0.78  | 0.67   | 0.37   | 0.31   | 0.27   | 0       |
| 88       | 11.8  | 0.79  | 0.67   | 0.38   | 0.33   | 0.28   | 0       |
| 89       | 11.94 | 0.79  | 0.67   | 0.4    | 0.34   | 0.29   | 0       |
| 90       | 12    | 0.79  | 0.67   | 0.39   | 0.33   | 0.28   | 0       |
| 91       | 12.2  | 0.8   | 0.68   | 0.41   | 0.35   | 0.3    | 0       |
| 92       | 12.4  | 0.8   | 0.68   | 0.58   | 0.49   | 0.42   | 0       |
| 93       | 12.6  | 0.81  | 0.68   | 0.58   | 0.49   | 0.42   | 0       |
| 94       | 12.8  | 0.68  | 0.58   | 0.49   | 0.42   | 0.36   | 0       |
| 95       | 13    | 0.66  | 0.56   | 0.48   | 0.41   | 0.35   | 0       |
| 96       | 13.2  | 0.67  | 0.57   | 0.48   | 0.41   | 0.35   | 0       |
| 97       | 13.4  | 0.61  | 0.52   | 0.44   | 0.38   | 0.32   | 0       |
| 98       | 13.6  | 0.61  | 0.52   | 0.44   | 0.38   | 0.32   | 0       |
| 99       | 13.8  | 0.22  | 0.18   | 0.16   | 0.13   | 0.11   | 0       |
| 100      | 14    | 0.06  | 0.05   | 0.05   | 0.04   | 0.03   | 0       |
| 101      | 14.2  | 0.09  | 0.07   | 0.06   | 0.05   | 0.04   | 0       |
| 102      | 14.4  | 0.13  | 0.11   | 0.09   | 0.08   | 0.07   | 0       |
| 103      | 14.6  | 0.14  | 0.12   | 0.1    | 0.08   | 0.07   | 0       |
| 104      | 14.8  | 0.15  | 0.13   | 0.11   | 0.09   | 0.08   | 0       |
| 105      | 15    | 0.17  | 0.14   | 0.12   | 0.1    | 0.09   | 0       |
| 106      | 15.2  | 0.19  | 0.16   | 0.14   | 0.12   | 0.1    | 0       |
| 107      | 15.25 | 0.19  | 0.17   | 0.14   | 0.12   | 0.1    | 0       |
| 108      | 15.4  | 0.21  | 0.18   | 0.15   | 0.13   | 0.11   | 0       |
| 109      | 15.6  | 0.23  | 0.2    | 0.17   | 0.14   | 0.12   | 0       |
| 110      | 15.8  | 0.25  | 0.21   | 0.18   | 0.15   | 0.13   | 0       |
| 111      | 16    | 0.27  | 0.23   | 0.2    | 0.17   | 0.14   | 0       |
| 112      | 16.2  | 0.29  | 0.25   | 0.21   | 0.18   | 0.15   | 0       |
| 113      | 16.4  | 0.31  | 0.26   | 0.22   | 0.19   | 0.16   | 0       |
| 114      | 16.6  | 0.33  | 0.28   | 0.24   | 0.2    | 0.17   | 0       |
| 115      | 16.8  | 0.35  | 0.3    | 0.25   | 0.22   | 0.18   | 0       |
| 116      | 17    | 0.37  | 0.32   | 0.27   | 0.23   | 0.19   | 0       |
| 117      | 17.2  | 0.39  | 0.33   | 0.28   | 0.24   | 0.21   | 0       |
| 118      | 17.4  | 0.41  | 0.35   | 0.3    | 0.25   | 0.22   | 0       |
| 119      | 17.6  | 0.43  | 0.37   | 0.31   | 0.27   | 0.23   | 0       |
| 120      | 17.8  | 0.45  | 0.39   | 0.33   | 0.28   | 0.24   | 0       |

Table 40

FIG. 64

| Design # | SNRs | 5.00% | 15.00% | 30.00% | 45.00% | 60.00% | 100.00% |
|---|---|---|---|---|---|---|---|
| 121 | 18 | 0.47 | 0.4 | 0.34 | 0.29 | 0.25 | 0 |
| 122 | 18.2 | 0.49 | 0.42 | 0.35 | 0.3 | 0.25 | 0 |
| 123 | 18.4 | 0.46 | 0.39 | 0.33 | 0.28 | 0.24 | 0 |
| 124 | 18.59 | 0.48 | 0.41 | 0.31 | 0.27 | 0.23 | 0 |
| 125 | 18.6 | 0.48 | 0.41 | 0.31 | 0.27 | 0.23 | 0 |
| 126 | 18.8 | 0.45 | 0.38 | 0.3 | 0.25 | 0.21 | 0 |
| 127 | 19 | 0.46 | 0.39 | 0.28 | 0.24 | 0.21 | 0 |
| 128 | 19.2 | 0.43 | 0.37 | 0.28 | 0.24 | 0.21 | 0 |
| 129 | 19.4 | 0.4 | 0.34 | 0.28 | 0.24 | 0.2 | 0 |
| 130 | 19.6 | 0.41 | 0.35 | 0.28 | 0.24 | 0.2 | 0 |
| 131 | 19.8 | 0.35 | 0.3 | 0.25 | 0.22 | 0.18 | 0 |
| 132 | 20 | 0.33 | 0.28 | 0.24 | 0.2 | 0.17 | 0 |
| 133 | 20.2 | 0.34 | 0.29 | 0.25 | 0.21 | 0.18 | 0 |
| 134 | 20.4 | 0.32 | 0.27 | 0.23 | 0.2 | 0.17 | 0 |
| 135 | 20.6 | 0.3 | 0.26 | 0.22 | 0.18 | 0.16 | 0 |
| 136 | 20.8 | 0.31 | 0.26 | 0.22 | 0.19 | 0.15 | 0 |
| 137 | 21 | 0.26 | 0.22 | 0.19 | 0.16 | 0.14 | 0 |
| 138 | 21.2 | 0.27 | 0.23 | 0.19 | 0.17 | 0.14 | 0 |
| 139 | 21.4 | 0.25 | 0.21 | 0.18 | 0.15 | 0.13 | 0 |
| 140 | 21.6 | 0.24 | 0.2 | 0.17 | 0.15 | 0.11 | 0 |
| 141 | 21.8 | 0.21 | 0.18 | 0.15 | 0.13 | 0.11 | 0 |
| 142 | 22 | 0.2 | 0.17 | 0.14 | 0.12 | 0.1 | 0 |
| 143 | 22.12 | 0.22 | 0.18 | 0.16 | 0.13 | 0.1 | 0 |
| 144 | 22.2 | 0.19 | 0.16 | 0.14 | 0.12 | 0.1 | 0 |
| 145 | 22.4 | 0.18 | 0.16 | 0.13 | 0.11 | 0.1 | 0 |
| 146 | 22.6 | 0.18 | 0.15 | 0.13 | 0.11 | 0.09 | 0 |
| 147 | 22.8 | 0.17 | 0.14 | 0.12 | 0.1 | 0.09 | 0 |
| 148 | 23 | 0.14 | 0.12 | 0.1 | 0.09 | 0.08 | 0 |
| 149 | 23.2 | 0.15 | 0.13 | 0.11 | 0.09 | 0.07 | 0 |
| 150 | 23.4 | 0.13 | 0.11 | 0.09 | 0.08 | 0.07 | 0 |
| 151 | 23.6 | 0.14 | 0.12 | 0.1 | 0.09 | 0.07 | 0 |
| 152 | 23.8 | 0.13 | 0.11 | 0.1 | 0.08 | 0.07 | 0 |
| 153 | 24 | 0.13 | 0.11 | 0.09 | 0.08 | 0.06 | 0 |
| 154 | 24.2 | 0.11 | 0.09 | 0.08 | 0.07 | 0.06 | 0 |
| 155 | 24.4 | 0.1 | 0.09 | 0.08 | 0.06 | 0.05 | 0 |
| 156 | 24.6 | 0.1 | 0.08 | 0.07 | 0.06 | 0.05 | 0 |
| 157 | 24.8 | 0.09 | 0.08 | 0.07 | 0.06 | 0.05 | 0 |
| 158 | 25 | 0.09 | 0.08 | 0.07 | 0.06 | 0.05 | 0 |
| 159 | 25.2 | 0.09 | 0.07 | 0.06 | 0.05 | 0.05 | 0 |
| 160 | 25.4 | 0.08 | 0.07 | 0.06 | 0.05 | 0.04 | 0 |

Table 41

FIG. 65

| Design # | SNRs | 5.00% | 15.00% | 30.00% | 45.00% | 60.00% | 100.00% |
|---|---|---|---|---|---|---|---|
| 161 | 25.6 | 0.08 | 0.07 | 0.06 | 0.05 | 0.04 | 0 |
| 162 | 25.8 | 0.08 | 0.06 | 0.05 | 0.05 | 0.04 | 0 |
| 163 | 26 | 0.07 | 0.06 | 0.05 | 0.04 | 0.04 | 0 |
| 164 | 26.2 | 0.07 | 0.06 | 0.05 | 0.04 | 0.04 | 0 |
| 165 | 26.4 | 0.07 | 0.06 | 0.05 | 0.04 | 0.03 | 0 |
| 166 | 26.6 | 0.06 | 0.05 | 0.05 | 0.04 | 0.03 | 0 |
| 167 | 26.8 | 0.05 | 0.05 | 0.04 | 0.03 | 0.03 | 0 |
| 168 | 27 | 0.06 | 0.05 | 0.04 | 0.04 | 0.03 | 0 |
| 169 | 27.2 | 0.06 | 0.05 | 0.04 | 0.03 | 0.03 | 0 |
| 170 | 27.4 | 0.05 | 0.04 | 0.04 | 0.03 | 0.03 | 0 |
| 171 | 27.6 | 0.05 | 0.04 | 0.04 | 0.03 | 0.03 | 0 |
| 172 | 27.8 | 0.05 | 0.04 | 0.03 | 0.03 | 0.02 | 0 |
| 173 | 28 | 0.04 | 0.04 | 0.03 | 0.03 | 0.02 | 0 |
| 174 | 28.2 | 0.04 | 0.04 | 0.03 | 0.03 | 0.02 | 0 |
| 175 | 28.4 | 0.04 | 0.04 | 0.03 | 0.03 | 0.02 | 0 |
| 176 | 28.6 | 0.04 | 0.03 | 0.03 | 0.02 | 0.02 | 0 |
| 177 | 28.8 | 0.03 | 0.03 | 0.03 | 0.02 | 0.02 | 0 |
| 178 | 29 | 0.04 | 0.03 | 0.03 | 0.02 | 0.02 | 0 |
| 179 | 29.2 | 0.04 | 0.03 | 0.03 | 0.02 | 0.02 | 0 |
| 180 | 29.4 | 0.03 | 0.03 | 0.02 | 0.02 | 0.02 | 0 |

Table 42

FIG. 66

| Design # | SNR | Opt. Cap | Std. Cap | Gain [bits] | Gain % |
|---|---|---|---|---|---|
| 1 | -5.0000 | 0.1977 | 0.1576 | 0.0401 | 25.4629 |
| 2 | -4.8000 | 0.2058 | 0.1643 | 0.0415 | 25.2261 |
| 3 | -4.6000 | 0.2141 | 0.1713 | 0.0428 | 24.9841 |
| 4 | -4.4000 | 0.2227 | 0.1785 | 0.0442 | 24.7360 |
| 5 | -4.2000 | 0.2316 | 0.1860 | 0.0455 | 24.4818 |
| 6 | -4.0000 | 0.2407 | 0.1938 | 0.0469 | 24.2216 |
| 7 | -3.8000 | 0.2502 | 0.2019 | 0.0484 | 23.9548 |
| 8 | -3.6000 | 0.2600 | 0.2102 | 0.0498 | 23.6816 |
| 9 | -3.4000 | 0.2700 | 0.2188 | 0.0512 | 23.4016 |
| 10 | -3.2000 | 0.2804 | 0.2277 | 0.0526 | 23.1144 |
| 11 | -3.0000 | 0.2910 | 0.2370 | 0.0541 | 22.8200 |
| 12 | -2.8000 | 0.3020 | 0.2465 | 0.0555 | 22.5180 |
| 13 | -2.6000 | 0.3133 | 0.2563 | 0.0569 | 22.2080 |
| 14 | -2.4000 | 0.3248 | 0.2665 | 0.0583 | 21.8898 |
| 15 | -2.2000 | 0.3367 | 0.2770 | 0.0597 | 21.5628 |
| 16 | -2.0000 | 0.3489 | 0.2878 | 0.0611 | 21.2267 |
| 17 | -1.8000 | 0.3613 | 0.2989 | 0.0624 | 20.8808 |
| 18 | -1.6000 | 0.3741 | 0.3104 | 0.0637 | 20.5252 |
| 19 | -1.4000 | 0.3872 | 0.3222 | 0.0650 | 20.1587 |
| 20 | -1.2000 | 0.4005 | 0.3344 | 0.0661 | 19.7810 |
| 21 | -1.0000 | 0.4141 | 0.3469 | 0.0673 | 19.3912 |
| 22 | -0.8000 | 0.4280 | 0.3597 | 0.0683 | 18.9893 |
| 23 | -0.6000 | 0.4421 | 0.3729 | 0.0693 | 18.5739 |
| 24 | -0.4000 | 0.4565 | 0.3864 | 0.0701 | 18.1444 |
| 25 | -0.2000 | 0.4711 | 0.4003 | 0.0708 | 17.7001 |
| 26 | 0.0000 | 0.4859 | 0.4145 | 0.0715 | 17.2401 |
| 27 | 0.2000 | 0.5010 | 0.4291 | 0.0719 | 16.7635 |
| 28 | 0.4000 | 0.5162 | 0.4440 | 0.0722 | 16.2693 |
| 29 | 0.6000 | 0.5316 | 0.4592 | 0.0724 | 15.7567 |
| 30 | 0.8000 | 0.5471 | 0.4748 | 0.0723 | 15.2244 |
| 31 | 1.0000 | 0.5628 | 0.4908 | 0.0720 | 14.6717 |
| 32 | 1.2000 | 0.5786 | 0.5071 | 0.0715 | 14.0974 |
| 33 | 1.4000 | 0.5944 | 0.5237 | 0.0707 | 13.5004 |
| 34 | 1.6000 | 0.6104 | 0.5407 | 0.0698 | 12.9055 |
| 35 | 1.8000 | 0.6270 | 0.5580 | 0.0691 | 12.3775 |
| 36 | 2.0000 | 0.6442 | 0.5756 | 0.0686 | 11.9162 |
| 37 | 2.2000 | 0.6619 | 0.5936 | 0.0684 | 11.5177 |
| 38 | 2.4000 | 0.6802 | 0.6118 | 0.0684 | 11.1782 |
| 39 | 2.6000 | 0.6991 | 0.6305 | 0.0687 | 10.8936 |
| 40 | 2.8000 | 0.7186 | 0.6494 | 0.0692 | 10.6597 |

Table 43

FIG. 67

| Design # | SNR | Opt. Cap | Std. Cap | Gain [bits] | Gain % |
|---|---|---|---|---|---|
| 41 | 3.0000 | 0.7386 | 0.6686 | 0.0700 | 10.4722 |
| 42 | 3.2000 | 0.7593 | 0.6882 | 0.0711 | 10.3265 |
| 43 | 3.4000 | 0.7804 | 0.7081 | 0.0724 | 10.2182 |
| 44 | 3.6000 | 0.8021 | 0.7282 | 0.0739 | 10.1425 |
| 45 | 3.8000 | 0.8243 | 0.7487 | 0.0756 | 10.0945 |
| 46 | 4.0000 | 0.8470 | 0.7695 | 0.0775 | 10.0696 |
| 47 | 4.2000 | 0.8702 | 0.7906 | 0.0796 | 10.0628 |
| 48 | 4.4000 | 0.8938 | 0.8120 | 0.0818 | 10.0689 |
| 49 | 4.6000 | 0.9178 | 0.8337 | 0.0841 | 10.0835 |
| 50 | 4.8000 | 0.9421 | 0.8557 | 0.0864 | 10.1016 |
| 51 | 5.0000 | 0.9668 | 0.8780 | 0.0888 | 10.1186 |
| 52 | 5.2000 | 0.9917 | 0.9005 | 0.0912 | 10.1305 |
| 53 | 5.4000 | 1.0169 | 0.9234 | 0.0936 | 10.1329 |
| 54 | 5.6000 | 1.0423 | 0.9465 | 0.0958 | 10.1224 |
| 55 | 5.8000 | 1.0678 | 0.9699 | 0.0979 | 10.0957 |
| 56 | 6.0000 | 1.0934 | 0.9936 | 0.0999 | 10.0497 |
| 57 | 6.2000 | 1.1191 | 1.0175 | 0.1016 | 9.9824 |
| 58 | 6.4000 | 1.1448 | 1.0417 | 0.1030 | 9.8921 |
| 59 | 6.6000 | 1.1704 | 1.0662 | 0.1042 | 9.7773 |
| 60 | 6.8000 | 1.1960 | 1.0909 | 0.1051 | 9.6380 |
| 61 | 7.0000 | 1.2216 | 1.1159 | 0.1057 | 9.4739 |
| 62 | 7.2000 | 1.2470 | 1.1411 | 0.1060 | 9.2859 |
| 63 | 7.4000 | 1.2725 | 1.1665 | 0.1060 | 9.0866 |
| 64 | 7.6000 | 1.2988 | 1.1922 | 0.1067 | 8.9466 |
| 65 | 7.8000 | 1.3259 | 1.2180 | 0.1079 | 8.8548 |
| 66 | 8.0000 | 1.3535 | 1.2441 | 0.1094 | 8.7928 |
| 67 | 8.2000 | 1.3814 | 1.2704 | 0.1110 | 8.7338 |
| 68 | 8.4000 | 1.4094 | 1.2969 | 0.1125 | 8.6745 |
| 69 | 8.6000 | 1.4376 | 1.3236 | 0.1140 | 8.6134 |
| 70 | 8.8000 | 1.4696 | 1.3505 | 0.1191 | 8.8172 |
| 71 | 9.0000 | 1.4999 | 1.3776 | 0.1223 | 8.8779 |
| 72 | 9.0008 | 1.5000 | 1.3777 | 0.1223 | 8.8771 |
| 73 | 9.2000 | 1.5300 | 1.4048 | 0.1252 | 8.9121 |
| 74 | 9.4000 | 1.5600 | 1.4323 | 0.1278 | 8.9202 |
| 75 | 9.6000 | 1.5899 | 1.4599 | 0.1300 | 8.9029 |
| 76 | 9.8000 | 1.6195 | 1.4877 | 0.1318 | 8.8608 |
| 77 | 10.0000 | 1.6490 | 1.5157 | 0.1333 | 8.7947 |
| 78 | 10.2000 | 1.6784 | 1.5439 | 0.1345 | 8.7124 |
| 79 | 10.4000 | 1.7079 | 1.5722 | 0.1357 | 8.6296 |
| 80 | 10.6000 | 1.7376 | 1.6008 | 0.1368 | 8.5474 |

Table 44

FIG. 68

| Design # | SNR | Opt. Cap | Std. Cap | Gain [bits] | Gain % |
|---|---|---|---|---|---|
| 81 | 10.8000 | 1.7719 | 1.6296 | 0.1424 | 8.7355 |
| 82 | 11.0000 | 1.8033 | 1.6586 | 0.1447 | 8.7246 |
| 83 | 11.2000 | 1.8346 | 1.6877 | 0.1468 | 8.6985 |
| 84 | 11.4000 | 1.8659 | 1.7172 | 0.1487 | 8.6597 |
| 85 | 11.6000 | 1.8972 | 1.7468 | 0.1504 | 8.6109 |
| 86 | 11.8000 | 1.9287 | 1.7767 | 0.1520 | 8.5555 |
| 87 | 12.0000 | 1.9603 | 1.8068 | 0.1535 | 8.4959 |
| 88 | 12.2000 | 1.9920 | 1.8371 | 0.1549 | 8.4335 |
| 89 | 12.2496 | 2.0000 | 1.8447 | 0.1553 | 8.4187 |
| 90 | 12.4000 | 2.0240 | 1.8677 | 0.1563 | 8.3688 |
| 91 | 12.6000 | 2.0561 | 1.8985 | 0.1576 | 8.2996 |
| 92 | 12.8000 | 2.0883 | 1.9296 | 0.1587 | 8.2232 |
| 93 | 13.0000 | 2.1205 | 1.9609 | 0.1596 | 8.1376 |
| 94 | 13.2000 | 2.1527 | 1.9925 | 0.1602 | 8.0402 |
| 95 | 13.4000 | 2.1848 | 2.0242 | 0.1605 | 7.9297 |
| 96 | 13.6000 | 2.2167 | 2.0563 | 0.1605 | 7.8050 |
| 97 | 13.8000 | 2.2486 | 2.0885 | 0.1601 | 7.6656 |
| 98 | 14.0000 | 2.2803 | 2.1209 | 0.1593 | 7.5115 |
| 99 | 14.2000 | 2.3117 | 2.1536 | 0.1581 | 7.3434 |
| 100 | 14.4000 | 2.3430 | 2.1864 | 0.1566 | 7.1620 |
| 101 | 14.6000 | 2.3741 | 2.2194 | 0.1547 | 6.9689 |
| 102 | 14.8000 | 2.4050 | 2.2526 | 0.1524 | 6.7660 |
| 103 | 15.0000 | 2.4358 | 2.2859 | 0.1499 | 6.5558 |
| 104 | 15.2000 | 2.4664 | 2.3194 | 0.1471 | 6.3410 |
| 105 | 15.4000 | 2.4971 | 2.3529 | 0.1441 | 6.1245 |
| 106 | 15.4192 | 2.5000 | 2.3562 | 0.1438 | 6.1030 |
| 107 | 15.6000 | 2.5276 | 2.3866 | 0.1410 | 5.9087 |
| 108 | 15.8000 | 2.5582 | 2.4204 | 0.1379 | 5.6954 |
| 109 | 16.0000 | 2.5888 | 2.4542 | 0.1346 | 5.4854 |
| 110 | 16.2000 | 2.6194 | 2.4881 | 0.1313 | 5.2791 |
| 111 | 16.4000 | 2.6500 | 2.5220 | 0.1280 | 5.0762 |
| 112 | 16.6000 | 2.6806 | 2.5560 | 0.1246 | 4.8762 |
| 113 | 16.8000 | 2.7111 | 2.5899 | 0.1212 | 4.6790 |
| 114 | 17.0000 | 2.7415 | 2.6238 | 0.1177 | 4.4842 |
| 115 | 17.2000 | 2.7718 | 2.6577 | 0.1141 | 4.2915 |
| 116 | 17.4000 | 2.8020 | 2.6916 | 0.1104 | 4.1009 |
| 117 | 17.6000 | 2.8321 | 2.7254 | 0.1066 | 3.9130 |
| 118 | 17.8000 | 2.8620 | 2.7591 | 0.1029 | 3.7285 |
| 119 | 18.0000 | 2.8919 | 2.7928 | 0.0991 | 3.5488 |
| 120 | 18.2000 | 2.9218 | 2.8263 | 0.0954 | 3.3762 |

Table 45

FIG. 69

| Design # | SNR | Opt. Cap | Std. Cap | Gain [bits] | Gain % |
|---|---|---|---|---|---|
| 121 | 18.4000 | 2.9517 | 2.8598 | 0.0919 | 3.2131 |
| 122 | 18.6000 | 2.9817 | 2.8931 | 0.0886 | 3.0622 |
| 123 | 18.7214 | 3.0000 | 2.9133 | 0.0867 | 2.9760 |
| 124 | 18.8000 | 3.0119 | 2.9263 | 0.0856 | 2.9259 |
| 125 | 19.0000 | 3.0423 | 2.9593 | 0.0830 | 2.8046 |
| 126 | 19.2000 | 3.0729 | 2.9922 | 0.0807 | 2.6964 |
| 127 | 19.4000 | 3.1035 | 3.0249 | 0.0786 | 2.5978 |
| 128 | 19.6000 | 3.1341 | 3.0575 | 0.0766 | 2.5058 |
| 129 | 19.8000 | 3.1646 | 3.0899 | 0.0747 | 2.4178 |
| 130 | 20.0000 | 3.1949 | 3.1221 | 0.0728 | 2.3321 |
| 131 | 20.2000 | 3.2250 | 3.1541 | 0.0709 | 2.2472 |
| 132 | 20.4000 | 3.2548 | 3.1859 | 0.0689 | 2.1625 |
| 133 | 20.6000 | 3.2844 | 3.2176 | 0.0668 | 2.0772 |
| 134 | 20.8000 | 3.3137 | 3.2490 | 0.0647 | 1.9911 |
| 135 | 21.0000 | 3.3427 | 3.2802 | 0.0625 | 1.9039 |
| 136 | 21.2000 | 3.3714 | 3.3112 | 0.0601 | 1.8158 |
| 137 | 21.4000 | 3.3997 | 3.3420 | 0.0577 | 1.7270 |
| 138 | 21.6000 | 3.4276 | 3.3724 | 0.0552 | 1.6377 |
| 139 | 21.8000 | 3.4553 | 3.4026 | 0.0527 | 1.5483 |
| 140 | 22.0000 | 3.4825 | 3.4324 | 0.0501 | 1.4593 |
| 141 | 22.1304 | 3.5000 | 3.4516 | 0.0484 | 1.4022 |
| 142 | 22.2000 | 3.5093 | 3.4618 | 0.0475 | 1.3712 |
| 143 | 22.4000 | 3.5357 | 3.4909 | 0.0448 | 1.2844 |
| 144 | 22.6000 | 3.5616 | 3.5194 | 0.0422 | 1.1994 |
| 145 | 22.8000 | 3.5871 | 3.5475 | 0.0396 | 1.1167 |
| 146 | 23.0000 | 3.6120 | 3.5750 | 0.0371 | 1.0366 |
| 147 | 23.2000 | 3.6364 | 3.6019 | 0.0346 | 0.9594 |
| 148 | 23.4000 | 3.6602 | 3.6281 | 0.0321 | 0.8854 |
| 149 | 23.6000 | 3.6834 | 3.6536 | 0.0298 | 0.8148 |
| 150 | 23.8000 | 3.7059 | 3.6784 | 0.0275 | 0.7476 |
| 151 | 24.0000 | 3.7277 | 3.7023 | 0.0253 | 0.6839 |
| 152 | 24.2000 | 3.7487 | 3.7254 | 0.0232 | 0.6237 |
| 153 | 24.4000 | 3.7689 | 3.7476 | 0.0213 | 0.5670 |
| 154 | 24.6000 | 3.7882 | 3.7688 | 0.0194 | 0.5139 |
| 155 | 24.8000 | 3.8067 | 3.7891 | 0.0176 | 0.4641 |
| 156 | 25.0000 | 3.8242 | 3.8083 | 0.0159 | 0.4176 |
| 157 | 25.2000 | 3.8409 | 3.8266 | 0.0143 | 0.3744 |
| 158 | 25.4000 | 3.8566 | 3.8437 | 0.0129 | 0.3344 |
| 159 | 25.6000 | 3.8713 | 3.8598 | 0.0115 | 0.2974 |
| 160 | 25.8000 | 3.8851 | 3.8749 | 0.0102 | 0.2634 |

Table 46

FIG. 70

| Design # | SNR | Opt. Cap | Std. Cap | Gain [bits] | Gain % |
|---|---|---|---|---|---|
| 161 | 26.0000 | 3.8979 | 3.8889 | 0.0090 | 0.2323 |
| 162 | 26.2000 | 3.9097 | 3.9018 | 0.0079 | 0.2037 |
| 163 | 26.4000 | 3.9207 | 3.9137 | 0.0070 | 0.1779 |
| 164 | 26.6000 | 3.9306 | 3.9246 | 0.0061 | 0.1545 |
| 165 | 26.8000 | 3.9397 | 3.9345 | 0.0052 | 0.1334 |
| 166 | 27.0000 | 3.9479 | 3.9434 | 0.0045 | 0.1145 |
| 167 | 27.2000 | 3.9553 | 3.9515 | 0.0039 | 0.0977 |
| 168 | 27.4000 | 3.9619 | 3.9587 | 0.0033 | 0.0829 |
| 169 | 27.6000 | 3.9678 | 3.9650 | 0.0028 | 0.0698 |
| 170 | 27.8000 | 3.9729 | 3.9706 | 0.0023 | 0.0584 |
| 171 | 28.0000 | 3.9775 | 3.9755 | 0.0019 | 0.0485 |
| 172 | 28.2000 | 3.9814 | 3.9798 | 0.0016 | 0.0399 |
| 173 | 28.4000 | 3.9847 | 3.9834 | 0.0013 | 0.0326 |
| 174 | 28.6000 | 3.9876 | 3.9865 | 0.0011 | 0.0264 |
| 175 | 28.8000 | 3.9900 | 3.9892 | 0.0008 | 0.0212 |
| 176 | 29.0000 | 3.9920 | 3.9914 | 0.0007 | 0.0169 |
| 177 | 29.2000 | 3.9937 | 3.9932 | 0.0005 | 0.0134 |
| 178 | 29.4000 | 3.9951 | 3.9947 | 0.0004 | 0.0103 |

Table 47

FIG. 71

|  | Label | | | | | | | |
|---|---|---|---|---|---|---|---|---|
|  | 0 | 1 | 2 | 3 | 4 | 5 | 6 | 7 |
| Design # | | | | | | | | |
| 1 | -9.221 | -9.221 | -9.221 | -9.221 | -9.216 | -9.216 | -9.221 | -9.221 |
| 2 | -9.253 | -9.252 | -9.200 | -9.252 | -9.200 | -9.200 | -9.200 | -9.200 |
| 3 | -9.232 | -9.222 | -9.216 | -9.222 | -9.216 | -9.216 | -9.216 | -9.216 |
| 4 | -9.224 | -9.220 | -9.219 | -9.219 | -9.219 | -9.219 | -9.219 | -9.219 |
| 5 | -9.226 | -9.226 | -9.226 | -9.226 | -9.195 | -9.219 | -9.220 | -9.220 |
| 6 | -9.230 | -9.225 | -9.218 | -9.218 | -9.217 | -9.217 | -9.217 | -9.217 |
| 7 | -9.229 | -9.224 | -9.224 | -9.224 | -9.214 | -9.214 | -9.214 | -9.214 |
| 8 | -9.225 | -9.225 | -9.225 | -9.225 | -9.192 | -9.219 | -9.225 | -9.219 |
| 9 | -9.225 | -9.224 | -9.219 | -9.219 | -9.215 | -9.218 | -9.219 | -9.218 |
| 10 | -9.227 | -9.227 | -9.227 | -9.227 | -9.193 | -9.200 | -9.227 | -9.227 |
| 11 | -9.221 | -9.221 | -9.221 | -9.221 | -9.214 | -9.218 | -9.221 | -9.220 |
| 12 | -9.220 | -9.220 | -9.220 | -9.220 | -9.217 | -9.217 | -9.220 | -9.220 |
| 13 | -9.228 | -9.228 | -9.215 | -9.228 | -9.215 | -9.215 | -9.215 | -9.215 |
| 14 | -9.221 | -9.221 | -9.221 | -9.221 | -9.216 | -9.216 | -9.221 | -9.220 |
| 15 | -9.220 | -9.220 | -9.220 | -9.220 | -9.219 | -9.219 | -9.219 | -9.219 |
| 16 | -9.220 | -9.220 | -9.220 | -9.220 | -9.219 | -9.219 | -9.219 | -9.219 |
| 17 | -9.232 | -9.232 | -9.232 | -9.232 | -9.189 | -9.189 | -9.231 | -9.219 |
| 18 | -9.224 | -9.224 | -9.224 | -9.224 | -9.211 | -9.212 | -9.224 | -9.212 |
| 19 | -9.222 | -9.220 | -9.220 | -9.220 | -9.219 | -9.219 | -9.220 | -9.219 |
| 20 | -9.223 | -9.220 | -9.219 | -9.220 | -9.217 | -9.219 | -9.219 | -9.219 |
| 21 | -9.220 | -9.220 | -9.220 | -9.220 | -9.219 | -9.219 | -9.220 | -9.220 |
| 22 | -9.222 | -9.222 | -9.220 | -9.220 | -9.218 | -9.219 | -9.219 | -9.219 |
| 23 | -9.229 | -9.223 | -9.219 | -9.219 | -9.217 | -9.217 | -9.217 | -9.217 |
| 24 | -9.225 | -9.219 | -9.219 | -9.219 | -9.219 | -9.219 | -9.219 | -9.219 |
| 25 | -9.224 | -9.222 | -9.220 | -9.221 | -9.217 | -9.217 | -9.217 | -9.217 |
| 26 | -9.223 | -9.223 | -9.223 | -9.223 | -9.210 | -9.212 | -9.222 | -9.222 |
| 27 | -9.222 | -9.221 | -9.221 | -9.221 | -9.217 | -9.217 | -9.220 | -9.218 |
| 28 | -9.235 | -9.235 | -9.230 | -9.235 | -9.203 | -9.206 | -9.207 | -9.207 |
| 29 | -9.226 | -9.220 | -9.219 | -9.219 | -9.218 | -9.218 | -9.218 | -9.218 |
| 30 | -9.236 | -9.236 | -9.211 | -9.235 | -9.207 | -9.210 | -9.210 | -9.210 |
| 31 | -9.225 | -9.225 | -9.216 | -9.225 | -9.216 | -9.216 | -9.216 | -9.216 |
| 32 | -9.226 | -9.226 | -9.224 | -9.225 | -9.214 | -9.214 | -9.214 | -9.214 |
| 33 | -9.221 | -9.221 | -9.220 | -9.220 | -9.219 | -9.219 | -9.219 | -9.219 |
| 34 | -10.280 | -10.279 | -10.279 | -10.279 | -8.021 | -8.021 | -8.021 | -8.021 |
| 35 | -10.773 | -10.773 | -10.772 | -10.772 | -7.346 | -7.346 | -7.346 | -7.346 |
| 36 | -11.094 | -11.094 | -11.094 | -11.094 | -6.850 | -6.850 | -6.850 | -6.850 |
| 37 | -11.336 | -11.336 | -11.336 | -11.336 | -6.442 | -6.442 | -6.442 | -6.442 |
| 38 | -11.527 | -11.527 | -11.527 | -11.527 | -6.094 | -6.094 | -6.094 | -6.094 |
| 39 | -11.684 | -11.684 | -11.684 | -11.684 | -5.786 | -5.786 | -5.786 | -5.786 |
| 40 | -11.817 | -11.816 | -11.816 | -11.816 | -5.512 | -5.512 | -5.512 | -5.512 |

Table 48

FIG. 72

|  | Label | | | | | | | |
|---|---|---|---|---|---|---|---|---|
|  | 8 | 9 | 10 | 11 | 12 | 13 | 14 | 15 |
| Design # | | | | | | | | |
| 1 | 9.220 | 9.220 | 9.220 | 9.220 | 9.220 | 9.220 | 9.220 | 9.220 |
| 2 | 9.220 | 9.220 | 9.220 | 9.220 | 9.218 | 9.218 | 9.220 | 9.220 |
| 3 | 9.232 | 9.233 | 9.232 | 9.232 | 9.205 | 9.205 | 9.210 | 9.207 |
| 4 | 9.223 | 9.223 | 9.223 | 9.223 | 9.193 | 9.223 | 9.223 | 9.223 |
| 5 | 9.226 | 9.219 | 9.219 | 9.219 | 9.219 | 9.219 | 9.219 | 9.219 |
| 6 | 9.220 | 9.220 | 9.220 | 9.220 | 9.218 | 9.220 | 9.220 | 9.220 |
| 7 | 9.225 | 9.225 | 9.225 | 9.225 | 9.197 | 9.208 | 9.225 | 9.225 |
| 8 | 9.220 | 9.220 | 9.219 | 9.219 | 9.219 | 9.219 | 9.219 | 9.219 |
| 9 | 9.221 | 9.221 | 9.219 | 9.221 | 9.218 | 9.218 | 9.219 | 9.219 |
| 10 | 9.227 | 9.221 | 9.221 | 9.221 | 9.214 | 9.215 | 9.221 | 9.217 |
| 11 | 9.229 | 9.229 | 9.214 | 9.229 | 9.214 | 9.214 | 9.214 | 9.214 |
| 12 | 9.224 | 9.224 | 9.217 | 9.224 | 9.217 | 9.217 | 9.217 | 9.217 |
| 13 | 9.228 | 9.221 | 9.217 | 9.221 | 9.217 | 9.217 | 9.217 | 9.217 |
| 14 | 9.221 | 9.219 | 9.219 | 9.219 | 9.219 | 9.219 | 9.219 | 9.219 |
| 15 | 9.222 | 9.220 | 9.220 | 9.220 | 9.219 | 9.219 | 9.220 | 9.219 |
| 16 | 9.233 | 9.218 | 9.218 | 9.218 | 9.218 | 9.218 | 9.218 | 9.218 |
| 17 | 9.232 | 9.225 | 9.223 | 9.223 | 9.213 | 9.213 | 9.214 | 9.214 |
| 18 | 9.226 | 9.224 | 9.224 | 9.224 | 9.214 | 9.214 | 9.218 | 9.214 |
| 19 | 9.222 | 9.222 | 9.221 | 9.222 | 9.217 | 9.218 | 9.218 | 9.218 |
| 20 | 9.223 | 9.219 | 9.219 | 9.219 | 9.219 | 9.219 | 9.219 | 9.219 |
| 21 | 9.246 | 9.246 | 9.247 | 9.246 | 9.193 | 9.193 | 9.193 | 9.193 |
| 22 | 9.222 | 9.220 | 9.220 | 9.220 | 9.219 | 9.219 | 9.219 | 9.219 |
| 23 | 9.228 | 9.228 | 9.217 | 9.217 | 9.217 | 9.217 | 9.217 | 9.217 |
| 24 | 9.223 | 9.223 | 9.219 | 9.219 | 9.218 | 9.218 | 9.218 | 9.218 |
| 25 | 9.224 | 9.224 | 9.220 | 9.224 | 9.214 | 9.214 | 9.220 | 9.214 |
| 26 | 9.224 | 9.224 | 9.224 | 9.224 | 9.199 | 9.217 | 9.223 | 9.224 |
| 27 | 9.222 | 9.219 | 9.219 | 9.219 | 9.219 | 9.219 | 9.219 | 9.219 |
| 28 | 9.235 | 9.228 | 9.226 | 9.228 | 9.210 | 9.210 | 9.210 | 9.210 |
| 29 | 9.220 | 9.220 | 9.220 | 9.220 | 9.219 | 9.219 | 9.219 | 9.219 |
| 30 | 9.227 | 9.225 | 9.224 | 9.225 | 9.214 | 9.214 | 9.214 | 9.214 |
| 31 | 9.222 | 9.222 | 9.221 | 9.221 | 9.218 | 9.218 | 9.218 | 9.218 |
| 32 | 9.229 | 9.229 | 9.214 | 9.229 | 9.214 | 9.214 | 9.214 | 9.214 |
| 33 | 9.222 | 9.222 | 9.222 | 9.222 | 9.217 | 9.217 | 9.218 | 9.217 |
| 34 | 10.279 | 10.279 | 10.279 | 10.279 | 8.021 | 8.021 | 8.022 | 8.021 |
| 35 | 10.773 | 10.773 | 10.773 | 10.773 | 7.345 | 7.345 | 7.345 | 7.345 |
| 36 | 11.096 | 11.096 | 11.089 | 11.096 | 6.850 | 6.850 | 6.850 | 6.850 |
| 37 | 11.336 | 11.334 | 11.334 | 11.334 | 6.443 | 6.443 | 6.443 | 6.443 |
| 38 | 11.527 | 11.527 | 11.527 | 11.527 | 6.094 | 6.094 | 6.094 | 6.094 |
| 39 | 11.684 | 11.684 | 11.684 | 11.684 | 5.786 | 5.786 | 5.786 | 5.786 |
| 40 | 11.817 | 11.816 | 11.815 | 11.815 | 5.512 | 5.512 | 5.512 | 5.512 |

Table 49

FIG. 73

|  | Label | | | | | | | |
|---|---|---|---|---|---|---|---|---|
|  | 0 | 1 | 2 | 3 | 4 | 5 | 6 | 7 |
| Design # | | | | | | | | |
| 41 | -11.928 | -11.928 | -11.928 | -11.928 | -5.265 | -5.265 | -5.265 | -5.265 |
| 42 | -12.025 | -12.025 | -12.023 | -12.025 | -5.042 | -5.042 | -5.042 | -5.042 |
| 43 | -12.108 | -12.108 | -12.107 | -12.108 | -4.838 | -4.838 | -4.838 | -4.838 |
| 44 | -12.181 | -12.180 | -12.180 | -12.180 | -4.652 | -4.652 | -4.652 | -4.652 |
| 45 | -12.244 | -12.244 | -12.244 | -12.244 | -4.482 | -4.482 | -4.482 | -4.482 |
| 46 | -12.300 | -12.300 | -12.300 | -12.300 | -4.327 | -4.327 | -4.327 | -4.327 |
| 47 | -12.348 | -12.348 | -12.348 | -12.348 | -4.187 | -4.187 | -4.187 | -4.187 |
| 48 | -12.391 | -12.391 | -12.390 | -12.390 | -4.058 | -4.058 | -4.058 | -4.058 |
| 49 | -12.429 | -12.429 | -12.428 | -12.428 | -3.942 | -3.942 | -3.942 | -3.942 |
| 50 | -12.461 | -12.461 | -12.461 | -12.461 | -3.837 | -3.837 | -3.837 | -3.837 |
| 51 | -12.491 | -12.490 | -12.489 | -12.489 | -3.743 | -3.743 | -3.743 | -3.743 |
| 52 | -12.515 | -12.515 | -12.514 | -12.514 | -3.660 | -3.660 | -3.660 | -3.660 |
| 53 | -12.541 | -12.541 | -12.517 | -12.522 | -3.592 | -3.592 | -3.594 | -3.594 |
| 54 | -12.556 | -12.552 | -12.552 | -12.552 | -3.524 | -3.524 | -3.524 | -3.524 |
| 55 | -12.568 | -12.568 | -12.568 | -12.568 | -3.471 | -3.471 | -3.471 | -3.471 |
| 56 | -12.586 | -12.586 | -12.569 | -12.582 | -3.426 | -3.426 | -3.427 | -3.426 |
| 57 | -12.595 | -12.595 | -12.582 | -12.587 | -3.391 | -3.391 | -3.393 | -3.392 |
| 58 | -12.605 | -12.605 | -12.575 | -12.602 | -3.366 | -3.366 | -3.368 | -3.366 |
| 59 | -12.605 | -12.605 | -12.595 | -12.602 | -3.349 | -3.349 | -3.350 | -3.349 |
| 60 | -12.606 | -12.606 | -12.593 | -12.605 | -3.340 | -3.341 | -3.343 | -3.342 |
| 61 | -12.615 | -12.605 | -12.596 | -12.596 | -3.339 | -3.340 | -3.340 | -3.340 |
| 62 | -12.669 | -12.669 | -12.531 | -12.538 | -3.334 | -3.334 | -3.357 | -3.356 |
| 63 | -16.220 | -12.525 | -10.823 | -10.823 | -2.815 | -3.060 | -3.520 | -3.520 |
| 64 | -12.374 | -12.374 | -12.374 | -12.374 | -3.419 | -3.419 | -3.419 | -3.419 |
| 65 | -16.429 | -12.067 | -10.510 | -10.510 | -2.915 | -3.151 | -3.545 | -3.545 |
| 66 | -16.646 | -11.953 | -10.412 | -10.412 | -2.868 | -3.118 | -3.554 | -3.554 |
| 67 | -16.808 | -11.873 | -10.335 | -10.335 | -2.828 | -3.086 | -3.564 | -3.564 |
| 68 | -16.934 | -11.816 | -10.270 | -10.270 | -2.793 | -3.054 | -3.575 | -3.575 |
| 69 | -17.032 | -11.780 | -10.213 | -10.213 | -2.763 | -3.021 | -3.588 | -3.588 |
| 70 | -15.874 | -15.874 | -7.431 | -7.431 | 15.874 | 15.874 | -5.725 | -5.725 |
| 71 | -15.852 | -15.845 | -7.463 | -7.464 | 15.852 | 15.845 | -5.752 | -5.752 |
| 72 | -15.850 | -15.850 | -7.460 | -7.460 | 15.850 | 15.850 | -5.750 | -5.750 |
| 73 | -15.822 | -15.820 | -7.500 | -7.500 | 15.822 | 15.822 | -5.777 | -5.777 |
| 74 | -15.793 | -15.792 | -7.542 | -7.542 | 15.794 | 15.791 | -5.800 | -5.800 |
| 75 | -15.765 | -15.761 | -7.587 | -7.588 | 15.765 | 15.759 | -5.821 | -5.821 |
| 76 | -15.758 | -15.702 | -7.633 | -7.648 | 15.757 | 15.703 | -5.837 | -5.837 |
| 77 | -15.738 | -15.654 | -7.688 | -7.710 | 15.738 | 15.654 | -5.850 | -5.850 |
| 78 | -16.426 | -14.932 | -7.512 | -7.920 | 16.426 | 14.932 | -5.820 | -5.820 |
| 79 | -16.777 | -14.559 | -7.409 | -8.036 | 16.778 | 14.559 | -5.775 | -5.775 |
| 80 | -17.021 | -14.296 | -7.335 | -8.129 | 17.021 | 14.296 | -5.726 | -5.726 |

Table 50

FIG. 74

|          | Label  |        |        |        |       |       |        |        |
|----------|--------|--------|--------|--------|-------|-------|--------|--------|
|          | 8      | 9      | 10     | 11     | 12    | 13    | 14     | 15     |
| Design # |        |        |        |        |       |       |        |        |
| 41       | 11.928 | 11.928 | 11.928 | 11.928 | 5.265 | 5.265 | 5.265  | 5.265  |
| 42       | 12.025 | 12.025 | 12.023 | 12.023 | 5.042 | 5.042 | 5.042  | 5.042  |
| 43       | 12.108 | 12.108 | 12.108 | 12.108 | 4.838 | 4.838 | 4.838  | 4.838  |
| 44       | 12.181 | 12.181 | 12.181 | 12.181 | 4.652 | 4.652 | 4.652  | 4.652  |
| 45       | 12.244 | 12.244 | 12.244 | 12.244 | 4.482 | 4.482 | 4.482  | 4.482  |
| 46       | 12.299 | 12.299 | 12.299 | 12.299 | 4.328 | 4.328 | 4.328  | 4.328  |
| 47       | 12.348 | 12.348 | 12.348 | 12.348 | 4.187 | 4.187 | 4.187  | 4.187  |
| 48       | 12.391 | 12.392 | 12.390 | 12.391 | 4.058 | 4.058 | 4.058  | 4.058  |
| 49       | 12.429 | 12.429 | 12.429 | 12.429 | 3.941 | 3.941 | 3.941  | 3.941  |
| 50       | 12.461 | 12.461 | 12.461 | 12.461 | 3.837 | 3.837 | 3.837  | 3.837  |
| 51       | 12.491 | 12.491 | 12.489 | 12.489 | 3.743 | 3.743 | 3.743  | 3.743  |
| 52       | 12.515 | 12.515 | 12.514 | 12.514 | 3.660 | 3.660 | 3.660  | 3.660  |
| 53       | 12.540 | 12.540 | 12.540 | 12.540 | 3.583 | 3.583 | 3.585  | 3.583  |
| 54       | 12.556 | 12.556 | 12.547 | 12.555 | 3.523 | 3.523 | 3.524  | 3.523  |
| 55       | 12.569 | 12.569 | 12.568 | 12.569 | 3.470 | 3.470 | 3.471  | 3.471  |
| 56       | 12.581 | 12.581 | 12.579 | 12.579 | 3.427 | 3.427 | 3.427  | 3.427  |
| 57       | 12.595 | 12.588 | 12.587 | 12.587 | 3.392 | 3.393 | 3.393  | 3.393  |
| 58       | 12.599 | 12.596 | 12.595 | 12.595 | 3.366 | 3.367 | 3.367  | 3.367  |
| 59       | 12.600 | 12.600 | 12.600 | 12.600 | 3.351 | 3.351 | 3.351  | 3.351  |
| 60       | 12.604 | 12.604 | 12.603 | 12.604 | 3.341 | 3.341 | 3.341  | 3.341  |
| 61       | 12.607 | 12.607 | 12.597 | 12.607 | 3.338 | 3.338 | 3.339  | 3.338  |
| 62       | 12.602 | 12.602 | 12.602 | 12.602 | 3.345 | 3.345 | 3.345  | 3.345  |
| 63       | 12.424 | 12.424 | 12.424 | 12.424 | 3.403 | 3.403 | 3.403  | 3.403  |
| 64       | 16.734 | 12.329 | 10.663 | 10.663 | 2.735 | 3.014 | 3.518  | 3.518  |
| 65       | 16.429 | 12.066 | 10.511 | 10.511 | 2.915 | 3.151 | 3.545  | 3.545  |
| 66       | 16.646 | 11.953 | 10.412 | 10.412 | 2.868 | 3.118 | 3.554  | 3.554  |
| 67       | 16.808 | 11.873 | 10.335 | 10.335 | 2.828 | 3.086 | 3.564  | 3.564  |
| 68       | 16.933 | 11.816 | 10.270 | 10.270 | 2.793 | 3.054 | 3.575  | 3.575  |
| 69       | 17.033 | 11.780 | 10.213 | 10.213 | 2.762 | 3.022 | 3.588  | 3.588  |
| 70       | 5.725  | 5.725  | 0.168  | 0.168  | 7.431 | 7.431 | -0.168 | -0.168 |
| 71       | 5.752  | 5.752  | 0.200  | 0.200  | 7.464 | 7.465 | -0.200 | -0.200 |
| 72       | 5.750  | 5.750  | 0.200  | 0.200  | 7.460 | 7.460 | -0.200 | -0.200 |
| 73       | 5.777  | 5.777  | 0.231  | 0.231  | 7.501 | 7.501 | -0.232 | -0.232 |
| 74       | 5.800  | 5.800  | 0.264  | 0.264  | 7.542 | 7.542 | -0.264 | -0.264 |
| 75       | 5.821  | 5.821  | 0.297  | 0.297  | 7.587 | 7.589 | -0.297 | -0.297 |
| 76       | 5.837  | 5.837  | 0.333  | 0.333  | 7.633 | 7.648 | -0.333 | -0.333 |
| 77       | 5.850  | 5.850  | 0.372  | 0.372  | 7.687 | 7.710 | -0.371 | -0.371 |
| 78       | 5.820  | 5.820  | 0.403  | 0.403  | 7.512 | 7.920 | -0.403 | -0.403 |
| 79       | 5.775  | 5.775  | 0.435  | 0.435  | 7.409 | 8.036 | -0.435 | -0.435 |
| 80       | 5.726  | 5.726  | 0.469  | 0.469  | 7.335 | 8.129 | -0.469 | -0.469 |

Table 51

FIG. 75

|   | Label | | | | | | | |
|---|---|---|---|---|---|---|---|---|
|   | 0 | 1 | 2 | 3 | 4 | 5 | 6 | 7 |
| Design # | | | | | | | | |
| 81 | -18.783 | -12.062 | 18.197 | -10.830 | -3.578 | -5.451 | -3.578 | -5.645 |
| 82 | -18.750 | -12.045 | 18.134 | -10.833 | -3.574 | -5.494 | -3.574 | -5.700 |
| 83 | -18.705 | -12.026 | 18.079 | -10.832 | -3.567 | -5.547 | -3.567 | -5.764 |
| 84 | -18.646 | -12.005 | 18.034 | -10.825 | -3.556 | -5.611 | -3.556 | -5.837 |
| 85 | -18.574 | -11.980 | 17.998 | -10.814 | -3.540 | -5.687 | -3.540 | -5.920 |
| 86 | -18.490 | -11.954 | 17.970 | -10.798 | -3.520 | -5.774 | -3.520 | -6.011 |
| 87 | -18.398 | -11.926 | 17.948 | -10.779 | -3.496 | -5.869 | -3.496 | -6.108 |
| 88 | -18.302 | -11.901 | 17.929 | -10.761 | -3.470 | -5.966 | -3.470 | -6.205 |
| 89 | -18.280 | -11.900 | 17.920 | -10.760 | -3.460 | -5.990 | -3.460 | -6.230 |
| 90 | -18.207 | -11.880 | 17.909 | -10.744 | -3.444 | -6.061 | -3.444 | -6.299 |
| 91 | -18.120 | -11.867 | 17.886 | -10.731 | -3.418 | -6.149 | -3.418 | -6.386 |
| 92 | -18.040 | -11.861 | 17.859 | -10.721 | -3.393 | -6.227 | -3.393 | -6.465 |
| 93 | -17.966 | -11.862 | 17.829 | -10.715 | -3.371 | -6.294 | -3.371 | -6.537 |
| 94 | -17.899 | -11.872 | 17.796 | -10.711 | -3.351 | -6.352 | -3.351 | -6.600 |
| 95 | -17.837 | -11.888 | 17.761 | -10.709 | -3.333 | -6.400 | -3.333 | -6.658 |
| 96 | -17.780 | -11.911 | 17.724 | -10.708 | -3.317 | -6.440 | -3.317 | -6.709 |
| 97 | -17.724 | -11.941 | 17.688 | -10.705 | -3.304 | -6.472 | -3.304 | -6.756 |
| 98 | -17.680 | -11.982 | 17.639 | -10.701 | -3.291 | -6.494 | -3.291 | -6.798 |
| 99 | -17.625 | -12.022 | 17.609 | -10.691 | -3.282 | -6.514 | -3.281 | -6.839 |
| 100 | -17.580 | -12.076 | 17.569 | -10.677 | -3.277 | -6.522 | -3.265 | -6.877 |
| 101 | -17.536 | -12.137 | 17.532 | -10.655 | -3.274 | -6.524 | -3.250 | -6.913 |
| 102 | -17.500 | -12.211 | 17.494 | -10.623 | -3.270 | -6.513 | -3.233 | -6.947 |
| 103 | -17.466 | -12.295 | 17.462 | -10.581 | -3.267 | -6.491 | -3.214 | -6.979 |
| 104 | -17.441 | -12.388 | 17.434 | -10.529 | -3.263 | -6.456 | -3.192 | -7.006 |
| 105 | -17.421 | -12.484 | 17.414 | -10.470 | -3.259 | -6.413 | -3.168 | -7.028 |
| 106 | -17.420 | -12.490 | 17.410 | -10.460 | -3.260 | -6.410 | -3.170 | -7.030 |
| 107 | -17.407 | -12.577 | 17.398 | -10.411 | -3.255 | -6.363 | -3.142 | -7.046 |
| 108 | -17.395 | -12.663 | 17.388 | -10.354 | -3.252 | -6.313 | -3.115 | -7.061 |
| 109 | -17.385 | -12.740 | 17.378 | -10.304 | -3.251 | -6.266 | -3.089 | -7.074 |
| 110 | -17.374 | -12.807 | 17.370 | -10.261 | -3.252 | -6.224 | -3.063 | -7.087 |
| 111 | -17.363 | -12.865 | 17.359 | -10.225 | -3.256 | -6.186 | -3.039 | -7.101 |
| 112 | -17.346 | -12.915 | 17.346 | -10.197 | -3.264 | -6.156 | -3.017 | -7.119 |
| 113 | -17.335 | -12.960 | 17.333 | -10.172 | -3.273 | -6.124 | -2.993 | -7.137 |
| 114 | -17.317 | -12.998 | 17.316 | -10.153 | -3.287 | -6.098 | -2.970 | -7.162 |
| 115 | -17.296 | -13.031 | 17.295 | -10.140 | -3.305 | -6.074 | -2.945 | -7.193 |
| 116 | -17.272 | -13.058 | 17.272 | -10.131 | -3.328 | -6.051 | -2.919 | -7.232 |
| 117 | -17.244 | -13.082 | 17.244 | -10.127 | -3.356 | -6.029 | -2.888 | -7.279 |
| 118 | -17.211 | -13.101 | 17.211 | -10.128 | -3.393 | -6.006 | -2.852 | -7.338 |
| 119 | -17.172 | -13.115 | 17.172 | -10.134 | -3.438 | -5.983 | -2.811 | -7.406 |
| 120 | -17.126 | -13.125 | 17.126 | -10.146 | -3.496 | -5.964 | -2.765 | -7.483 |

Table 52

FIG. 76

|  | Label | | | | | | | |
|---|---|---|---|---|---|---|---|---|
|  | 8 | 9 | 10 | 11 | 12 | 13 | 14 | 15 |
| Design # | | | | | | | | |
| 81 | 8.945 | 7.590 | 10.894 | 7.590 | 1.248 | 2.166 | 1.131 | 2.166 |
| 82 | 9.040 | 7.532 | 11.014 | 7.532 | 1.186 | 2.227 | 1.081 | 2.227 |
| 83 | 9.154 | 7.464 | 11.131 | 7.464 | 1.111 | 2.291 | 1.022 | 2.291 |
| 84 | 9.291 | 7.388 | 11.242 | 7.388 | 1.022 | 2.360 | 0.950 | 2.360 |
| 85 | 9.452 | 7.304 | 11.344 | 7.304 | 0.918 | 2.436 | 0.865 | 2.436 |
| 86 | 9.629 | 7.215 | 11.435 | 7.215 | 0.803 | 2.516 | 0.768 | 2.516 |
| 87 | 9.809 | 7.127 | 11.512 | 7.127 | 0.683 | 2.601 | 0.664 | 2.601 |
| 88 | 9.978 | 7.055 | 11.580 | 7.036 | 0.566 | 2.685 | 0.560 | 2.685 |
| 89 | 10.020 | 7.040 | 11.600 | 7.010 | 0.540 | 2.710 | 0.540 | 2.710 |
| 90 | 10.127 | 7.007 | 11.643 | 6.939 | 0.461 | 2.766 | 0.461 | 2.766 |
| 91 | 10.247 | 6.969 | 11.696 | 6.864 | 0.372 | 2.841 | 0.372 | 2.841 |
| 92 | 10.344 | 6.939 | 11.742 | 6.805 | 0.297 | 2.909 | 0.297 | 2.909 |
| 93 | 10.423 | 6.918 | 11.784 | 6.758 | 0.234 | 2.968 | 0.234 | 2.968 |
| 94 | 10.486 | 6.904 | 11.823 | 6.722 | 0.183 | 3.019 | 0.183 | 3.019 |
| 95 | 10.536 | 6.897 | 11.861 | 6.694 | 0.141 | 3.063 | 0.141 | 3.063 |
| 96 | 10.575 | 6.897 | 11.898 | 6.673 | 0.108 | 3.099 | 0.108 | 3.099 |
| 97 | 10.604 | 6.901 | 11.939 | 6.655 | 0.082 | 3.128 | 0.082 | 3.128 |
| 98 | 10.626 | 6.911 | 11.977 | 6.646 | 0.065 | 3.153 | 0.065 | 3.153 |
| 99 | 10.633 | 6.924 | 12.029 | 6.627 | 0.045 | 3.166 | 0.045 | 3.173 |
| 100 | 10.633 | 6.941 | 12.082 | 6.613 | 0.034 | 3.175 | 0.034 | 3.193 |
| 101 | 10.623 | 6.961 | 12.144 | 6.595 | 0.025 | 3.178 | 0.025 | 3.207 |
| 102 | 10.600 | 6.983 | 12.213 | 6.572 | 0.019 | 3.178 | 0.019 | 3.220 |
| 103 | 10.565 | 7.004 | 12.293 | 6.541 | 0.015 | 3.172 | 0.015 | 3.228 |
| 104 | 10.518 | 7.024 | 12.381 | 6.500 | 0.012 | 3.160 | 0.012 | 3.234 |
| 105 | 10.464 | 7.041 | 12.474 | 6.451 | 0.009 | 3.143 | 0.009 | 3.237 |
| 106 | 10.460 | 7.040 | 12.480 | 6.450 | 0.010 | 3.140 | 0.010 | 3.240 |
| 107 | 10.407 | 7.055 | 12.566 | 6.397 | 0.008 | 3.123 | 0.008 | 3.238 |
| 108 | 10.352 | 7.067 | 12.653 | 6.342 | 0.010 | 3.101 | 0.002 | 3.239 |
| 109 | 10.303 | 7.079 | 12.731 | 6.291 | 0.015 | 3.077 | -0.006 | 3.241 |
| 110 | 10.260 | 7.090 | 12.800 | 6.244 | 0.021 | 3.054 | -0.015 | 3.244 |
| 111 | 10.225 | 7.103 | 12.860 | 6.202 | 0.029 | 3.031 | -0.025 | 3.250 |
| 112 | 10.197 | 7.121 | 12.913 | 6.167 | 0.038 | 3.010 | -0.037 | 3.259 |
| 113 | 10.172 | 7.139 | 12.958 | 6.134 | 0.050 | 2.987 | -0.048 | 3.269 |
| 114 | 10.153 | 7.163 | 12.997 | 6.105 | 0.063 | 2.965 | -0.063 | 3.284 |
| 115 | 10.140 | 7.194 | 13.030 | 6.080 | 0.079 | 2.942 | -0.079 | 3.303 |
| 116 | 10.131 | 7.232 | 13.058 | 6.056 | 0.098 | 2.916 | -0.099 | 3.326 |
| 117 | 10.127 | 7.280 | 13.082 | 6.032 | 0.122 | 2.885 | -0.122 | 3.355 |
| 118 | 10.128 | 7.338 | 13.101 | 6.008 | 0.151 | 2.850 | -0.152 | 3.392 |
| 119 | 10.135 | 7.407 | 13.115 | 5.985 | 0.188 | 2.809 | -0.189 | 3.438 |
| 120 | 10.147 | 7.484 | 13.125 | 5.965 | 0.235 | 2.763 | -0.236 | 3.496 |

Table 53

FIG. 77

|  | Label | | | | | | | |
|---|---|---|---|---|---|---|---|---|
|  | 0 | 1 | 2 | 3 | 4 | 5 | 6 | 7 |
| Design # | | | | | | | | |
| 121 | -17.073 | -13.130 | 17.073 | -10.163 | -3.570 | -5.950 | -2.716 | -7.565 |
| 122 | -17.011 | -13.129 | 17.012 | -10.183 | -3.661 | -5.947 | -2.667 | -7.649 |
| 123 | -16.970 | -13.130 | 16.970 | -10.200 | -3.720 | -5.950 | -2.640 | -7.700 |
| 124 | -16.945 | -13.125 | 16.945 | -10.205 | -3.765 | -5.954 | -2.624 | -7.729 |
| 125 | -16.879 | -13.119 | 16.879 | -10.228 | -3.867 | -5.968 | -2.591 | -7.798 |
| 126 | -16.817 | -13.115 | 16.817 | -10.249 | -3.954 | -5.984 | -2.568 | -7.856 |
| 127 | -16.763 | -13.114 | 16.763 | -10.271 | -4.022 | -5.999 | -2.551 | -7.903 |
| 128 | -16.713 | -13.115 | 16.713 | -10.292 | -4.074 | -6.013 | -2.539 | -7.942 |
| 129 | -16.667 | -13.117 | 16.667 | -10.313 | -4.116 | -6.026 | -2.531 | -7.975 |
| 130 | -16.624 | -13.120 | 16.624 | -10.334 | -4.149 | -6.039 | -2.526 | -8.005 |
| 131 | -16.582 | -13.123 | 16.582 | -10.356 | -4.176 | -6.053 | -2.524 | -8.033 |
| 132 | -16.540 | -13.127 | 16.541 | -10.378 | -4.199 | -6.067 | -2.524 | -8.060 |
| 133 | -16.499 | -13.129 | 16.500 | -10.400 | -4.220 | -6.083 | -2.525 | -8.087 |
| 134 | -16.459 | -13.132 | 16.458 | -10.422 | -4.238 | -6.100 | -2.528 | -8.113 |
| 135 | -16.418 | -13.134 | 16.417 | -10.444 | -4.256 | -6.119 | -2.532 | -8.140 |
| 136 | -16.375 | -13.134 | 16.376 | -10.466 | -4.275 | -6.139 | -2.539 | -8.167 |
| 137 | -16.335 | -13.135 | 16.332 | -10.487 | -4.293 | -6.162 | -2.545 | -8.195 |
| 138 | -16.291 | -13.134 | 16.290 | -10.508 | -4.312 | -6.186 | -2.555 | -8.223 |
| 139 | -16.249 | -13.132 | 16.247 | -10.528 | -4.332 | -6.212 | -2.565 | -8.251 |
| 140 | -16.204 | -13.129 | 16.204 | -10.548 | -4.354 | -6.239 | -2.577 | -8.280 |
| 141 | -16.180 | -13.130 | 16.180 | -10.560 | -4.370 | -6.260 | -2.590 | -8.300 |
| 142 | -16.160 | -13.126 | 16.161 | -10.567 | -4.377 | -6.267 | -2.590 | -8.309 |
| 143 | -16.117 | -13.122 | 16.117 | -10.585 | -4.400 | -6.296 | -2.604 | -8.337 |
| 144 | -16.074 | -13.117 | 16.074 | -10.603 | -4.424 | -6.324 | -2.619 | -8.365 |
| 145 | -16.031 | -13.112 | 16.032 | -10.620 | -4.448 | -6.353 | -2.635 | -8.393 |
| 146 | -15.989 | -13.107 | 15.989 | -10.636 | -4.472 | -6.382 | -2.650 | -8.419 |
| 147 | -15.948 | -13.102 | 15.949 | -10.652 | -4.497 | -6.410 | -2.666 | -8.445 |
| 148 | -15.910 | -13.098 | 15.908 | -10.667 | -4.519 | -6.437 | -2.681 | -8.470 |
| 149 | -15.872 | -13.092 | 15.869 | -10.682 | -4.542 | -6.463 | -2.696 | -8.495 |
| 150 | -15.833 | -13.087 | 15.833 | -10.695 | -4.565 | -6.489 | -2.712 | -8.518 |
| 151 | -15.797 | -13.082 | 15.797 | -10.708 | -4.586 | -6.513 | -2.726 | -8.540 |
| 152 | -15.763 | -13.078 | 15.763 | -10.721 | -4.606 | -6.536 | -2.739 | -8.562 |
| 153 | -15.730 | -13.073 | 15.730 | -10.733 | -4.625 | -6.559 | -2.752 | -8.582 |
| 154 | -15.698 | -13.069 | 15.698 | -10.745 | -4.643 | -6.580 | -2.764 | -8.601 |
| 155 | -15.668 | -13.066 | 15.668 | -10.756 | -4.660 | -6.599 | -2.776 | -8.619 |
| 156 | -15.639 | -13.062 | 15.639 | -10.767 | -4.677 | -6.618 | -2.787 | -8.637 |
| 157 | -15.610 | -13.059 | 15.610 | -10.777 | -4.692 | -6.637 | -2.797 | -8.654 |
| 158 | -15.584 | -13.056 | 15.584 | -10.787 | -4.707 | -6.654 | -2.807 | -8.670 |
| 159 | -15.559 | -13.053 | 15.559 | -10.796 | -4.721 | -6.670 | -2.816 | -8.685 |
| 160 | -15.535 | -13.050 | 15.535 | -10.805 | -4.734 | -6.685 | -2.825 | -8.699 |

Table 54

FIG. 78

| Design # | Label | | | | | | | |
|---|---|---|---|---|---|---|---|---|
| | 8 | 9 | 10 | 11 | 12 | 13 | 14 | 15 |
| 121 | 10.163 | 7.566 | 13.130 | 5.951 | 0.294 | 2.713 | -0.295 | 3.570 |
| 122 | 10.184 | 7.650 | 13.130 | 5.947 | 0.368 | 2.666 | -0.369 | 3.661 |
| 123 | 10.200 | 7.700 | 13.130 | 5.950 | 0.420 | 2.640 | -0.420 | 3.720 |
| 124 | 10.206 | 7.729 | 13.125 | 5.954 | 0.452 | 2.623 | -0.452 | 3.765 |
| 125 | 10.228 | 7.799 | 13.120 | 5.969 | 0.534 | 2.590 | -0.534 | 3.867 |
| 126 | 10.250 | 7.856 | 13.115 | 5.985 | 0.604 | 2.567 | -0.604 | 3.954 |
| 127 | 10.271 | 7.903 | 13.114 | 6.000 | 0.658 | 2.550 | -0.659 | 4.022 |
| 128 | 10.292 | 7.942 | 13.115 | 6.013 | 0.700 | 2.539 | -0.700 | 4.074 |
| 129 | 10.313 | 7.975 | 13.117 | 6.026 | 0.732 | 2.531 | -0.732 | 4.116 |
| 130 | 10.334 | 8.005 | 13.120 | 6.039 | 0.757 | 2.526 | -0.757 | 4.149 |
| 131 | 10.356 | 8.033 | 13.123 | 6.053 | 0.776 | 2.524 | -0.776 | 4.176 |
| 132 | 10.378 | 8.060 | 13.127 | 6.067 | 0.791 | 2.523 | -0.791 | 4.199 |
| 133 | 10.400 | 8.087 | 13.130 | 6.083 | 0.803 | 2.525 | -0.803 | 4.220 |
| 134 | 10.422 | 8.113 | 13.132 | 6.100 | 0.813 | 2.528 | -0.813 | 4.238 |
| 135 | 10.444 | 8.140 | 13.133 | 6.119 | 0.822 | 2.533 | -0.821 | 4.257 |
| 136 | 10.466 | 8.167 | 13.135 | 6.139 | 0.828 | 2.538 | -0.828 | 4.274 |
| 137 | 10.487 | 8.195 | 13.134 | 6.163 | 0.835 | 2.547 | -0.834 | 4.294 |
| 138 | 10.508 | 8.223 | 13.134 | 6.186 | 0.840 | 2.555 | -0.840 | 4.312 |
| 139 | 10.528 | 8.251 | 13.131 | 6.212 | 0.846 | 2.566 | -0.845 | 4.333 |
| 140 | 10.548 | 8.280 | 13.129 | 6.239 | 0.851 | 2.577 | -0.850 | 4.354 |
| 141 | 10.560 | 8.300 | 13.130 | 6.260 | 0.850 | 2.590 | -0.850 | 4.370 |
| 142 | 10.567 | 8.309 | 13.126 | 6.267 | 0.856 | 2.590 | -0.856 | 4.376 |
| 143 | 10.585 | 8.337 | 13.122 | 6.296 | 0.861 | 2.604 | -0.861 | 4.400 |
| 144 | 10.603 | 8.365 | 13.117 | 6.324 | 0.867 | 2.619 | -0.866 | 4.424 |
| 145 | 10.620 | 8.392 | 13.113 | 6.353 | 0.872 | 2.634 | -0.872 | 4.448 |
| 146 | 10.636 | 8.419 | 13.107 | 6.382 | 0.878 | 2.650 | -0.878 | 4.472 |
| 147 | 10.652 | 8.446 | 13.102 | 6.410 | 0.883 | 2.666 | -0.884 | 4.496 |
| 148 | 10.667 | 8.471 | 13.096 | 6.437 | 0.890 | 2.682 | -0.888 | 4.520 |
| 149 | 10.681 | 8.495 | 13.091 | 6.464 | 0.895 | 2.697 | -0.894 | 4.543 |
| 150 | 10.695 | 8.518 | 13.087 | 6.489 | 0.899 | 2.711 | -0.900 | 4.565 |
| 151 | 10.709 | 8.540 | 13.082 | 6.513 | 0.904 | 2.726 | -0.904 | 4.586 |
| 152 | 10.721 | 8.561 | 13.078 | 6.537 | 0.909 | 2.739 | -0.909 | 4.606 |
| 153 | 10.733 | 8.582 | 13.073 | 6.559 | 0.914 | 2.752 | -0.914 | 4.625 |
| 154 | 10.745 | 8.601 | 13.070 | 6.580 | 0.918 | 2.764 | -0.918 | 4.643 |
| 155 | 10.756 | 8.619 | 13.066 | 6.599 | 0.922 | 2.776 | -0.922 | 4.661 |
| 156 | 10.767 | 8.637 | 13.062 | 6.618 | 0.926 | 2.787 | -0.926 | 4.677 |
| 157 | 10.777 | 8.654 | 13.059 | 6.637 | 0.929 | 2.797 | -0.929 | 4.692 |
| 158 | 10.787 | 8.670 | 13.056 | 6.654 | 0.933 | 2.807 | -0.933 | 4.707 |
| 159 | 10.796 | 8.685 | 13.053 | 6.670 | 0.936 | 2.816 | -0.936 | 4.721 |
| 160 | 10.805 | 8.699 | 13.050 | 6.685 | 0.939 | 2.825 | -0.939 | 4.734 |

Table 55

FIG. 79

|  | Label | | | | | | | |
|---|---|---|---|---|---|---|---|---|
|  | 0 | 1 | 2 | 3 | 4 | 5 | 6 | 7 |
| Design # | | | | | | | | |
| 161 | -15.512 | -13.048 | 15.512 | -10.814 | -4.746 | -6.700 | -2.833 | -8.713 |
| 162 | -15.489 | -13.045 | 15.489 | -10.822 | -4.758 | -6.713 | -2.841 | -8.726 |
| 163 | -15.468 | -13.043 | 15.468 | -10.829 | -4.770 | -6.727 | -2.848 | -8.738 |
| 164 | -15.447 | -13.040 | 15.447 | -10.837 | -4.781 | -6.739 | -2.856 | -8.750 |
| 165 | -15.428 | -13.038 | 15.428 | -10.844 | -4.790 | -6.751 | -2.862 | -8.761 |
| 166 | -15.408 | -13.036 | 15.409 | -10.851 | -4.801 | -6.763 | -2.869 | -8.773 |
| 167 | -15.393 | -13.034 | 15.392 | -10.857 | -4.809 | -6.773 | -2.875 | -8.782 |
| 168 | -15.375 | -13.033 | 15.374 | -10.864 | -4.818 | -6.784 | -2.880 | -8.792 |
| 169 | -15.358 | -13.032 | 15.358 | -10.870 | -4.826 | -6.793 | -2.886 | -8.801 |
| 170 | -15.344 | -13.030 | 15.344 | -10.875 | -4.834 | -6.802 | -2.891 | -8.810 |
| 171 | -15.328 | -13.028 | 15.328 | -10.881 | -4.842 | -6.811 | -2.896 | -8.819 |
| 172 | -15.312 | -13.026 | 15.313 | -10.886 | -4.850 | -6.821 | -2.902 | -8.827 |
| 173 | -15.299 | -13.025 | 15.299 | -10.891 | -4.856 | -6.829 | -2.906 | -8.835 |
| 174 | -15.288 | -13.024 | 15.288 | -10.895 | -4.862 | -6.836 | -2.910 | -8.841 |
| 175 | -15.276 | -13.024 | 15.276 | -10.901 | -4.867 | -6.843 | -2.912 | -8.849 |
| 176 | -15.263 | -13.023 | 15.261 | -10.905 | -4.874 | -6.850 | -2.917 | -8.856 |
| 177 | -15.252 | -13.022 | 15.251 | -10.909 | -4.879 | -6.856 | -2.921 | -8.862 |
| 178 | -15.242 | -13.021 | 15.241 | -10.913 | -4.885 | -6.863 | -2.923 | -8.869 |

Table 56

FIG. 80

|  | Label | | | | | | | |
|---|---|---|---|---|---|---|---|---|
|  | 8 | 9 | 10 | 11 | 12 | 13 | 14 | 15 |
| Design # | | | | | | | | |
| 161 | 10.813 | 8.712 | 13.047 | 6.699 | 0.942 | 2.833 | -0.942 | 4.747 |
| 162 | 10.822 | 8.726 | 13.045 | 6.713 | 0.945 | 2.841 | -0.945 | 4.758 |
| 163 | 10.829 | 8.738 | 13.042 | 6.727 | 0.947 | 2.848 | -0.947 | 4.770 |
| 164 | 10.837 | 8.750 | 13.040 | 6.740 | 0.950 | 2.856 | -0.950 | 4.781 |
| 165 | 10.844 | 8.761 | 13.038 | 6.751 | 0.952 | 2.862 | -0.952 | 4.790 |
| 166 | 10.852 | 8.773 | 13.037 | 6.763 | 0.954 | 2.869 | -0.955 | 4.801 |
| 167 | 10.857 | 8.782 | 13.035 | 6.773 | 0.956 | 2.874 | -0.957 | 4.809 |
| 168 | 10.864 | 8.792 | 13.033 | 6.784 | 0.959 | 2.881 | -0.958 | 4.818 |
| 169 | 10.870 | 8.801 | 13.032 | 6.793 | 0.960 | 2.886 | -0.960 | 4.826 |
| 170 | 10.875 | 8.810 | 13.030 | 6.802 | 0.962 | 2.891 | -0.962 | 4.834 |
| 171 | 10.881 | 8.819 | 13.029 | 6.811 | 0.964 | 2.896 | -0.964 | 4.842 |
| 172 | 10.887 | 8.828 | 13.027 | 6.821 | 0.965 | 2.901 | -0.967 | 4.849 |
| 173 | 10.891 | 8.835 | 13.025 | 6.829 | 0.967 | 2.906 | -0.967 | 4.856 |
| 174 | 10.896 | 8.842 | 13.025 | 6.836 | 0.968 | 2.909 | -0.969 | 4.862 |
| 175 | 10.899 | 8.848 | 13.023 | 6.843 | 0.971 | 2.914 | -0.969 | 4.868 |
| 176 | 10.905 | 8.856 | 13.022 | 6.851 | 0.972 | 2.918 | -0.971 | 4.875 |
| 177 | 10.909 | 8.861 | 13.021 | 6.857 | 0.973 | 2.921 | -0.972 | 4.880 |
| 178 | 10.911 | 8.867 | 13.019 | 6.863 | 0.975 | 2.926 | -0.972 | 4.886 |

Table 57

FIG. 81

| Design # | SNRs | 5.00% | 40.00% | 50.00% | 60.00% | 70.00% | 100.00% |
|---|---|---|---|---|---|---|---|
| 63 | 7.4 | 1.36 | 1.23 | 1.1 | 0.99 | 0.65 | 0 |
| 64 | 7.6 | 1.35 | 1.22 | 1.1 | 0.99 | 0.65 | 0 |
| 65 | 7.8 | 1.24 | 1.11 | 1 | 0.9 | 0.59 | 0 |
| 66 | 8 | 1.17 | 1.06 | 0.95 | 0.85 | 0.56 | 0 |
| 67 | 8.2 | 1.14 | 1.02 | 0.92 | 0.83 | 0.54 | 0 |
| 68 | 8.4 | 1.12 | 1.01 | 0.91 | 0.82 | 0.59 | 0 |
| 69 | 8.6 | 1.23 | 1.1 | 0.99 | 0.8 | 0.53 | 0 |
| 70 | 8.8 | 1.17 | 0.65 | 0.58 | 0.53 | 0.47 | 0 |
| 71 | 9 | 1.17 | 0.64 | 0.57 | 0.52 | 0.47 | 0 |
| 72 | 9 | 1.17 | 0.64 | 0.57 | 0.52 | 0.47 | 0 |
| 73 | 9.2 | 1.17 | 0.63 | 0.56 | 0.51 | 0.46 | 0 |
| 74 | 9.4 | 1.16 | 0.61 | 0.55 | 0.49 | 0.45 | 0 |
| 75 | 9.6 | 1.16 | 0.6 | 0.54 | 0.48 | 0.44 | 0 |
| 76 | 9.8 | 1.15 | 0.59 | 0.53 | 0.48 | 0.43 | 0 |
| 77 | 10 | 1.14 | 0.58 | 0.52 | 0.47 | 0.42 | 0 |
| 78 | 10.2 | 1.18 | 0.79 | 0.71 | 0.64 | 0.57 | 0 |
| 79 | 10.4 | 1.1 | 0.91 | 0.82 | 0.73 | 0.54 | 0 |
| 80 | 10.6 | 1.08 | 0.97 | 0.87 | 0.79 | 0.57 | 0 |
| 81 | 10.8 | 1.04 | 0.93 | 0.84 | 0.68 | 0.5 | 0 |
| 82 | 11 | 1 | 0.9 | 0.81 | 0.73 | 0.53 | 0 |
| 83 | 11.2 | 1.07 | 0.96 | 0.87 | 0.7 | 0.51 | 0 |
| 84 | 11.4 | 1.03 | 0.92 | 0.83 | 0.75 | 0.55 | 0 |
| 85 | 11.6 | 1.09 | 0.98 | 0.88 | 0.71 | 0.52 | 0 |
| 86 | 11.8 | 1.03 | 0.92 | 0.83 | 0.75 | 0.49 | 0 |
| 87 | 12 | 0.97 | 0.87 | 0.78 | 0.7 | 0.51 | 0 |
| 88 | 12.2 | 1.01 | 0.9 | 0.81 | 0.73 | 0.48 | 0 |
| 89 | 12.25 | 0.99 | 0.89 | 0.8 | 0.72 | 0.52 | 0 |
| 90 | 12.4 | 0.94 | 0.84 | 0.76 | 0.68 | 0.5 | 0 |
| 91 | 12.6 | 0.97 | 0.88 | 0.79 | 0.71 | 0.47 | 0 |
| 92 | 12.8 | 0.93 | 0.83 | 0.75 | 0.67 | 0.49 | 0 |
| 93 | 13 | 0.89 | 0.8 | 0.72 | 0.65 | 0.47 | 0 |
| 94 | 13.2 | 0.86 | 0.77 | 0.7 | 0.63 | 0.46 | 0 |
| 95 | 13.4 | 0.93 | 0.83 | 0.75 | 0.68 | 0.44 | 0 |
| 96 | 13.6 | 0.9 | 0.81 | 0.73 | 0.66 | 0.43 | 0 |
| 97 | 13.8 | 0.88 | 0.79 | 0.71 | 0.64 | 0.42 | 0 |
| 98 | 14 | 0.87 | 0.78 | 0.69 | 0.62 | 0.45 | 0 |
| 99 | 14.2 | 0.77 | 0.69 | 0.62 | 0.56 | 0.45 | 0 |
| 100 | 14.4 | 0.83 | 0.75 | 0.63 | 0.57 | 0.41 | 0 |
| 101 | 14.6 | 0.73 | 0.66 | 0.59 | 0.53 | 0.39 | 0 |
| 102 | 14.8 | 0.72 | 0.65 | 0.55 | 0.5 | 0.4 | 0 |
| 103 | 15 | 0.71 | 0.64 | 0.52 | 0.47 | 0.38 | 0 |

Table 58

FIG. 82

| Design # | SNRs | 5.00% | 40.00% | 50.00% | 60.00% | 70.00% | 100.00% |
|---|---|---|---|---|---|---|---|
| 104 | 15.2 | 0.7 | 0.63 | 0.49 | 0.44 | 0.36 | 0 |
| 105 | 15.4 | 0.68 | 0.61 | 0.47 | 0.43 | 0.34 | 0 |
| 106 | 15.42 | 0.68 | 0.61 | 0.47 | 0.42 | 0.38 | 0 |
| 107 | 15.6 | 0.67 | 0.6 | 0.47 | 0.42 | 0.34 | 0 |
| 108 | 15.8 | 0.72 | 0.65 | 0.46 | 0.41 | 0.33 | 0 |
| 109 | 16 | 0.63 | 0.57 | 0.45 | 0.41 | 0.33 | 0 |
| 110 | 16.2 | 0.61 | 0.55 | 0.44 | 0.4 | 0.32 | 0 |
| 111 | 16.4 | 0.6 | 0.54 | 0.43 | 0.39 | 0.32 | 0 |
| 112 | 16.6 | 0.58 | 0.53 | 0.42 | 0.38 | 0.31 | 0 |
| 113 | 16.8 | 0.57 | 0.52 | 0.41 | 0.37 | 0.3 | 0 |
| 114 | 17 | 0.56 | 0.5 | 0.4 | 0.36 | 0.26 | 0 |
| 115 | 17.2 | 0.49 | 0.44 | 0.38 | 0.35 | 0.28 | 0 |
| 116 | 17.4 | 0.53 | 0.47 | 0.37 | 0.33 | 0.27 | 0 |
| 117 | 17.6 | 0.51 | 0.46 | 0.35 | 0.31 | 0.25 | 0 |
| 118 | 17.8 | 0.48 | 0.43 | 0.32 | 0.29 | 0.23 | 0 |
| 119 | 18 | 0.46 | 0.41 | 0.34 | 0.3 | 0.25 | 0 |
| 120 | 18.2 | 0.43 | 0.39 | 0.35 | 0.31 | 0.23 | 0 |
| 121 | 18.4 | 0.4 | 0.36 | 0.33 | 0.29 | 0.21 | 0 |
| 122 | 18.6 | 0.42 | 0.38 | 0.34 | 0.31 | 0.2 | 0 |
| 123 | 18.72 | 0.39 | 0.35 | 0.31 | 0.28 | 0.21 | 0 |
| 124 | 18.8 | 0.39 | 0.35 | 0.32 | 0.29 | 0.21 | 0 |
| 125 | 19 | 0.37 | 0.33 | 0.3 | 0.27 | 0.2 | 0 |
| 126 | 19.2 | 0.39 | 0.35 | 0.3 | 0.27 | 0.2 | 0 |
| 127 | 19.4 | 0.37 | 0.33 | 0.28 | 0.25 | 0.18 | 0 |
| 128 | 19.6 | 0.34 | 0.31 | 0.26 | 0.24 | 0.19 | 0 |
| 129 | 19.8 | 0.36 | 0.32 | 0.25 | 0.23 | 0.18 | 0 |
| 130 | 20 | 0.33 | 0.3 | 0.27 | 0.24 | 0.18 | 0 |
| 131 | 20.2 | 0.34 | 0.31 | 0.28 | 0.23 | 0.16 | 0 |
| 132 | 20.4 | 0.32 | 0.29 | 0.26 | 0.23 | 0.17 | 0 |
| 133 | 20.6 | 0.3 | 0.27 | 0.24 | 0.22 | 0.16 | 0 |
| 134 | 20.8 | 0.27 | 0.25 | 0.22 | 0.2 | 0.15 | 0 |
| 135 | 21 | 0.28 | 0.25 | 0.23 | 0.21 | 0.14 | 0 |
| 136 | 21.2 | 0.26 | 0.24 | 0.21 | 0.19 | 0.14 | 0 |
| 137 | 21.4 | 0.26 | 0.23 | 0.21 | 0.19 | 0.14 | 0 |
| 138 | 21.6 | 0.25 | 0.22 | 0.2 | 0.18 | 0.12 | 0 |
| 139 | 21.8 | 0.24 | 0.21 | 0.19 | 0.17 | 0.13 | 0 |
| 140 | 22 | 0.23 | 0.21 | 0.19 | 0.17 | 0.11 | 0 |
| 141 | 22.13 | 0.2 | 0.18 | 0.16 | 0.15 | 0.11 | 0 |
| 142 | 22.2 | 0.2 | 0.18 | 0.16 | 0.14 | 0.11 | 0 |
| 143 | 22.4 | 0.19 | 0.17 | 0.15 | 0.14 | 0.1 | 0 |
| 144 | 22.6 | 0.18 | 0.17 | 0.15 | 0.13 | 0.1 | 0 |

Table 59

FIG. 83

| Design # | SNRs | 5.00% | 40.00% | 50.00% | 60.00% | 70.00% | 100.00% |
|---|---|---|---|---|---|---|---|
| 145 | 22.8 | 0.18 | 0.16 | 0.14 | 0.13 | 0.09 | 0 |
| 146 | 23 | 0.17 | 0.15 | 0.14 | 0.12 | 0.09 | 0 |
| 147 | 23.2 | 0.16 | 0.14 | 0.13 | 0.12 | 0.08 | 0 |
| 148 | 23.4 | 0.15 | 0.14 | 0.12 | 0.11 | 0.08 | 0 |
| 149 | 23.6 | 0.13 | 0.12 | 0.11 | 0.1 | 0.07 | 0 |
| 150 | 23.8 | 0.14 | 0.13 | 0.11 | 0.1 | 0.07 | 0 |
| 151 | 24 | 0.12 | 0.11 | 0.1 | 0.09 | 0.06 | 0 |
| 152 | 24.2 | 0.12 | 0.1 | 0.09 | 0.08 | 0.06 | 0 |
| 153 | 24.4 | 0.11 | 0.1 | 0.09 | 0.08 | 0.06 | 0 |
| 154 | 24.6 | 0.11 | 0.09 | 0.09 | 0.08 | 0.06 | 0 |
| 155 | 24.8 | 0.1 | 0.09 | 0.08 | 0.07 | 0.05 | 0 |
| 156 | 25 | 0.1 | 0.09 | 0.08 | 0.07 | 0.05 | 0 |
| 157 | 25.2 | 0.09 | 0.08 | 0.07 | 0.07 | 0.05 | 0 |
| 158 | 25.4 | 0.09 | 0.08 | 0.07 | 0.06 | 0.05 | 0 |
| 159 | 25.6 | 0.08 | 0.08 | 0.07 | 0.06 | 0.04 | 0 |
| 160 | 25.8 | 0.08 | 0.07 | 0.06 | 0.06 | 0.04 | 0 |
| 161 | 26 | 0.08 | 0.07 | 0.06 | 0.06 | 0.04 | 0 |
| 162 | 26.2 | 0.07 | 0.07 | 0.06 | 0.05 | 0.04 | 0 |
| 163 | 26.4 | 0.07 | 0.06 | 0.06 | 0.05 | 0.04 | 0 |
| 164 | 26.6 | 0.07 | 0.06 | 0.05 | 0.05 | 0.04 | 0 |
| 165 | 26.8 | 0.06 | 0.06 | 0.05 | 0.05 | 0.03 | 0 |
| 166 | 27 | 0.06 | 0.05 | 0.05 | 0.04 | 0.03 | 0 |
| 167 | 27.2 | 0.05 | 0.05 | 0.04 | 0.04 | 0.03 | 0 |
| 168 | 27.4 | 0.06 | 0.05 | 0.05 | 0.04 | 0.03 | 0 |
| 169 | 27.6 | 0.05 | 0.05 | 0.04 | 0.04 | 0.03 | 0 |
| 170 | 27.8 | 0.05 | 0.04 | 0.04 | 0.03 | 0.02 | 0 |
| 171 | 28 | 0.05 | 0.04 | 0.04 | 0.04 | 0.03 | 0 |
| 172 | 28.2 | 0.05 | 0.04 | 0.04 | 0.03 | 0.02 | 0 |
| 173 | 28.4 | 0.04 | 0.04 | 0.03 | 0.03 | 0.02 | 0 |
| 174 | 28.6 | 0.04 | 0.04 | 0.03 | 0.03 | 0.02 | 0 |
| 175 | 28.8 | 0.04 | 0.03 | 0.03 | 0.03 | 0.02 | 0 |
| 176 | 29 | 0.03 | 0.03 | 0.03 | 0.03 | 0.02 | 0 |
| 177 | 29.2 | 0.03 | 0.03 | 0.03 | 0.02 | 0.02 | 0 |
| 178 | 29.4 | 0.03 | 0.03 | 0.03 | 0.02 | 0.02 | 0 |

Table 60

FIG. 84

| Design # | SNR | Opt. Cap | Std. Cap | Gain [bits] | Gain % |
|---|---|---|---|---|---|
| 1 | -5.000 | 0.1982 | 0.1980 | 0.0002 | 0.0804 |
| 2 | -4.800 | 0.2063 | 0.2061 | 0.0002 | 0.0894 |
| 3 | -4.600 | 0.2147 | 0.2145 | 0.0002 | 0.0992 |
| 4 | -4.400 | 0.2234 | 0.2232 | 0.0002 | 0.1099 |
| 5 | -4.200 | 0.2324 | 0.2322 | 0.0003 | 0.1217 |
| 6 | -4.000 | 0.2417 | 0.2414 | 0.0003 | 0.1346 |
| 7 | -3.800 | 0.2514 | 0.2510 | 0.0004 | 0.1488 |
| 8 | -3.600 | 0.2613 | 0.2609 | 0.0004 | 0.1642 |
| 9 | -3.400 | 0.2715 | 0.2711 | 0.0005 | 0.1809 |
| 10 | -3.200 | 0.2821 | 0.2816 | 0.0006 | 0.1992 |
| 11 | -3.000 | 0.2931 | 0.2924 | 0.0006 | 0.2190 |
| 12 | -2.800 | 0.3043 | 0.3036 | 0.0007 | 0.2405 |
| 13 | -2.600 | 0.3159 | 0.3151 | 0.0008 | 0.2637 |
| 14 | -2.400 | 0.3279 | 0.3269 | 0.0009 | 0.2888 |
| 15 | -2.200 | 0.3402 | 0.3391 | 0.0011 | 0.3159 |
| 16 | -2.000 | 0.3529 | 0.3516 | 0.0012 | 0.3451 |
| 17 | -1.800 | 0.3659 | 0.3645 | 0.0014 | 0.3764 |
| 18 | -1.600 | 0.3793 | 0.3777 | 0.0015 | 0.4100 |
| 19 | -1.400 | 0.3931 | 0.3913 | 0.0017 | 0.4460 |
| 20 | -1.200 | 0.4072 | 0.4052 | 0.0020 | 0.4845 |
| 21 | -1.000 | 0.4217 | 0.4195 | 0.0022 | 0.5255 |
| 22 | -0.800 | 0.4366 | 0.4341 | 0.0025 | 0.5692 |
| 23 | -0.600 | 0.4519 | 0.4491 | 0.0028 | 0.6155 |
| 24 | -0.400 | 0.4675 | 0.4644 | 0.0031 | 0.6647 |
| 25 | -0.200 | 0.4836 | 0.4801 | 0.0034 | 0.7167 |
| 26 | 0.000 | 0.5000 | 0.4962 | 0.0038 | 0.7716 |
| 27 | 0.200 | 0.5168 | 0.5125 | 0.0043 | 0.8294 |
| 28 | 0.400 | 0.5340 | 0.5292 | 0.0047 | 0.8902 |
| 29 | 0.600 | 0.5515 | 0.5463 | 0.0052 | 0.9540 |
| 30 | 0.800 | 0.5695 | 0.5637 | 0.0058 | 1.0207 |
| 31 | 1.000 | 0.5878 | 0.5814 | 0.0063 | 1.0903 |
| 32 | 1.200 | 0.6065 | 0.5995 | 0.0070 | 1.1629 |
| 33 | 1.400 | 0.6255 | 0.6179 | 0.0077 | 1.2383 |
| 34 | 1.600 | 0.6450 | 0.6366 | 0.0084 | 1.3165 |
| 35 | 1.800 | 0.6648 | 0.6556 | 0.0092 | 1.3973 |
| 36 | 2.000 | 0.6850 | 0.6750 | 0.0100 | 1.4807 |
| 37 | 2.200 | 0.7055 | 0.6946 | 0.0109 | 1.5665 |
| 38 | 2.400 | 0.7264 | 0.7146 | 0.0118 | 1.6545 |
| 39 | 2.600 | 0.7476 | 0.7348 | 0.0128 | 1.7448 |
| 40 | 2.800 | 0.7692 | 0.7553 | 0.0139 | 1.8370 |

Table 61

FIG. 85

| Design # | SNR | Opt. Cap | Std. Cap | Gain [bits] | Gain % |
|---|---|---|---|---|---|
| 41 | 3.000 | 0.7912 | 0.7762 | 0.0150 | 1.9309 |
| 42 | 3.200 | 0.8134 | 0.7973 | 0.0162 | 2.0265 |
| 43 | 3.400 | 0.8360 | 0.8186 | 0.0174 | 2.1237 |
| 44 | 3.600 | 0.8589 | 0.8403 | 0.0187 | 2.2223 |
| 45 | 3.800 | 0.8822 | 0.8622 | 0.0200 | 2.3216 |
| 46 | 4.000 | 0.9057 | 0.8843 | 0.0214 | 2.4217 |
| 47 | 4.200 | 0.9296 | 0.9067 | 0.0229 | 2.5225 |
| 48 | 4.400 | 0.9538 | 0.9294 | 0.0244 | 2.6237 |
| 49 | 4.600 | 0.9782 | 0.9523 | 0.0260 | 2.7253 |
| 50 | 4.776 | 1.0000 | 0.9726 | 0.0274 | 2.8172 |
| 51 | 4.800 | 1.0030 | 0.9754 | 0.0276 | 2.8268 |
| 52 | 5.000 | 1.0280 | 0.9988 | 0.0292 | 2.9281 |
| 53 | 5.200 | 1.0533 | 1.0223 | 0.0310 | 3.0290 |
| 54 | 5.400 | 1.0789 | 1.0461 | 0.0327 | 3.1291 |
| 55 | 5.600 | 1.1047 | 1.0702 | 0.0345 | 3.2281 |
| 56 | 5.800 | 1.1308 | 1.0944 | 0.0364 | 3.3258 |
| 57 | 6.000 | 1.1571 | 1.1188 | 0.0383 | 3.4217 |
| 58 | 6.200 | 1.1836 | 1.1434 | 0.0402 | 3.5157 |
| 59 | 6.400 | 1.2104 | 1.1682 | 0.0422 | 3.6083 |
| 60 | 6.600 | 1.2374 | 1.1932 | 0.0441 | 3.6994 |
| 61 | 6.800 | 1.2646 | 1.2184 | 0.0462 | 3.7888 |
| 62 | 7.000 | 1.2920 | 1.2438 | 0.0482 | 3.8764 |
| 63 | 7.200 | 1.3197 | 1.2694 | 0.0503 | 3.9615 |
| 64 | 7.400 | 1.3475 | 1.2951 | 0.0524 | 4.0439 |
| 65 | 7.600 | 1.3755 | 1.3210 | 0.0545 | 4.1236 |
| 66 | 7.800 | 1.4037 | 1.3471 | 0.0566 | 4.2007 |
| 67 | 8.000 | 1.4320 | 1.3733 | 0.0587 | 4.2754 |
| 68 | 8.200 | 1.4605 | 1.3997 | 0.0609 | 4.3475 |
| 69 | 8.400 | 1.4892 | 1.4262 | 0.0630 | 4.4169 |
| 70 | 8.475 | 1.5000 | 1.4362 | 0.0638 | 4.4423 |
| 71 | 8.600 | 1.5180 | 1.4529 | 0.0651 | 4.4836 |
| 72 | 8.800 | 1.5470 | 1.4797 | 0.0673 | 4.5478 |
| 73 | 9.000 | 1.5762 | 1.5067 | 0.0695 | 4.6094 |
| 74 | 9.200 | 1.6054 | 1.5338 | 0.0716 | 4.6679 |
| 75 | 9.400 | 1.6348 | 1.5611 | 0.0737 | 4.7231 |
| 76 | 9.600 | 1.6643 | 1.5885 | 0.0758 | 4.7749 |
| 77 | 9.800 | 1.6940 | 1.6160 | 0.0779 | 4.8235 |
| 78 | 10.000 | 1.7237 | 1.6437 | 0.0800 | 4.8693 |
| 79 | 10.200 | 1.7536 | 1.6715 | 0.0821 | 4.9121 |
| 80 | 10.400 | 1.7835 | 1.6994 | 0.0842 | 4.9523 |

Table 62

FIG. 86

| Design # | SNR | Opt. Cap | Std. Cap | Gain [bits] | Gain % |
|---|---|---|---|---|---|
| 81 | 10.600 | 1.8136 | 1.7274 | 0.0862 | 4.9903 |
| 82 | 10.800 | 1.8437 | 1.7555 | 0.0882 | 5.0256 |
| 83 | 11.000 | 1.8740 | 1.7838 | 0.0902 | 5.0582 |
| 84 | 11.200 | 1.9043 | 1.8121 | 0.0922 | 5.0883 |
| 85 | 11.400 | 1.9348 | 1.8406 | 0.0942 | 5.1158 |
| 86 | 11.600 | 1.9653 | 1.8692 | 0.0961 | 5.1407 |
| 87 | 11.800 | 1.9959 | 1.8979 | 0.0980 | 5.1630 |
| 88 | 11.827 | 2.0000 | 1.9018 | 0.0982 | 5.1635 |
| 89 | 12.000 | 2.0265 | 1.9267 | 0.0998 | 5.1824 |
| 90 | 12.200 | 2.0572 | 1.9555 | 0.1017 | 5.1988 |
| 91 | 12.400 | 2.0880 | 1.9845 | 0.1034 | 5.2121 |
| 92 | 12.600 | 2.1188 | 2.0136 | 0.1052 | 5.2225 |
| 93 | 12.800 | 2.1496 | 2.0428 | 0.1069 | 5.2307 |
| 94 | 13.000 | 2.1805 | 2.0720 | 0.1085 | 5.2365 |
| 95 | 13.200 | 2.2115 | 2.1014 | 0.1101 | 5.2400 |
| 96 | 13.400 | 2.2425 | 2.1308 | 0.1117 | 5.2417 |
| 97 | 13.600 | 2.2736 | 2.1603 | 0.1132 | 5.2416 |
| 98 | 13.800 | 2.3047 | 2.1899 | 0.1147 | 5.2398 |
| 99 | 14.000 | 2.3358 | 2.2196 | 0.1162 | 5.2362 |
| 100 | 14.200 | 2.3670 | 2.2494 | 0.1177 | 5.2310 |
| 101 | 14.400 | 2.3983 | 2.2792 | 0.1191 | 5.2241 |
| 102 | 14.600 | 2.4296 | 2.3091 | 0.1204 | 5.2155 |
| 103 | 14.800 | 2.4609 | 2.3391 | 0.1218 | 5.2052 |
| 104 | 15.000 | 2.4922 | 2.3692 | 0.1230 | 5.1934 |
| 105 | 15.050 | 2.5000 | 2.3766 | 0.1234 | 5.1923 |
| 106 | 15.200 | 2.5236 | 2.3993 | 0.1243 | 5.1802 |
| 107 | 15.400 | 2.5550 | 2.4295 | 0.1255 | 5.1654 |
| 108 | 15.600 | 2.5864 | 2.4598 | 0.1267 | 5.1492 |
| 109 | 15.800 | 2.6179 | 2.4901 | 0.1278 | 5.1316 |
| 110 | 16.000 | 2.6493 | 2.5205 | 0.1289 | 5.1124 |
| 111 | 16.200 | 2.6808 | 2.5509 | 0.1299 | 5.0918 |
| 112 | 16.400 | 2.7123 | 2.5814 | 0.1309 | 5.0696 |
| 113 | 16.600 | 2.7438 | 2.6120 | 0.1318 | 5.0459 |
| 114 | 16.800 | 2.7753 | 2.6426 | 0.1327 | 5.0207 |
| 115 | 17.000 | 2.8068 | 2.6733 | 0.1335 | 4.9940 |
| 116 | 17.200 | 2.8383 | 2.7041 | 0.1343 | 4.9658 |
| 117 | 17.400 | 2.8698 | 2.7348 | 0.1350 | 4.9361 |
| 118 | 17.600 | 2.9013 | 2.7657 | 0.1357 | 4.9051 |
| 119 | 17.800 | 2.9329 | 2.7966 | 0.1363 | 4.8727 |
| 120 | 18.000 | 2.9643 | 2.8275 | 0.1368 | 4.8389 |

Table 63

FIG. 87

|  | SNR | Opt. Cap | Std. Cap | Gain [bits] | Gain % |
|---|---|---|---|---|---|
| Design # | | | | | |
| 121 | 18.200 | 2.9958 | 2.8585 | 0.1373 | 4.8038 |
| 122 | 18.226 | 3.0000 | 2.8626 | 0.1374 | 4.7998 |
| 123 | 18.400 | 3.0273 | 2.8896 | 0.1378 | 4.7674 |
| 124 | 18.600 | 3.0588 | 2.9206 | 0.1381 | 4.7297 |
| 125 | 18.800 | 3.0902 | 2.9518 | 0.1385 | 4.6907 |
| 126 | 19.000 | 3.1217 | 2.9830 | 0.1387 | 4.6505 |
| 127 | 19.200 | 3.1531 | 3.0142 | 0.1389 | 4.6090 |
| 128 | 19.400 | 3.1845 | 3.0454 | 0.1391 | 4.5663 |
| 129 | 19.600 | 3.2159 | 3.0767 | 0.1391 | 4.5223 |
| 130 | 19.800 | 3.2472 | 3.1081 | 0.1392 | 4.4772 |
| 131 | 20.000 | 3.2786 | 3.1395 | 0.1391 | 4.4307 |
| 132 | 20.200 | 3.3099 | 3.1709 | 0.1390 | 4.3831 |
| 133 | 20.400 | 3.3411 | 3.2023 | 0.1388 | 4.3342 |
| 134 | 20.600 | 3.3723 | 3.2338 | 0.1385 | 4.2841 |
| 135 | 20.800 | 3.4035 | 3.2653 | 0.1382 | 4.2328 |
| 136 | 21.000 | 3.4347 | 3.2969 | 0.1378 | 4.1802 |
| 137 | 21.200 | 3.4658 | 3.3285 | 0.1373 | 4.1265 |
| 138 | 21.400 | 3.4969 | 3.3601 | 0.1368 | 4.0714 |
| 139 | 21.420 | 3.5000 | 3.3633 | 0.1367 | 4.0645 |
| 140 | 21.600 | 3.5279 | 3.3917 | 0.1362 | 4.0151 |
| 141 | 21.800 | 3.5589 | 3.4234 | 0.1355 | 3.9576 |
| 142 | 22.000 | 3.5898 | 3.4551 | 0.1347 | 3.8988 |
| 143 | 22.200 | 3.6207 | 3.4869 | 0.1338 | 3.8386 |
| 144 | 22.400 | 3.6515 | 3.5186 | 0.1329 | 3.7772 |
| 145 | 22.600 | 3.6823 | 3.5504 | 0.1319 | 3.7144 |
| 146 | 22.800 | 3.7130 | 3.5823 | 0.1308 | 3.6503 |
| 147 | 23.000 | 3.7437 | 3.6141 | 0.1296 | 3.5848 |
| 148 | 23.200 | 3.7742 | 3.6460 | 0.1283 | 3.5179 |
| 149 | 23.400 | 3.8047 | 3.6779 | 0.1269 | 3.4495 |
| 150 | 23.600 | 3.8351 | 3.7098 | 0.1254 | 3.3797 |
| 151 | 23.800 | 3.8655 | 3.7417 | 0.1238 | 3.3084 |
| 152 | 24.000 | 3.8958 | 3.7737 | 0.1221 | 3.2356 |
| 153 | 24.200 | 3.9259 | 3.8056 | 0.1203 | 3.1611 |
| 154 | 24.400 | 3.9560 | 3.8376 | 0.1184 | 3.0851 |
| 155 | 24.600 | 3.9860 | 3.8696 | 0.1164 | 3.0074 |
| 156 | 24.694 | 4.0000 | 3.8846 | 0.1154 | 2.9707 |
| 157 | 24.800 | 4.0159 | 3.9016 | 0.1142 | 2.9280 |
| 158 | 25.000 | 4.0457 | 3.9337 | 0.1120 | 2.8470 |
| 159 | 25.200 | 4.0753 | 3.9657 | 0.1096 | 2.7642 |
| 160 | 25.400 | 4.1049 | 3.9978 | 0.1071 | 2.6798 |

Table 64

FIG. 88

| Design # | SNR | Opt. Cap | Std. Cap | Gain [bits] | Gain % |
|---|---|---|---|---|---|
| 161 | 25.600 | 4.1343 | 4.0298 | 0.1045 | 2.5936 |
| 162 | 25.800 | 4.1636 | 4.0618 | 0.1018 | 2.5059 |
| 163 | 26.000 | 4.1928 | 4.0938 | 0.0989 | 2.4166 |
| 164 | 26.200 | 4.2218 | 4.1258 | 0.0960 | 2.3259 |
| 165 | 26.400 | 4.2507 | 4.1578 | 0.0929 | 2.2339 |
| 166 | 26.600 | 4.2793 | 4.1896 | 0.0897 | 2.1408 |
| 167 | 26.800 | 4.3079 | 4.2214 | 0.0864 | 2.0470 |
| 168 | 27.000 | 4.3362 | 4.2531 | 0.0830 | 1.9525 |
| 169 | 27.200 | 4.3643 | 4.2847 | 0.0796 | 1.8579 |
| 170 | 27.400 | 4.3922 | 4.3161 | 0.0761 | 1.7634 |
| 171 | 27.600 | 4.4199 | 4.3473 | 0.0726 | 1.6694 |
| 172 | 27.800 | 4.4473 | 4.3782 | 0.0690 | 1.5763 |
| 173 | 28.000 | 4.4744 | 4.4089 | 0.0655 | 1.4846 |
| 174 | 28.192 | 4.5000 | 4.4380 | 0.0620 | 1.3970 |
| 175 | 28.200 | 4.5011 | 4.4392 | 0.0619 | 1.3945 |
| 176 | 28.400 | 4.5276 | 4.4692 | 0.0584 | 1.3065 |
| 177 | 28.600 | 4.5536 | 4.4987 | 0.0549 | 1.2209 |
| 178 | 28.800 | 4.5793 | 4.5277 | 0.0515 | 1.1379 |
| 179 | 29.000 | 4.6044 | 4.5562 | 0.0482 | 1.0577 |
| 180 | 29.200 | 4.6290 | 4.5841 | 0.0450 | 0.9806 |
| 181 | 29.400 | 4.6531 | 4.6113 | 0.0418 | 0.9067 |
| 182 | 29.600 | 4.6765 | 4.6378 | 0.0388 | 0.8361 |
| 183 | 29.800 | 4.6993 | 4.6635 | 0.0359 | 0.7687 |
| 184 | 30.000 | 4.7214 | 4.6884 | 0.0330 | 0.7048 |
| 185 | 30.200 | 4.7427 | 4.7124 | 0.0304 | 0.6442 |
| 186 | 30.400 | 4.7632 | 4.7354 | 0.0278 | 0.5870 |
| 187 | 30.600 | 4.7829 | 4.7575 | 0.0254 | 0.5332 |
| 188 | 30.800 | 4.8017 | 4.7786 | 0.0231 | 0.4826 |
| 189 | 31.000 | 4.8196 | 4.7987 | 0.0209 | 0.4352 |
| 190 | 31.200 | 4.8366 | 4.8177 | 0.0188 | 0.3910 |
| 191 | 31.400 | 4.8526 | 4.8356 | 0.0169 | 0.3500 |
| 192 | 31.600 | 4.8676 | 4.8525 | 0.0151 | 0.3119 |
| 193 | 31.800 | 4.8817 | 4.8682 | 0.0135 | 0.2768 |
| 194 | 32.000 | 4.8948 | 4.8828 | 0.0119 | 0.2445 |
| 195 | 32.200 | 4.9069 | 4.8964 | 0.0105 | 0.2149 |
| 196 | 32.400 | 4.9181 | 4.9088 | 0.0092 | 0.1880 |
| 197 | 32.600 | 4.9283 | 4.9203 | 0.0080 | 0.1636 |
| 198 | 32.800 | 4.9376 | 4.9307 | 0.0070 | 0.1415 |
| 199 | 33.000 | 4.9461 | 4.9401 | 0.0060 | 0.1217 |
| 200 | 33.200 | 4.9537 | 4.9485 | 0.0051 | 0.1041 |

Table 65

FIG. 89

| Design # | SNR | Opt. Cap | Std. Cap | Gain [bits] | Gain % |
|---|---|---|---|---|---|
| 201 | 33.400 | 4.9605 | 4.9561 | 0.0044 | 0.0884 |
| 202 | 33.600 | 4.9665 | 4.9628 | 0.0037 | 0.0746 |
| 203 | 33.800 | 4.9718 | 4.9687 | 0.0031 | 0.0625 |
| 204 | 34.000 | 4.9765 | 4.9739 | 0.0026 | 0.0520 |
| 205 | 34.200 | 4.9805 | 4.9784 | 0.0021 | 0.0429 |
| 206 | 34.400 | 4.9840 | 4.9823 | 0.0017 | 0.0351 |
| 207 | 34.600 | 4.9870 | 4.9856 | 0.0014 | 0.0285 |
| 208 | 34.800 | 4.9895 | 4.9884 | 0.0011 | 0.0229 |
| 209 | 35.000 | 4.9916 | 4.9907 | 0.0009 | 0.0183 |
| 210 | 35.200 | 4.9934 | 4.9927 | 0.0007 | 0.0144 |
| 211 | 35.400 | 4.9948 | 4.9943 | 0.0006 | 0.0112 |
| 212 | 35.600 | 4.9960 | 4.9956 | 0.0004 | 0.0087 |

Table 66

FIG. 90

|  | Label | | | | | | | |
|---|---|---|---|---|---|---|---|---|
|  | 0 | 1 | 2 | 3 | 4 | 5 | 6 | 7 |
| Design # | | | | | | | | |
| 1 | -45.343 | -24.394 | -22.729 | -22.548 | -19.985 | -18.269 | -17.663 | -14.325 |
| 2 | -45.283 | -24.883 | -23.866 | -21.906 | -18.916 | -18.279 | -17.226 | -15.598 |
| 3 | -45.204 | -23.374 | -22.109 | -19.418 | -20.610 | -22.694 | -19.681 | -19.323 |
| 4 | -45.358 | -20.100 | -20.409 | -20.348 | -20.339 | -20.192 | -20.138 | -20.147 |
| 5 | -45.157 | -29.835 | -16.217 | -16.186 | -16.191 | -16.174 | -16.180 | -16.171 |
| 6 | -45.052 | -27.227 | -26.705 | -14.338 | -14.246 | -14.277 | -14.357 | -14.108 |
| 7 | -45.255 | -18.839 | -23.089 | -23.230 | -19.868 | -21.696 | -21.424 | -13.250 |
| 8 | -24.362 | -45.114 | -22.442 | -22.568 | -19.567 | -15.644 | 3.330 | -1.541 |
| 9 | -45.303 | -21.093 | -20.986 | -19.939 | -20.641 | -20.205 | -20.253 | -19.419 |
| 10 | -45.073 | -21.391 | -21.412 | -21.316 | -21.414 | -21.401 | -21.433 | -21.295 |
| 11 | -45.215 | -21.016 | -21.354 | -21.801 | -21.401 | -21.841 | -20.198 | -16.773 |
| 12 | -45.219 | -19.542 | -19.569 | -20.712 | -21.194 | -20.510 | -20.220 | -21.190 |
| 13 | -17.864 | -45.095 | -24.540 | -22.942 | -23.784 | -18.452 | -13.887 | -17.940 |
| 14 | -45.158 | -20.872 | -20.650 | -20.889 | -20.103 | -20.425 | -20.291 | -20.430 |
| 15 | -45.118 | -20.368 | -20.347 | -20.452 | -20.577 | -20.637 | -20.511 | -20.575 |
| 16 | -45.172 | -20.834 | -19.751 | -20.049 | -20.844 | -19.309 | -20.258 | -21.056 |
| 17 | -45.108 | -20.531 | -20.445 | -20.446 | -20.492 | -20.508 | -20.508 | -20.518 |
| 18 | -45.094 | -22.132 | -22.129 | -21.433 | -21.433 | -21.450 | -16.562 | -16.560 |
| 19 | -45.032 | -20.649 | -20.648 | -20.648 | -20.650 | -20.558 | -20.552 | -20.553 |
| 20 | -45.043 | -20.498 | -20.551 | -20.740 | -20.638 | -20.664 | -20.223 | -20.505 |
| 21 | -44.984 | -20.591 | -20.757 | -20.602 | -20.753 | -20.530 | -20.561 | -20.568 |
| 22 | -44.957 | -20.684 | -20.684 | -20.657 | -20.646 | -20.650 | -20.652 | -20.652 |
| 23 | -44.931 | -20.682 | -20.682 | -20.682 | -20.682 | -20.682 | -20.682 | -20.672 |
| 24 | -44.914 | -20.681 | -20.681 | -20.681 | -20.681 | -20.681 | -20.681 | -20.681 |
| 25 | -44.884 | -20.700 | -20.710 | -20.704 | -20.706 | -20.699 | -20.706 | -20.712 |
| 26 | -44.850 | -20.750 | -20.740 | -20.740 | -20.740 | -20.740 | -20.740 | -20.740 |
| 27 | -44.829 | -20.756 | -20.756 | -20.756 | -20.756 | -20.756 | -20.756 | -20.756 |
| 28 | -44.817 | -20.760 | -20.760 | -20.760 | -20.762 | -20.762 | -20.762 | -20.752 |
| 29 | -44.805 | -20.765 | -20.764 | -20.764 | -20.764 | -20.762 | -20.761 | -20.764 |
| 30 | -44.786 | -20.777 | -20.781 | -20.775 | -20.772 | -20.794 | -20.766 | -20.790 |
| 31 | -44.736 | -21.134 | -21.019 | -21.139 | -21.139 | -21.111 | -21.114 | -21.123 |
| 32 | -44.702 | -21.199 | -21.183 | -21.183 | -21.183 | -21.183 | -21.183 | -21.183 |
| 33 | -44.668 | -21.250 | -21.250 | -21.247 | -21.249 | -21.253 | -21.255 | -21.248 |
| 34 | -44.635 | -21.306 | -21.306 | -21.306 | -21.306 | -21.306 | -21.301 | -21.300 |
| 35 | -44.604 | -21.353 | -21.353 | -21.353 | -21.353 | -21.351 | -21.351 | -21.351 |
| 36 | -44.573 | -21.391 | -21.391 | -21.391 | -21.391 | -21.395 | -21.395 | -21.395 |
| 37 | -44.543 | -21.431 | -21.430 | -21.430 | -21.430 | -21.430 | -21.428 | -21.428 |
| 38 | -44.486 | -21.617 | -21.657 | -21.541 | -21.590 | -21.608 | -21.546 | -21.516 |
| 39 | -44.404 | -21.764 | -21.767 | -21.777 | -21.785 | -21.778 | -21.774 | -21.770 |
| 40 | -44.380 | -21.767 | -21.794 | -21.780 | -21.780 | -21.788 | -21.789 | -21.789 |

Table 67

FIG. 91

|  | Label | | | | | | | |
|---|---|---|---|---|---|---|---|---|
|  | 8 | 9 | 10 | 11 | 12 | 13 | 14 | 15 |
| Design # | | | | | | | | |
| 1 | -13.635 | -11.934 | -8.649 | -6.824 | -5.114 | -4.635 | -3.002 | -1.841 |
| 2 | -12.831 | -10.336 | -9.442 | -8.114 | -5.012 | -3.798 | -3.272 | -2.251 |
| 3 | -4.779 | -3.027 | -3.096 | -2.272 | -0.919 | -1.470 | -2.114 | -0.429 |
| 4 | -20.325 | -7.492 | -2.105 | -1.838 | -1.625 | -1.116 | -1.116 | -1.127 |
| 5 | -16.199 | -16.203 | -13.514 | -11.005 | -8.551 | -7.350 | -4.689 | -3.100 |
| 6 | -14.280 | -14.036 | -14.051 | -14.399 | -12.854 | -1.255 | -0.433 | 1.263 |
| 7 | -11.272 | -14.648 | -4.877 | -6.864 | -0.261 | -3.154 | -4.705 | -2.791 |
| 8 | 2.680 | -0.839 | -22.596 | -17.342 | -9.498 | -9.135 | -3.810 | -5.056 |
| 9 | -19.872 | -5.248 | -1.888 | -1.112 | -1.283 | -1.245 | -1.367 | -0.633 |
| 10 | -4.409 | -4.056 | -3.087 | -3.109 | -3.056 | -2.997 | -2.974 | -2.994 |
| 11 | -15.579 | -10.382 | -7.645 | -2.175 | -1.624 | -0.887 | -1.247 | -1.441 |
| 12 | -19.896 | -8.370 | -2.717 | -2.138 | -0.283 | -0.277 | -0.303 | -1.010 |
| 13 | -15.407 | -15.505 | -3.399 | -2.573 | -3.270 | -3.907 | 2.693 | 0.560 |
| 14 | -20.141 | -4.751 | -2.071 | -1.303 | -0.418 | -0.959 | -1.139 | -0.930 |
| 15 | -20.770 | -2.574 | -0.053 | -1.009 | -1.099 | -0.986 | -1.226 | -0.812 |
| 16 | -20.343 | -12.201 | 0.377 | 1.140 | -0.046 | 1.530 | 0.760 | 0.683 |
| 17 | -20.495 | -7.614 | -1.738 | -1.162 | -0.583 | -0.540 | -0.526 | -0.545 |
| 18 | -16.560 | -16.560 | -0.513 | 0.198 | 0.226 | 0.659 | 1.095 | 1.087 |
| 19 | -20.552 | -1.210 | -0.755 | -0.754 | -0.754 | -0.756 | -0.756 | -0.756 |
| 20 | -20.469 | -8.598 | 1.013 | 1.057 | 0.913 | 0.724 | 0.947 | 0.744 |
| 21 | -20.712 | -1.009 | -0.885 | -1.016 | -0.934 | -0.885 | -0.996 | -0.906 |
| 22 | -20.652 | -0.569 | -0.569 | -0.569 | -0.569 | -0.569 | -0.569 | -0.532 |
| 23 | -20.673 | -0.459 | -0.460 | -0.459 | -0.459 | -0.459 | -0.459 | -0.459 |
| 24 | -20.681 | -5.138 | 0.198 | 0.198 | 0.198 | 0.198 | 0.198 | 0.198 |
| 25 | -20.742 | -4.073 | 0.302 | 0.292 | 0.297 | 0.291 | 0.302 | 0.293 |
| 26 | -20.730 | -0.420 | -0.380 | -0.360 | -0.320 | -0.300 | -0.280 | -0.230 |
| 27 | -20.756 | -0.082 | 0.006 | 0.006 | 0.006 | 0.006 | 0.006 | 0.006 |
| 28 | -20.752 | -0.007 | -0.007 | -0.007 | -0.010 | 0.001 | -0.010 | 0.000 |
| 29 | -20.754 | -0.001 | -0.002 | -0.001 | -0.002 | -0.003 | -0.004 | -0.002 |
| 30 | -20.715 | 0.011 | 0.013 | 0.011 | 0.014 | 0.012 | 0.011 | 0.010 |
| 31 | -18.293 | 0.011 | -0.004 | 0.004 | -0.005 | 0.008 | -0.020 | -0.001 |
| 32 | -17.778 | -0.004 | -0.004 | -0.004 | -0.004 | -0.004 | -0.004 | 0.003 |
| 33 | -17.315 | -0.003 | 0.000 | -0.004 | 0.001 | 0.000 | -0.002 | 0.003 |
| 34 | -16.932 | -0.005 | -0.005 | 0.001 | 0.001 | 0.001 | 0.001 | 0.001 |
| 35 | -16.587 | -0.013 | -0.010 | -0.008 | -0.009 | 0.004 | 0.004 | 0.004 |
| 36 | -16.301 | -0.017 | -0.011 | -0.011 | 0.004 | 0.004 | 0.004 | 0.004 |
| 37 | -16.041 | -0.004 | -0.004 | -0.004 | -0.004 | -0.004 | -0.004 | -0.004 |
| 38 | -13.874 | -3.119 | -3.130 | -2.370 | 0.046 | 0.224 | 0.372 | -0.010 |
| 39 | -4.540 | -4.609 | -4.579 | -4.575 | -4.642 | -4.538 | -4.465 | -4.463 |
| 40 | -4.516 | -4.521 | -4.550 | -4.546 | -4.540 | -4.557 | -4.537 | -4.536 |

Table 68

FIG. 92

|  | Label | | | | | | | |
|---|---|---|---|---|---|---|---|---|
|  | 16 | 17 | 18 | 19 | 20 | 21 | 22 | 23 |
| Design # | | | | | | | | |
| 1 | 0.559 | 0.878 | 1.628 | 7.378 | 8.322 | 13.022 | 13.872 | 13.904 |
| 2 | -1.704 | 3.042 | 3.725 | 7.812 | 9.088 | 9.252 | 9.824 | 13.966 |
| 3 | -3.795 | -5.863 | -7.934 | -6.868 | 18.715 | 18.996 | 20.161 | 15.141 |
| 4 | -1.369 | -0.980 | -0.902 | -0.750 | -0.105 | 11.883 | 15.567 | 15.460 |
| 5 | 6.651 | 7.690 | 12.424 | 12.446 | 12.429 | 12.433 | 12.427 | 12.454 |
| 6 | 1.620 | 3.323 | 3.412 | 4.223 | 6.954 | 8.333 | 13.210 | 16.400 |
| 7 | 0.423 | -0.188 | 1.768 | 1.979 | 5.146 | 12.533 | 19.507 | 17.546 |
| 8 | -5.326 | -5.776 | -6.925 | 8.076 | -0.329 | 7.836 | 21.080 | 19.904 |
| 9 | -1.159 | -2.404 | -1.143 | -1.834 | 18.015 | -1.591 | 16.255 | 16.368 |
| 10 | -3.042 | -3.091 | -3.066 | -2.633 | 4.068 | 9.019 | 19.530 | 19.493 |
| 11 | 1.066 | 1.431 | 1.863 | 2.221 | 3.093 | 5.760 | 8.956 | 15.215 |
| 12 | -0.833 | -1.102 | 1.022 | 0.334 | 1.654 | 5.346 | 8.910 | 19.145 |
| 13 | -1.453 | -0.557 | -1.031 | 4.251 | -1.363 | 19.205 | 23.735 | 17.787 |
| 14 | -0.890 | -0.800 | -0.582 | 0.426 | 0.057 | 2.811 | 14.025 | 15.501 |
| 15 | -0.834 | -0.404 | -0.640 | -0.676 | -0.608 | 0.390 | 12.322 | 20.810 |
| 16 | 1.356 | 1.543 | 0.606 | 0.849 | 0.368 | 0.937 | 0.269 | 20.383 |
| 17 | -0.104 | -0.019 | 0.225 | 0.802 | 2.289 | 3.473 | 5.851 | 20.505 |
| 18 | 1.097 | 1.095 | 1.102 | 1.095 | 1.095 | 1.095 | 1.090 | 19.720 |
| 19 | -0.756 | -0.755 | -0.494 | -0.414 | -0.413 | -0.174 | 9.614 | 20.386 |
| 20 | 0.904 | 0.792 | 0.627 | 0.791 | 0.617 | -0.641 | -0.520 | 20.637 |
| 21 | -1.020 | -0.917 | -0.884 | -1.015 | 5.030 | 5.165 | 20.457 | 20.734 |
| 22 | -0.569 | -0.532 | -0.545 | -0.557 | -0.542 | -0.072 | 7.122 | 20.594 |
| 23 | -0.459 | -0.459 | -0.460 | -0.459 | -0.459 | -0.459 | 6.213 | 20.636 |
| 24 | 0.238 | 0.249 | 0.653 | 0.668 | 0.668 | 0.668 | 0.668 | 20.696 |
| 25 | 0.303 | 0.298 | 0.313 | 0.318 | 0.321 | 0.324 | 0.351 | 20.731 |
| 26 | -0.160 | -0.070 | -0.030 | -0.030 | -0.010 | 0.010 | 2.590 | 20.730 |
| 27 | 0.006 | 0.006 | 0.006 | 0.006 | 0.006 | 0.006 | 0.006 | 20.734 |
| 28 | -0.008 | 0.005 | 0.010 | 0.006 | 0.006 | 0.011 | 0.009 | 20.762 |
| 29 | -0.003 | -0.003 | -0.003 | -0.003 | -0.003 | 0.014 | 0.016 | 20.734 |
| 30 | 0.009 | 0.006 | 0.008 | 0.014 | 0.012 | 0.010 | 0.016 | 18.707 |
| 31 | -0.001 | 0.017 | -0.021 | 0.023 | -0.011 | 21.115 | 21.080 | -0.032 |
| 32 | 0.003 | 0.003 | 0.003 | 0.003 | 0.003 | 0.003 | 0.003 | 17.791 |
| 33 | -0.001 | 0.000 | 0.001 | 0.000 | 0.001 | 0.001 | 0.003 | 17.320 |
| 34 | 0.001 | 0.001 | 0.001 | 0.001 | 0.001 | 0.001 | 0.002 | 16.920 |
| 35 | 0.004 | 0.004 | 0.004 | 0.004 | 0.004 | 0.004 | 0.004 | 16.590 |
| 36 | 0.004 | 0.003 | 0.003 | 0.003 | 0.003 | 0.003 | 0.003 | 16.298 |
| 37 | -0.004 | -0.004 | -0.004 | -0.004 | 0.015 | 0.015 | 0.015 | 16.041 |
| 38 | -0.001 | -0.158 | -0.092 | 0.249 | 2.273 | 2.631 | 3.034 | 13.943 |
| 39 | 4.450 | 4.538 | 4.602 | 4.675 | 4.557 | 4.555 | 4.550 | 4.485 |
| 40 | 4.533 | 4.547 | 4.538 | 4.524 | 4.524 | 4.538 | 4.568 | 4.532 |

Table 69

FIG. 93

|  | Label | | | | | | | |
|---|---|---|---|---|---|---|---|---|
|  | 24 | 25 | 26 | 27 | 28 | 29 | 30 | 31 |
| Design # | | | | | | | | |
| 1 | 16.228 | 16.944 | 17.064 | 17.457 | 18.036 | 23.620 | 26.682 | 45.294 |
| 2 | 17.928 | 17.982 | 18.192 | 19.553 | 20.125 | 20.783 | 26.101 | 45.344 |
| 3 | 19.782 | 17.858 | 12.125 | 20.371 | 5.939 | 19.767 | 20.586 | 45.539 |
| 4 | 18.190 | 18.596 | 18.715 | 18.637 | 18.711 | 22.562 | 24.189 | 45.372 |
| 5 | 12.433 | 12.435 | 12.444 | 12.434 | 12.433 | 28.408 | 28.406 | 44.777 |
| 6 | 18.299 | 18.306 | 18.313 | 18.364 | 18.214 | 18.234 | 27.926 | 45.223 |
| 7 | 16.584 | 18.303 | 17.321 | 14.171 | 18.208 | 19.779 | 26.886 | 45.258 |
| 8 | 14.532 | 23.670 | 18.114 | 16.877 | 22.057 | 16.800 | 17.548 | 45.369 |
| 9 | 17.625 | 16.310 | 16.764 | 16.787 | 17.047 | 21.555 | 26.663 | 45.231 |
| 10 | 19.360 | 19.413 | 19.361 | 19.445 | 19.349 | 19.391 | 19.391 | 45.431 |
| 11 | 19.561 | 21.712 | 21.119 | 21.344 | 20.929 | 21.212 | 19.875 | 45.222 |
| 12 | 21.093 | 20.712 | 20.654 | 19.848 | 20.639 | 19.954 | 20.537 | 45.233 |
| 13 | 25.021 | 18.153 | 20.805 | 16.034 | 13.962 | 13.485 | 12.121 | 45.159 |
| 14 | 19.945 | 21.365 | 21.592 | 20.221 | 20.547 | 20.507 | 20.601 | 45.201 |
| 15 | 20.279 | 20.327 | 20.400 | 20.168 | 20.126 | 20.118 | 20.137 | 45.198 |
| 16 | 20.621 | 20.677 | 20.467 | 20.558 | 20.568 | 20.490 | 20.580 | 45.102 |
| 17 | 20.519 | 20.515 | 20.448 | 20.613 | 20.475 | 20.513 | 20.556 | 45.098 |
| 18 | 20.462 | 20.637 | 20.639 | 20.641 | 20.665 | 20.633 | 21.019 | 45.074 |
| 19 | 20.448 | 20.510 | 20.513 | 20.511 | 20.509 | 20.514 | 20.507 | 45.077 |
| 20 | 20.696 | 20.484 | 20.699 | 20.605 | 20.653 | 20.514 | 20.663 | 45.008 |
| 21 | 20.547 | 20.590 | 20.655 | 20.626 | 20.600 | 0.532 | 20.590 | 45.000 |
| 22 | 20.596 | 20.604 | 20.603 | 20.607 | 20.627 | 20.628 | 20.636 | 44.979 |
| 23 | 20.637 | 20.636 | 20.636 | 20.651 | 20.661 | 20.661 | 20.661 | 44.947 |
| 24 | 20.696 | 20.697 | 20.697 | 20.697 | 20.697 | 20.707 | 20.707 | 44.905 |
| 25 | 20.710 | 20.714 | 20.719 | 20.714 | 20.717 | 20.743 | 20.708 | 44.879 |
| 26 | 20.730 | 20.724 | 20.736 | 20.742 | 20.742 | 20.738 | 20.746 | 44.852 |
| 27 | 20.747 | 20.758 | 20.758 | 20.758 | 20.758 | 20.762 | 20.768 | 44.829 |
| 28 | 20.757 | 20.757 | 20.759 | 20.758 | 20.760 | 20.762 | 20.757 | 44.817 |
| 29 | 20.733 | 20.760 | 20.760 | 20.760 | 20.761 | 20.760 | 20.830 | 44.805 |
| 30 | 21.012 | 21.041 | 21.063 | 21.047 | 21.040 | 21.063 | 21.058 | 44.767 |
| 31 | 18.509 | 21.040 | 21.141 | 21.071 | 20.994 | -0.005 | 21.154 | 44.740 |
| 32 | 21.184 | 21.184 | 21.184 | 21.184 | 21.184 | 21.184 | 21.184 | 44.702 |
| 33 | 21.240 | 21.248 | 21.251 | 21.252 | 21.254 | 21.250 | 21.252 | 44.668 |
| 34 | 21.305 | 21.305 | 21.305 | 21.305 | 21.305 | 21.305 | 21.309 | 44.635 |
| 35 | 21.350 | 21.352 | 21.352 | 21.352 | 21.353 | 21.352 | 21.352 | 44.604 |
| 36 | 21.379 | 21.387 | 21.395 | 21.399 | 21.400 | 21.398 | 21.394 | 44.573 |
| 37 | 21.427 | 21.427 | 21.427 | 21.432 | 21.432 | 21.432 | 21.432 | 44.543 |
| 38 | 21.535 | 21.638 | 21.561 | 21.528 | 21.640 | 21.580 | 21.575 | 44.487 |
| 39 | 21.768 | 21.771 | 21.771 | 21.773 | 21.761 | 21.796 | 21.773 | 44.404 |
| 40 | 21.783 | 21.784 | 21.779 | 21.783 | 21.786 | 21.784 | 21.787 | 44.380 |

Table 70

FIG. 94

|  | Label | | | | | | | |
|---|---|---|---|---|---|---|---|---|
|  | 0 | 1 | 2 | 3 | 4 | 5 | 6 | 7 |
| Design # | | | | | | | | |
| 41 | -44.331 | -22.050 | -22.075 | -22.065 | -22.069 | -22.039 | -22.053 | -20.292 |
| 42 | -44.215 | -22.590 | -22.587 | -22.587 | -22.587 | -22.587 | -22.586 | -15.296 |
| 43 | -44.114 | -22.822 | -22.823 | -22.822 | -22.822 | -22.821 | -22.821 | -7.777 |
| 44 | -44.082 | -22.838 | -22.838 | -22.838 | -22.838 | -22.838 | -22.838 | -6.530 |
| 45 | -44.052 | -22.851 | -22.851 | -22.851 | -22.851 | -22.849 | -22.847 | -6.521 |
| 46 | -43.976 | -23.394 | -23.394 | -23.392 | -23.391 | -23.391 | -19.819 | -6.612 |
| 47 | -43.890 | -23.657 | -23.657 | -23.657 | -23.657 | -23.655 | -17.939 | -6.749 |
| 48 | -43.769 | -23.993 | -23.993 | -23.992 | -23.992 | -23.992 | -12.510 | -8.124 |
| 49 | -43.747 | -23.932 | -23.932 | -23.932 | -23.932 | -23.932 | -15.409 | -7.000 |
| 50 | -43.690 | -24.010 | -24.010 | -24.010 | -24.010 | -24.010 | -14.480 | -7.110 |
| 51 | -43.685 | -24.022 | -24.021 | -24.021 | -24.021 | -24.021 | -14.359 | -7.122 |
| 52 | -43.628 | -24.091 | -24.091 | -24.091 | -24.091 | -24.091 | -13.389 | -7.240 |
| 53 | -43.575 | -24.146 | -24.148 | -24.147 | -24.146 | -24.147 | -12.479 | -7.354 |
| 54 | -43.526 | -24.191 | -24.191 | -24.191 | -24.191 | -24.191 | -11.630 | -7.457 |
| 55 | -43.480 | -24.223 | -24.225 | -24.227 | -24.223 | -24.227 | -7.537 | -7.562 |
| 56 | -43.435 | -24.253 | -24.251 | -24.252 | -24.253 | -24.252 | -8.209 | -8.208 |
| 57 | -43.393 | -24.270 | -24.269 | -24.269 | -24.269 | -24.269 | -8.182 | -8.170 |
| 58 | -43.323 | -24.795 | -24.795 | -24.795 | -24.795 | -21.912 | -8.434 | -8.432 |
| 59 | -43.224 | -25.171 | -25.171 | -25.170 | -25.170 | -19.536 | -9.211 | -9.200 |
| 60 | -43.143 | -25.366 | -25.366 | -25.366 | -25.366 | -17.669 | -10.066 | -10.066 |
| 61 | -43.058 | -25.545 | -25.545 | -25.545 | -25.545 | -11.874 | -11.891 | -11.892 |
| 62 | -43.009 | -25.568 | -25.568 | -25.568 | -25.569 | -11.884 | -11.875 | -11.875 |
| 63 | -42.959 | -25.586 | -25.586 | -25.586 | -25.586 | -11.885 | -11.885 | -11.885 |
| 64 | -42.907 | -25.604 | -25.604 | -25.604 | -25.604 | -11.890 | -11.889 | -11.890 |
| 65 | -42.832 | -26.175 | -26.175 | -26.175 | -23.810 | -11.947 | -11.947 | -11.947 |
| 66 | -42.761 | -26.407 | -26.407 | -26.407 | -23.008 | -12.221 | -12.221 | -12.221 |
| 67 | -42.685 | -26.623 | -26.623 | -26.623 | -22.127 | -12.457 | -12.457 | -12.457 |
| 68 | -42.617 | -26.762 | -26.762 | -26.762 | -21.528 | -12.600 | -12.600 | -12.600 |
| 69 | -42.547 | -26.909 | -26.909 | -26.909 | -20.691 | -12.903 | -12.905 | -12.910 |
| 70 | -42.530 | -26.930 | -26.930 | -26.930 | -20.620 | -12.920 | -12.920 | -12.920 |
| 71 | -42.477 | -27.050 | -27.050 | -27.050 | -19.462 | -13.823 | -13.823 | -13.822 |
| 72 | -42.415 | -27.121 | -27.121 | -27.121 | -18.901 | -14.000 | -14.000 | -13.989 |
| 73 | -42.351 | -27.211 | -27.212 | -27.211 | -15.640 | -15.640 | -15.640 | -15.640 |
| 74 | -42.293 | -27.236 | -27.236 | -27.236 | -15.640 | -15.639 | -15.639 | -15.639 |
| 75 | -42.232 | -27.259 | -27.259 | -27.259 | -15.648 | -15.648 | -15.648 | -15.648 |
| 76 | -42.169 | -27.280 | -27.279 | -27.279 | -15.663 | -15.663 | -15.663 | -15.663 |
| 77 | -42.094 | -27.964 | -27.964 | -25.850 | -15.745 | -15.745 | -15.745 | -15.745 |
| 78 | -42.024 | -28.222 | -28.222 | -25.276 | -15.825 | -15.826 | -15.826 | -15.825 |
| 79 | -41.959 | -28.366 | -28.366 | -24.979 | -15.860 | -15.858 | -15.860 | -15.860 |
| 80 | -41.887 | -28.620 | -28.620 | -24.173 | -16.615 | -16.615 | -16.616 | -16.615 |

Table 71

FIG. 95

| Design # | Label | | | | | | | |
|---|---|---|---|---|---|---|---|---|
| | 8 | 9 | 10 | 11 | 12 | 13 | 14 | 15 |
| 41 | -3.639 | -3.628 | -3.647 | -3.629 | -3.641 | -3.634 | -3.627 | -3.653 |
| 42 | -4.609 | -4.609 | -4.609 | -4.609 | -4.609 | -4.609 | -4.609 | -4.609 |
| 43 | -6.370 | -6.373 | -6.369 | -6.369 | -6.369 | -6.370 | -6.368 | -6.370 |
| 44 | -6.527 | -6.527 | -6.527 | -6.527 | -6.527 | -6.527 | -6.524 | -6.524 |
| 45 | -6.521 | -6.521 | -6.521 | -6.521 | -6.521 | -6.521 | -6.521 | -6.521 |
| 46 | -6.612 | -6.612 | -6.612 | -6.612 | -6.612 | -6.610 | -6.610 | -6.610 |
| 47 | -6.749 | -6.749 | -6.749 | -6.748 | -6.748 | -6.747 | -6.746 | -6.744 |
| 48 | -8.124 | -8.124 | -8.124 | -8.124 | -8.121 | -8.121 | -8.121 | 6.031 |
| 49 | -7.000 | -7.000 | -7.000 | -7.000 | -7.000 | -7.000 | -7.000 | -6.998 |
| 50 | -7.110 | -7.110 | -7.110 | -7.110 | -7.100 | -7.100 | -7.100 | -7.100 |
| 51 | -7.122 | -7.122 | -7.122 | -7.122 | -7.122 | -7.122 | -7.116 | -7.114 |
| 52 | -7.240 | -7.239 | -7.239 | -7.239 | -7.239 | -7.234 | -7.234 | -7.233 |
| 53 | -7.312 | -7.406 | -7.344 | -7.380 | -7.341 | -7.346 | -7.335 | -7.327 |
| 54 | -7.457 | -7.457 | -7.457 | -7.457 | -7.457 | -7.457 | -7.450 | -7.451 |
| 55 | -7.675 | -7.559 | -7.013 | -7.420 | -10.845 | -7.658 | -7.783 | -7.752 |
| 56 | -8.209 | -8.208 | -8.209 | -8.209 | -8.206 | -8.172 | -8.158 | -4.855 |
| 57 | -8.166 | -8.166 | -8.166 | -8.166 | -8.166 | -8.166 | -8.166 | -5.244 |
| 58 | -8.432 | -8.432 | -8.432 | -8.432 | -8.432 | -8.432 | -8.432 | 0.000 |
| 59 | -9.200 | -9.200 | -9.200 | -9.200 | -9.200 | -9.200 | 0.506 | 0.519 |
| 60 | -10.066 | -10.066 | -10.063 | -10.057 | -10.057 | -0.011 | -0.010 | 0.005 |
| 61 | -11.893 | -11.892 | -11.892 | -11.892 | -0.308 | -0.308 | -0.308 | -0.310 |
| 62 | -11.874 | -11.874 | -11.874 | -11.870 | -2.509 | 0.345 | 0.345 | 0.345 |
| 63 | -11.884 | -11.885 | -11.885 | -11.885 | -0.377 | -0.376 | -0.376 | -0.371 |
| 64 | -11.890 | -11.890 | -11.890 | -11.890 | -0.365 | -0.365 | -0.365 | -0.365 |
| 65 | -11.947 | -11.947 | -11.947 | -11.946 | -0.003 | 0.000 | 0.000 | 0.000 |
| 66 | -12.221 | -12.221 | -12.221 | -10.474 | -0.012 | -0.012 | -0.012 | -0.012 |
| 67 | -12.456 | -12.456 | -12.456 | -9.335 | 0.000 | 0.000 | 0.000 | 0.000 |
| 68 | -12.600 | -12.600 | -12.600 | -8.667 | -0.002 | -0.001 | -0.001 | 0.000 |
| 69 | -12.901 | -12.897 | -12.902 | -3.081 | -3.046 | -3.034 | -3.074 | -3.000 |
| 70 | -12.910 | -12.910 | -12.910 | -3.110 | -3.080 | -3.020 | -3.000 | -2.950 |
| 71 | -13.822 | -13.823 | -5.103 | -5.055 | -5.055 | -5.054 | -5.054 | 2.768 |
| 72 | -13.987 | -13.987 | -4.360 | -4.360 | -4.360 | -4.360 | -4.360 | -4.360 |
| 73 | -15.640 | -9.495 | -4.617 | -4.616 | -4.616 | -4.617 | -4.616 | -4.614 |
| 74 | -15.640 | -9.565 | -4.609 | -4.609 | -4.609 | -4.609 | -4.609 | -4.608 |
| 75 | -15.648 | -9.562 | -4.613 | -4.613 | -4.613 | -4.613 | -4.613 | -4.613 |
| 76 | -15.663 | -9.504 | -4.627 | -4.626 | -4.626 | -4.626 | -4.626 | -4.626 |
| 77 | -15.745 | -8.854 | -4.726 | -4.724 | -4.724 | -4.724 | -4.724 | -4.724 |
| 78 | -15.825 | -6.846 | -5.638 | -5.642 | -5.644 | -5.641 | -5.659 | 0.068 |
| 79 | -15.859 | -5.840 | -5.840 | -5.840 | -5.840 | -5.840 | -5.839 | -0.179 |
| 80 | -12.278 | -6.699 | -6.692 | -6.691 | -6.694 | -6.690 | 0.001 | 0.002 |

Table 72

FIG. 96

|  | Label | | | | | | | |
|---|---|---|---|---|---|---|---|---|
|  | 16 | 17 | 18 | 19 | 20 | 21 | 22 | 23 |
| Design # | | | | | | | | |
| 41 | -3.686 | -3.668 | 6.587 | 6.464 | 6.471 | 6.465 | 6.464 | 6.507 |
| 42 | -4.609 | 6.228 | 6.228 | 6.229 | 6.229 | 6.229 | 6.246 | 6.269 |
| 43 | 5.753 | 5.801 | 6.614 | 6.773 | 6.758 | 6.762 | 6.762 | 6.750 |
| 44 | 6.524 | 6.524 | 6.524 | 6.524 | 6.528 | 6.528 | 6.528 | 6.528 |
| 45 | 6.519 | 6.519 | 6.519 | 6.519 | 6.523 | 6.523 | 6.523 | 6.523 |
| 46 | 6.611 | 6.611 | 6.611 | 6.611 | 6.611 | 6.611 | 6.611 | 6.611 |
| 47 | 6.741 | 6.746 | 6.746 | 6.749 | 6.749 | 6.749 | 6.749 | 6.749 |
| 48 | 6.031 | 6.031 | 6.031 | 6.032 | 6.032 | 6.032 | 6.033 | 6.035 |
| 49 | 7.000 | 7.000 | 7.000 | 7.000 | 7.000 | 7.000 | 7.000 | 7.000 |
| 50 | 7.100 | 7.100 | 7.100 | 7.100 | 7.110 | 7.110 | 7.110 | 7.110 |
| 51 | 7.120 | 7.120 | 7.120 | 7.121 | 7.121 | 7.121 | 7.121 | 7.121 |
| 52 | 7.237 | 7.237 | 7.237 | 7.237 | 7.237 | 7.238 | 7.238 | 7.238 |
| 53 | 7.399 | 7.365 | 7.267 | 7.327 | 7.392 | 7.354 | 7.264 | 7.414 |
| 54 | 7.444 | 7.457 | 7.457 | 7.457 | 7.457 | 7.457 | 7.457 | 7.457 |
| 55 | 7.469 | 7.260 | 7.080 | 8.013 | 10.246 | 9.165 | 7.233 | 8.013 |
| 56 | 4.856 | 8.207 | 8.190 | 8.190 | 8.202 | 8.210 | 8.186 | 8.196 |
| 57 | 5.244 | 8.168 | 8.168 | 8.168 | 8.168 | 8.168 | 8.168 | 8.168 |
| 58 | 0.000 | 8.432 | 8.432 | 8.432 | 8.432 | 8.432 | 8.432 | 8.432 |
| 59 | 0.524 | 0.524 | 3.854 | 9.711 | 9.711 | 9.711 | 9.711 | 9.711 |
| 60 | 0.005 | 0.005 | 0.005 | 10.061 | 10.061 | 10.061 | 10.064 | 10.064 |
| 61 | -0.310 | -0.311 | -0.310 | 2.201 | 11.885 | 11.885 | 11.886 | 11.885 |
| 62 | 0.345 | 0.345 | 0.345 | 0.384 | 11.884 | 11.884 | 11.885 | 11.885 |
| 63 | -0.353 | -0.353 | -0.354 | 2.624 | 11.874 | 11.874 | 11.874 | 11.874 |
| 64 | -0.365 | -0.365 | -0.340 | 2.595 | 11.879 | 11.879 | 11.879 | 11.879 |
| 65 | 0.000 | 0.000 | 0.000 | 0.002 | 11.947 | 11.947 | 11.947 | 11.947 |
| 66 | -0.012 | -0.012 | -0.012 | -0.012 | 11.972 | 11.973 | 11.975 | 11.975 |
| 67 | -0.001 | 0.000 | 0.000 | 0.002 | 9.338 | 12.455 | 12.456 | 12.456 |
| 68 | -0.001 | -0.001 | 0.002 | 0.004 | 8.664 | 12.601 | 12.601 | 12.601 |
| 69 | 2.963 | 3.151 | 3.052 | 3.030 | 3.041 | 12.913 | 12.904 | 12.896 |
| 70 | 2.900 | 2.900 | 3.040 | 3.090 | 3.240 | 12.910 | 12.910 | 12.910 |
| 71 | 2.768 | 2.768 | 2.769 | 2.767 | 2.768 | 9.507 | 13.611 | 13.611 |
| 72 | 4.357 | 4.357 | 4.362 | 4.362 | 4.362 | 4.362 | 13.979 | 13.996 |
| 73 | 4.613 | 4.617 | 4.617 | 4.617 | 4.616 | 4.617 | 9.495 | 15.639 |
| 74 | 4.607 | 4.609 | 4.610 | 4.608 | 4.608 | 4.609 | 9.565 | 15.639 |
| 75 | 4.613 | 4.613 | 4.613 | 4.613 | 4.613 | 4.614 | 9.562 | 15.647 |
| 76 | 4.626 | 4.626 | 4.626 | 4.626 | 4.626 | 4.626 | 9.504 | 15.663 |
| 77 | 4.723 | 4.724 | 4.724 | 4.724 | 4.725 | 4.725 | 8.854 | 15.745 |
| 78 | 0.039 | 4.532 | 5.978 | 6.085 | 6.071 | 6.159 | 6.139 | 15.825 |
| 79 | 0.179 | 5.839 | 5.840 | 5.839 | 5.840 | 5.841 | 5.841 | 15.859 |
| 80 | 0.002 | -0.004 | 6.686 | 6.685 | 6.689 | 6.695 | 6.709 | 12.278 |

Table 73

FIG. 97

|         | Label  |        |        |        |        |        |        |        |
|---------|--------|--------|--------|--------|--------|--------|--------|--------|
|         | 24     | 25     | 26     | 27     | 28     | 29     | 30     | 31     |
| Design # |        |        |        |        |        |        |        |        |
| 41      | 15.111 | 22.519 | 22.506 | 22.519 | 22.521 | 22.511 | 22.503 | 44.275 |
| 42      | 12.543 | 22.685 | 22.685 | 22.686 | 22.686 | 22.688 | 22.688 | 44.193 |
| 43      | 6.754  | 22.824 | 22.822 | 22.823 | 22.823 | 22.824 | 22.823 | 44.113 |
| 44      | 6.535  | 22.837 | 22.838 | 22.838 | 22.838 | 22.838 | 22.838 | 44.082 |
| 45      | 6.523  | 22.848 | 22.849 | 22.849 | 22.851 | 22.851 | 22.851 | 44.051 |
| 46      | 6.611  | 19.820 | 23.392 | 23.392 | 23.392 | 23.392 | 23.392 | 43.976 |
| 47      | 6.749  | 17.938 | 23.656 | 23.656 | 23.656 | 23.657 | 23.657 | 43.890 |
| 48      | 6.044  | 19.120 | 23.583 | 23.583 | 23.583 | 23.583 | 23.583 | 43.859 |
| 49      | 7.000  | 15.409 | 23.932 | 23.932 | 23.932 | 23.932 | 23.932 | 43.747 |
| 50      | 7.120  | 14.480 | 24.010 | 24.010 | 24.010 | 24.010 | 24.010 | 43.690 |
| 51      | 7.121  | 14.359 | 24.022 | 24.021 | 24.021 | 24.021 | 24.021 | 43.685 |
| 52      | 7.238  | 13.389 | 24.091 | 24.091 | 24.091 | 24.091 | 24.091 | 43.628 |
| 53      | 12.477 | 7.364  | 24.146 | 24.146 | 24.147 | 24.147 | 24.148 | 43.575 |
| 54      | 7.457  | 11.630 | 24.191 | 24.191 | 24.191 | 24.191 | 24.191 | 43.526 |
| 55      | 7.057  | 7.253  | 24.230 | 24.230 | 24.227 | 24.226 | 24.227 | 43.479 |
| 56      | 8.190  | 8.214  | 24.253 | 24.252 | 24.252 | 24.252 | 24.252 | 43.435 |
| 57      | 8.168  | 8.168  | 24.269 | 24.269 | 24.269 | 24.270 | 24.270 | 43.393 |
| 58      | 8.432  | 8.433  | 21.911 | 24.795 | 24.795 | 24.795 | 24.795 | 43.323 |
| 59      | 9.711  | 9.711  | 19.089 | 25.210 | 25.210 | 25.210 | 25.210 | 43.219 |
| 60      | 10.064 | 10.064 | 17.669 | 25.366 | 25.366 | 25.366 | 25.366 | 43.143 |
| 61      | 11.883 | 11.882 | 11.878 | 25.546 | 25.546 | 25.546 | 25.546 | 43.058 |
| 62      | 11.885 | 11.885 | 11.885 | 25.567 | 25.567 | 25.566 | 25.566 | 43.010 |
| 63      | 11.874 | 11.874 | 11.874 | 25.588 | 25.588 | 25.588 | 25.588 | 42.959 |
| 64      | 11.879 | 11.879 | 11.879 | 25.606 | 25.606 | 25.606 | 25.606 | 42.907 |
| 65      | 11.947 | 11.947 | 11.947 | 23.810 | 26.175 | 26.175 | 26.175 | 42.832 |
| 66      | 11.975 | 11.975 | 11.977 | 23.203 | 26.366 | 26.366 | 26.366 | 42.764 |
| 67      | 12.456 | 12.456 | 12.456 | 22.128 | 26.622 | 26.622 | 26.622 | 42.685 |
| 68      | 12.600 | 12.601 | 12.600 | 21.527 | 26.762 | 26.762 | 26.762 | 42.617 |
| 69      | 12.895 | 12.899 | 12.910 | 20.692 | 26.909 | 26.910 | 26.909 | 42.547 |
| 70      | 12.920 | 12.920 | 12.920 | 20.620 | 26.930 | 26.930 | 26.930 | 42.530 |
| 71      | 13.612 | 13.613 | 13.612 | 19.786 | 27.028 | 27.028 | 27.028 | 42.479 |
| 72      | 13.996 | 13.996 | 13.996 | 18.901 | 27.121 | 27.121 | 27.121 | 42.415 |
| 73      | 15.640 | 15.640 | 15.640 | 15.640 | 27.211 | 27.211 | 27.212 | 42.351 |
| 74      | 15.639 | 15.641 | 15.639 | 15.640 | 27.236 | 27.236 | 27.236 | 42.293 |
| 75      | 15.647 | 15.648 | 15.648 | 15.648 | 27.259 | 27.259 | 27.259 | 42.232 |
| 76      | 15.663 | 15.663 | 15.663 | 15.663 | 27.279 | 27.279 | 27.279 | 42.169 |
| 77      | 15.745 | 15.745 | 15.745 | 15.745 | 25.850 | 27.964 | 27.964 | 42.094 |
| 78      | 15.825 | 15.824 | 15.825 | 15.825 | 25.278 | 28.221 | 28.221 | 42.024 |
| 79      | 15.859 | 15.859 | 15.859 | 15.860 | 24.979 | 28.366 | 28.366 | 41.959 |
| 80      | 16.616 | 16.615 | 16.615 | 16.615 | 24.173 | 28.620 | 28.620 | 41.887 |

Table 74

FIG. 98

| Design # | Label | | | | | | | |
|---|---|---|---|---|---|---|---|---|
| | 0 | 1 | 2 | 3 | 4 | 5 | 6 | 7 |
| 81 | -41.821 | -28.769 | -28.769 | -23.684 | -16.845 | -16.844 | -16.842 | -16.844 |
| 82 | -41.760 | -28.848 | -28.848 | -23.491 | -16.906 | -16.906 | -16.905 | -16.904 |
| 83 | -41.699 | -28.961 | -28.960 | -23.010 | -17.629 | -17.630 | -17.631 | -14.794 |
| 84 | -41.639 | -29.050 | -29.050 | -22.578 | -17.973 | -17.973 | -17.974 | -13.458 |
| 85 | -41.579 | -29.119 | -29.119 | -22.235 | -18.205 | -18.206 | -18.207 | -10.709 |
| 86 | -41.521 | -29.202 | -29.202 | -19.869 | -20.914 | -19.870 | -15.504 | -11.049 |
| 87 | -41.459 | -29.236 | -29.236 | -20.250 | -20.250 | -20.250 | -11.081 | -15.369 |
| 88 | -41.470 | -29.230 | -29.230 | -20.250 | -20.250 | -20.250 | -15.360 | -11.090 |
| 89 | -41.393 | -29.263 | -29.263 | -20.260 | -20.261 | -20.262 | -15.380 | -11.085 |
| 90 | -41.326 | -29.287 | -29.287 | -20.278 | -20.278 | -20.277 | -15.368 | -11.099 |
| 91 | -41.255 | -29.310 | -29.310 | -20.298 | -20.298 | -20.299 | -15.342 | -11.114 |
| 92 | -41.186 | -29.946 | -28.676 | -20.382 | -20.382 | -20.382 | -14.423 | -12.070 |
| 93 | -41.122 | -30.267 | -28.358 | -20.437 | -20.437 | -20.437 | -11.520 | -13.125 |
| 94 | -41.060 | -30.466 | -28.172 | -20.467 | -20.467 | -20.467 | -13.048 | -13.053 |
| 95 | -41.000 | -30.689 | -27.922 | -20.987 | -20.987 | -19.413 | -13.248 | -13.248 |
| 96 | -40.942 | -30.884 | -27.690 | -21.251 | -21.251 | -18.827 | -13.445 | -13.445 |
| 97 | -40.887 | -31.034 | -27.518 | -21.408 | -21.408 | -18.464 | -13.580 | -13.581 |
| 98 | -40.834 | -31.159 | -27.377 | -21.533 | -21.533 | -18.136 | -13.737 | -13.737 |
| 99 | -40.781 | -31.262 | -27.270 | -21.623 | -21.623 | -17.864 | -14.270 | -14.266 |
| 100 | -40.731 | -31.355 | -27.173 | -21.712 | -21.712 | -17.499 | -14.653 | -14.653 |
| 101 | -40.680 | -31.436 | -27.096 | -21.782 | -21.782 | -17.099 | -15.016 | -15.016 |
| 102 | -40.629 | -31.502 | -27.043 | -21.827 | -21.827 | -16.360 | -16.383 | -14.324 |
| 103 | -40.578 | -31.565 | -26.989 | -22.249 | -21.434 | -16.400 | -16.400 | -14.293 |
| 104 | -40.531 | -31.636 | -26.895 | -22.684 | -20.972 | -16.569 | -16.575 | -13.874 |
| 105 | -40.520 | -31.650 | -26.880 | -22.740 | -20.910 | -16.600 | -16.600 | -13.820 |
| 106 | -40.482 | -31.696 | -26.823 | -22.912 | -20.724 | -16.706 | -16.696 | -13.471 |
| 107 | -40.433 | -31.749 | -26.769 | -23.062 | -20.561 | -16.800 | -16.805 | -12.532 |
| 108 | -40.382 | -31.796 | -26.724 | -23.204 | -20.335 | -17.642 | -15.980 | -12.703 |
| 109 | -40.330 | -31.839 | -26.687 | -23.329 | -20.047 | -18.214 | -14.661 | -14.680 |
| 110 | -40.275 | -31.875 | -26.675 | -23.385 | -19.954 | -18.338 | -14.629 | -14.608 |
| 111 | -40.217 | -31.906 | -26.677 | -23.414 | -19.937 | -18.371 | -14.621 | -14.621 |
| 112 | -40.157 | -31.935 | -26.689 | -23.430 | -19.948 | -18.379 | -14.631 | -14.631 |
| 113 | -40.096 | -31.960 | -26.708 | -23.437 | -19.986 | -18.357 | -14.674 | -14.638 |
| 114 | -40.032 | -31.984 | -26.733 | -23.437 | -20.035 | -18.325 | -14.686 | -14.686 |
| 115 | -39.966 | -32.007 | -26.761 | -23.435 | -20.089 | -18.291 | -14.717 | -14.717 |
| 116 | -39.899 | -32.028 | -26.791 | -23.436 | -20.126 | -18.282 | -14.727 | -14.734 |
| 117 | -39.830 | -32.048 | -26.825 | -23.430 | -20.191 | -18.225 | -15.093 | -14.397 |
| 118 | -39.760 | -32.067 | -26.861 | -23.423 | -20.255 | -18.167 | -15.279 | -14.232 |
| 119 | -39.689 | -32.086 | -26.898 | -23.419 | -20.312 | -18.119 | -15.410 | -14.123 |
| 120 | -39.616 | -32.103 | -26.934 | -23.418 | -20.360 | -18.084 | -15.506 | -14.041 |

Table 75

FIG. 99

|  | Label | | | | | | | |
|---|---|---|---|---|---|---|---|---|
|  | 8 | 9 | 10 | 11 | 12 | 13 | 14 | 15 |
| Design # | | | | | | | | |
| 81 | -10.064 | -4.016 | -7.749 | -7.790 | -7.745 | -7.783 | 0.710 | 0.600 |
| 82 | -8.314 | -8.314 | -8.314 | -8.314 | -8.314 | -2.668 | 0.000 | 0.000 |
| 83 | -8.424 | -8.424 | -8.425 | -8.424 | -8.425 | -2.035 | -0.010 | -0.010 |
| 84 | -9.139 | -9.131 | -9.148 | -9.133 | -5.714 | -1.273 | -1.253 | -1.255 |
| 85 | -10.708 | -10.711 | -10.709 | -7.012 | -2.943 | -2.947 | -2.946 | -2.946 |
| 86 | -10.979 | -11.029 | -11.133 | -2.350 | -3.921 | -3.938 | -4.265 | -4.066 |
| 87 | -11.077 | -11.070 | -11.079 | -4.614 | -3.298 | -3.771 | -3.624 | -3.316 |
| 88 | -11.080 | -11.070 | -11.070 | -4.470 | -3.850 | -3.740 | -3.630 | -2.900 |
| 89 | -11.087 | -11.083 | -11.081 | -4.419 | -4.105 | -3.440 | -3.137 | -3.531 |
| 90 | -11.105 | -11.095 | -11.095 | -3.757 | -3.409 | -3.572 | -3.471 | -4.449 |
| 91 | -11.115 | -11.118 | -11.122 | -3.938 | -3.922 | -3.779 | -3.779 | -3.260 |
| 92 | -12.114 | -12.134 | -7.676 | -5.315 | -5.314 | -5.318 | -0.787 | -0.790 |
| 93 | -13.127 | -13.129 | -5.948 | -5.949 | -5.948 | -5.948 | -0.345 | -0.320 |
| 94 | -13.052 | -11.799 | -5.914 | -5.916 | -5.916 | -5.916 | -1.319 | 0.426 |
| 95 | -13.248 | -11.225 | -5.983 | -5.983 | -5.982 | -5.983 | -0.233 | -0.148 |
| 96 | -13.446 | -10.590 | -6.363 | -6.363 | -6.363 | -5.062 | -0.001 | -0.001 |
| 97 | -13.580 | -6.575 | -10.100 | -6.574 | -4.630 | -6.577 | 0.002 | 0.000 |
| 98 | -13.731 | -8.188 | -8.183 | -8.185 | -5.489 | -2.226 | -2.219 | -2.231 |
| 99 | -12.752 | -8.255 | -8.253 | -8.253 | -5.304 | -2.266 | -2.266 | -2.266 |
| 100 | -12.010 | -8.425 | -8.425 | -8.425 | -4.723 | -2.483 | -2.393 | -2.393 |
| 101 | -10.050 | -10.047 | -10.050 | -5.349 | -5.160 | -5.018 | -1.627 | -0.546 |
| 102 | -10.084 | -10.073 | -10.052 | -4.892 | -5.291 | -5.290 | -1.843 | -0.211 |
| 103 | -10.075 | -10.081 | -10.079 | -5.181 | -5.085 | -5.214 | -1.847 | -0.022 |
| 104 | -10.625 | -10.633 | -9.069 | -5.233 | -5.235 | -5.234 | -1.098 | -1.100 |
| 105 | -10.670 | -10.640 | -9.040 | -5.270 | -5.230 | -5.180 | -1.690 | -0.020 |
| 106 | -10.976 | -10.978 | -8.219 | -6.210 | -5.838 | -3.678 | -1.657 | -1.383 |
| 107 | -12.532 | -10.313 | -7.356 | -7.377 | -5.724 | -2.519 | -2.613 | -1.587 |
| 108 | -12.703 | -9.852 | -7.796 | -7.617 | -4.400 | -4.277 | -2.310 | -0.288 |
| 109 | -11.046 | -10.598 | -8.374 | -6.228 | -5.911 | -2.886 | -2.891 | -0.761 |
| 110 | -11.630 | -9.544 | -9.075 | -6.528 | -4.747 | -4.441 | -1.922 | 2.042 |
| 111 | -11.639 | -9.258 | -9.417 | -6.176 | -5.514 | -3.923 | -1.628 | -1.313 |
| 112 | -11.636 | -9.367 | -9.337 | -5.875 | -5.869 | -3.813 | -1.898 | -1.040 |
| 113 | -11.521 | -9.916 | -8.843 | -5.892 | -5.967 | -3.727 | -1.210 | -1.836 |
| 114 | -11.349 | -10.251 | -8.607 | -5.991 | -5.990 | -3.645 | -1.592 | -1.552 |
| 115 | -10.977 | -10.743 | -8.400 | -6.068 | -6.061 | -3.492 | -1.877 | -1.380 |
| 116 | -10.870 | -10.866 | -8.385 | -6.096 | -6.093 | -2.911 | -2.905 | -0.561 |
| 117 | -10.896 | -10.898 | -8.337 | -6.306 | -5.924 | -2.887 | -2.924 | -0.568 |
| 118 | -10.944 | -10.946 | -8.124 | -6.860 | -5.436 | -3.346 | -2.594 | -0.489 |
| 119 | -10.991 | -10.989 | -7.699 | -7.441 | -5.086 | -3.647 | -2.493 | -0.229 |
| 120 | -11.297 | -10.718 | -7.592 | -7.592 | -5.023 | -3.732 | -2.449 | -0.229 |

Table 76

FIG. 100

|  | Label | | | | | | | |
| --- | --- | --- | --- | --- | --- | --- | --- | --- |
|  | 16 | 17 | 18 | 19 | 20 | 21 | 22 | 23 |
| Design # | | | | | | | | |
| 81 | 0.645 | 0.697 | 0.666 | 8.351 | 8.351 | 8.355 | 8.360 | 8.348 |
| 82 | 0.000 | 0.001 | 2.667 | 8.314 | 8.314 | 8.314 | 8.314 | 8.313 |
| 83 | -0.009 | -0.010 | 2.080 | 8.423 | 8.423 | 8.423 | 8.423 | 8.422 |
| 84 | -1.110 | 2.734 | 2.911 | 4.726 | 9.212 | 9.223 | 9.217 | 9.219 |
| 85 | 2.943 | 2.949 | 2.944 | 2.948 | 7.012 | 10.711 | 10.708 | 10.709 |
| 86 | 3.314 | 3.315 | 3.187 | 3.641 | 5.117 | 11.020 | 11.009 | 11.046 |
| 87 | 4.672 | 3.541 | 3.560 | 3.537 | 3.314 | 11.074 | 11.083 | 11.073 |
| 88 | 2.870 | 3.480 | 3.890 | 4.110 | 4.250 | 11.070 | 11.070 | 11.080 |
| 89 | 3.414 | 3.445 | 3.365 | 3.791 | 4.620 | 11.084 | 11.081 | 11.085 |
| 90 | 3.381 | 3.458 | 3.883 | 4.403 | 3.534 | 11.099 | 11.096 | 11.098 |
| 91 | 3.241 | 3.862 | 3.858 | 3.858 | 3.859 | 11.118 | 11.118 | 11.119 |
| 92 | -0.794 | 2.871 | 5.049 | 5.048 | 5.062 | 8.046 | 12.065 | 12.058 |
| 93 | -0.342 | 1.023 | 5.944 | 5.943 | 5.943 | 5.941 | 11.537 | 13.123 |
| 94 | 0.432 | 0.426 | 5.927 | 5.927 | 5.928 | 5.928 | 11.755 | 13.064 |
| 95 | -0.134 | 0.518 | 5.981 | 5.982 | 5.982 | 5.982 | 11.228 | 13.247 |
| 96 | 0.001 | 0.001 | 5.059 | 6.361 | 6.366 | 6.366 | 10.589 | 13.446 |
| 97 | -0.002 | 0.000 | 4.630 | 6.569 | 6.570 | 6.586 | 10.100 | 13.580 |
| 98 | 2.256 | 2.211 | 2.210 | 5.488 | 8.196 | 8.184 | 8.177 | 13.741 |
| 99 | 2.266 | 2.266 | 2.266 | 5.305 | 8.254 | 8.254 | 8.254 | 12.753 |
| 100 | 2.412 | 2.423 | 2.433 | 4.725 | 8.424 | 8.424 | 8.427 | 12.010 |
| 101 | 0.292 | 1.989 | 4.607 | 5.235 | 5.585 | 10.018 | 10.058 | 10.061 |
| 102 | 0.199 | 1.862 | 4.857 | 5.294 | 5.316 | 10.059 | 10.067 | 10.082 |
| 103 | 0.027 | 1.840 | 5.158 | 5.161 | 5.163 | 10.081 | 10.077 | 10.076 |
| 104 | 0.507 | 1.769 | 5.187 | 5.185 | 5.194 | 9.676 | 9.674 | 11.026 |
| 105 | 0.020 | 1.690 | 5.210 | 5.230 | 5.240 | 9.040 | 10.650 | 10.660 |
| 106 | 1.491 | 1.542 | 3.681 | 6.008 | 6.031 | 8.239 | 11.040 | 10.907 |
| 107 | 1.618 | 2.523 | 2.564 | 5.792 | 7.592 | 7.091 | 10.313 | 12.546 |
| 108 | 0.281 | 2.326 | 4.252 | 4.414 | 7.640 | 7.776 | 9.850 | 12.681 |
| 109 | 1.329 | 1.578 | 3.802 | 5.883 | 5.951 | 10.149 | 11.333 | 8.689 |
| 110 | -0.655 | 0.583 | 4.770 | 4.332 | 6.606 | 9.687 | 8.910 | 11.611 |
| 111 | 1.225 | 1.746 | 3.838 | 5.773 | 5.960 | 9.394 | 9.297 | 11.633 |
| 112 | 1.917 | 1.027 | 3.804 | 5.827 | 5.920 | 9.356 | 9.346 | 11.637 |
| 113 | 1.236 | 1.801 | 3.741 | 5.929 | 5.922 | 8.854 | 9.904 | 11.524 |
| 114 | 1.564 | 1.580 | 3.645 | 6.016 | 5.964 | 8.608 | 10.249 | 11.350 |
| 115 | 1.608 | 1.607 | 3.559 | 5.819 | 6.299 | 8.379 | 10.867 | 10.860 |
| 116 | 0.588 | 2.629 | 3.173 | 6.054 | 6.117 | 8.394 | 10.870 | 10.863 |
| 117 | 0.566 | 2.894 | 2.920 | 5.893 | 6.340 | 8.330 | 10.898 | 10.898 |
| 118 | 0.521 | 2.446 | 3.520 | 5.319 | 6.968 | 8.070 | 10.908 | 10.993 |
| 119 | 0.235 | 2.468 | 3.679 | 5.067 | 7.472 | 7.673 | 10.990 | 10.989 |
| 120 | 0.226 | 2.460 | 3.717 | 5.033 | 7.568 | 7.612 | 10.729 | 11.285 |

Table 77

FIG. 101

| Design # | Label | | | | | | | |
|---|---|---|---|---|---|---|---|---|
| | 24 | 25 | 26 | 27 | 28 | 29 | 30 | 31 |
| 81 | 16.864 | 16.864 | 16.864 | 16.864 | 23.655 | 28.775 | 28.775 | 41.821 |
| 82 | 16.904 | 16.904 | 16.906 | 16.906 | 23.491 | 28.848 | 28.848 | 41.760 |
| 83 | 14.802 | 17.628 | 17.628 | 17.628 | 23.011 | 28.960 | 28.960 | 41.699 |
| 84 | 13.339 | 17.988 | 17.988 | 17.988 | 22.564 | 29.051 | 29.051 | 41.639 |
| 85 | 10.707 | 18.208 | 18.205 | 18.205 | 22.235 | 29.119 | 29.119 | 41.579 |
| 86 | 11.056 | 15.550 | 20.962 | 19.857 | 19.813 | 29.201 | 29.201 | 41.521 |
| 87 | 11.074 | 15.370 | 20.252 | 20.248 | 20.251 | 29.236 | 29.236 | 41.459 |
| 88 | 11.090 | 15.360 | 20.250 | 20.250 | 20.250 | 29.230 | 29.230 | 41.470 |
| 89 | 11.082 | 15.382 | 20.261 | 20.261 | 20.260 | 29.263 | 29.263 | 41.393 |
| 90 | 11.101 | 15.368 | 20.277 | 20.278 | 20.278 | 29.287 | 29.287 | 41.326 |
| 91 | 11.113 | 15.342 | 20.298 | 20.298 | 20.299 | 29.310 | 29.310 | 41.255 |
| 92 | 12.054 | 14.489 | 20.380 | 20.379 | 20.380 | 28.682 | 29.941 | 41.186 |
| 93 | 13.123 | 13.122 | 20.437 | 20.437 | 20.437 | 28.357 | 30.267 | 41.122 |
| 94 | 13.060 | 13.065 | 20.466 | 20.466 | 20.467 | 28.173 | 30.465 | 41.060 |
| 95 | 13.247 | 13.247 | 19.415 | 20.987 | 20.986 | 27.922 | 30.688 | 41.000 |
| 96 | 13.445 | 13.446 | 18.826 | 21.251 | 21.251 | 27.690 | 30.884 | 40.942 |
| 97 | 13.580 | 13.580 | 18.464 | 21.408 | 21.408 | 27.518 | 31.034 | 40.887 |
| 98 | 13.732 | 13.732 | 18.136 | 21.534 | 21.533 | 27.377 | 31.159 | 40.834 |
| 99 | 14.267 | 14.269 | 17.864 | 21.623 | 21.623 | 27.270 | 31.262 | 40.781 |
| 100 | 14.653 | 14.653 | 17.499 | 21.712 | 21.712 | 27.173 | 31.355 | 40.731 |
| 101 | 15.019 | 15.019 | 17.095 | 21.783 | 21.782 | 27.095 | 31.436 | 40.680 |
| 102 | 14.325 | 16.399 | 16.342 | 21.827 | 21.827 | 27.043 | 31.502 | 40.629 |
| 103 | 14.293 | 16.400 | 16.400 | 21.434 | 22.249 | 26.989 | 31.565 | 40.578 |
| 104 | 13.899 | 16.562 | 16.562 | 20.987 | 22.674 | 26.897 | 31.635 | 40.530 |
| 105 | 13.820 | 16.600 | 16.600 | 20.910 | 22.740 | 26.880 | 31.650 | 40.520 |
| 106 | 13.473 | 16.699 | 16.702 | 20.724 | 22.912 | 26.823 | 31.696 | 40.482 |
| 107 | 12.517 | 16.811 | 16.794 | 20.560 | 23.062 | 26.769 | 31.749 | 40.433 |
| 108 | 12.727 | 15.977 | 17.644 | 20.334 | 23.205 | 26.724 | 31.796 | 40.382 |
| 109 | 14.629 | 14.688 | 18.227 | 20.039 | 23.331 | 26.686 | 31.839 | 40.330 |
| 110 | 14.610 | 14.629 | 18.338 | 19.954 | 23.385 | 26.675 | 31.875 | 40.275 |
| 111 | 14.628 | 14.617 | 18.369 | 19.939 | 23.413 | 26.678 | 31.906 | 40.217 |
| 112 | 14.629 | 14.632 | 18.379 | 19.947 | 23.430 | 26.689 | 31.935 | 40.158 |
| 113 | 14.658 | 14.654 | 18.357 | 19.986 | 23.437 | 26.708 | 31.960 | 40.096 |
| 114 | 14.686 | 14.686 | 18.325 | 20.035 | 23.437 | 26.733 | 31.984 | 40.032 |
| 115 | 14.716 | 14.719 | 18.290 | 20.089 | 23.435 | 26.761 | 32.007 | 39.966 |
| 116 | 14.734 | 14.728 | 18.280 | 20.126 | 23.436 | 26.791 | 32.028 | 39.899 |
| 117 | 14.392 | 15.097 | 18.224 | 20.191 | 23.429 | 26.825 | 32.048 | 39.830 |
| 118 | 14.220 | 15.290 | 18.164 | 20.256 | 23.423 | 26.861 | 32.067 | 39.760 |
| 119 | 14.124 | 15.410 | 18.119 | 20.312 | 23.419 | 26.898 | 32.086 | 39.689 |
| 120 | 14.045 | 15.504 | 18.085 | 20.360 | 23.418 | 26.934 | 32.103 | 39.616 |

Table 78

FIG. 102

|  | Label | | | | | | | |
|---|---|---|---|---|---|---|---|---|
|  | 0 | 1 | 2 | 3 | 4 | 5 | 6 | 7 |
| Design # | | | | | | | | |
| 121 | -39.542 | -32.120 | -26.971 | -23.419 | -20.406 | -18.051 | -15.604 | -13.944 |
| 122 | -39.530 | -32.120 | -26.980 | -23.420 | -20.410 | -18.050 | -15.620 | -13.930 |
| 123 | -39.467 | -32.136 | -27.007 | -23.423 | -20.446 | -18.027 | -15.684 | -13.860 |
| 124 | -39.390 | -32.151 | -27.044 | -23.431 | -20.479 | -18.015 | -15.738 | -13.811 |
| 125 | -39.312 | -32.165 | -27.080 | -23.442 | -20.509 | -18.011 | -15.782 | -13.773 |
| 126 | -39.233 | -32.177 | -27.115 | -23.457 | -20.535 | -18.015 | -15.810 | -13.761 |
| 127 | -39.152 | -32.188 | -27.151 | -23.475 | -20.558 | -18.026 | -15.831 | -13.764 |
| 128 | -39.070 | -32.198 | -27.186 | -23.496 | -20.579 | -18.041 | -15.846 | -13.776 |
| 129 | -38.986 | -32.206 | -27.221 | -23.519 | -20.600 | -18.059 | -15.859 | -13.792 |
| 130 | -38.901 | -32.212 | -27.256 | -23.544 | -20.620 | -18.079 | -15.871 | -13.810 |
| 131 | -38.814 | -32.217 | -27.292 | -23.572 | -20.641 | -18.100 | -15.884 | -13.828 |
| 132 | -38.725 | -32.219 | -27.326 | -23.602 | -20.662 | -18.122 | -15.897 | -13.847 |
| 133 | -38.635 | -32.220 | -27.361 | -23.633 | -20.684 | -18.145 | -15.912 | -13.865 |
| 134 | -38.544 | -32.219 | -27.396 | -23.666 | -20.706 | -18.168 | -15.928 | -13.883 |
| 135 | -38.451 | -32.216 | -27.430 | -23.700 | -20.731 | -18.192 | -15.945 | -13.900 |
| 136 | -38.357 | -32.212 | -27.464 | -23.736 | -20.756 | -18.216 | -15.964 | -13.918 |
| 137 | -38.261 | -32.205 | -27.497 | -23.773 | -20.783 | -18.241 | -15.984 | -13.936 |
| 138 | -38.164 | -32.196 | -27.529 | -23.812 | -20.812 | -18.266 | -16.005 | -13.955 |
| 139 | -38.150 | -32.190 | -27.530 | -23.820 | -20.820 | -18.270 | -16.010 | -13.960 |
| 140 | -38.065 | -32.185 | -27.561 | -23.851 | -20.843 | -18.292 | -16.028 | -13.974 |
| 141 | -37.965 | -32.172 | -27.592 | -23.892 | -20.876 | -18.319 | -16.051 | -13.993 |
| 142 | -37.863 | -32.157 | -27.621 | -23.933 | -20.910 | -18.348 | -16.076 | -14.014 |
| 143 | -37.760 | -32.140 | -27.650 | -23.975 | -20.946 | -18.377 | -16.102 | -14.036 |
| 144 | -37.656 | -32.120 | -27.677 | -24.017 | -20.984 | -18.408 | -16.129 | -14.058 |
| 145 | -37.550 | -32.099 | -27.702 | -24.060 | -21.024 | -18.441 | -16.157 | -14.082 |
| 146 | -37.443 | -32.075 | -27.727 | -24.104 | -21.066 | -18.475 | -16.186 | -14.107 |
| 147 | -37.334 | -32.049 | -27.749 | -24.147 | -21.110 | -18.511 | -16.217 | -14.133 |
| 148 | -37.224 | -32.021 | -27.770 | -24.190 | -21.155 | -18.549 | -16.249 | -14.161 |
| 149 | -37.112 | -31.990 | -27.789 | -24.233 | -21.201 | -18.589 | -16.283 | -14.190 |
| 150 | -37.000 | -31.957 | -27.806 | -24.276 | -21.249 | -18.631 | -16.318 | -14.220 |
| 151 | -36.886 | -31.923 | -27.822 | -24.318 | -21.298 | -18.676 | -16.356 | -14.252 |
| 152 | -36.770 | -31.885 | -27.835 | -24.359 | -21.348 | -18.722 | -16.395 | -14.286 |
| 153 | -36.654 | -31.846 | -27.846 | -24.399 | -21.399 | -18.771 | -16.437 | -14.321 |
| 154 | -36.536 | -31.805 | -27.855 | -24.438 | -21.450 | -18.821 | -16.481 | -14.359 |
| 155 | -36.417 | -31.761 | -27.862 | -24.476 | -21.502 | -18.873 | -16.527 | -14.398 |
| 156 | -36.360 | -31.740 | -27.860 | -24.490 | -21.530 | -18.900 | -16.550 | -14.420 |
| 157 | -36.296 | -31.715 | -27.867 | -24.513 | -21.554 | -18.927 | -16.576 | -14.440 |
| 158 | -36.175 | -31.667 | -27.869 | -24.548 | -21.605 | -18.983 | -16.627 | -14.484 |
| 159 | -36.052 | -31.617 | -27.869 | -24.581 | -21.657 | -19.039 | -16.681 | -14.531 |
| 160 | -35.928 | -31.565 | -27.867 | -24.613 | -21.708 | -19.097 | -16.737 | -14.581 |

Table 79

FIG. 103

|  | Label | | | | | | | |
|---|---|---|---|---|---|---|---|---|
|  | 8 | 9 | 10 | 11 | 12 | 13 | 14 | 15 |
| Design # | | | | | | | | |
| 121 | -11.514 | -10.528 | -7.664 | -7.612 | -4.476 | -4.476 | -1.815 | -1.123 |
| 122 | -11.550 | -10.490 | -7.830 | -7.450 | -4.490 | -4.480 | -1.730 | -1.220 |
| 123 | -11.692 | -10.348 | -8.097 | -7.207 | -4.776 | -4.237 | -1.668 | -1.313 |
| 124 | -11.793 | -10.248 | -8.253 | -7.066 | -4.948 | -4.085 | -1.837 | -1.141 |
| 125 | -11.881 | -10.145 | -8.428 | -6.865 | -5.234 | -3.784 | -2.185 | -0.797 |
| 126 | -11.924 | -10.105 | -8.499 | -6.786 | -5.342 | -3.663 | -2.325 | -0.650 |
| 127 | -11.945 | -10.098 | -8.526 | -6.766 | -5.376 | -3.631 | -2.364 | -0.611 |
| 128 | -11.955 | -10.110 | -8.527 | -6.781 | -5.367 | -3.652 | -2.346 | -0.634 |
| 129 | -11.960 | -10.127 | -8.523 | -6.804 | -5.351 | -3.681 | -2.320 | -0.665 |
| 130 | -11.964 | -10.147 | -8.517 | -6.828 | -5.335 | -3.709 | -2.295 | -0.694 |
| 131 | -11.970 | -10.165 | -8.515 | -6.848 | -5.324 | -3.731 | -2.277 | -0.716 |
| 132 | -11.977 | -10.182 | -8.515 | -6.865 | -5.318 | -3.748 | -2.265 | -0.731 |
| 133 | -11.985 | -10.198 | -8.518 | -6.879 | -5.316 | -3.760 | -2.259 | -0.741 |
| 134 | -11.996 | -10.212 | -8.524 | -6.890 | -5.317 | -3.768 | -2.257 | -0.746 |
| 135 | -12.008 | -10.225 | -8.531 | -6.900 | -5.321 | -3.775 | -2.257 | -0.750 |
| 136 | -12.021 | -10.238 | -8.540 | -6.909 | -5.326 | -3.780 | -2.258 | -0.752 |
| 137 | -12.036 | -10.251 | -8.550 | -6.917 | -5.332 | -3.785 | -2.261 | -0.753 |
| 138 | -12.051 | -10.264 | -8.561 | -6.926 | -5.339 | -3.790 | -2.263 | -0.754 |
| 139 | -12.050 | -10.270 | -8.560 | -6.930 | -5.340 | -3.790 | -2.260 | -0.750 |
| 140 | -12.067 | -10.278 | -8.572 | -6.935 | -5.346 | -3.795 | -2.266 | -0.754 |
| 141 | -12.085 | -10.292 | -8.584 | -6.944 | -5.353 | -3.799 | -2.270 | -0.755 |
| 142 | -12.103 | -10.307 | -8.597 | -6.954 | -5.361 | -3.805 | -2.273 | -0.756 |
| 143 | -12.121 | -10.322 | -8.610 | -6.964 | -5.369 | -3.810 | -2.276 | -0.757 |
| 144 | -12.141 | -10.338 | -8.623 | -6.975 | -5.377 | -3.816 | -2.280 | -0.758 |
| 145 | -12.161 | -10.355 | -8.637 | -6.986 | -5.386 | -3.822 | -2.284 | -0.760 |
| 146 | -12.182 | -10.373 | -8.652 | -6.998 | -5.395 | -3.829 | -2.287 | -0.761 |
| 147 | -12.205 | -10.392 | -8.668 | -7.011 | -5.404 | -3.835 | -2.291 | -0.762 |
| 148 | -12.228 | -10.411 | -8.684 | -7.024 | -5.414 | -3.842 | -2.296 | -0.764 |
| 149 | -12.252 | -10.432 | -8.701 | -7.037 | -5.425 | -3.850 | -2.300 | -0.765 |
| 150 | -12.278 | -10.454 | -8.719 | -7.052 | -5.436 | -3.858 | -2.305 | -0.767 |
| 151 | -12.305 | -10.477 | -8.738 | -7.067 | -5.447 | -3.866 | -2.310 | -0.768 |
| 152 | -12.334 | -10.501 | -8.757 | -7.083 | -5.460 | -3.874 | -2.315 | -0.770 |
| 153 | -12.364 | -10.526 | -8.778 | -7.099 | -5.472 | -3.883 | -2.320 | -0.772 |
| 154 | -12.396 | -10.553 | -8.800 | -7.117 | -5.486 | -3.893 | -2.326 | -0.774 |
| 155 | -12.429 | -10.581 | -8.823 | -7.136 | -5.500 | -3.903 | -2.332 | -0.776 |
| 156 | -12.450 | -10.590 | -8.830 | -7.140 | -5.510 | -3.910 | -2.330 | -0.780 |
| 157 | -12.465 | -10.611 | -8.848 | -7.155 | -5.515 | -3.914 | -2.338 | -0.778 |
| 158 | -12.503 | -10.642 | -8.874 | -7.176 | -5.531 | -3.925 | -2.345 | -0.780 |
| 159 | -12.542 | -10.676 | -8.902 | -7.199 | -5.548 | -3.937 | -2.352 | -0.782 |
| 160 | -12.585 | -10.711 | -8.931 | -7.222 | -5.567 | -3.950 | -2.360 | -0.785 |

Table 80

FIG. 104

|  | Label | | | | | | | |
|---|---|---|---|---|---|---|---|---|
|  | 16 | 17 | 18 | 19 | 20 | 21 | 22 | 23 |
| Design # | | | | | | | | |
| 121 | 1.123 | 1.815 | 4.476 | 4.476 | 7.632 | 7.643 | 10.529 | 11.513 |
| 122 | 1.210 | 1.740 | 4.470 | 4.490 | 7.490 | 7.790 | 10.500 | 11.540 |
| 123 | 1.486 | 1.475 | 4.503 | 4.505 | 7.296 | 8.017 | 10.382 | 11.668 |
| 124 | 1.115 | 1.879 | 4.030 | 5.005 | 7.029 | 8.282 | 10.233 | 11.802 |
| 125 | 0.797 | 2.183 | 3.787 | 5.231 | 6.868 | 8.426 | 10.146 | 11.880 |
| 126 | 0.650 | 2.325 | 3.663 | 5.342 | 6.786 | 8.500 | 10.105 | 11.924 |
| 127 | 0.611 | 2.364 | 3.631 | 5.376 | 6.766 | 8.526 | 10.098 | 11.945 |
| 128 | 0.634 | 2.346 | 3.652 | 5.367 | 6.781 | 8.528 | 10.110 | 11.955 |
| 129 | 0.665 | 2.320 | 3.681 | 5.351 | 6.804 | 8.523 | 10.127 | 11.960 |
| 130 | 0.694 | 2.295 | 3.709 | 5.335 | 6.828 | 8.517 | 10.147 | 11.964 |
| 131 | 0.716 | 2.277 | 3.731 | 5.324 | 6.848 | 8.515 | 10.165 | 11.970 |
| 132 | 0.731 | 2.265 | 3.748 | 5.318 | 6.865 | 8.515 | 10.182 | 11.977 |
| 133 | 0.741 | 2.259 | 3.760 | 5.316 | 6.879 | 8.518 | 10.198 | 11.985 |
| 134 | 0.746 | 2.257 | 3.768 | 5.317 | 6.890 | 8.524 | 10.212 | 11.996 |
| 135 | 0.750 | 2.257 | 3.775 | 5.321 | 6.900 | 8.531 | 10.225 | 12.008 |
| 136 | 0.752 | 2.258 | 3.780 | 5.326 | 6.909 | 8.540 | 10.238 | 12.021 |
| 137 | 0.753 | 2.261 | 3.785 | 5.332 | 6.917 | 8.550 | 10.251 | 12.036 |
| 138 | 0.754 | 2.263 | 3.790 | 5.339 | 6.926 | 8.561 | 10.264 | 12.051 |
| 139 | 0.750 | 2.260 | 3.790 | 5.340 | 6.930 | 8.560 | 10.270 | 12.050 |
| 140 | 0.754 | 2.266 | 3.795 | 5.346 | 6.935 | 8.572 | 10.278 | 12.067 |
| 141 | 0.755 | 2.270 | 3.799 | 5.353 | 6.944 | 8.584 | 10.292 | 12.085 |
| 142 | 0.756 | 2.273 | 3.805 | 5.361 | 6.954 | 8.597 | 10.307 | 12.103 |
| 143 | 0.757 | 2.276 | 3.810 | 5.369 | 6.964 | 8.610 | 10.322 | 12.121 |
| 144 | 0.758 | 2.280 | 3.816 | 5.377 | 6.975 | 8.623 | 10.338 | 12.141 |
| 145 | 0.760 | 2.284 | 3.822 | 5.386 | 6.986 | 8.637 | 10.355 | 12.161 |
| 146 | 0.761 | 2.287 | 3.829 | 5.395 | 6.998 | 8.652 | 10.373 | 12.182 |
| 147 | 0.762 | 2.291 | 3.835 | 5.404 | 7.011 | 8.668 | 10.392 | 12.205 |
| 148 | 0.764 | 2.296 | 3.842 | 5.414 | 7.024 | 8.684 | 10.411 | 12.228 |
| 149 | 0.765 | 2.300 | 3.850 | 5.425 | 7.037 | 8.701 | 10.432 | 12.252 |
| 150 | 0.767 | 2.305 | 3.858 | 5.436 | 7.052 | 8.719 | 10.454 | 12.278 |
| 151 | 0.768 | 2.310 | 3.866 | 5.447 | 7.067 | 8.738 | 10.477 | 12.305 |
| 152 | 0.770 | 2.315 | 3.874 | 5.460 | 7.083 | 8.757 | 10.501 | 12.334 |
| 153 | 0.772 | 2.320 | 3.883 | 5.472 | 7.099 | 8.778 | 10.526 | 12.364 |
| 154 | 0.774 | 2.326 | 3.893 | 5.486 | 7.117 | 8.800 | 10.553 | 12.396 |
| 155 | 0.776 | 2.332 | 3.903 | 5.500 | 7.136 | 8.823 | 10.581 | 12.429 |
| 156 | 0.780 | 2.330 | 3.910 | 5.510 | 7.140 | 8.830 | 10.590 | 12.450 |
| 157 | 0.778 | 2.338 | 3.914 | 5.515 | 7.155 | 8.848 | 10.611 | 12.465 |
| 158 | 0.780 | 2.345 | 3.925 | 5.531 | 7.176 | 8.874 | 10.642 | 12.503 |
| 159 | 0.782 | 2.352 | 3.937 | 5.548 | 7.199 | 8.902 | 10.676 | 12.542 |
| 160 | 0.785 | 2.360 | 3.950 | 5.567 | 7.222 | 8.931 | 10.711 | 12.585 |

Table 81

FIG. 105

|  | Label | | | | | | | |
|---|---|---|---|---|---|---|---|---|
|  | 24 | 25 | 26 | 27 | 28 | 29 | 30 | 31 |
| Design # | | | | | | | | |
| 121 | 13.944 | 15.604 | 18.051 | 20.406 | 23.419 | 26.971 | 32.120 | 39.542 |
| 122 | 13.930 | 15.620 | 18.050 | 20.410 | 23.420 | 26.980 | 32.120 | 39.530 |
| 123 | 13.870 | 15.679 | 18.028 | 20.445 | 23.423 | 27.007 | 32.136 | 39.467 |
| 124 | 13.807 | 15.740 | 18.014 | 20.479 | 23.431 | 27.044 | 32.151 | 39.390 |
| 125 | 13.774 | 15.782 | 18.011 | 20.509 | 23.442 | 27.079 | 32.165 | 39.312 |
| 126 | 13.761 | 15.810 | 18.015 | 20.535 | 23.457 | 27.115 | 32.177 | 39.233 |
| 127 | 13.764 | 15.831 | 18.026 | 20.558 | 23.475 | 27.151 | 32.188 | 39.152 |
| 128 | 13.776 | 15.846 | 18.041 | 20.580 | 23.496 | 27.186 | 32.198 | 39.070 |
| 129 | 13.792 | 15.859 | 18.059 | 20.600 | 23.519 | 27.221 | 32.206 | 38.986 |
| 130 | 13.810 | 15.871 | 18.079 | 20.620 | 23.544 | 27.256 | 32.212 | 38.901 |
| 131 | 13.828 | 15.884 | 18.100 | 20.641 | 23.572 | 27.292 | 32.217 | 38.814 |
| 132 | 13.847 | 15.897 | 18.122 | 20.662 | 23.602 | 27.326 | 32.219 | 38.725 |
| 133 | 13.865 | 15.912 | 18.145 | 20.684 | 23.633 | 27.361 | 32.220 | 38.635 |
| 134 | 13.883 | 15.928 | 18.168 | 20.706 | 23.666 | 27.396 | 32.219 | 38.544 |
| 135 | 13.900 | 15.945 | 18.192 | 20.731 | 23.700 | 27.430 | 32.216 | 38.451 |
| 136 | 13.918 | 15.964 | 18.216 | 20.756 | 23.736 | 27.464 | 32.212 | 38.357 |
| 137 | 13.936 | 15.984 | 18.241 | 20.783 | 23.773 | 27.497 | 32.205 | 38.261 |
| 138 | 13.955 | 16.005 | 18.266 | 20.812 | 23.812 | 27.529 | 32.196 | 38.164 |
| 139 | 13.960 | 16.010 | 18.270 | 20.820 | 23.820 | 27.530 | 32.190 | 38.150 |
| 140 | 13.974 | 16.028 | 18.292 | 20.843 | 23.851 | 27.561 | 32.185 | 38.065 |
| 141 | 13.993 | 16.051 | 18.319 | 20.876 | 23.892 | 27.592 | 32.172 | 37.965 |
| 142 | 14.014 | 16.076 | 18.348 | 20.910 | 23.933 | 27.621 | 32.157 | 37.863 |
| 143 | 14.036 | 16.102 | 18.377 | 20.946 | 23.975 | 27.650 | 32.140 | 37.760 |
| 144 | 14.058 | 16.129 | 18.408 | 20.984 | 24.017 | 27.677 | 32.120 | 37.656 |
| 145 | 14.082 | 16.157 | 18.441 | 21.024 | 24.060 | 27.702 | 32.099 | 37.550 |
| 146 | 14.107 | 16.186 | 18.475 | 21.066 | 24.104 | 27.727 | 32.075 | 37.443 |
| 147 | 14.133 | 16.217 | 18.511 | 21.110 | 24.147 | 27.749 | 32.049 | 37.334 |
| 148 | 14.161 | 16.249 | 18.549 | 21.155 | 24.190 | 27.770 | 32.021 | 37.224 |
| 149 | 14.190 | 16.283 | 18.589 | 21.201 | 24.233 | 27.789 | 31.990 | 37.112 |
| 150 | 14.220 | 16.318 | 18.631 | 21.249 | 24.276 | 27.806 | 31.957 | 37.000 |
| 151 | 14.252 | 16.356 | 18.676 | 21.298 | 24.318 | 27.822 | 31.923 | 36.886 |
| 152 | 14.286 | 16.395 | 18.722 | 21.348 | 24.359 | 27.835 | 31.885 | 36.770 |
| 153 | 14.321 | 16.437 | 18.771 | 21.399 | 24.399 | 27.846 | 31.846 | 36.654 |
| 154 | 14.359 | 16.481 | 18.821 | 21.450 | 24.438 | 27.855 | 31.805 | 36.536 |
| 155 | 14.398 | 16.527 | 18.873 | 21.502 | 24.476 | 27.862 | 31.761 | 36.416 |
| 156 | 14.420 | 16.550 | 18.900 | 21.530 | 24.490 | 27.860 | 31.740 | 36.360 |
| 157 | 14.440 | 16.576 | 18.927 | 21.554 | 24.513 | 27.867 | 31.715 | 36.296 |
| 158 | 14.484 | 16.627 | 18.983 | 21.605 | 24.548 | 27.869 | 31.667 | 36.175 |
| 159 | 14.531 | 16.681 | 19.039 | 21.657 | 24.581 | 27.869 | 31.617 | 36.052 |
| 160 | 14.581 | 16.737 | 19.097 | 21.708 | 24.613 | 27.867 | 31.565 | 35.928 |

Table 82

FIG. 106

|  | Label | | | | | | | |
|---|---|---|---|---|---|---|---|---|
|  | 0 | 1 | 2 | 3 | 4 | 5 | 6 | 7 |
| Design # | | | | | | | | |
| 161 | -35.803 | -31.511 | -27.863 | -24.643 | -21.758 | -19.156 | -16.795 | -14.633 |
| 162 | -35.678 | -31.455 | -27.856 | -24.671 | -21.808 | -19.215 | -16.854 | -14.688 |
| 163 | -35.551 | -31.397 | -27.847 | -24.697 | -21.856 | -19.275 | -16.916 | -14.745 |
| 164 | -35.424 | -31.337 | -27.836 | -24.721 | -21.903 | -19.335 | -16.979 | -14.805 |
| 165 | -35.296 | -31.275 | -27.823 | -24.743 | -21.949 | -19.394 | -17.043 | -14.867 |
| 166 | -35.167 | -31.212 | -27.808 | -24.763 | -21.994 | -19.453 | -17.108 | -14.932 |
| 167 | -35.038 | -31.147 | -27.790 | -24.781 | -22.037 | -19.512 | -17.174 | -14.998 |
| 168 | -34.909 | -31.081 | -27.771 | -24.797 | -22.078 | -19.569 | -17.240 | -15.065 |
| 169 | -34.779 | -31.014 | -27.750 | -24.811 | -22.117 | -19.626 | -17.306 | -15.134 |
| 170 | -34.650 | -30.946 | -27.728 | -24.823 | -22.155 | -19.681 | -17.372 | -15.203 |
| 171 | -34.522 | -30.877 | -27.704 | -24.833 | -22.191 | -19.735 | -17.436 | -15.273 |
| 172 | -34.394 | -30.808 | -27.679 | -24.842 | -22.226 | -19.788 | -17.501 | -15.342 |
| 173 | -34.268 | -30.739 | -27.653 | -24.850 | -22.259 | -19.839 | -17.563 | -15.411 |
| 174 | -34.150 | -30.670 | -27.630 | -24.860 | -22.290 | -19.890 | -17.620 | -15.480 |
| 175 | -34.144 | -30.671 | -27.627 | -24.856 | -22.290 | -19.888 | -17.625 | -15.479 |
| 176 | -34.022 | -30.603 | -27.601 | -24.862 | -22.320 | -19.936 | -17.685 | -15.546 |
| 177 | -33.902 | -30.537 | -27.574 | -24.866 | -22.348 | -19.982 | -17.743 | -15.611 |
| 178 | -33.785 | -30.472 | -27.548 | -24.870 | -22.375 | -20.026 | -17.799 | -15.673 |
| 179 | -33.672 | -30.409 | -27.522 | -24.874 | -22.401 | -20.069 | -17.853 | -15.734 |
| 180 | -33.562 | -30.347 | -27.497 | -24.877 | -22.426 | -20.110 | -17.905 | -15.793 |
| 181 | -33.455 | -30.288 | -27.474 | -24.880 | -22.450 | -20.149 | -17.954 | -15.849 |
| 182 | -33.353 | -30.231 | -27.450 | -24.883 | -22.473 | -20.187 | -18.002 | -15.903 |
| 183 | -33.254 | -30.176 | -27.428 | -24.886 | -22.495 | -20.223 | -18.048 | -15.954 |
| 184 | -33.160 | -30.124 | -27.407 | -24.889 | -22.516 | -20.257 | -18.091 | -16.003 |
| 185 | -33.068 | -30.073 | -27.387 | -24.892 | -22.536 | -20.290 | -18.133 | -16.050 |
| 186 | -32.981 | -30.026 | -27.368 | -24.895 | -22.556 | -20.321 | -18.172 | -16.094 |
| 187 | -32.898 | -29.980 | -27.350 | -24.898 | -22.574 | -20.351 | -18.210 | -16.136 |
| 188 | -32.817 | -29.936 | -27.333 | -24.901 | -22.592 | -20.380 | -18.246 | -16.176 |
| 189 | -32.740 | -29.894 | -27.317 | -24.904 | -22.609 | -20.407 | -18.280 | -16.214 |
| 190 | -32.666 | -29.854 | -27.301 | -24.906 | -22.626 | -20.434 | -18.313 | -16.250 |
| 191 | -32.595 | -29.816 | -27.287 | -24.910 | -22.642 | -20.459 | -18.344 | -16.285 |
| 192 | -32.527 | -29.780 | -27.273 | -24.913 | -22.657 | -20.483 | -18.374 | -16.318 |
| 193 | -32.464 | -29.746 | -27.260 | -24.915 | -22.671 | -20.505 | -18.401 | -16.348 |
| 194 | -32.400 | -29.712 | -27.248 | -24.918 | -22.686 | -20.528 | -18.429 | -16.379 |
| 195 | -32.342 | -29.681 | -27.236 | -24.921 | -22.699 | -20.548 | -18.454 | -16.406 |
| 196 | -32.285 | -29.652 | -27.225 | -24.924 | -22.712 | -20.568 | -18.478 | -16.433 |
| 197 | -32.230 | -29.623 | -27.215 | -24.927 | -22.724 | -20.587 | -18.502 | -16.459 |
| 198 | -32.178 | -29.595 | -27.204 | -24.929 | -22.736 | -20.605 | -18.524 | -16.483 |
| 199 | -32.127 | -29.568 | -27.194 | -24.932 | -22.747 | -20.623 | -18.546 | -16.507 |
| 200 | -32.075 | -29.542 | -27.185 | -24.935 | -22.759 | -20.640 | -18.567 | -16.530 |

Table 83

FIG. 107

|  | Label | | | | | | | |
|---|---|---|---|---|---|---|---|---|
|  | 8 | 9 | 10 | 11 | 12 | 13 | 14 | 15 |
| Design # | | | | | | | | |
| 161 | -12.630 | -10.749 | -8.963 | -7.247 | -5.586 | -3.963 | -2.368 | -0.788 |
| 162 | -12.678 | -10.790 | -8.996 | -7.274 | -5.606 | -3.978 | -2.376 | -0.790 |
| 163 | -12.728 | -10.833 | -9.032 | -7.303 | -5.628 | -3.993 | -2.386 | -0.794 |
| 164 | -12.782 | -10.879 | -9.070 | -7.334 | -5.652 | -4.010 | -2.396 | -0.797 |
| 165 | -12.838 | -10.927 | -9.111 | -7.367 | -5.677 | -4.028 | -2.406 | -0.800 |
| 166 | -12.897 | -10.979 | -9.154 | -7.402 | -5.704 | -4.047 | -2.418 | -0.804 |
| 167 | -12.959 | -11.034 | -9.201 | -7.440 | -5.734 | -4.068 | -2.430 | -0.808 |
| 168 | -13.023 | -11.091 | -9.250 | -7.480 | -5.765 | -4.090 | -2.443 | -0.813 |
| 169 | -13.089 | -11.151 | -9.302 | -7.523 | -5.798 | -4.114 | -2.458 | -0.817 |
| 170 | -13.157 | -11.214 | -9.356 | -7.568 | -5.834 | -4.140 | -2.473 | -0.823 |
| 171 | -13.226 | -11.278 | -9.413 | -7.616 | -5.871 | -4.167 | -2.489 | -0.828 |
| 172 | -13.295 | -11.344 | -9.472 | -7.666 | -5.911 | -4.195 | -2.507 | -0.834 |
| 173 | -13.365 | -11.410 | -9.532 | -7.717 | -5.952 | -4.225 | -2.525 | -0.840 |
| 174 | -13.430 | -11.470 | -9.590 | -7.770 | -5.990 | -4.250 | -2.540 | -0.850 |
| 175 | -13.435 | -11.477 | -9.593 | -7.769 | -5.994 | -4.256 | -2.543 | -0.846 |
| 176 | -13.503 | -11.544 | -9.654 | -7.822 | -6.037 | -4.287 | -2.562 | -0.852 |
| 177 | -13.570 | -11.609 | -9.714 | -7.875 | -6.080 | -4.319 | -2.582 | -0.859 |
| 178 | -13.636 | -11.673 | -9.774 | -7.927 | -6.122 | -4.350 | -2.601 | -0.865 |
| 179 | -13.699 | -11.735 | -9.832 | -7.978 | -6.164 | -4.381 | -2.620 | -0.872 |
| 180 | -13.760 | -11.796 | -9.888 | -8.027 | -6.204 | -4.411 | -2.638 | -0.878 |
| 181 | -13.819 | -11.853 | -9.942 | -8.075 | -6.243 | -4.440 | -2.656 | -0.884 |
| 182 | -13.875 | -11.909 | -9.993 | -8.120 | -6.281 | -4.468 | -2.673 | -0.890 |
| 183 | -13.929 | -11.961 | -10.043 | -8.164 | -6.317 | -4.495 | -2.690 | -0.895 |
| 184 | -13.980 | -12.011 | -10.089 | -8.205 | -6.351 | -4.520 | -2.705 | -0.901 |
| 185 | -14.028 | -12.059 | -10.134 | -8.244 | -6.383 | -4.544 | -2.720 | -0.906 |
| 186 | -14.074 | -12.104 | -10.176 | -8.281 | -6.413 | -4.566 | -2.734 | -0.910 |
| 187 | -14.118 | -12.147 | -10.216 | -8.316 | -6.442 | -4.588 | -2.747 | -0.915 |
| 188 | -14.160 | -12.188 | -10.253 | -8.349 | -6.469 | -4.608 | -2.760 | -0.919 |
| 189 | -14.199 | -12.226 | -10.289 | -8.381 | -6.495 | -4.627 | -2.771 | -0.923 |
| 190 | -14.237 | -12.263 | -10.323 | -8.411 | -6.520 | -4.645 | -2.783 | -0.927 |
| 191 | -14.272 | -12.298 | -10.355 | -8.439 | -6.543 | -4.662 | -2.793 | -0.930 |
| 192 | -14.306 | -12.331 | -10.386 | -8.465 | -6.565 | -4.679 | -2.803 | -0.934 |
| 193 | -14.337 | -12.361 | -10.414 | -8.490 | -6.585 | -4.694 | -2.812 | -0.937 |
| 194 | -14.369 | -12.392 | -10.442 | -8.515 | -6.605 | -4.709 | -2.821 | -0.940 |
| 195 | -14.397 | -12.419 | -10.467 | -8.537 | -6.623 | -4.722 | -2.830 | -0.943 |
| 196 | -14.424 | -12.446 | -10.492 | -8.558 | -6.640 | -4.735 | -2.837 | -0.945 |
| 197 | -14.451 | -12.472 | -10.516 | -8.579 | -6.658 | -4.747 | -2.845 | -0.948 |
| 198 | -14.476 | -12.496 | -10.538 | -8.598 | -6.673 | -4.759 | -2.852 | -0.950 |
| 199 | -14.500 | -12.519 | -10.560 | -8.618 | -6.689 | -4.771 | -2.860 | -0.953 |
| 200 | -14.524 | -12.542 | -10.581 | -8.636 | -6.704 | -4.782 | -2.866 | -0.955 |

Table 84

FIG. 108

|  | Label | | | | | | | |
|---|---|---|---|---|---|---|---|---|
|  | 16 | 17 | 18 | 19 | 20 | 21 | 22 | 23 |
| Design # | | | | | | | | |
| 161 | 0.788 | 2.368 | 3.963 | 5.586 | 7.247 | 8.963 | 10.749 | 12.630 |
| 162 | 0.790 | 2.376 | 3.978 | 5.606 | 7.274 | 8.996 | 10.790 | 12.678 |
| 163 | 0.794 | 2.386 | 3.993 | 5.628 | 7.303 | 9.032 | 10.833 | 12.728 |
| 164 | 0.797 | 2.396 | 4.010 | 5.652 | 7.334 | 9.070 | 10.879 | 12.782 |
| 165 | 0.800 | 2.406 | 4.028 | 5.677 | 7.367 | 9.111 | 10.927 | 12.838 |
| 166 | 0.804 | 2.418 | 4.047 | 5.704 | 7.402 | 9.154 | 10.979 | 12.897 |
| 167 | 0.808 | 2.430 | 4.068 | 5.734 | 7.440 | 9.201 | 11.034 | 12.959 |
| 168 | 0.813 | 2.443 | 4.090 | 5.765 | 7.480 | 9.250 | 11.091 | 13.023 |
| 169 | 0.817 | 2.458 | 4.114 | 5.798 | 7.523 | 9.302 | 11.151 | 13.089 |
| 170 | 0.823 | 2.473 | 4.140 | 5.834 | 7.568 | 9.356 | 11.214 | 13.157 |
| 171 | 0.828 | 2.489 | 4.167 | 5.871 | 7.616 | 9.413 | 11.278 | 13.226 |
| 172 | 0.834 | 2.506 | 4.195 | 5.911 | 7.666 | 9.472 | 11.344 | 13.295 |
| 173 | 0.840 | 2.525 | 4.225 | 5.952 | 7.717 | 9.532 | 11.410 | 13.365 |
| 174 | 0.850 | 2.540 | 4.250 | 5.990 | 7.770 | 9.590 | 11.470 | 13.430 |
| 175 | 0.846 | 2.543 | 4.256 | 5.994 | 7.769 | 9.593 | 11.477 | 13.435 |
| 176 | 0.853 | 2.562 | 4.287 | 6.037 | 7.822 | 9.654 | 11.544 | 13.503 |
| 177 | 0.859 | 2.582 | 4.319 | 6.080 | 7.875 | 9.714 | 11.609 | 13.570 |
| 178 | 0.865 | 2.601 | 4.350 | 6.122 | 7.927 | 9.774 | 11.673 | 13.636 |
| 179 | 0.872 | 2.620 | 4.381 | 6.164 | 7.978 | 9.832 | 11.735 | 13.699 |
| 180 | 0.878 | 2.638 | 4.411 | 6.204 | 8.027 | 9.888 | 11.796 | 13.760 |
| 181 | 0.884 | 2.656 | 4.440 | 6.244 | 8.075 | 9.942 | 11.853 | 13.819 |
| 182 | 0.890 | 2.673 | 4.468 | 6.281 | 8.120 | 9.993 | 11.909 | 13.875 |
| 183 | 0.896 | 2.690 | 4.495 | 6.317 | 8.164 | 10.043 | 11.961 | 13.929 |
| 184 | 0.901 | 2.705 | 4.520 | 6.351 | 8.205 | 10.089 | 12.011 | 13.980 |
| 185 | 0.906 | 2.720 | 4.544 | 6.383 | 8.244 | 10.134 | 12.059 | 14.028 |
| 186 | 0.910 | 2.734 | 4.566 | 6.413 | 8.281 | 10.176 | 12.105 | 14.074 |
| 187 | 0.915 | 2.747 | 4.588 | 6.442 | 8.316 | 10.216 | 12.147 | 14.118 |
| 188 | 0.919 | 2.760 | 4.608 | 6.469 | 8.349 | 10.253 | 12.188 | 14.160 |
| 189 | 0.923 | 2.771 | 4.627 | 6.495 | 8.381 | 10.289 | 12.226 | 14.199 |
| 190 | 0.927 | 2.783 | 4.645 | 6.520 | 8.411 | 10.323 | 12.263 | 14.237 |
| 191 | 0.930 | 2.793 | 4.662 | 6.543 | 8.439 | 10.355 | 12.298 | 14.272 |
| 192 | 0.934 | 2.803 | 4.679 | 6.565 | 8.466 | 10.386 | 12.331 | 14.306 |
| 193 | 0.937 | 2.812 | 4.694 | 6.585 | 8.490 | 10.414 | 12.361 | 14.337 |
| 194 | 0.940 | 2.821 | 4.709 | 6.605 | 8.515 | 10.442 | 12.392 | 14.369 |
| 195 | 0.943 | 2.830 | 4.722 | 6.623 | 8.537 | 10.467 | 12.419 | 14.397 |
| 196 | 0.945 | 2.837 | 4.735 | 6.640 | 8.558 | 10.492 | 12.446 | 14.424 |
| 197 | 0.948 | 2.845 | 4.747 | 6.658 | 8.579 | 10.516 | 12.472 | 14.451 |
| 198 | 0.950 | 2.852 | 4.759 | 6.673 | 8.598 | 10.538 | 12.496 | 14.476 |
| 199 | 0.953 | 2.860 | 4.771 | 6.689 | 8.618 | 10.560 | 12.519 | 14.500 |
| 200 | 0.955 | 2.866 | 4.782 | 6.704 | 8.636 | 10.580 | 12.542 | 14.524 |

Table 85

FIG. 109

|   | Label | | | | | | | |
|---|---|---|---|---|---|---|---|---|
|   | 24 | 25 | 26 | 27 | 28 | 29 | 30 | 31 |
| Design # | | | | | | | | |
| 161 | 14.633 | 16.795 | 19.156 | 21.758 | 24.643 | 27.863 | 31.511 | 35.803 |
| 162 | 14.688 | 16.854 | 19.215 | 21.808 | 24.671 | 27.856 | 31.455 | 35.678 |
| 163 | 14.745 | 16.916 | 19.275 | 21.856 | 24.697 | 27.847 | 31.397 | 35.551 |
| 164 | 14.805 | 16.979 | 19.335 | 21.903 | 24.721 | 27.836 | 31.337 | 35.424 |
| 165 | 14.867 | 17.043 | 19.394 | 21.949 | 24.743 | 27.823 | 31.275 | 35.296 |
| 166 | 14.932 | 17.108 | 19.453 | 21.994 | 24.763 | 27.808 | 31.212 | 35.167 |
| 167 | 14.998 | 17.174 | 19.512 | 22.037 | 24.781 | 27.790 | 31.147 | 35.038 |
| 168 | 15.065 | 17.240 | 19.569 | 22.078 | 24.797 | 27.771 | 31.081 | 34.909 |
| 169 | 15.134 | 17.306 | 19.626 | 22.117 | 24.811 | 27.750 | 31.014 | 34.779 |
| 170 | 15.203 | 17.372 | 19.681 | 22.155 | 24.823 | 27.728 | 30.946 | 34.650 |
| 171 | 15.273 | 17.436 | 19.735 | 22.191 | 24.833 | 27.704 | 30.877 | 34.522 |
| 172 | 15.342 | 17.501 | 19.788 | 22.226 | 24.842 | 27.679 | 30.808 | 34.394 |
| 173 | 15.411 | 17.563 | 19.839 | 22.259 | 24.850 | 27.653 | 30.739 | 34.268 |
| 174 | 15.480 | 17.620 | 19.890 | 22.290 | 24.860 | 27.630 | 30.670 | 34.150 |
| 175 | 15.479 | 17.625 | 19.888 | 22.290 | 24.856 | 27.627 | 30.671 | 34.144 |
| 176 | 15.546 | 17.685 | 19.936 | 22.320 | 24.862 | 27.601 | 30.603 | 34.022 |
| 177 | 15.611 | 17.743 | 19.982 | 22.348 | 24.866 | 27.574 | 30.537 | 33.902 |
| 178 | 15.673 | 17.799 | 20.026 | 22.375 | 24.870 | 27.548 | 30.472 | 33.785 |
| 179 | 15.734 | 17.853 | 20.069 | 22.401 | 24.874 | 27.522 | 30.409 | 33.672 |
| 180 | 15.793 | 17.905 | 20.110 | 22.426 | 24.877 | 27.497 | 30.347 | 33.562 |
| 181 | 15.849 | 17.954 | 20.149 | 22.450 | 24.880 | 27.473 | 30.288 | 33.455 |
| 182 | 15.903 | 18.002 | 20.187 | 22.473 | 24.883 | 27.450 | 30.231 | 33.353 |
| 183 | 15.954 | 18.048 | 20.223 | 22.495 | 24.886 | 27.428 | 30.176 | 33.254 |
| 184 | 16.003 | 18.091 | 20.257 | 22.516 | 24.889 | 27.407 | 30.124 | 33.160 |
| 185 | 16.050 | 18.133 | 20.290 | 22.536 | 24.892 | 27.387 | 30.073 | 33.068 |
| 186 | 16.094 | 18.172 | 20.321 | 22.556 | 24.895 | 27.368 | 30.025 | 32.981 |
| 187 | 16.136 | 18.210 | 20.351 | 22.574 | 24.898 | 27.350 | 29.980 | 32.898 |
| 188 | 16.176 | 18.246 | 20.380 | 22.592 | 24.901 | 27.333 | 29.936 | 32.817 |
| 189 | 16.214 | 18.280 | 20.407 | 22.609 | 24.904 | 27.317 | 29.894 | 32.740 |
| 190 | 16.250 | 18.313 | 20.434 | 22.626 | 24.906 | 27.301 | 29.854 | 32.666 |
| 191 | 16.285 | 18.344 | 20.459 | 22.642 | 24.910 | 27.287 | 29.816 | 32.595 |
| 192 | 16.318 | 18.374 | 20.483 | 22.657 | 24.913 | 27.273 | 29.780 | 32.527 |
| 193 | 16.348 | 18.401 | 20.505 | 22.671 | 24.915 | 27.260 | 29.746 | 32.464 |
| 194 | 16.379 | 18.429 | 20.528 | 22.686 | 24.918 | 27.248 | 29.712 | 32.400 |
| 195 | 16.406 | 18.454 | 20.548 | 22.699 | 24.921 | 27.236 | 29.681 | 32.342 |
| 196 | 16.433 | 18.478 | 20.568 | 22.712 | 24.924 | 27.225 | 29.652 | 32.285 |
| 197 | 16.459 | 18.502 | 20.587 | 22.724 | 24.927 | 27.215 | 29.623 | 32.230 |
| 198 | 16.483 | 18.524 | 20.605 | 22.736 | 24.929 | 27.204 | 29.595 | 32.178 |
| 199 | 16.507 | 18.546 | 20.623 | 22.747 | 24.932 | 27.194 | 29.568 | 32.127 |
| 200 | 16.530 | 18.567 | 20.640 | 22.759 | 24.935 | 27.185 | 29.542 | 32.075 |

Table 86

FIG. 110

|  | Label | | | | | | | |
| --- | --- | --- | --- | --- | --- | --- | --- | --- |
|  | 0 | 1 | 2 | 3 | 4 | 5 | 6 | 7 |
| Design # | | | | | | | | |
| 201 | -32.030 | -29.518 | -27.177 | -24.937 | -22.770 | -20.656 | -18.586 | -16.551 |
| 202 | -31.991 | -29.497 | -27.169 | -24.939 | -22.778 | -20.670 | -18.603 | -16.570 |
| 203 | -31.943 | -29.472 | -27.160 | -24.941 | -22.788 | -20.686 | -18.623 | -16.592 |
| 204 | -31.897 | -29.450 | -27.153 | -24.944 | -22.799 | -20.701 | -18.641 | -16.611 |
| 205 | -31.863 | -29.431 | -27.146 | -24.946 | -22.808 | -20.714 | -18.656 | -16.627 |
| 206 | -31.831 | -29.416 | -27.141 | -24.948 | -22.814 | -20.724 | -18.668 | -16.641 |
| 207 | -31.803 | -29.401 | -27.135 | -24.950 | -22.821 | -20.734 | -18.681 | -16.654 |
| 208 | -31.800 | -29.402 | -27.142 | -24.960 | -22.834 | -20.749 | -18.697 | -16.670 |
| 209 | -31.732 | -29.365 | -27.122 | -24.953 | -22.836 | -20.757 | -18.709 | -16.686 |
| 210 | -31.670 | -29.332 | -27.107 | -24.951 | -22.843 | -20.771 | -18.727 | -16.706 |
| 211 | -31.644 | -29.307 | -27.086 | -24.937 | -22.838 | -20.774 | -18.735 | -16.718 |
| 212 | -31.640 | -29.319 | -27.107 | -24.959 | -22.856 | -20.788 | -18.746 | -16.727 |

Table 87

FIG. 111

|  | Label | | | | | | | |
|---|---|---|---|---|---|---|---|---|
|  | 8 | 9 | 10 | 11 | 12 | 13 | 14 | 15 |
| Design # | | | | | | | | |
| 201 | -14.545 | -12.563 | -10.599 | -8.652 | -6.717 | -4.791 | -2.872 | -0.957 |
| 202 | -14.564 | -12.581 | -10.617 | -8.667 | -6.730 | -4.801 | -2.878 | -0.959 |
| 203 | -14.587 | -12.603 | -10.637 | -8.684 | -6.743 | -4.811 | -2.884 | -0.961 |
| 204 | -14.606 | -12.622 | -10.655 | -8.701 | -6.757 | -4.821 | -2.891 | -0.963 |
| 205 | -14.622 | -12.637 | -10.668 | -8.712 | -6.766 | -4.827 | -2.894 | -0.964 |
| 206 | -14.637 | -12.652 | -10.681 | -8.723 | -6.775 | -4.834 | -2.899 | -0.966 |
| 207 | -14.650 | -12.664 | -10.692 | -8.733 | -6.784 | -4.841 | -2.902 | -0.967 |
| 208 | -14.664 | -12.676 | -10.701 | -8.737 | -6.783 | -4.835 | -2.893 | -0.954 |
| 209 | -14.683 | -12.696 | -10.722 | -8.759 | -6.804 | -4.856 | -2.912 | -0.970 |
| 210 | -14.704 | -12.716 | -10.741 | -8.776 | -6.819 | -4.868 | -2.922 | -0.978 |
| 211 | -14.717 | -12.731 | -10.757 | -8.793 | -6.836 | -4.884 | -2.936 | -0.990 |
| 212 | -14.724 | -12.735 | -10.758 | -8.790 | -6.830 | -4.875 | -2.923 | -0.974 |

Table 88

FIG. 112

|  | Label | | | | | | | |
|---|---|---|---|---|---|---|---|---|
|  | 16 | 17 | 18 | 19 | 20 | 21 | 22 | 23 |
| Design # | | | | | | | | |
| 201 | 0.957 | 2.872 | 4.791 | 6.717 | 8.652 | 10.599 | 12.563 | 14.545 |
| 202 | 0.959 | 2.878 | 4.801 | 6.730 | 8.667 | 10.617 | 12.581 | 14.564 |
| 203 | 0.961 | 2.884 | 4.811 | 6.743 | 8.684 | 10.637 | 12.603 | 14.587 |
| 204 | 0.963 | 2.891 | 4.821 | 6.757 | 8.701 | 10.655 | 12.622 | 14.606 |
| 205 | 0.964 | 2.894 | 4.827 | 6.766 | 8.712 | 10.668 | 12.637 | 14.622 |
| 206 | 0.966 | 2.899 | 4.834 | 6.775 | 8.723 | 10.681 | 12.652 | 14.637 |
| 207 | 0.967 | 2.902 | 4.841 | 6.784 | 8.733 | 10.692 | 12.664 | 14.650 |
| 208 | 0.984 | 2.922 | 4.862 | 6.807 | 8.758 | 10.718 | 12.689 | 14.674 |
| 209 | 0.970 | 2.912 | 4.856 | 6.804 | 8.759 | 10.722 | 12.696 | 14.683 |
| 210 | 0.966 | 2.910 | 4.857 | 6.808 | 8.765 | 10.729 | 12.704 | 14.692 |
| 211 | 0.956 | 2.904 | 4.855 | 6.809 | 8.769 | 10.735 | 12.712 | 14.701 |
| 212 | 0.974 | 2.923 | 4.875 | 6.830 | 8.790 | 10.758 | 12.735 | 14.724 |

Table 89

FIG. 113

|  | Label | | | | | | | |
|---|---|---|---|---|---|---|---|---|
|  | 24 | 25 | 26 | 27 | 28 | 29 | 30 | 31 |
| Design # | | | | | | | | |
| 201 | 16.551 | 18.586 | 20.656 | 22.770 | 24.937 | 27.177 | 29.518 | 32.030 |
| 202 | 16.570 | 18.603 | 20.670 | 22.778 | 24.939 | 27.169 | 29.497 | 31.991 |
| 203 | 16.592 | 18.623 | 20.686 | 22.788 | 24.941 | 27.160 | 29.472 | 31.943 |
| 204 | 16.611 | 18.641 | 20.701 | 22.799 | 24.945 | 27.153 | 29.450 | 31.897 |
| 205 | 16.627 | 18.656 | 20.714 | 22.808 | 24.946 | 27.146 | 29.431 | 31.863 |
| 206 | 16.641 | 18.668 | 20.724 | 22.814 | 24.948 | 27.141 | 29.416 | 31.831 |
| 207 | 16.654 | 18.681 | 20.734 | 22.821 | 24.950 | 27.135 | 29.401 | 31.803 |
| 208 | 16.676 | 18.699 | 20.746 | 22.825 | 24.943 | 27.113 | 29.357 | 31.723 |
| 209 | 16.686 | 18.709 | 20.757 | 22.836 | 24.953 | 27.122 | 29.365 | 31.732 |
| 210 | 16.697 | 18.720 | 20.768 | 22.845 | 24.959 | 27.124 | 29.362 | 31.726 |
| 211 | 16.706 | 18.729 | 20.775 | 22.850 | 24.962 | 27.127 | 29.366 | 31.729 |
| 212 | 16.727 | 18.746 | 20.788 | 22.856 | 24.959 | 27.107 | 29.318 | 31.639 |

Table 90

FIG. 114

| Design # | SNRs | 5.00% | 15.00% | 30.00% | 45.00% | 60.00% | 100.00% |
|---|---|---|---|---|---|---|---|
| 1 | -5 | 0.87 | 0.74 | 0.63 | 0.53 | 0.41 | 0 |
| 2 | -4.8 | 1.02 | 0.78 | 0.67 | 0.57 | 0.43 | 0 |
| 3 | -4.6 | 0.86 | 0.73 | 0.62 | 0.53 | 0.45 | 0 |
| 4 | -4.4 | 0.76 | 0.65 | 0.55 | 0.47 | 0.4 | 0 |
| 5 | -4.2 | 1.03 | 0.88 | 0.75 | 0.63 | 0.54 | 0 |
| 6 | -4 | 1 | 0.85 | 0.72 | 0.61 | 0.52 | 0 |
| 7 | -3.8 | 1.18 | 0.9 | 0.77 | 0.65 | 0.55 | 0 |
| 8 | -3.6 | 1.14 | 0.97 | 0.83 | 0.7 | 0.6 | 0 |
| 9 | -3.4 | 1.19 | 1.01 | 0.86 | 0.73 | 0.62 | 0 |
| 10 | -3.2 | 1.41 | 1.2 | 1.02 | 0.87 | 0.66 | 0 |
| 11 | -3 | 1.33 | 1.13 | 0.96 | 0.81 | 0.62 | 0 |
| 12 | -2.8 | 1.49 | 1.14 | 0.97 | 0.82 | 0.63 | 0 |
| 13 | -2.6 | 1.43 | 1.22 | 1.03 | 0.88 | 0.75 | 0 |
| 14 | -2.4 | 1.74 | 1.48 | 1.26 | 1.07 | 0.91 | 0 |
| 15 | -2.2 | 1.44 | 1.23 | 1.04 | 0.89 | 0.75 | 0 |
| 16 | -2 | 1.45 | 1.23 | 1.05 | 0.89 | 0.76 | 0 |
| 17 | -1.8 | 1.81 | 1.54 | 1.31 | 1.11 | 0.85 | 0 |
| 18 | -1.6 | 1.87 | 1.59 | 1.35 | 1.15 | 0.88 | 0 |
| 19 | -1.4 | 1.82 | 1.55 | 1.32 | 1.12 | 0.95 | 0 |
| 20 | -1.2 | 2.01 | 1.7 | 1.45 | 1.23 | 1.05 | 0 |
| 21 | -1 | 2.01 | 1.71 | 1.45 | 1.23 | 0.94 | 0 |
| 22 | -0.8 | 2.03 | 1.73 | 1.47 | 1.25 | 1.06 | 0 |
| 23 | -0.6 | 2.04 | 1.73 | 1.47 | 1.25 | 1.06 | 0 |
| 24 | -0.4 | 2.27 | 1.93 | 1.64 | 1.39 | 1.18 | 0 |
| 25 | -0.2 | 2.26 | 1.93 | 1.64 | 1.39 | 1.06 | 0 |
| 26 | 0 | 2.27 | 1.93 | 1.64 | 1.39 | 1.18 | 0 |
| 27 | 0 | 2.27 | 1.93 | 1.64 | 1.39 | 1.18 | 0 |
| 28 | 0.2 | 2.29 | 1.95 | 1.66 | 1.41 | 1.2 | 0 |
| 29 | 0.4 | 2.83 | 2.4 | 2.04 | 1.74 | 1.48 | 0 |
| 30 | 0.6 | 2.55 | 2.16 | 1.84 | 1.56 | 1.33 | 0 |
| 31 | 0.8 | 2.54 | 2.16 | 1.84 | 1.56 | 1.19 | 0 |
| 32 | 1 | 3.26 | 2.77 | 2.35 | 2 | 1.53 | 0 |
| 33 | 1.2 | 3.29 | 2.79 | 2.37 | 2.02 | 1.72 | 0 |
| 34 | 1.4 | 3.3 | 2.8 | 2.38 | 2.02 | 1.55 | 0 |
| 35 | 1.6 | 2.97 | 2.53 | 2.15 | 1.83 | 1.55 | 0 |
| 36 | 1.8 | 3.31 | 2.82 | 2.39 | 2.03 | 1.73 | 0 |
| 37 | 2 | 3.69 | 3.13 | 2.66 | 2.26 | 1.73 | 0 |
| 38 | 2.2 | 3.69 | 2.83 | 2.4 | 2.04 | 1.74 | 0 |
| 39 | 2.4 | 3.84 | 3.26 | 2.77 | 2.36 | 1.8 | 0 |
| 40 | 2.6 | 3.89 | 3.31 | 2.81 | 2.39 | 1.83 | 0 |

Table 91

FIG. 115

| Design # | SNRs | 5.00% | 15.00% | 30.00% | 45.00% | 60.00% | 100.00% |
|---|---|---|---|---|---|---|---|
| 41 | 2.8 | 3.51 | 2.98 | 2.53 | 2.15 | 1.65 | 0 |
| 42 | 3 | 3.49 | 2.97 | 2.52 | 2.15 | 1.64 | 0 |
| 43 | 3.2 | 3.86 | 3.28 | 2.79 | 2.37 | 1.63 | 0 |
| 44 | 3.4 | 3.48 | 2.96 | 2.51 | 2.14 | 1.63 | 0 |
| 45 | 3.6 | 3.48 | 2.96 | 2.51 | 2.14 | 1.63 | 0 |
| 46 | 3.8 | 3.48 | 2.96 | 2.51 | 2.14 | 1.64 | 0 |
| 47 | 4 | 3.63 | 3.08 | 2.62 | 2.23 | 1.7 | 0 |
| 48 | 4.2 | 3.67 | 3.12 | 2.65 | 2.25 | 1.72 | 0 |
| 49 | 4.4 | 3.5 | 2.98 | 2.53 | 2.15 | 1.65 | 0 |
| 50 | 4.6 | 3.45 | 2.94 | 2.5 | 2.12 | 1.62 | 0 |
| 51 | 4.78 | 3.72 | 3.16 | 2.68 | 2.28 | 1.75 | 0 |
| 52 | 4.8 | 3.64 | 3.1 | 2.63 | 2.24 | 1.71 | 0 |
| 53 | 5 | 3.42 | 2.9 | 2.47 | 2.1 | 1.6 | 0 |
| 54 | 5.2 | 2.82 | 2.4 | 2.04 | 1.73 | 1.47 | 0 |
| 55 | 5.4 | 2.27 | 1.93 | 1.64 | 1.4 | 1.19 | 0 |
| 56 | 5.6 | 1.77 | 1.5 | 1.28 | 1.08 | 0.92 | 0 |
| 57 | 5.8 | 2.71 | 2.31 | 1.96 | 1.67 | 1.42 | 0 |
| 58 | 6 | 2.43 | 2.07 | 1.76 | 1.49 | 1.27 | 0 |
| 59 | 6.2 | 3.53 | 3 | 2.55 | 2.17 | 1.66 | 0 |
| 60 | 6.4 | 3.58 | 3.04 | 2.58 | 2.2 | 1.68 | 0 |
| 61 | 6.6 | 3.8 | 3.23 | 2.74 | 2.33 | 1.78 | 0 |
| 62 | 6.8 | 3.87 | 3.29 | 2.8 | 2.38 | 1.64 | 0 |
| 63 | 7 | 3.49 | 2.97 | 2.52 | 2.14 | 1.82 | 0 |
| 64 | 7.2 | 3.5 | 2.97 | 2.53 | 2.15 | 1.83 | 0 |
| 65 | 7.4 | 3.15 | 2.68 | 2.28 | 1.94 | 1.65 | 0 |
| 66 | 7.6 | 3.69 | 3.14 | 2.67 | 2.27 | 1.73 | 0 |
| 67 | 7.8 | 3.33 | 2.83 | 2.41 | 2.04 | 1.74 | 0 |
| 68 | 8 | 3.75 | 3.19 | 2.71 | 2.3 | 1.76 | 0 |
| 69 | 8.2 | 3.77 | 3.2 | 2.72 | 2.32 | 1.59 | 0 |
| 70 | 8.4 | 3.55 | 3.02 | 2.57 | 2.18 | 1.85 | 0 |
| 71 | 8.48 | 3.56 | 3.02 | 2.57 | 2.18 | 1.86 | 0 |
| 72 | 8.6 | 3.54 | 3.01 | 2.56 | 2.17 | 1.66 | 0 |
| 73 | 8.8 | 3.54 | 3.01 | 2.56 | 2.17 | 1.66 | 0 |
| 74 | 9 | 3.72 | 3.16 | 2.68 | 2.28 | 1.75 | 0 |
| 75 | 9.2 | 3.35 | 2.85 | 2.42 | 2.06 | 1.75 | 0 |
| 76 | 9.4 | 3.36 | 2.85 | 2.43 | 2.06 | 1.75 | 0 |
| 77 | 9.6 | 3.36 | 2.85 | 2.43 | 2.06 | 1.75 | 0 |
| 78 | 9.8 | 3.55 | 3.01 | 2.56 | 2.18 | 1.67 | 0 |
| 79 | 10 | 3.56 | 3.03 | 2.57 | 2.19 | 1.67 | 0 |
| 80 | 10.2 | 3.57 | 3.04 | 2.58 | 2.19 | 1.68 | 0 |

Table 92

FIG. 116

| Design # | SNRs | 5.00% | 15.00% | 30.00% | 45.00% | 60.00% | 100.00% |
|---|---|---|---|---|---|---|---|
| 81 | 10.4 | 2.77 | 2.35 | 2 | 1.7 | 1.44 | 0 |
| 82 | 10.6 | 2.83 | 2.41 | 2.05 | 1.74 | 1.48 | 0 |
| 83 | 10.8 | 2.87 | 2.44 | 2.07 | 1.76 | 1.5 | 0 |
| 84 | 11 | 2.76 | 2.35 | 1.99 | 1.7 | 1.44 | 0 |
| 85 | 11.2 | 2.17 | 1.84 | 1.57 | 1.33 | 1.13 | 0 |
| 86 | 11.4 | 2.35 | 2 | 1.7 | 1.44 | 1.23 | 0 |
| 87 | 11.6 | 2.22 | 1.89 | 1.6 | 1.36 | 1.16 | 0 |
| 88 | 11.8 | 2.34 | 1.99 | 1.69 | 1.43 | 1.22 | 0 |
| 89 | 11.83 | 2.33 | 1.98 | 1.69 | 1.43 | 1.22 | 0 |
| 90 | 12 | 2.34 | 1.99 | 1.69 | 1.44 | 1.22 | 0 |
| 91 | 12.2 | 2.34 | 1.99 | 1.69 | 1.44 | 1.22 | 0 |
| 92 | 12.4 | 2.43 | 2.06 | 1.75 | 1.49 | 1.27 | 0 |
| 93 | 12.6 | 2.25 | 1.92 | 1.63 | 1.38 | 1.18 | 0 |
| 94 | 12.8 | 2.26 | 1.92 | 1.63 | 1.39 | 1.18 | 0 |
| 95 | 13 | 2.26 | 1.92 | 1.63 | 1.39 | 1.18 | 0 |
| 96 | 13.2 | 1.96 | 1.67 | 1.42 | 1.21 | 1.03 | 0 |
| 97 | 13.4 | 1.81 | 1.54 | 1.31 | 1.11 | 0.94 | 0 |
| 98 | 13.6 | 1.83 | 1.55 | 1.32 | 1.12 | 0.95 | 0 |
| 99 | 13.8 | 1.64 | 1.39 | 1.18 | 1 | 0.85 | 0 |
| 100 | 14 | 1.39 | 1.18 | 1.01 | 0.86 | 0.73 | 0 |
| 101 | 14.2 | 1.42 | 1.21 | 1.03 | 0.87 | 0.74 | 0 |
| 102 | 14.4 | 1.44 | 1.23 | 1.04 | 0.89 | 0.75 | 0 |
| 103 | 14.6 | 1.44 | 1.22 | 1.04 | 0.88 | 0.75 | 0 |
| 104 | 14.8 | 1.45 | 1.23 | 1.04 | 0.89 | 0.75 | 0 |
| 105 | 15 | 1.31 | 1.12 | 0.95 | 0.81 | 0.69 | 0 |
| 106 | 15.05 | 1.29 | 1.09 | 0.93 | 0.79 | 0.67 | 0 |
| 107 | 15.2 | 0.93 | 0.79 | 0.67 | 0.57 | 0.48 | 0 |
| 108 | 15.4 | 0.98 | 0.83 | 0.71 | 0.6 | 0.51 | 0 |
| 109 | 15.6 | 0.79 | 0.67 | 0.57 | 0.48 | 0.41 | 0 |
| 110 | 15.8 | 0.84 | 0.72 | 0.61 | 0.52 | 0.44 | 0 |
| 111 | 16 | 0.84 | 0.71 | 0.61 | 0.52 | 0.44 | 0 |
| 112 | 16.2 | 0.85 | 0.72 | 0.61 | 0.52 | 0.44 | 0 |
| 113 | 16.4 | 0.85 | 0.72 | 0.61 | 0.52 | 0.44 | 0 |
| 114 | 16.6 | 0.85 | 0.72 | 0.61 | 0.52 | 0.44 | 0 |
| 115 | 16.8 | 0.85 | 0.72 | 0.61 | 0.52 | 0.44 | 0 |
| 116 | 17 | 0.85 | 0.72 | 0.62 | 0.52 | 0.45 | 0 |
| 117 | 17.2 | 0.85 | 0.72 | 0.62 | 0.52 | 0.44 | 0 |
| 118 | 17.4 | 0.74 | 0.63 | 0.54 | 0.45 | 0.39 | 0 |
| 119 | 17.6 | 0.75 | 0.64 | 0.54 | 0.46 | 0.39 | 0 |
| 120 | 17.8 | 0.79 | 0.67 | 0.57 | 0.49 | 0.41 | 0 |

Table 93

FIG. 117

| Design # | SNRs | 5.00% | 15.00% | 30.00% | 45.00% | 60.00% | 100.00% |
|---|---|---|---|---|---|---|---|
| 121 | 18 | 0.7 | 0.6 | 0.51 | 0.43 | 0.37 | 0 |
| 122 | 18.2 | 0.74 | 0.63 | 0.54 | 0.46 | 0.39 | 0 |
| 123 | 18.23 | 0.67 | 0.57 | 0.49 | 0.41 | 0.35 | 0 |
| 124 | 18.4 | 0.69 | 0.59 | 0.5 | 0.43 | 0.36 | 0 |
| 125 | 18.6 | 0.72 | 0.61 | 0.52 | 0.44 | 0.37 | 0 |
| 126 | 18.8 | 0.75 | 0.64 | 0.54 | 0.46 | 0.39 | 0 |
| 127 | 19 | 0.79 | 0.67 | 0.57 | 0.48 | 0.41 | 0 |
| 128 | 19.2 | 0.82 | 0.7 | 0.6 | 0.51 | 0.43 | 0 |
| 129 | 19.4 | 0.86 | 0.73 | 0.62 | 0.53 | 0.45 | 0 |
| 130 | 19.6 | 0.89 | 0.76 | 0.65 | 0.55 | 0.47 | 0 |
| 131 | 19.8 | 0.93 | 0.79 | 0.67 | 0.57 | 0.48 | 0 |
| 132 | 20 | 0.96 | 0.82 | 0.7 | 0.59 | 0.5 | 0 |
| 133 | 20.2 | 1 | 0.85 | 0.72 | 0.61 | 0.52 | 0 |
| 134 | 20.4 | 1.03 | 0.88 | 0.75 | 0.63 | 0.54 | 0 |
| 135 | 20.6 | 1.07 | 0.91 | 0.77 | 0.65 | 0.56 | 0 |
| 136 | 20.8 | 0.99 | 0.84 | 0.71 | 0.61 | 0.52 | 0 |
| 137 | 21 | 1.14 | 0.97 | 0.82 | 0.7 | 0.52 | 0 |
| 138 | 21.2 | 1.07 | 0.91 | 0.77 | 0.65 | 0.56 | 0 |
| 139 | 21.4 | 1 | 0.85 | 0.72 | 0.61 | 0.52 | 0 |
| 140 | 21.42 | 1 | 0.85 | 0.73 | 0.62 | 0.52 | 0 |
| 141 | 21.6 | 1.04 | 0.88 | 0.75 | 0.64 | 0.49 | 0 |
| 142 | 21.8 | 0.97 | 0.83 | 0.7 | 0.6 | 0.51 | 0 |
| 143 | 22 | 1.01 | 0.86 | 0.73 | 0.62 | 0.47 | 0 |
| 144 | 22.2 | 0.94 | 0.8 | 0.68 | 0.58 | 0.44 | 0 |
| 145 | 22.4 | 0.87 | 0.74 | 0.63 | 0.54 | 0.41 | 0 |
| 146 | 22.6 | 0.9 | 0.77 | 0.65 | 0.55 | 0.42 | 0 |
| 147 | 22.8 | 0.84 | 0.71 | 0.61 | 0.52 | 0.44 | 0 |
| 148 | 23 | 0.78 | 0.66 | 0.56 | 0.48 | 0.41 | 0 |
| 149 | 23.2 | 0.8 | 0.68 | 0.58 | 0.49 | 0.38 | 0 |
| 150 | 23.4 | 0.74 | 0.63 | 0.54 | 0.46 | 0.35 | 0 |
| 151 | 23.6 | 0.76 | 0.65 | 0.55 | 0.47 | 0.36 | 0 |
| 152 | 23.8 | 0.7 | 0.6 | 0.51 | 0.43 | 0.37 | 0 |
| 153 | 24 | 0.65 | 0.55 | 0.47 | 0.4 | 0.34 | 0 |
| 154 | 24.2 | 0.66 | 0.56 | 0.48 | 0.41 | 0.31 | 0 |
| 155 | 24.4 | 0.61 | 0.52 | 0.44 | 0.38 | 0.29 | 0 |
| 156 | 24.6 | 0.56 | 0.48 | 0.41 | 0.35 | 0.26 | 0 |
| 157 | 24.69 | 0.57 | 0.48 | 0.41 | 0.35 | 0.3 | 0 |
| 158 | 24.8 | 0.58 | 0.49 | 0.42 | 0.36 | 0.27 | 0 |
| 159 | 25 | 0.54 | 0.45 | 0.39 | 0.33 | 0.28 | 0 |
| 160 | 25.2 | 0.49 | 0.42 | 0.36 | 0.3 | 0.26 | 0 |

Table 94

FIG. 118

| Design # | SNRs | 5.00% | 15.00% | 30.00% | 45.00% | 60.00% | 100.00% |
|---|---|---|---|---|---|---|---|
| 161 | 25.4 | 0.51 | 0.43 | 0.37 | 0.31 | 0.26 | 0 |
| 162 | 25.6 | 0.47 | 0.4 | 0.34 | 0.29 | 0.24 | 0 |
| 163 | 25.8 | 0.48 | 0.41 | 0.35 | 0.29 | 0.22 | 0 |
| 164 | 26 | 0.44 | 0.37 | 0.32 | 0.27 | 0.23 | 0 |
| 165 | 26.2 | 0.41 | 0.34 | 0.29 | 0.25 | 0.21 | 0 |
| 166 | 26.4 | 0.41 | 0.35 | 0.3 | 0.25 | 0.21 | 0 |
| 167 | 26.6 | 0.4 | 0.34 | 0.29 | 0.24 | 0.19 | 0 |
| 168 | 26.8 | 0.35 | 0.3 | 0.25 | 0.21 | 0.18 | 0 |
| 169 | 27 | 0.34 | 0.29 | 0.24 | 0.21 | 0.18 | 0 |
| 170 | 27.2 | 0.32 | 0.28 | 0.23 | 0.2 | 0.17 | 0 |
| 171 | 27.4 | 0.31 | 0.27 | 0.23 | 0.19 | 0.16 | 0 |
| 172 | 27.6 | 0.27 | 0.23 | 0.2 | 0.17 | 0.14 | 0 |
| 173 | 27.8 | 0.26 | 0.22 | 0.19 | 0.16 | 0.14 | 0 |
| 174 | 28 | 0.25 | 0.21 | 0.18 | 0.15 | 0.13 | 0 |
| 175 | 28.19 | 0.24 | 0.2 | 0.17 | 0.15 | 0.13 | 0 |
| 176 | 28.2 | 0.24 | 0.2 | 0.17 | 0.15 | 0.13 | 0 |
| 177 | 28.4 | 0.23 | 0.2 | 0.17 | 0.14 | 0.12 | 0 |
| 178 | 28.6 | 0.22 | 0.19 | 0.16 | 0.14 | 0.12 | 0 |
| 179 | 28.8 | 0.21 | 0.18 | 0.15 | 0.13 | 0.11 | 0 |
| 180 | 29 | 0.2 | 0.17 | 0.15 | 0.12 | 0.1 | 0 |
| 181 | 29.2 | 0.17 | 0.15 | 0.13 | 0.11 | 0.09 | 0 |
| 182 | 29.4 | 0.17 | 0.14 | 0.12 | 0.1 | 0.09 | 0 |
| 183 | 29.6 | 0.16 | 0.14 | 0.12 | 0.1 | 0.08 | 0 |
| 184 | 29.8 | 0.15 | 0.13 | 0.11 | 0.09 | 0.08 | 0 |
| 185 | 30 | 0.15 | 0.12 | 0.11 | 0.09 | 0.08 | 0 |
| 186 | 30.2 | 0.14 | 0.12 | 0.1 | 0.09 | 0.07 | 0 |
| 187 | 30.4 | 0.13 | 0.11 | 0.1 | 0.08 | 0.07 | 0 |
| 188 | 30.6 | 0.13 | 0.11 | 0.09 | 0.08 | 0.07 | 0 |
| 189 | 30.8 | 0.12 | 0.1 | 0.09 | 0.07 | 0.06 | 0 |
| 190 | 31 | 0.12 | 0.1 | 0.08 | 0.07 | 0.05 | 0 |
| 191 | 31.2 | 0.1 | 0.08 | 0.07 | 0.06 | 0.05 | 0 |
| 192 | 31.4 | 0.1 | 0.08 | 0.07 | 0.06 | 0.05 | 0 |
| 193 | 31.6 | 0.09 | 0.08 | 0.07 | 0.06 | 0.05 | 0 |
| 194 | 31.8 | 0.09 | 0.07 | 0.06 | 0.05 | 0.05 | 0 |
| 195 | 32 | 0.08 | 0.07 | 0.06 | 0.05 | 0.04 | 0 |
| 196 | 32.2 | 0.08 | 0.07 | 0.06 | 0.05 | 0.04 | 0 |
| 197 | 32.4 | 0.08 | 0.07 | 0.06 | 0.05 | 0.04 | 0 |
| 198 | 32.6 | 0.07 | 0.06 | 0.05 | 0.04 | 0.04 | 0 |
| 199 | 32.8 | 0.07 | 0.06 | 0.05 | 0.04 | 0.04 | 0 |
| 200 | 33 | 0.07 | 0.06 | 0.05 | 0.04 | 0.03 | 0 |

Table 95

FIG. 119

| Design # | SNRs | 5.00% | 15.00% | 30.00% | 45.00% | 60.00% | 100.00% |
|---|---|---|---|---|---|---|---|
| 201 | 33.2 | 0.06 | 0.05 | 0.05 | 0.04 | 0.03 | 0 |
| 202 | 33.4 | 0.06 | 0.05 | 0.04 | 0.04 | 0.03 | 0 |
| 203 | 33.6 | 0.06 | 0.05 | 0.04 | 0.04 | 0.03 | 0 |
| 204 | 33.8 | 0.06 | 0.05 | 0.04 | 0.03 | 0.03 | 0 |
| 205 | 34 | 0.05 | 0.04 | 0.04 | 0.03 | 0.03 | 0 |
| 206 | 34.2 | 0.05 | 0.04 | 0.04 | 0.03 | 0.03 | 0 |
| 207 | 34.4 | 0.05 | 0.04 | 0.04 | 0.03 | 0.03 | 0 |
| 208 | 34.6 | 0.05 | 0.04 | 0.03 | 0.03 | 0.02 | 0 |
| 209 | 34.8 | 0.05 | 0.04 | 0.03 | 0.03 | 0.02 | 0 |
| 210 | 35 | 0.04 | 0.04 | 0.03 | 0.03 | 0.02 | 0 |
| 211 | 35.2 | 0.04 | 0.04 | 0.03 | 0.03 | 0.02 | 0 |
| 212 | 35.4 | 0.04 | 0.03 | 0.03 | 0.02 | 0.02 | 0 |
| 213 | 35.6 | 0.04 | 0.03 | 0.03 | 0.02 | 0.02 | 0 |

Table 96

FIG. 120

| Design # | SNR | Opt. Cap | Std. Cap | Gain [bits] | Gain % |
|---|---|---|---|---|---|
| 1 | -5.0000 | 0.1977 | 0.1571 | 0.0407 | 25.9021 |
| 2 | -4.8000 | 0.2058 | 0.1637 | 0.0420 | 25.6676 |
| 3 | -4.6000 | 0.2141 | 0.1707 | 0.0434 | 25.4273 |
| 4 | -4.4000 | 0.2227 | 0.1779 | 0.0448 | 25.1813 |
| 5 | -4.2000 | 0.2316 | 0.1854 | 0.0462 | 24.9291 |
| 6 | -4.0000 | 0.2407 | 0.1931 | 0.0476 | 24.6715 |
| 7 | -3.8000 | 0.2502 | 0.2011 | 0.0491 | 24.4072 |
| 8 | -3.6000 | 0.2600 | 0.2094 | 0.0505 | 24.1364 |
| 9 | -3.4000 | 0.2700 | 0.2180 | 0.0520 | 23.8588 |
| 10 | -3.2000 | 0.2804 | 0.2269 | 0.0535 | 23.5744 |
| 11 | -3.0000 | 0.2910 | 0.2361 | 0.0550 | 23.2828 |
| 12 | -2.8000 | 0.3020 | 0.2456 | 0.0564 | 22.9836 |
| 13 | -2.6000 | 0.3133 | 0.2554 | 0.0579 | 22.6764 |
| 14 | -2.4000 | 0.3248 | 0.2655 | 0.0594 | 22.3611 |
| 15 | -2.2000 | 0.3367 | 0.2759 | 0.0608 | 22.0374 |
| 16 | -2.0000 | 0.3489 | 0.2867 | 0.0622 | 21.7045 |
| 17 | -1.8000 | 0.3613 | 0.2977 | 0.0636 | 21.3620 |
| 18 | -1.6000 | 0.3741 | 0.3092 | 0.0650 | 21.0097 |
| 19 | -1.4000 | 0.3872 | 0.3209 | 0.0663 | 20.6467 |
| 20 | -1.2000 | 0.4005 | 0.3330 | 0.0675 | 20.2727 |
| 21 | -1.0000 | 0.4141 | 0.3454 | 0.0687 | 19.8868 |
| 22 | -0.8000 | 0.4280 | 0.3582 | 0.0698 | 19.4885 |
| 23 | -0.6000 | 0.4421 | 0.3713 | 0.0708 | 19.0766 |
| 24 | -0.4000 | 0.4565 | 0.3847 | 0.0718 | 18.6515 |
| 25 | -0.2000 | 0.4711 | 0.3985 | 0.0726 | 18.2112 |
| 26 | 0.0000 | 0.4859 | 0.4127 | 0.0733 | 17.7556 |
| 27 | 0.1871 | 0.5 | 0.4262 | 0.0738 | 17.3143 |
| 28 | 0.2000 | 0.5010 | 0.4272 | 0.0738 | 17.2830 |
| 29 | 0.4000 | 0.5162 | 0.4420 | 0.0742 | 16.7935 |
| 30 | 0.6000 | 0.5316 | 0.4571 | 0.0744 | 16.2853 |
| 31 | 0.8000 | 0.5471 | 0.4726 | 0.0745 | 15.7577 |
| 32 | 1.0000 | 0.5628 | 0.4885 | 0.0743 | 15.2096 |
| 33 | 1.2000 | 0.5786 | 0.5047 | 0.0739 | 14.6402 |
| 34 | 1.4000 | 0.5944 | 0.5212 | 0.0732 | 14.0480 |
| 35 | 1.6000 | 0.6104 | 0.5380 | 0.0724 | 13.4584 |
| 36 | 1.8000 | 0.6270 | 0.5552 | 0.0718 | 12.9362 |
| 37 | 2.0000 | 0.6442 | 0.5727 | 0.0715 | 12.4812 |
| 38 | 2.2000 | 0.6619 | 0.5905 | 0.0714 | 12.0896 |
| 39 | 2.4000 | 0.6802 | 0.6087 | 0.0716 | 11.7577 |
| 40 | 2.6000 | 0.6991 | 0.6271 | 0.0720 | 11.4812 |

Table 97

FIG. 121

| | SNR | Opt. Cap | Std. Cap | Gain [bits] | Gain % |
|---|---|---|---|---|---|
| Design # | | | | | |
| 41 | 2.8000 | 0.7186 | 0.6459 | 0.0727 | 11.2561 |
| 42 | 3.0000 | 0.7386 | 0.6650 | 0.0737 | 11.0780 |
| 43 | 3.2000 | 0.7593 | 0.6844 | 0.0749 | 10.9425 |
| 44 | 3.4000 | 0.7804 | 0.7041 | 0.0764 | 10.8448 |
| 45 | 3.6000 | 0.8021 | 0.7241 | 0.0781 | 10.7804 |
| 46 | 3.8000 | 0.8243 | 0.7443 | 0.0800 | 10.7445 |
| 47 | 4.0000 | 0.8470 | 0.7649 | 0.0821 | 10.7322 |
| 48 | 4.2000 | 0.8702 | 0.7858 | 0.0844 | 10.7388 |
| 49 | 4.4000 | 0.8938 | 0.8070 | 0.0868 | 10.7590 |
| 50 | 4.6000 | 0.9178 | 0.8284 | 0.0894 | 10.7882 |
| 51 | 4.8000 | 0.9421 | 0.8501 | 0.0920 | 10.8216 |
| 52 | 5.0000 | 0.9668 | 0.8721 | 0.0947 | 10.8545 |
| 53 | 5.2000 | 0.9917 | 0.8944 | 0.0973 | 10.8828 |
| 54 | 5.2657 | 1.0000 | 0.9018 | 0.0982 | 10.8905 |
| 55 | 5.4000 | 1.0169 | 0.9170 | 0.1000 | 10.9024 |
| 56 | 5.6000 | 1.0423 | 0.9398 | 0.1025 | 10.9096 |
| 57 | 5.8000 | 1.0678 | 0.9628 | 0.1050 | 10.9012 |
| 58 | 6.0000 | 1.0934 | 0.9862 | 0.1072 | 10.8741 |
| 59 | 6.2000 | 1.1191 | 1.0098 | 0.1093 | 10.8262 |
| 60 | 6.4000 | 1.1448 | 1.0336 | 0.1112 | 10.7558 |
| 61 | 6.6000 | 1.1704 | 1.0577 | 0.1128 | 10.6614 |
| 62 | 6.8000 | 1.1960 | 1.0820 | 0.1141 | 10.5429 |
| 63 | 7.0000 | 1.2210 | 1.1065 | 0.1145 | 10.3491 |
| 64 | 7.2000 | 1.2477 | 1.1312 | 0.1164 | 10.2925 |
| 65 | 7.4000 | 1.2747 | 1.1562 | 0.1185 | 10.2474 |
| 66 | 7.6000 | 1.3026 | 1.1814 | 0.1212 | 10.2619 |
| 67 | 7.8000 | 1.3306 | 1.2067 | 0.1239 | 10.2665 |
| 68 | 8.0000 | 1.3587 | 1.2323 | 0.1264 | 10.2601 |
| 69 | 8.2000 | 1.3869 | 1.2580 | 0.1288 | 10.2420 |
| 70 | 8.4000 | 1.4150 | 1.2839 | 0.1311 | 10.2121 |
| 71 | 8.6000 | 1.4432 | 1.3100 | 0.1332 | 10.1702 |
| 72 | 8.8000 | 1.4714 | 1.3362 | 0.1352 | 10.1178 |
| 73 | 8.9903 | 1.4984 | 1.3613 | 0.1371 | 10.0694 |
| 74 | 9.0000 | 1.4999 | 1.3626 | 0.1373 | 10.0734 |
| 75 | 9.2000 | 1.5300 | 1.3892 | 0.1409 | 10.1412 |
| 76 | 9.4000 | 1.5600 | 1.4159 | 0.1442 | 10.1840 |
| 77 | 9.6000 | 1.5899 | 1.4427 | 0.1472 | 10.2025 |
| 78 | 9.8000 | 1.6195 | 1.4697 | 0.1499 | 10.1975 |
| 79 | 10.0000 | 1.6491 | 1.4968 | 0.1523 | 10.1750 |
| 80 | 10.2000 | 1.6796 | 1.5240 | 0.1555 | 10.2052 |

Table 98

FIG. 122

| Design # | SNR | Opt. Cap | Std. Cap | Gain [bits] | Gain % |
|---|---|---|---|---|---|
| 81 | 10.4000 | 1.7104 | 1.5514 | 0.1590 | 10.2461 |
| 82 | 10.6000 | 1.7413 | 1.5790 | 0.1623 | 10.2771 |
| 83 | 10.8000 | 1.7721 | 1.6067 | 0.1654 | 10.2967 |
| 84 | 11.0000 | 1.8037 | 1.6345 | 0.1692 | 10.3523 |
| 85 | 11.2000 | 1.8362 | 1.6625 | 0.1737 | 10.4487 |
| 86 | 11.4000 | 1.8686 | 1.6906 | 0.1779 | 10.5249 |
| 87 | 11.6000 | 1.9009 | 1.7189 | 0.1819 | 10.5824 |
| 88 | 11.8000 | 1.9330 | 1.7474 | 0.1856 | 10.6235 |
| 89 | 12.0000 | 1.9652 | 1.7760 | 0.1892 | 10.6515 |
| 90 | 12.2000 | 1.9974 | 1.8048 | 0.1926 | 10.6705 |
| 91 | 12.2081 | 1.9987 | 1.8060 | 0.1927 | 10.6711 |
| 92 | 12.4000 | 2.0297 | 1.8338 | 0.1959 | 10.6843 |
| 93 | 12.6000 | 2.0621 | 1.8629 | 0.1993 | 10.6962 |
| 94 | 12.8000 | 2.0947 | 1.8921 | 0.2026 | 10.7072 |
| 95 | 13.0000 | 2.1275 | 1.9215 | 0.2059 | 10.7170 |
| 96 | 13.2000 | 2.1604 | 1.9511 | 0.2093 | 10.7247 |
| 97 | 13.4000 | 2.1934 | 1.9808 | 0.2125 | 10.7283 |
| 98 | 13.6000 | 2.2264 | 2.0107 | 0.2157 | 10.7258 |
| 99 | 13.8000 | 2.2594 | 2.0407 | 0.2187 | 10.7156 |
| 100 | 14.0000 | 2.2924 | 2.0709 | 0.2215 | 10.6966 |
| 101 | 14.2000 | 2.3253 | 2.1011 | 0.2242 | 10.6682 |
| 102 | 14.4000 | 2.3581 | 2.1315 | 0.2266 | 10.6302 |
| 103 | 14.6000 | 2.3908 | 2.1620 | 0.2288 | 10.5831 |
| 104 | 14.8000 | 2.4234 | 2.1926 | 0.2308 | 10.5273 |
| 105 | 15.0000 | 2.4559 | 2.2233 | 0.2326 | 10.4639 |
| 106 | 15.2000 | 2.4884 | 2.2541 | 0.2343 | 10.3941 |
| 107 | 15.2711 | 2.4999 | 2.2651 | 0.2348 | 10.3676 |
| 108 | 15.4000 | 2.5207 | 2.2850 | 0.2357 | 10.3170 |
| 109 | 15.6000 | 2.5530 | 2.3160 | 0.2370 | 10.2322 |
| 110 | 15.8000 | 2.5851 | 2.3471 | 0.2380 | 10.1392 |
| 111 | 16.0000 | 2.6171 | 2.3783 | 0.2387 | 10.0379 |
| 112 | 16.2000 | 2.6489 | 2.4097 | 0.2392 | 9.9288 |
| 113 | 16.4000 | 2.6806 | 2.4411 | 0.2395 | 9.8122 |
| 114 | 16.6000 | 2.7122 | 2.4727 | 0.2396 | 9.6892 |
| 115 | 16.8000 | 2.7438 | 2.5043 | 0.2394 | 9.5605 |
| 116 | 17.0000 | 2.7756 | 2.5362 | 0.2394 | 9.4386 |
| 117 | 17.2000 | 2.8075 | 2.5682 | 0.2393 | 9.3185 |
| 118 | 17.4000 | 2.8392 | 2.6003 | 0.2389 | 9.1891 |
| 119 | 17.6000 | 2.8709 | 2.6326 | 0.2383 | 9.0518 |
| 120 | 17.8000 | 2.9025 | 2.6651 | 0.2374 | 8.9078 |

Table 99

FIG. 123

| Design # | SNR | Opt. Cap | Std. Cap | Gain [bits] | Gain % |
|---|---|---|---|---|---|
| 121 | 18.0000 | 2.9341 | 2.6977 | 0.2364 | 8.7621 |
| 122 | 18.2000 | 2.9657 | 2.7306 | 0.2351 | 8.6105 |
| 123 | 18.4000 | 2.9973 | 2.7637 | 0.2336 | 8.4532 |
| 124 | 18.4172 | 3.0000 | 2.7665 | 0.2335 | 8.4394 |
| 125 | 18.6000 | 3.0288 | 2.7969 | 0.2319 | 8.2922 |
| 126 | 18.8000 | 3.0605 | 2.8304 | 0.2301 | 8.1301 |
| 127 | 19.0000 | 3.0923 | 2.8640 | 0.2282 | 7.9695 |
| 128 | 19.2000 | 3.1243 | 2.8979 | 0.2264 | 7.8128 |
| 129 | 19.4000 | 3.1566 | 2.9320 | 0.2246 | 7.6606 |
| 130 | 19.6000 | 3.1891 | 2.9662 | 0.2228 | 7.5114 |
| 131 | 19.8000 | 3.2216 | 3.0007 | 0.2209 | 7.3626 |
| 132 | 20.0000 | 3.2543 | 3.0353 | 0.2189 | 7.2125 |
| 133 | 20.2000 | 3.2870 | 3.0701 | 0.2169 | 7.0633 |
| 134 | 20.4000 | 3.3197 | 3.1051 | 0.2146 | 6.9116 |
| 135 | 20.6000 | 3.3523 | 3.1402 | 0.2121 | 6.7543 |
| 136 | 20.8000 | 3.3847 | 3.1754 | 0.2093 | 6.5913 |
| 137 | 21.0000 | 3.4170 | 3.2108 | 0.2062 | 6.4231 |
| 138 | 21.2000 | 3.4491 | 3.2462 | 0.2029 | 6.2502 |
| 139 | 21.4000 | 3.4811 | 3.2817 | 0.1993 | 6.0734 |
| 140 | 21.5191 | 3.5000 | 3.3029 | 0.1971 | 5.9667 |
| 141 | 21.6000 | 3.5128 | 3.3173 | 0.1955 | 5.8936 |
| 142 | 21.8000 | 3.5445 | 3.3530 | 0.1915 | 5.7115 |
| 143 | 22.0000 | 3.5760 | 3.3887 | 0.1873 | 5.5275 |
| 144 | 22.2000 | 3.6073 | 3.4244 | 0.1829 | 5.3421 |
| 145 | 22.4000 | 3.6385 | 3.4601 | 0.1784 | 5.1557 |
| 146 | 22.6000 | 3.6695 | 3.4958 | 0.1737 | 4.9688 |
| 147 | 22.8000 | 3.7003 | 3.5314 | 0.1689 | 4.7819 |
| 148 | 23.0000 | 3.7310 | 3.5670 | 0.1639 | 4.5957 |
| 149 | 23.2000 | 3.7615 | 3.6026 | 0.1589 | 4.4107 |
| 150 | 23.4000 | 3.7919 | 3.6381 | 0.1538 | 4.2274 |
| 151 | 23.6000 | 3.8221 | 3.6734 | 0.1486 | 4.0462 |
| 152 | 23.8000 | 3.8522 | 3.7087 | 0.1434 | 3.8675 |
| 153 | 24.0000 | 3.8821 | 3.7439 | 0.1382 | 3.6919 |
| 154 | 24.2000 | 3.9119 | 3.7789 | 0.1330 | 3.5202 |
| 155 | 24.4000 | 3.9417 | 3.8138 | 0.1279 | 3.3529 |
| 156 | 24.6000 | 3.9714 | 3.8485 | 0.1228 | 3.1909 |
| 157 | 24.7934 | 4.0000 | 3.8820 | 0.1180 | 3.0401 |
| 158 | 24.8000 | 4.0010 | 3.8831 | 0.1179 | 3.0351 |
| 159 | 25.0000 | 4.0306 | 3.9175 | 0.1131 | 2.8869 |
| 160 | 25.2000 | 4.0603 | 3.9517 | 0.1086 | 2.7487 |

Table 100

FIG. 124

| | SNR | Opt. Cap | Std. Cap | Gain [bits] | Gain % |
|---|---|---|---|---|---|
| Design # | | | | | |
| 161 | 25.4000 | 4.0904 | 3.9858 | 0.1046 | 2.6251 |
| 162 | 25.6000 | 4.1208 | 4.0196 | 0.1012 | 2.5185 |
| 163 | 25.8000 | 4.1514 | 4.0532 | 0.0982 | 2.4225 |
| 164 | 26.0000 | 4.1820 | 4.0867 | 0.0953 | 2.3319 |
| 165 | 26.2000 | 4.2124 | 4.1199 | 0.0925 | 2.2443 |
| 166 | 26.4000 | 4.2426 | 4.1529 | 0.0896 | 2.1580 |
| 167 | 26.6000 | 4.2725 | 4.1857 | 0.0867 | 2.0723 |
| 168 | 26.8000 | 4.3021 | 4.2183 | 0.0838 | 1.9866 |
| 169 | 27.0000 | 4.3315 | 4.2507 | 0.0808 | 1.9006 |
| 170 | 27.2000 | 4.3605 | 4.2828 | 0.0777 | 1.8141 |
| 171 | 27.4000 | 4.3892 | 4.3146 | 0.0745 | 1.7273 |
| 172 | 27.6000 | 4.4175 | 4.3462 | 0.0713 | 1.6404 |
| 173 | 27.8000 | 4.4454 | 4.3774 | 0.0680 | 1.5535 |
| 174 | 28.0000 | 4.4730 | 4.4083 | 0.0647 | 1.4670 |
| 175 | 28.1991 | 4.5000 | 4.4387 | 0.0613 | 1.3817 |
| 176 | 28.2000 | 4.5001 | 4.4388 | 0.0613 | 1.3813 |
| 177 | 28.4000 | 4.5268 | 4.4689 | 0.0580 | 1.2968 |
| 178 | 28.6000 | 4.5531 | 4.4985 | 0.0546 | 1.2139 |
| 179 | 28.8000 | 4.5789 | 4.5276 | 0.0513 | 1.1330 |
| 180 | 29.0000 | 4.6042 | 4.5561 | 0.0480 | 1.0544 |
| 181 | 29.2000 | 4.6289 | 4.5840 | 0.0449 | 0.9784 |
| 182 | 29.4000 | 4.6530 | 4.6112 | 0.0417 | 0.9053 |
| 183 | 29.6000 | 4.6765 | 4.6377 | 0.0387 | 0.8352 |
| 184 | 29.8000 | 4.6993 | 4.6635 | 0.0358 | 0.7682 |
| 185 | 30.0000 | 4.7214 | 4.6883 | 0.0330 | 0.7045 |

Table 101

FIG. 125

|  | Label | | | | | | | |
|---|---|---|---|---|---|---|---|---|
|  | 0 | 1 | 2 | 3 | 4 | 5 | 6 | 7 |
| Design # | | | | | | | | |
| 1 | -18.468 | -18.468 | -18.468 | -18.468 | -18.466 | -18.466 | -18.468 | -18.468 |
| 2 | -18.487 | -18.487 | -18.464 | -18.464 | -18.463 | -18.463 | -18.464 | -18.463 |
| 3 | -18.502 | -18.466 | -18.466 | -18.466 | -18.466 | -18.466 | -18.466 | -18.466 |
| 4 | -18.502 | -18.480 | -18.480 | -18.480 | -18.460 | -18.460 | -18.463 | -18.460 |
| 5 | -18.513 | -18.513 | -18.513 | -18.513 | -18.443 | -18.464 | -18.513 | -18.468 |
| 6 | -18.472 | -18.466 | -18.466 | -18.466 | -18.466 | -18.466 | -18.466 | -18.466 |
| 7 | -18.510 | -18.483 | -18.483 | -18.483 | -18.466 | -18.466 | -18.483 | -18.474 |
| 8 | -18.478 | -18.478 | -18.472 | -18.472 | -18.472 | -18.472 | -18.472 | -18.472 |
| 9 | -18.494 | -18.466 | -18.464 | -18.465 | -18.464 | -18.464 | -18.464 | -18.464 |
| 10 | -18.477 | -18.477 | -18.475 | -18.475 | -18.474 | -18.474 | -18.475 | -18.475 |
| 11 | -18.489 | -18.478 | -18.478 | -18.478 | -18.475 | -18.475 | -18.478 | -18.478 |
| 12 | -18.509 | -18.479 | -18.465 | -18.465 | -18.465 | -18.465 | -18.465 | -18.465 |
| 13 | -18.540 | -18.529 | -18.451 | -18.527 | -18.451 | -18.451 | -18.451 | -18.451 |
| 14 | -18.529 | -18.514 | -18.459 | -18.459 | -18.459 | -18.459 | -18.459 | -18.459 |
| 15 | -18.506 | -18.505 | -18.494 | -18.505 | -18.444 | -18.480 | -18.494 | -18.480 |
| 16 | -18.529 | -18.504 | -18.461 | -18.461 | -18.459 | -18.461 | -18.461 | -18.461 |
| 17 | -18.471 | -18.470 | -18.470 | -18.470 | -18.470 | -18.470 | -18.470 | -18.470 |
| 18 | -18.506 | -18.505 | -18.468 | -18.468 | -18.465 | -18.468 | -18.468 | -18.468 |
| 19 | -18.476 | -18.476 | -18.476 | -18.476 | -18.476 | -18.476 | -18.476 | -18.476 |
| 20 | -18.482 | -18.482 | -18.482 | -18.482 | -18.454 | -18.482 | -18.482 | -18.482 |
| 21 | -18.474 | -18.466 | -18.466 | -18.466 | -18.466 | -18.466 | -18.466 | -18.466 |
| 22 | -18.478 | -18.474 | -18.474 | -18.474 | -18.464 | -18.474 | -18.474 | -18.474 |
| 23 | -18.524 | -18.524 | -18.524 | -18.524 | -18.524 | -18.524 | -18.524 | -18.524 |
| 24 | -18.483 | -18.479 | -18.479 | -18.479 | -18.461 | -18.466 | -18.479 | -18.479 |
| 25 | -18.496 | -18.496 | -18.496 | -18.496 | -18.496 | -18.496 | -18.496 | -18.496 |
| 26 | -18.467 | -18.467 | -18.467 | -18.467 | -18.467 | -18.467 | -18.467 | -18.467 |
| 27 | -18.474 | -18.471 | -18.471 | -18.471 | -18.471 | -18.471 | -18.471 | -18.471 |
| 28 | -18.538 | -18.537 | -18.537 | -18.537 | -18.446 | -18.446 | -18.446 | -18.446 |
| 29 | -18.499 | -18.499 | -18.467 | -18.467 | -18.466 | -18.466 | -18.466 | -18.466 |
| 30 | -18.495 | -18.495 | -18.495 | -18.495 | -18.453 | -18.459 | -18.486 | -18.460 |
| 31 | -18.494 | -18.494 | -18.485 | -18.485 | -18.485 | -18.485 | -18.485 | -18.485 |
| 32 | -18.528 | -18.528 | -18.528 | -18.528 | -18.528 | -18.528 | -18.528 | -18.528 |
| 33 | -18.488 | -18.488 | -18.488 | -18.488 | -18.488 | -18.488 | -18.488 | -18.488 |
| 34 | -18.536 | -18.535 | -18.464 | -18.464 | -18.464 | -18.464 | -18.464 | -18.464 |
| 35 | -20.584 | -20.584 | -20.584 | -20.584 | -20.584 | -20.584 | -20.584 | -20.584 |
| 36 | -21.574 | -21.574 | -21.574 | -21.574 | -21.573 | -21.573 | -21.574 | -21.573 |
| 37 | -22.222 | -22.222 | -22.222 | -22.222 | -22.220 | -22.222 | -22.222 | -22.222 |
| 38 | -22.705 | -22.705 | -22.704 | -22.705 | -22.703 | -22.703 | -22.703 | -22.703 |
| 39 | -23.088 | -23.087 | -23.087 | -23.087 | -23.087 | -23.087 | -23.087 | -23.087 |
| 40 | -23.404 | -23.404 | -23.404 | -23.404 | -23.402 | -23.404 | -23.404 | -23.404 |

Table 102

FIG. 126

|         | Label   |         |         |         |         |         |         |         |
|---------|---------|---------|---------|---------|---------|---------|---------|---------|
|         | 8       | 9       | 10      | 11      | 12      | 13      | 14      | 15      |
| Design # |         |         |         |         |         |         |         |         |
| 1       | -18.462 | -18.463 | -18.466 | -18.463 | -18.466 | -18.466 | -18.466 | -18.466 |
| 2       | -18.462 | -18.462 | -18.463 | -18.463 | -18.463 | -18.463 | -18.463 | -18.463 |
| 3       | -18.445 | -18.455 | -18.466 | -18.462 | -18.466 | -18.466 | -18.466 | -18.466 |
| 4       | -18.459 | -18.459 | -18.459 | -18.459 | -18.460 | -18.459 | -18.459 | -18.459 |
| 5       | -18.436 | -18.438 | -18.438 | -18.438 | -18.442 | -18.442 | -18.442 | -18.442 |
| 6       | -18.460 | -18.466 | -18.466 | -18.466 | -18.466 | -18.466 | -18.466 | -18.466 |
| 7       | -18.449 | -18.450 | -18.450 | -18.450 | -18.466 | -18.450 | -18.450 | -18.450 |
| 8       | -18.391 | -18.447 | -18.472 | -18.472 | -18.472 | -18.472 | -18.472 | -18.472 |
| 9       | -18.464 | -18.464 | -18.464 | -18.464 | -18.464 | -18.464 | -18.464 | -18.464 |
| 10      | -18.444 | -18.459 | -18.459 | -18.459 | -18.459 | -18.459 | -18.459 | -18.459 |
| 11      | -18.424 | -18.431 | -18.456 | -18.450 | -18.472 | -18.469 | -18.458 | -18.468 |
| 12      | -18.428 | -18.463 | -18.463 | -18.463 | -18.465 | -18.465 | -18.465 | -18.465 |
| 13      | -18.451 | -18.451 | -18.451 | -18.451 | -18.451 | -18.451 | -18.451 | -18.451 |
| 14      | -18.453 | -18.459 | -18.459 | -18.459 | -18.459 | -18.459 | -18.459 | -18.459 |
| 15      | -18.444 | -18.444 | -18.444 | -18.444 | -18.444 | -18.444 | -18.444 | -18.444 |
| 16      | -18.458 | -18.458 | -18.458 | -18.458 | -18.459 | -18.459 | -18.458 | -18.458 |
| 17      | -18.415 | -18.463 | -18.470 | -18.469 | -18.470 | -18.470 | -18.470 | -18.470 |
| 18      | -18.456 | -18.456 | -18.456 | -18.456 | -18.456 | -18.456 | -18.456 | -18.456 |
| 19      | -18.455 | -18.455 | -18.457 | -18.457 | -18.457 | -18.457 | -18.457 | -18.457 |
| 20      | -18.454 | -18.454 | -18.454 | -18.454 | -18.454 | -18.454 | -18.454 | -18.454 |
| 21      | -18.465 | -18.465 | -18.465 | -18.465 | -18.465 | -18.465 | -18.465 | -18.465 |
| 22      | -18.459 | -18.459 | -18.459 | -18.459 | -18.459 | -18.459 | -18.459 | -18.459 |
| 23      | -18.391 | -18.391 | -18.391 | -18.391 | -18.456 | -18.456 | -18.394 | -18.394 |
| 24      | -18.452 | -18.457 | -18.457 | -18.457 | -18.457 | -18.457 | -18.457 | -18.457 |
| 25      | -18.399 | -18.418 | -18.420 | -18.420 | -18.495 | -18.495 | -18.422 | -18.426 |
| 26      | -18.465 | -18.465 | -18.465 | -18.465 | -18.467 | -18.465 | -18.465 | -18.465 |
| 27      | -18.459 | -18.459 | -18.459 | -18.459 | -18.465 | -18.463 | -18.462 | -18.462 |
| 28      | -18.408 | -18.445 | -18.445 | -18.445 | -18.445 | -18.445 | -18.445 | -18.445 |
| 29      | -18.456 | -18.456 | -18.457 | -18.456 | -18.461 | -18.461 | -18.458 | -18.459 |
| 30      | -18.453 | -18.453 | -18.453 | -18.453 | -18.453 | -18.453 | -18.453 | -18.453 |
| 31      | -18.440 | -18.440 | -18.440 | -18.440 | -18.484 | -18.440 | -18.440 | -18.440 |
| 32      | -18.389 | -18.389 | -18.390 | -18.390 | -18.419 | -18.419 | -18.419 | -18.419 |
| 33      | -18.428 | -18.429 | -18.430 | -18.429 | -18.486 | -18.455 | -18.449 | -18.449 |
| 34      | -18.450 | -18.450 | -18.450 | -18.450 | -18.452 | -18.450 | -18.450 | -18.450 |
| 35      | -16.071 | -16.073 | -16.073 | -16.073 | -16.073 | -16.073 | -16.073 | -16.073 |
| 36      | -14.716 | -14.716 | -14.716 | -14.716 | -14.722 | -14.722 | -14.717 | -14.717 |
| 37      | -13.720 | -13.720 | -13.720 | -13.720 | -13.720 | -13.720 | -13.720 | -13.720 |
| 38      | -12.905 | -12.905 | -12.905 | -12.905 | -12.905 | -12.905 | -12.905 | -12.905 |
| 39      | -12.206 | -12.206 | -12.206 | -12.206 | -12.206 | -12.206 | -12.206 | -12.206 |
| 40      | -11.589 | -11.589 | -11.589 | -11.589 | -11.589 | -11.589 | -11.589 | -11.589 |

Table 103

FIG. 127

|  | Label | | | | | | | |
|---|---|---|---|---|---|---|---|---|
|  | 16 | 17 | 18 | 19 | 20 | 21 | 22 | 23 |
| Design # | | | | | | | | |
| 1 | 18.471 | 18.471 | 18.466 | 18.466 | 18.466 | 18.466 | 18.466 | 18.466 |
| 2 | 18.479 | 18.469 | 18.469 | 18.469 | 18.468 | 18.468 | 18.469 | 18.468 |
| 3 | 18.502 | 18.502 | 18.497 | 18.502 | 18.481 | 18.497 | 18.497 | 18.497 |
| 4 | 18.502 | 18.502 | 18.483 | 18.483 | 18.483 | 18.483 | 18.483 | 18.483 |
| 5 | 18.481 | 18.481 | 18.481 | 18.481 | 18.481 | 18.481 | 18.481 | 18.481 |
| 6 | 18.471 | 18.471 | 18.471 | 18.471 | 18.471 | 18.471 | 18.471 | 18.471 |
| 7 | 18.509 | 18.468 | 18.468 | 18.468 | 18.468 | 18.468 | 18.468 | 18.468 |
| 8 | 18.478 | 18.467 | 18.467 | 18.467 | 18.466 | 18.466 | 18.467 | 18.466 |
| 9 | 18.496 | 18.496 | 18.496 | 18.496 | 18.496 | 18.496 | 18.496 | 18.496 |
| 10 | 18.541 | 18.542 | 18.478 | 18.479 | 18.452 | 18.452 | 18.452 | 18.452 |
| 11 | 18.489 | 18.468 | 18.467 | 18.467 | 18.465 | 18.465 | 18.467 | 18.465 |
| 12 | 18.509 | 18.484 | 18.484 | 18.484 | 18.466 | 18.466 | 18.466 | 18.466 |
| 13 | 18.540 | 18.499 | 18.469 | 18.469 | 18.469 | 18.469 | 18.469 | 18.469 |
| 14 | 18.528 | 18.528 | 18.528 | 18.528 | 18.476 | 18.476 | 18.528 | 18.476 |
| 15 | 18.505 | 18.464 | 18.464 | 18.464 | 18.464 | 18.464 | 18.464 | 18.464 |
| 16 | 18.528 | 18.471 | 18.466 | 18.469 | 18.460 | 18.462 | 18.465 | 18.462 |
| 17 | 18.543 | 18.544 | 18.456 | 18.456 | 18.455 | 18.455 | 18.455 | 18.455 |
| 18 | 18.505 | 18.505 | 18.505 | 18.505 | 18.440 | 18.505 | 18.505 | 18.505 |
| 19 | 18.541 | 18.542 | 18.471 | 18.471 | 18.453 | 18.453 | 18.453 | 18.453 |
| 20 | 18.474 | 18.474 | 18.474 | 18.474 | 18.468 | 18.468 | 18.474 | 18.468 |
| 21 | 18.477 | 18.477 | 18.467 | 18.474 | 18.466 | 18.466 | 18.467 | 18.466 |
| 22 | 18.478 | 18.478 | 18.478 | 18.478 | 18.478 | 18.478 | 18.478 | 18.478 |
| 23 | 18.524 | 18.491 | 18.491 | 18.491 | 18.491 | 18.491 | 18.491 | 18.491 |
| 24 | 18.484 | 18.484 | 18.484 | 18.484 | 18.484 | 18.484 | 18.484 | 18.484 |
| 25 | 18.483 | 18.483 | 18.474 | 18.474 | 18.474 | 18.474 | 18.474 | 18.474 |
| 26 | 18.468 | 18.468 | 18.468 | 18.468 | 18.468 | 18.468 | 18.468 | 18.468 |
| 27 | 18.470 | 18.468 | 18.468 | 18.468 | 18.468 | 18.468 | 18.468 | 18.468 |
| 28 | 18.519 | 18.481 | 18.481 | 18.481 | 18.481 | 18.481 | 18.481 | 18.481 |
| 29 | 18.500 | 18.474 | 18.474 | 18.474 | 18.474 | 18.474 | 18.474 | 18.474 |
| 30 | 18.495 | 18.495 | 18.495 | 18.495 | 18.495 | 18.495 | 18.495 | 18.495 |
| 31 | 18.483 | 18.481 | 18.481 | 18.481 | 18.481 | 18.481 | 18.481 | 18.481 |
| 32 | 18.528 | 18.520 | 18.499 | 18.499 | 18.473 | 18.477 | 18.499 | 18.499 |
| 33 | 18.488 | 18.485 | 18.485 | 18.485 | 18.485 | 18.485 | 18.485 | 18.485 |
| 34 | 18.534 | 18.488 | 18.488 | 18.488 | 18.487 | 18.487 | 18.487 | 18.487 |
| 35 | 20.584 | 20.583 | 20.583 | 20.583 | 20.583 | 20.583 | 20.583 | 20.583 |
| 36 | 21.574 | 21.572 | 21.571 | 21.571 | 21.571 | 21.571 | 21.571 | 21.571 |
| 37 | 22.218 | 22.218 | 22.218 | 22.218 | 22.208 | 22.209 | 22.218 | 22.217 |
| 38 | 22.705 | 22.705 | 22.705 | 22.705 | 22.702 | 22.702 | 22.705 | 22.704 |
| 39 | 23.088 | 23.088 | 23.088 | 23.088 | 23.088 | 23.088 | 23.088 | 23.088 |
| 40 | 23.404 | 23.404 | 23.404 | 23.404 | 23.401 | 23.401 | 23.401 | 23.401 |

Table 104

FIG. 128

|  | Label | | | | | | | |
|---|---|---|---|---|---|---|---|---|
|  | 24 | 25 | 26 | 27 | 28 | 29 | 30 | 31 |
| Design # | | | | | | | | |
| 1 | 18.465 | 18.465 | 18.465 | 18.465 | 18.466 | 18.466 | 18.466 | 18.466 |
| 2 | 18.452 | 18.463 | 18.463 | 18.463 | 18.468 | 18.464 | 18.463 | 18.463 |
| 3 | 18.434 | 18.434 | 18.436 | 18.435 | 18.437 | 18.437 | 18.437 | 18.437 |
| 4 | 18.410 | 18.410 | 18.445 | 18.410 | 18.483 | 18.483 | 18.445 | 18.472 |
| 5 | 18.309 | 18.456 | 18.460 | 18.460 | 18.481 | 18.481 | 18.481 | 18.481 |
| 6 | 18.438 | 18.445 | 18.466 | 18.453 | 18.471 | 18.471 | 18.471 | 18.471 |
| 7 | 18.433 | 18.451 | 18.462 | 18.462 | 18.468 | 18.468 | 18.463 | 18.466 |
| 8 | 18.464 | 18.464 | 18.464 | 18.464 | 18.465 | 18.465 | 18.464 | 18.464 |
| 9 | 18.408 | 18.408 | 18.420 | 18.420 | 18.496 | 18.497 | 18.420 | 18.420 |
| 10 | 18.452 | 18.452 | 18.452 | 18.452 | 18.452 | 18.452 | 18.452 | 18.452 |
| 11 | 18.461 | 18.464 | 18.464 | 18.464 | 18.465 | 18.464 | 18.464 | 18.464 |
| 12 | 18.453 | 18.453 | 18.455 | 18.453 | 18.455 | 18.455 | 18.455 | 18.455 |
| 13 | 18.448 | 18.448 | 18.448 | 18.448 | 18.469 | 18.448 | 18.448 | 18.448 |
| 14 | 18.404 | 18.417 | 18.418 | 18.418 | 18.476 | 18.419 | 18.418 | 18.418 |
| 15 | 18.457 | 18.462 | 18.464 | 18.462 | 18.464 | 18.464 | 18.464 | 18.464 |
| 16 | 18.458 | 18.460 | 18.460 | 18.460 | 18.460 | 18.460 | 18.460 | 18.460 |
| 17 | 18.455 | 18.455 | 18.455 | 18.455 | 18.455 | 18.455 | 18.455 | 18.455 |
| 18 | 18.421 | 18.432 | 18.437 | 18.437 | 18.439 | 18.439 | 18.439 | 18.439 |
| 19 | 18.452 | 18.452 | 18.452 | 18.452 | 18.453 | 18.453 | 18.452 | 18.452 |
| 20 | 18.455 | 18.455 | 18.455 | 18.455 | 18.467 | 18.467 | 18.466 | 18.467 |
| 21 | 18.459 | 18.460 | 18.461 | 18.460 | 18.466 | 18.466 | 18.462 | 18.465 |
| 22 | 18.426 | 18.432 | 18.432 | 18.432 | 18.478 | 18.478 | 18.478 | 18.478 |
| 23 | 18.428 | 18.428 | 18.428 | 18.428 | 18.490 | 18.440 | 18.428 | 18.428 |
| 24 | 18.415 | 18.418 | 18.429 | 18.419 | 18.484 | 18.483 | 18.472 | 18.473 |
| 25 | 18.456 | 18.456 | 18.456 | 18.456 | 18.456 | 18.456 | 18.456 | 18.456 |
| 26 | 18.465 | 18.465 | 18.465 | 18.465 | 18.465 | 18.465 | 18.465 | 18.465 |
| 27 | 18.464 | 18.464 | 18.464 | 18.464 | 18.464 | 18.464 | 18.464 | 18.464 |
| 28 | 18.437 | 18.437 | 18.453 | 18.437 | 18.453 | 18.453 | 18.453 | 18.453 |
| 29 | 18.453 | 18.453 | 18.453 | 18.453 | 18.473 | 18.453 | 18.453 | 18.453 |
| 30 | 18.427 | 18.438 | 18.438 | 18.438 | 18.445 | 18.438 | 18.438 | 18.438 |
| 31 | 18.451 | 18.451 | 18.451 | 18.451 | 18.455 | 18.451 | 18.451 | 18.451 |
| 32 | 18.428 | 18.428 | 18.429 | 18.428 | 18.451 | 18.437 | 18.429 | 18.434 |
| 33 | 18.447 | 18.447 | 18.447 | 18.447 | 18.448 | 18.448 | 18.447 | 18.447 |
| 34 | 18.439 | 18.439 | 18.439 | 18.439 | 18.440 | 18.439 | 18.439 | 18.439 |
| 35 | 16.071 | 16.071 | 16.072 | 16.071 | 16.085 | 16.072 | 16.072 | 16.072 |
| 36 | 14.720 | 14.720 | 14.720 | 14.720 | 14.720 | 14.720 | 14.720 | 14.720 |
| 37 | 13.722 | 13.722 | 13.728 | 13.728 | 13.731 | 13.728 | 13.728 | 13.728 |
| 38 | 12.905 | 12.905 | 12.905 | 12.905 | 12.905 | 12.905 | 12.905 | 12.905 |
| 39 | 12.205 | 12.205 | 12.205 | 12.205 | 12.205 | 12.205 | 12.205 | 12.205 |
| 40 | 11.590 | 11.590 | 11.590 | 11.590 | 11.590 | 11.590 | 11.590 | 11.590 |

Table 105

FIG. 129

|  | Label | | | | | | | |
|---|---|---|---|---|---|---|---|---|
|  | 0 | 1 | 2 | 3 | 4 | 5 | 6 | 7 |
| Design # | | | | | | | | |
| 41 | -23.669 | -23.669 | -23.669 | -23.669 | -23.662 | -23.662 | -23.665 | -23.665 |
| 42 | -23.892 | -23.892 | -23.892 | -23.892 | -23.891 | -23.891 | -23.892 | -23.891 |
| 43 | -24.086 | -24.086 | -24.086 | -24.086 | -24.085 | -24.085 | -24.086 | -24.085 |
| 44 | -24.254 | -24.254 | -24.253 | -24.254 | -24.245 | -24.250 | -24.253 | -24.253 |
| 45 | -24.397 | -24.397 | -24.397 | -24.397 | -24.395 | -24.395 | -24.397 | -24.397 |
| 46 | -24.525 | -24.524 | -24.524 | -24.524 | -24.524 | -24.524 | -24.524 | -24.524 |
| 47 | -24.635 | -24.635 | -24.635 | -24.635 | -24.633 | -24.634 | -24.635 | -24.635 |
| 48 | -24.738 | -24.738 | -24.730 | -24.738 | -24.727 | -24.729 | -24.730 | -24.730 |
| 49 | -24.821 | -24.821 | -24.816 | -24.816 | -24.816 | -24.816 | -24.816 | -24.816 |
| 50 | -24.897 | -24.897 | -24.892 | -24.897 | -24.890 | -24.891 | -24.892 | -24.892 |
| 51 | -24.963 | -24.960 | -24.960 | -24.960 | -24.955 | -24.960 | -24.960 | -24.960 |
| 52 | -25.024 | -25.023 | -25.015 | -25.015 | -25.015 | -25.015 | -25.015 | -25.015 |
| 53 | -25.074 | -25.074 | -25.074 | -25.074 | -25.038 | -25.041 | -25.061 | -25.061 |
| 54 | -25.083 | -25.082 | -25.082 | -25.082 | -25.078 | -25.078 | -25.078 | -25.078 |
| 55 | -25.109 | -25.109 | -25.108 | -25.108 | -25.108 | -25.108 | -25.108 | -25.108 |
| 56 | -25.148 | -25.147 | -25.143 | -25.144 | -25.143 | -25.143 | -25.143 | -25.143 |
| 57 | -25.176 | -25.174 | -25.174 | -25.174 | -25.173 | -25.173 | -25.173 | -25.173 |
| 58 | -25.202 | -25.202 | -25.202 | -25.202 | -25.189 | -25.192 | -25.197 | -25.195 |
| 59 | -25.220 | -25.220 | -25.215 | -25.215 | -25.214 | -25.214 | -25.215 | -25.214 |
| 60 | -25.238 | -25.236 | -25.236 | -25.236 | -25.226 | -25.226 | -25.235 | -25.228 |
| 61 | -25.243 | -25.243 | -25.243 | -25.243 | -25.222 | -25.222 | -25.233 | -25.230 |
| 62 | -25.243 | -25.243 | -25.243 | -25.243 | -25.243 | -25.243 | -25.243 | -25.243 |
| 63 | -24.792 | -24.792 | -24.792 | -24.792 | -24.792 | -24.792 | -24.792 | -24.792 |
| 64 | -24.737 | -24.737 | -24.737 | -24.737 | -24.737 | -24.737 | -24.737 | -24.737 |
| 65 | -38.698 | -26.007 | -23.569 | -23.569 | -21.371 | -21.371 | -21.371 | -21.371 |
| 66 | -39.014 | -25.904 | -23.497 | -23.497 | -21.322 | -21.322 | -21.322 | -21.322 |
| 67 | -39.276 | -25.788 | -23.433 | -23.433 | -21.281 | -21.281 | -21.281 | -21.281 |
| 68 | -39.422 | -25.843 | -23.419 | -23.419 | -21.222 | -21.222 | -21.222 | -21.222 |
| 69 | -39.538 | -25.889 | -23.430 | -23.430 | -21.156 | -21.156 | -21.156 | -21.156 |
| 70 | -39.608 | -26.034 | -23.434 | -23.434 | -21.077 | -21.077 | -21.077 | -21.077 |
| 71 | -39.643 | -26.177 | -23.477 | -23.477 | -20.995 | -20.995 | -20.995 | -20.995 |
| 72 | -39.643 | -26.413 | -23.533 | -23.533 | -20.878 | -20.878 | -20.878 | -20.878 |
| 73 | -31.746 | -31.746 | -31.746 | -31.746 | -14.945 | -14.945 | -14.945 | -14.945 |
| 74 | -31.751 | -31.751 | -31.734 | -31.746 | -14.948 | -14.948 | -14.952 | -14.949 |
| 75 | -31.689 | -31.689 | -31.688 | -31.688 | -15.023 | -15.023 | -15.024 | -15.024 |
| 76 | -31.638 | -31.638 | -31.622 | -31.622 | -15.108 | -15.108 | -15.110 | -15.110 |
| 77 | -31.574 | -31.574 | -31.564 | -31.570 | -15.198 | -15.198 | -15.201 | -15.200 |
| 78 | -31.554 | -31.547 | -31.456 | -31.456 | -15.296 | -15.297 | -15.310 | -15.310 |
| 79 | -38.428 | -31.170 | -28.865 | -28.865 | -14.205 | -14.668 | -15.742 | -15.742 |
| 80 | -38.361 | -30.759 | -28.491 | -28.491 | -14.105 | -14.576 | -15.661 | -15.661 |

Table 106

FIG. 130

|  | Label | | | | | | | |
|---|---|---|---|---|---|---|---|---|
|  | 8 | 9 | 10 | 11 | 12 | 13 | 14 | 15 |
| Design # | | | | | | | | |
| 41 | -11.041 | -11.041 | -11.041 | -11.041 | -11.041 | -11.041 | -11.041 | -11.041 |
| 42 | -10.545 | -10.545 | -10.545 | -10.545 | -10.545 | -10.545 | -10.545 | -10.545 |
| 43 | -10.096 | -10.096 | -10.096 | -10.096 | -10.096 | -10.096 | -10.096 | -10.096 |
| 44 | -9.688 | -9.688 | -9.688 | -9.688 | -9.688 | -9.688 | -9.688 | -9.688 |
| 45 | -9.317 | -9.317 | -9.317 | -9.317 | -9.317 | -9.317 | -9.317 | -9.317 |
| 46 | -8.977 | -8.977 | -8.977 | -8.977 | -8.977 | -8.977 | -8.977 | -8.977 |
| 47 | -8.668 | -8.668 | -8.668 | -8.668 | -8.669 | -8.668 | -8.668 | -8.668 |
| 48 | -8.385 | -8.385 | -8.385 | -8.385 | -8.385 | -8.385 | -8.385 | -8.385 |
| 49 | -8.128 | -8.128 | -8.128 | -8.128 | -8.129 | -8.129 | -8.128 | -8.129 |
| 50 | -7.892 | -7.892 | -7.892 | -7.892 | -7.897 | -7.896 | -7.896 | -7.896 |
| 51 | -7.685 | -7.685 | -7.685 | -7.685 | -7.685 | -7.685 | -7.685 | -7.685 |
| 52 | -7.494 | -7.496 | -7.496 | -7.496 | -7.497 | -7.497 | -7.496 | -7.496 |
| 53 | -7.337 | -7.337 | -7.337 | -7.337 | -7.346 | -7.337 | -7.337 | -7.337 |
| 54 | -7.280 | -7.280 | -7.280 | -7.280 | -7.280 | -7.280 | -7.280 | -7.280 |
| 55 | -7.183 | -7.183 | -7.183 | -7.183 | -7.183 | -7.183 | -7.183 | -7.183 |
| 56 | -7.054 | -7.054 | -7.057 | -7.056 | -7.058 | -7.058 | -7.057 | -7.057 |
| 57 | -6.949 | -6.949 | -6.950 | -6.950 | -6.951 | -6.951 | -6.951 | -6.951 |
| 58 | -6.860 | -6.860 | -6.860 | -6.860 | -6.869 | -6.866 | -6.860 | -6.866 |
| 59 | -6.789 | -6.794 | -6.794 | -6.794 | -6.797 | -6.797 | -6.797 | -6.797 |
| 60 | -6.738 | -6.739 | -6.739 | -6.739 | -6.742 | -6.742 | -6.741 | -6.741 |
| 61 | -6.715 | -6.715 | -6.715 | -6.715 | -6.718 | -6.717 | -6.715 | -6.715 |
| 62 | -6.695 | -6.696 | -6.696 | -6.696 | -6.698 | -6.698 | -6.698 | -6.698 |
| 63 | -6.815 | -6.815 | -6.815 | -6.815 | -6.815 | -6.815 | -6.815 | -6.815 |
| 64 | -6.812 | -6.812 | -6.812 | -6.812 | -6.812 | -6.812 | -6.812 | -6.812 |
| 65 | -5.930 | -6.162 | -6.424 | -6.424 | -6.878 | -6.878 | -6.878 | -6.878 |
| 66 | -5.857 | -6.089 | -6.361 | -6.361 | -6.860 | -6.860 | -6.860 | -6.860 |
| 67 | -5.810 | -6.038 | -6.309 | -6.309 | -6.851 | -6.851 | -6.851 | -6.851 |
| 68 | -5.751 | -5.969 | -6.255 | -6.255 | -6.862 | -6.862 | -6.862 | -6.862 |
| 69 | -5.707 | -5.913 | -6.203 | -6.203 | -6.880 | -6.880 | -6.880 | -6.880 |
| 70 | -5.674 | -5.865 | -6.164 | -6.164 | -6.913 | -6.913 | -6.913 | -6.913 |
| 71 | -5.641 | -5.816 | -6.119 | -6.119 | -6.957 | -6.957 | -6.957 | -6.957 |
| 72 | -5.601 | -5.760 | -6.071 | -6.071 | -7.015 | -7.015 | -7.015 | -7.015 |
| 73 | 31.747 | 31.747 | 31.746 | 31.746 | -11.518 | -11.518 | -11.518 | -11.518 |
| 74 | 31.742 | 31.742 | 31.742 | 31.742 | -11.521 | -11.521 | -11.521 | -11.521 |
| 75 | 31.700 | 31.700 | 31.674 | 31.677 | -11.571 | -11.571 | -11.571 | -11.571 |
| 76 | 31.637 | 31.638 | 31.625 | 31.631 | -11.616 | -11.616 | -11.616 | -11.616 |
| 77 | 31.574 | 31.574 | 31.564 | 31.570 | -11.658 | -11.658 | -11.658 | -11.658 |
| 78 | 31.553 | 31.553 | 31.441 | 31.484 | -11.695 | -11.695 | -11.695 | -11.695 |
| 79 | 31.181 | 31.181 | 31.181 | 31.181 | -11.375 | -11.375 | -11.375 | -11.375 |
| 80 | 38.361 | 30.758 | 28.491 | 28.491 | -11.302 | -11.302 | -11.302 | -11.302 |

Table 107

FIG. 131

|  | Label | | | | | | | |
| --- | --- | --- | --- | --- | --- | --- | --- | --- |
|  | 16 | 17 | 18 | 19 | 20 | 21 | 22 | 23 |
| Design # | | | | | | | | |
| 41 | 23.671 | 23.671 | 23.668 | 23.671 | 23.657 | 23.663 | 23.667 | 23.666 |
| 42 | 23.892 | 23.892 | 23.892 | 23.892 | 23.891 | 23.891 | 23.891 | 23.891 |
| 43 | 24.086 | 24.086 | 24.084 | 24.086 | 24.080 | 24.080 | 24.080 | 24.080 |
| 44 | 24.254 | 24.254 | 24.254 | 24.254 | 24.249 | 24.249 | 24.249 | 24.249 |
| 45 | 24.397 | 24.397 | 24.397 | 24.397 | 24.397 | 24.397 | 24.397 | 24.397 |
| 46 | 24.526 | 24.526 | 24.526 | 24.526 | 24.516 | 24.517 | 24.526 | 24.523 |
| 47 | 24.635 | 24.635 | 24.635 | 24.635 | 24.635 | 24.635 | 24.635 | 24.635 |
| 48 | 24.735 | 24.735 | 24.731 | 24.735 | 24.731 | 24.731 | 24.731 | 24.731 |
| 49 | 24.821 | 24.821 | 24.821 | 24.821 | 24.818 | 24.819 | 24.820 | 24.820 |
| 50 | 24.896 | 24.895 | 24.895 | 24.895 | 24.891 | 24.891 | 24.894 | 24.891 |
| 51 | 24.963 | 24.961 | 24.961 | 24.961 | 24.948 | 24.951 | 24.960 | 24.957 |
| 52 | 25.021 | 25.020 | 25.013 | 25.013 | 25.012 | 25.012 | 25.012 | 25.012 |
| 53 | 25.074 | 25.074 | 25.062 | 25.062 | 25.061 | 25.061 | 25.061 | 25.061 |
| 54 | 25.081 | 25.081 | 25.081 | 25.081 | 25.079 | 25.079 | 25.079 | 25.079 |
| 55 | 25.109 | 25.109 | 25.106 | 25.106 | 25.106 | 25.106 | 25.106 | 25.106 |
| 56 | 25.148 | 25.148 | 25.143 | 25.148 | 25.138 | 25.138 | 25.142 | 25.140 |
| 57 | 25.176 | 25.176 | 25.176 | 25.176 | 25.167 | 25.167 | 25.173 | 25.170 |
| 58 | 25.203 | 25.203 | 25.203 | 25.203 | 25.185 | 25.185 | 25.203 | 25.194 |
| 59 | 25.219 | 25.219 | 25.219 | 25.219 | 25.204 | 25.209 | 25.214 | 25.214 |
| 60 | 25.230 | 25.230 | 25.226 | 25.230 | 25.225 | 25.225 | 25.225 | 25.225 |
| 61 | 25.240 | 25.240 | 25.240 | 25.240 | 25.240 | 25.240 | 25.240 | 25.240 |
| 62 | 25.243 | 25.243 | 25.243 | 25.243 | 25.228 | 25.237 | 25.243 | 25.243 |
| 63 | 38.522 | 26.837 | 24.259 | 24.259 | 21.835 | 21.835 | 21.835 | 21.835 |
| 64 | 39.430 | 26.613 | 24.103 | 24.103 | 21.747 | 21.747 | 21.747 | 21.747 |
| 65 | 38.697 | 25.964 | 23.561 | 23.561 | 21.380 | 21.380 | 21.380 | 21.380 |
| 66 | 39.013 | 25.893 | 23.500 | 23.500 | 21.319 | 21.319 | 21.319 | 21.319 |
| 67 | 39.272 | 25.861 | 23.457 | 23.457 | 21.263 | 21.263 | 21.263 | 21.263 |
| 68 | 39.422 | 25.861 | 23.430 | 23.430 | 21.215 | 21.215 | 21.215 | 21.215 |
| 69 | 39.550 | 25.899 | 23.429 | 23.429 | 21.154 | 21.154 | 21.154 | 21.154 |
| 70 | 39.625 | 26.010 | 23.440 | 23.440 | 21.079 | 21.079 | 21.079 | 21.079 |
| 71 | 39.618 | 26.207 | 23.493 | 23.493 | 20.983 | 20.983 | 20.983 | 20.983 |
| 72 | 39.638 | 26.474 | 23.540 | 23.540 | 20.865 | 20.865 | 20.865 | 20.865 |
| 73 | 11.518 | 11.518 | 11.518 | 11.518 | 0.398 | 0.398 | 0.398 | 0.398 |
| 74 | 11.522 | 11.522 | 11.522 | 11.522 | 0.402 | 0.402 | 0.403 | 0.403 |
| 75 | 11.574 | 11.574 | 11.574 | 11.574 | 0.462 | 0.462 | 0.462 | 0.462 |
| 76 | 11.619 | 11.619 | 11.619 | 11.619 | 0.528 | 0.528 | 0.528 | 0.528 |
| 77 | 11.658 | 11.658 | 11.658 | 11.658 | 0.595 | 0.595 | 0.595 | 0.595 |
| 78 | 11.692 | 11.692 | 11.692 | 11.692 | 0.665 | 0.665 | 0.665 | 0.665 |
| 79 | 11.652 | 11.652 | 11.652 | 11.652 | 0.746 | 0.760 | 0.845 | 0.845 |
| 80 | 11.303 | 11.303 | 11.303 | 11.303 | 0.716 | 0.717 | 0.717 | 0.717 |

Table 108

FIG. 132

|  | Label | | | | | | | |
|---|---|---|---|---|---|---|---|---|
|  | 24 | 25 | 26 | 27 | 28 | 29 | 30 | 31 |
| Design # | | | | | | | | |
| 41 | 11.041 | 11.041 | 11.041 | 11.041 | 11.041 | 11.041 | 11.041 | 11.041 |
| 42 | 10.545 | 10.545 | 10.545 | 10.545 | 10.545 | 10.545 | 10.545 | 10.545 |
| 43 | 10.098 | 10.099 | 10.099 | 10.099 | 10.099 | 10.099 | 10.099 | 10.099 |
| 44 | 9.688 | 9.688 | 9.688 | 9.688 | 9.688 | 9.688 | 9.688 | 9.688 |
| 45 | 9.316 | 9.316 | 9.316 | 9.316 | 9.316 | 9.316 | 9.316 | 9.316 |
| 46 | 8.978 | 8.978 | 8.978 | 8.978 | 8.978 | 8.978 | 8.978 | 8.978 |
| 47 | 8.666 | 8.667 | 8.667 | 8.667 | 8.667 | 8.667 | 8.667 | 8.667 |
| 48 | 8.385 | 8.385 | 8.385 | 8.385 | 8.385 | 8.385 | 8.385 | 8.385 |
| 49 | 8.125 | 8.125 | 8.125 | 8.125 | 8.126 | 8.126 | 8.125 | 8.125 |
| 50 | 7.893 | 7.894 | 7.894 | 7.894 | 7.894 | 7.894 | 7.894 | 7.894 |
| 51 | 7.685 | 7.686 | 7.686 | 7.686 | 7.688 | 7.687 | 7.686 | 7.686 |
| 52 | 7.498 | 7.498 | 7.498 | 7.498 | 7.501 | 7.499 | 7.499 | 7.499 |
| 53 | 7.332 | 7.335 | 7.337 | 7.337 | 7.337 | 7.337 | 7.337 | 7.337 |
| 54 | 7.280 | 7.280 | 7.280 | 7.280 | 7.280 | 7.280 | 7.280 | 7.280 |
| 55 | 7.183 | 7.184 | 7.184 | 7.184 | 7.186 | 7.186 | 7.185 | 7.185 |
| 56 | 7.054 | 7.058 | 7.058 | 7.058 | 7.059 | 7.059 | 7.059 | 7.059 |
| 57 | 6.950 | 6.950 | 6.952 | 6.952 | 6.952 | 6.952 | 6.952 | 6.952 |
| 58 | 6.863 | 6.863 | 6.863 | 6.863 | 6.864 | 6.863 | 6.863 | 6.863 |
| 59 | 6.791 | 6.791 | 6.791 | 6.791 | 6.810 | 6.799 | 6.798 | 6.798 |
| 60 | 6.745 | 6.745 | 6.745 | 6.745 | 6.746 | 6.746 | 6.745 | 6.745 |
| 61 | 6.709 | 6.709 | 6.710 | 6.710 | 6.711 | 6.711 | 6.711 | 6.711 |
| 62 | 6.693 | 6.700 | 6.700 | 6.700 | 6.702 | 6.702 | 6.700 | 6.700 |
| 63 | 5.660 | 5.923 | 6.256 | 6.256 | 6.886 | 6.886 | 6.886 | 6.886 |
| 64 | 5.576 | 5.836 | 6.181 | 6.181 | 6.844 | 6.844 | 6.844 | 6.844 |
| 65 | 5.939 | 6.170 | 6.431 | 6.431 | 6.876 | 6.876 | 6.876 | 6.876 |
| 66 | 5.863 | 6.093 | 6.361 | 6.361 | 6.862 | 6.862 | 6.862 | 6.862 |
| 67 | 5.794 | 6.017 | 6.297 | 6.297 | 6.856 | 6.856 | 6.856 | 6.856 |
| 68 | 5.748 | 5.965 | 6.249 | 6.249 | 6.865 | 6.865 | 6.865 | 6.865 |
| 69 | 5.706 | 5.911 | 6.201 | 6.201 | 6.880 | 6.880 | 6.880 | 6.880 |
| 70 | 5.673 | 5.865 | 6.161 | 6.161 | 6.912 | 6.912 | 6.912 | 6.912 |
| 71 | 5.638 | 5.814 | 6.118 | 6.118 | 6.962 | 6.962 | 6.962 | 6.962 |
| 72 | 5.598 | 5.755 | 6.066 | 6.066 | 7.014 | 7.014 | 7.014 | 7.014 |
| 73 | 14.945 | 14.945 | 14.945 | 14.945 | -0.398 | -0.398 | -0.398 | -0.398 |
| 74 | 14.947 | 14.947 | 14.947 | 14.947 | -0.397 | -0.397 | -0.397 | -0.397 |
| 75 | 15.017 | 15.019 | 15.031 | 15.029 | -0.465 | -0.465 | -0.466 | -0.466 |
| 76 | 15.103 | 15.103 | 15.107 | 15.104 | -0.528 | -0.528 | -0.529 | -0.528 |
| 77 | 15.199 | 15.199 | 15.203 | 15.201 | -0.597 | -0.597 | -0.597 | -0.597 |
| 78 | 15.293 | 15.293 | 15.322 | 15.314 | -0.667 | -0.667 | -0.668 | -0.667 |
| 79 | 15.258 | 15.258 | 15.258 | 15.258 | -0.593 | -0.593 | -0.593 | -0.593 |
| 80 | 14.104 | 14.575 | 15.660 | 15.660 | -0.716 | -0.717 | -0.717 | -0.717 |

Table 109

FIG. 133

| Design # | Label | | | | | | | |
|---|---|---|---|---|---|---|---|---|
| | 0 | 1 | 2 | 3 | 4 | 5 | 6 | 7 |
| 81 | -38.770 | -30.565 | -28.305 | -28.305 | -14.112 | -14.591 | -15.728 | -15.728 |
| 82 | -39.045 | -30.428 | -28.150 | -28.150 | -14.151 | -14.629 | -15.813 | -15.813 |
| 83 | -39.237 | -30.332 | -28.008 | -28.008 | -14.213 | -14.681 | -15.922 | -15.922 |
| 84 | -42.842 | -27.881 | 42.842 | -25.702 | 29.062 | -24.594 | 31.203 | -24.594 |
| 85 | -42.655 | -27.882 | 42.853 | -25.687 | 29.031 | -24.553 | 31.121 | -24.553 |
| 86 | -42.464 | -27.897 | 42.842 | -25.674 | 29.001 | -24.507 | 31.047 | -24.507 |
| 87 | -42.259 | -27.918 | 42.803 | -25.658 | 28.972 | -24.450 | 30.979 | -24.450 |
| 88 | -42.044 | -27.950 | 42.732 | -25.640 | 28.944 | -24.384 | 30.918 | -24.384 |
| 89 | -41.810 | -27.996 | 42.639 | -25.619 | 28.920 | -24.309 | 30.866 | -24.309 |
| 90 | -41.564 | -28.049 | 42.521 | -25.594 | 28.899 | -24.226 | 30.820 | -24.226 |
| 91 | -41.554 | -28.060 | 42.517 | -25.592 | 28.899 | -24.218 | 30.819 | -24.218 |
| 92 | -41.313 | -28.130 | 42.382 | -25.568 | 28.883 | -24.131 | 30.781 | -24.131 |
| 93 | -41.061 | -28.204 | 42.235 | -25.546 | 28.871 | -24.041 | 30.748 | -24.041 |
| 94 | -40.815 | -28.281 | 42.094 | -25.529 | 28.867 | -23.954 | 30.725 | -23.954 |
| 95 | -40.588 | -28.384 | 41.955 | -25.523 | 28.866 | -23.867 | 30.704 | -23.867 |
| 96 | -40.382 | -28.507 | 41.826 | -25.531 | 28.868 | -23.781 | 30.688 | -23.781 |
| 97 | -40.205 | -28.658 | 41.701 | -25.556 | 28.869 | -23.693 | 30.674 | -23.693 |
| 98 | -40.054 | -28.809 | 41.580 | -25.607 | 28.865 | -23.609 | 30.656 | -23.609 |
| 99 | -39.931 | -28.990 | 41.461 | -25.677 | 28.857 | -23.523 | 30.638 | -23.523 |
| 100 | -39.837 | -29.167 | 41.338 | -25.777 | 28.842 | -23.437 | 30.617 | -23.437 |
| 101 | -39.769 | -29.347 | 41.210 | -25.909 | 28.820 | -23.348 | 30.594 | -23.348 |
| 102 | -39.729 | -29.519 | 41.072 | -26.092 | 28.790 | -23.251 | 30.569 | -23.251 |
| 103 | -39.717 | -29.676 | 40.928 | -26.350 | 28.749 | -23.144 | 30.538 | -23.144 |
| 104 | -39.740 | -29.838 | 40.770 | -26.653 | 28.695 | -23.030 | 30.504 | -23.030 |
| 105 | -39.801 | -30.016 | 40.599 | -27.009 | 28.627 | -22.860 | 30.464 | -22.947 |
| 106 | -39.861 | -30.186 | 40.421 | -27.323 | 28.552 | -22.705 | 30.427 | -22.896 |
| 107 | -39.873 | -30.238 | 40.366 | -27.420 | 28.529 | -22.658 | 30.421 | -22.880 |
| 108 | -39.892 | -30.332 | 40.263 | -27.572 | 28.484 | -22.588 | 30.408 | -22.856 |
| 109 | -39.907 | -30.471 | 40.107 | -27.763 | 28.409 | -22.501 | 30.409 | -22.830 |
| 110 | -39.901 | -30.592 | 39.964 | -27.911 | 28.334 | -22.431 | 30.432 | -22.810 |
| 111 | -39.885 | -30.712 | 39.825 | -28.026 | 28.255 | -22.368 | 30.473 | -22.799 |
| 112 | -39.845 | -30.817 | 39.722 | -28.095 | 28.173 | -22.304 | 30.566 | -22.787 |
| 113 | -39.795 | -30.919 | 39.633 | -28.136 | 28.094 | -22.240 | 30.679 | -22.778 |
| 114 | -39.727 | -31.016 | 39.585 | -28.134 | 28.013 | -22.164 | 30.850 | -22.763 |
| 115 | -39.632 | -31.098 | 39.588 | -28.106 | 27.930 | -22.083 | 31.071 | -22.749 |
| 116 | -40.170 | -32.458 | -24.267 | -26.000 | -15.469 | -15.469 | -18.490 | -17.922 |
| 117 | -40.113 | -32.438 | -24.253 | -26.017 | -15.428 | -15.428 | -18.613 | -18.023 |
| 118 | -40.042 | -32.414 | -24.246 | -26.045 | -15.378 | -15.378 | -18.749 | -18.141 |
| 119 | -39.959 | -32.389 | -24.245 | -26.083 | -15.323 | -15.323 | -18.892 | -18.271 |
| 120 | -39.866 | -32.361 | -24.251 | -26.129 | -15.266 | -15.266 | -19.035 | -18.407 |

Table 110

FIG. 134

|  | Label | | | | | | | |
|---|---|---|---|---|---|---|---|---|
|  | 8 | 9 | 10 | 11 | 12 | 13 | 14 | 15 |
| Design # | | | | | | | | |
| 81 | 38.770 | 30.564 | 28.304 | 28.304 | -11.260 | -11.260 | -11.260 | -11.260 |
| 82 | 39.045 | 30.428 | 28.150 | 28.150 | -11.220 | -11.220 | -11.220 | -11.220 |
| 83 | 39.236 | 30.328 | 28.011 | 28.011 | -11.174 | -11.174 | -11.174 | -11.174 |
| 84 | -8.991 | -12.436 | -8.991 | -12.638 | -8.991 | -13.018 | -8.991 | -13.018 |
| 85 | -8.995 | -12.533 | -8.995 | -12.741 | -8.995 | -13.146 | -8.995 | -13.146 |
| 86 | -8.991 | -12.638 | -8.991 | -12.852 | -8.991 | -13.286 | -8.991 | -13.286 |
| 87 | -8.970 | -12.766 | -8.970 | -12.985 | -8.970 | -13.450 | -8.970 | -13.450 |
| 88 | -8.931 | -12.915 | -8.931 | -13.140 | -8.931 | -13.637 | -8.931 | -13.637 |
| 89 | -8.879 | -13.083 | -8.879 | -13.313 | -8.879 | -13.842 | -8.879 | -13.842 |
| 90 | -8.810 | -13.271 | -8.810 | -13.505 | -8.810 | -14.064 | -8.810 | -14.064 |
| 91 | -8.807 | -13.276 | -8.807 | -13.512 | -8.807 | -14.073 | -8.807 | -14.073 |
| 92 | -8.729 | -13.463 | -8.729 | -13.703 | -8.729 | -14.290 | -8.729 | -14.290 |
| 93 | -8.644 | -13.658 | -8.644 | -13.899 | -8.644 | -14.508 | -8.644 | -14.508 |
| 94 | -8.563 | -13.841 | -8.563 | -14.081 | -8.563 | -14.707 | -8.563 | -14.707 |
| 95 | -8.488 | -13.996 | -8.488 | -14.234 | -8.488 | -14.882 | -8.488 | -14.882 |
| 96 | -8.419 | -14.121 | -8.419 | -14.357 | -8.419 | -15.032 | -8.419 | -15.032 |
| 97 | -8.355 | -14.215 | -8.355 | -14.447 | -8.355 | -15.161 | -8.355 | -15.161 |
| 98 | -8.299 | -14.289 | -8.299 | -14.513 | -8.299 | -15.273 | -8.299 | -15.273 |
| 99 | -8.244 | -14.335 | -8.244 | -14.548 | -8.244 | -15.366 | -8.244 | -15.366 |
| 100 | -8.199 | -14.363 | -8.199 | -14.561 | -8.185 | -15.447 | -8.190 | -15.447 |
| 101 | -8.165 | -14.372 | -8.165 | -14.551 | -8.123 | -15.519 | -8.124 | -15.519 |
| 102 | -8.133 | -14.360 | -8.132 | -14.514 | -8.059 | -15.585 | -8.059 | -15.585 |
| 103 | -8.103 | -14.325 | -8.101 | -14.448 | -7.991 | -15.648 | -7.991 | -15.648 |
| 104 | -8.070 | -14.265 | -8.067 | -14.358 | -7.916 | -15.702 | -7.916 | -15.702 |
| 105 | -8.033 | -14.180 | -8.031 | -14.237 | -7.833 | -15.746 | -7.833 | -15.746 |
| 106 | -8.001 | -14.102 | -7.999 | -14.128 | -7.755 | -15.782 | -7.755 | -15.782 |
| 107 | -7.994 | -14.077 | -7.990 | -14.094 | -7.730 | -15.794 | -7.730 | -15.794 |
| 108 | -7.980 | -14.038 | -7.978 | -14.041 | -7.687 | -15.814 | -7.687 | -15.814 |
| 109 | -7.965 | -13.981 | -7.963 | -13.981 | -7.628 | -15.842 | -7.628 | -15.842 |
| 110 | -7.959 | -13.935 | -7.957 | -13.935 | -7.578 | -15.871 | -7.578 | -15.871 |
| 111 | -7.958 | -13.895 | -7.957 | -13.895 | -7.531 | -15.907 | -7.531 | -15.892 |
| 112 | -7.967 | -13.861 | -7.967 | -13.861 | -7.491 | -15.947 | -7.495 | -15.905 |
| 113 | -7.981 | -13.829 | -7.981 | -13.829 | -7.455 | -15.990 | -7.459 | -15.920 |
| 114 | -8.002 | -13.795 | -8.002 | -13.795 | -7.423 | -16.030 | -7.431 | -15.932 |
| 115 | -8.027 | -13.760 | -8.027 | -13.760 | -7.397 | -16.076 | -7.403 | -15.949 |
| 116 | 40.170 | 32.459 | 24.267 | 26.000 | -9.724 | -9.724 | -8.849 | -8.881 |
| 117 | 40.113 | 32.438 | 24.253 | 26.016 | -9.774 | -9.774 | -8.798 | -8.827 |
| 118 | 40.041 | 32.414 | 24.246 | 26.044 | -9.829 | -9.829 | -8.735 | -8.760 |
| 119 | 39.958 | 32.388 | 24.245 | 26.081 | -9.889 | -9.889 | -8.662 | -8.682 |
| 120 | 39.865 | 32.360 | 24.250 | 26.128 | -9.954 | -9.954 | -8.580 | -8.596 |

Table 111

FIG. 135

|  | Label | | | | | | | |
|---|---|---|---|---|---|---|---|---|
|  | 16 | 17 | 18 | 19 | 20 | 21 | 22 | 23 |
| Design # | | | | | | | | |
| 81 | 11.260 | 11.260 | 11.260 | 11.260 | 0.782 | 0.782 | 0.782 | 0.782 |
| 82 | 11.219 | 11.219 | 11.219 | 11.219 | 0.855 | 0.855 | 0.855 | 0.855 |
| 83 | 11.176 | 11.176 | 11.176 | 11.176 | 0.939 | 0.939 | 0.939 | 0.939 |
| 84 | 14.917 | 12.616 | 14.917 | 12.616 | 18.770 | 12.616 | 18.440 | 12.616 |
| 85 | 15.029 | 12.559 | 15.029 | 12.559 | 18.943 | 12.559 | 18.598 | 12.559 |
| 86 | 15.158 | 12.498 | 15.158 | 12.498 | 19.110 | 12.498 | 18.752 | 12.498 |
| 87 | 15.323 | 12.421 | 15.323 | 12.421 | 19.290 | 12.421 | 18.924 | 12.421 |
| 88 | 15.528 | 12.328 | 15.528 | 12.328 | 19.470 | 12.328 | 19.102 | 12.328 |
| 89 | 15.765 | 12.227 | 15.765 | 12.227 | 19.641 | 12.227 | 19.272 | 12.227 |
| 90 | 16.040 | 12.111 | 16.040 | 12.111 | 19.803 | 12.111 | 19.434 | 12.111 |
| 91 | 16.050 | 12.107 | 16.050 | 12.107 | 19.810 | 12.107 | 19.440 | 12.107 |
| 92 | 16.334 | 11.988 | 16.334 | 11.988 | 19.950 | 11.988 | 19.582 | 11.988 |
| 93 | 16.630 | 11.865 | 16.630 | 11.865 | 20.081 | 11.865 | 19.714 | 11.865 |
| 94 | 16.908 | 11.750 | 16.908 | 11.750 | 20.189 | 11.750 | 19.819 | 11.750 |
| 95 | 17.152 | 11.664 | 17.152 | 11.657 | 20.285 | 11.630 | 19.911 | 11.630 |
| 96 | 17.361 | 11.607 | 17.361 | 11.606 | 20.372 | 11.494 | 19.990 | 11.494 |
| 97 | 17.532 | 11.562 | 17.532 | 11.562 | 20.447 | 11.378 | 20.055 | 11.385 |
| 98 | 17.667 | 11.531 | 17.667 | 11.531 | 20.512 | 11.289 | 20.106 | 11.300 |
| 99 | 17.779 | 11.505 | 17.779 | 11.505 | 20.569 | 11.210 | 20.149 | 11.229 |
| 100 | 17.870 | 11.489 | 17.870 | 11.489 | 20.621 | 11.149 | 20.185 | 11.172 |
| 101 | 17.942 | 11.482 | 17.942 | 11.482 | 20.671 | 11.099 | 20.215 | 11.126 |
| 102 | 18.000 | 11.481 | 18.000 | 11.481 | 20.721 | 11.059 | 20.244 | 11.089 |
| 103 | 18.041 | 11.488 | 18.041 | 11.488 | 20.769 | 11.027 | 20.268 | 11.061 |
| 104 | 18.070 | 11.499 | 18.070 | 11.499 | 20.816 | 11.000 | 20.288 | 11.037 |
| 105 | 18.084 | 11.513 | 18.084 | 11.513 | 20.863 | 10.978 | 20.303 | 11.017 |
| 106 | 18.089 | 11.536 | 18.089 | 11.536 | 20.917 | 10.958 | 20.324 | 11.000 |
| 107 | 18.091 | 11.544 | 18.091 | 11.544 | 20.940 | 10.950 | 20.331 | 10.993 |
| 108 | 18.090 | 11.562 | 18.090 | 11.562 | 20.986 | 10.937 | 20.352 | 10.981 |
| 109 | 18.081 | 11.593 | 18.081 | 11.593 | 21.073 | 10.915 | 20.385 | 10.961 |
| 110 | 18.062 | 11.627 | 18.062 | 11.627 | 21.179 | 10.887 | 20.428 | 10.936 |
| 111 | 18.031 | 11.666 | 18.031 | 11.666 | 21.300 | 10.854 | 20.480 | 10.904 |
| 112 | 17.983 | 11.700 | 17.983 | 11.700 | 21.446 | 10.807 | 20.532 | 10.857 |
| 113 | 17.921 | 11.735 | 17.921 | 11.735 | 21.603 | 10.747 | 20.598 | 10.796 |
| 114 | 17.840 | 11.763 | 17.840 | 11.763 | 21.778 | 10.668 | 20.661 | 10.715 |
| 115 | 17.747 | 11.779 | 17.747 | 11.779 | 21.949 | 10.577 | 20.706 | 10.623 |
| 116 | 9.724 | 9.724 | 8.849 | 8.880 | 2.894 | 2.894 | 3.101 | 3.098 |
| 117 | 9.774 | 9.774 | 8.798 | 8.827 | 2.866 | 2.866 | 3.128 | 3.126 |
| 118 | 9.829 | 9.829 | 8.736 | 8.760 | 2.831 | 2.831 | 3.159 | 3.157 |
| 119 | 9.889 | 9.889 | 8.662 | 8.683 | 2.787 | 2.787 | 3.194 | 3.192 |
| 120 | 9.954 | 9.954 | 8.581 | 8.596 | 2.735 | 2.735 | 3.234 | 3.232 |

Table 112

FIG. 136

|  | Label | | | | | | | |
|---|---|---|---|---|---|---|---|---|
|  | 24 | 25 | 26 | 27 | 28 | 29 | 30 | 31 |
| Design # | | | | | | | | |
| 81 | 14.114 | 14.594 | 15.729 | 15.729 | -0.783 | -0.783 | -0.783 | -0.783 |
| 82 | 14.152 | 14.629 | 15.814 | 15.814 | -0.856 | -0.856 | -0.856 | -0.856 |
| 83 | 14.215 | 14.684 | 15.916 | 15.916 | -0.939 | -0.939 | -0.939 | -0.939 |
| 84 | 0.734 | 2.397 | 0.734 | 2.397 | 0.504 | 2.397 | 0.515 | 2.397 |
| 85 | 0.628 | 2.487 | 0.628 | 2.487 | 0.412 | 2.487 | 0.424 | 2.487 |
| 86 | 0.514 | 2.585 | 0.514 | 2.585 | 0.316 | 2.585 | 0.329 | 2.585 |
| 87 | 0.375 | 2.700 | 0.375 | 2.700 | 0.203 | 2.700 | 0.215 | 2.700 |
| 88 | 0.211 | 2.836 | 0.211 | 2.836 | 0.069 | 2.836 | 0.082 | 2.836 |
| 89 | 0.029 | 2.988 | 0.029 | 2.988 | -0.079 | 2.988 | -0.067 | 2.988 |
| 90 | -0.178 | 3.161 | -0.178 | 3.161 | -0.250 | 3.161 | -0.239 | 3.161 |
| 91 | -0.186 | 3.167 | -0.186 | 3.167 | -0.257 | 3.167 | -0.246 | 3.167 |
| 92 | -0.395 | 3.346 | -0.395 | 3.346 | -0.435 | 3.346 | -0.424 | 3.346 |
| 93 | -0.612 | 3.534 | -0.612 | 3.534 | -0.625 | 3.534 | -0.614 | 3.534 |
| 94 | -0.808 | 3.712 | -0.808 | 3.712 | -0.808 | 3.712 | -0.808 | 3.712 |
| 95 | -0.978 | 3.870 | -0.978 | 3.870 | -0.978 | 3.870 | -0.978 | 3.870 |
| 96 | -1.124 | 4.007 | -1.124 | 4.007 | -1.124 | 4.007 | -1.124 | 4.007 |
| 97 | -1.244 | 4.122 | -1.244 | 4.122 | -1.244 | 4.122 | -1.244 | 4.122 |
| 98 | -1.336 | 4.218 | -1.336 | 4.218 | -1.336 | 4.218 | -1.336 | 4.218 |
| 99 | -1.409 | 4.297 | -1.409 | 4.297 | -1.409 | 4.297 | -1.409 | 4.297 |
| 100 | -1.464 | 4.365 | -1.464 | 4.365 | -1.464 | 4.365 | -1.464 | 4.365 |
| 101 | -1.501 | 4.420 | -1.501 | 4.420 | -1.501 | 4.420 | -1.501 | 4.420 |
| 102 | -1.524 | 4.465 | -1.524 | 4.465 | -1.524 | 4.465 | -1.524 | 4.465 |
| 103 | -1.533 | 4.505 | -1.533 | 4.505 | -1.533 | 4.505 | -1.533 | 4.505 |
| 104 | -1.530 | 4.540 | -1.530 | 4.540 | -1.530 | 4.540 | -1.530 | 4.540 |
| 105 | -1.514 | 4.570 | -1.514 | 4.571 | -1.514 | 4.571 | -1.514 | 4.571 |
| 106 | -1.495 | 4.593 | -1.495 | 4.593 | -1.495 | 4.609 | -1.495 | 4.609 |
| 107 | -1.490 | 4.596 | -1.490 | 4.596 | -1.490 | 4.619 | -1.490 | 4.618 |
| 108 | -1.480 | 4.604 | -1.480 | 4.604 | -1.480 | 4.639 | -1.480 | 4.638 |
| 109 | -1.466 | 4.612 | -1.466 | 4.612 | -1.466 | 4.669 | -1.466 | 4.666 |
| 110 | -1.456 | 4.614 | -1.456 | 4.614 | -1.456 | 4.693 | -1.456 | 4.691 |
| 111 | -1.435 | 4.610 | -1.436 | 4.610 | -1.456 | 4.719 | -1.456 | 4.716 |
| 112 | -1.421 | 4.592 | -1.422 | 4.592 | -1.468 | 4.737 | -1.468 | 4.733 |
| 113 | -1.407 | 4.566 | -1.408 | 4.566 | -1.484 | 4.751 | -1.484 | 4.748 |
| 114 | -1.401 | 4.525 | -1.401 | 4.525 | -1.511 | 4.757 | -1.510 | 4.754 |
| 115 | -1.397 | 4.473 | -1.397 | 4.473 | -1.545 | 4.759 | -1.545 | 4.753 |
| 116 | 15.469 | 15.469 | 18.491 | 17.923 | -2.894 | -2.894 | -3.101 | -3.099 |
| 117 | 15.428 | 15.428 | 18.613 | 18.023 | -2.866 | -2.866 | -3.128 | -3.126 |
| 118 | 15.378 | 15.378 | 18.749 | 18.141 | -2.831 | -2.831 | -3.159 | -3.157 |
| 119 | 15.324 | 15.324 | 18.891 | 18.272 | -2.787 | -2.787 | -3.194 | -3.192 |
| 120 | 15.266 | 15.266 | 19.034 | 18.406 | -2.735 | -2.735 | -3.233 | -3.232 |

Table 113

FIG. 137

| Design # | \multicolumn{8}{c}{Label} |
| | 0 | 1 | 2 | 3 | 4 | 5 | 6 | 7 |
|---|---|---|---|---|---|---|---|---|
| 121 | -39.738 | -32.309 | -24.163 | -26.205 | 39.739 | 32.310 | -19.642 | -19.232 |
| 122 | -39.649 | -32.294 | -24.211 | -26.262 | 39.652 | 32.295 | -19.652 | -19.205 |
| 123 | -39.536 | -32.264 | -24.242 | -26.313 | 39.558 | 32.276 | -19.673 | -19.189 |
| 124 | -39.535 | -32.267 | -24.247 | -26.323 | 39.535 | 32.267 | -19.676 | -19.188 |
| 125 | -39.425 | -32.234 | -24.266 | -26.372 | 39.425 | 32.235 | -19.705 | -19.182 |
| 126 | -39.280 | -32.184 | -24.279 | -26.420 | 39.280 | 32.185 | -19.748 | -19.190 |
| 127 | -39.115 | -32.122 | -24.285 | -26.466 | 39.114 | 32.120 | -19.802 | -19.206 |
| 128 | -38.948 | -32.053 | -24.274 | -26.504 | 38.949 | 32.054 | -19.853 | -19.220 |
| 129 | -38.784 | -31.991 | -24.260 | -26.553 | 38.784 | 31.991 | -19.906 | -19.230 |
| 130 | -38.640 | -31.943 | -24.236 | -26.616 | 38.640 | 31.943 | -19.954 | -19.226 |
| 131 | -38.523 | -31.917 | -24.206 | -26.700 | 38.522 | 31.915 | -19.999 | -19.205 |
| 132 | -38.424 | -31.907 | -24.169 | -26.796 | 38.425 | 31.908 | -20.038 | -19.169 |
| 133 | -38.432 | -32.010 | 38.436 | -27.388 | -17.451 | -21.330 | -17.003 | -22.982 |
| 134 | -38.350 | -32.013 | 38.356 | -27.381 | -17.487 | -21.326 | -16.995 | -23.037 |
| 135 | -38.274 | -32.018 | 38.274 | -27.382 | -17.524 | -21.318 | -16.982 | -23.104 |
| 136 | -38.195 | -32.021 | 38.202 | -27.387 | -17.562 | -21.304 | -16.961 | -23.182 |
| 137 | -38.121 | -32.028 | 38.125 | -27.401 | -17.603 | -21.285 | -16.930 | -23.274 |
| 138 | -38.052 | -32.040 | 38.050 | -27.427 | -17.643 | -21.261 | -16.888 | -23.380 |
| 139 | -37.977 | -32.047 | 37.977 | -27.455 | -17.685 | -21.234 | -16.841 | -23.485 |
| 140 | -37.932 | -32.052 | 37.936 | -27.475 | -17.710 | -21.218 | -16.811 | -23.549 |
| 141 | -37.904 | -32.056 | 37.909 | -27.490 | -17.726 | -21.207 | -16.788 | -23.592 |
| 142 | -37.835 | -32.069 | 37.833 | -27.533 | -17.771 | -21.185 | -16.735 | -23.696 |
| 143 | -37.760 | -32.075 | 37.765 | -27.574 | -17.819 | -21.165 | -16.683 | -23.789 |
| 144 | -37.689 | -32.084 | 37.687 | -27.619 | -17.873 | -21.153 | -16.633 | -23.875 |
| 145 | -37.610 | -32.087 | 37.614 | -27.661 | -17.935 | -21.147 | -16.586 | -23.953 |
| 146 | -37.532 | -32.090 | 37.534 | -27.705 | -18.009 | -21.151 | -16.540 | -24.027 |
| 147 | -37.452 | -32.088 | 37.452 | -27.746 | -18.093 | -21.162 | -16.497 | -24.094 |
| 148 | -37.366 | -32.082 | 37.368 | -27.784 | -18.187 | -21.184 | -16.457 | -24.159 |
| 149 | -37.280 | -32.074 | 37.279 | -27.821 | -18.284 | -21.215 | -16.423 | -24.220 |
| 150 | -37.189 | -32.062 | 37.189 | -27.855 | -18.380 | -21.253 | -16.398 | -24.278 |
| 151 | -37.094 | -32.045 | 37.094 | -27.885 | -18.474 | -21.299 | -16.383 | -24.334 |
| 152 | -36.994 | -32.023 | 36.996 | -27.912 | -18.564 | -21.350 | -16.383 | -24.388 |
| 153 | -36.891 | -31.997 | 36.891 | -27.935 | -18.649 | -21.405 | -16.394 | -24.439 |
| 154 | -36.781 | -31.964 | 36.781 | -27.953 | -18.731 | -21.462 | -16.421 | -24.487 |
| 155 | -36.668 | -31.927 | 36.666 | -27.965 | -18.808 | -21.519 | -16.460 | -24.531 |
| 156 | -36.538 | -31.876 | 36.541 | -27.969 | -18.887 | -21.579 | -16.517 | -24.571 |
| 157 | -36.412 | -31.824 | 36.413 | -27.969 | -18.956 | -21.631 | -16.575 | -24.605 |
| 158 | -36.408 | -31.822 | 36.408 | -27.968 | -18.959 | -21.633 | -16.577 | -24.606 |
| 159 | -36.258 | -31.750 | 36.259 | -27.953 | -19.032 | -21.685 | -16.653 | -24.631 |
| 160 | -36.085 | -31.658 | 36.082 | -27.921 | -19.106 | -21.732 | -16.740 | -24.645 |

Table 114

FIG. 138

|  | Label | | | | | | | |
|---|---|---|---|---|---|---|---|---|
|  | 8 | 9 | 10 | 11 | 12 | 13 | 14 | 15 |
| Design # | | | | | | | | |
| 121 | -6.470 | -6.470 | -11.613 | -11.613 | -5.566 | -5.562 | -13.954 | -14.014 |
| 122 | -6.536 | -6.536 | -11.556 | -11.556 | -5.489 | -5.486 | -14.052 | -14.129 |
| 123 | -6.623 | -6.623 | -11.505 | -11.505 | -5.407 | -5.404 | -14.171 | -14.262 |
| 124 | -6.629 | -6.629 | -11.499 | -11.499 | -5.397 | -5.393 | -14.181 | -14.273 |
| 125 | -6.729 | -6.729 | -11.456 | -11.456 | -5.311 | -5.308 | -14.303 | -14.405 |
| 126 | -6.870 | -6.870 | -11.425 | -11.425 | -5.212 | -5.210 | -14.452 | -14.563 |
| 127 | -7.045 | -7.045 | -11.413 | -11.413 | -5.115 | -5.114 | -14.605 | -14.723 |
| 128 | -7.239 | -7.239 | -11.420 | -11.420 | -5.034 | -5.033 | -14.742 | -14.866 |
| 129 | -7.422 | -7.422 | -11.438 | -11.438 | -4.968 | -4.967 | -14.857 | -14.991 |
| 130 | -7.572 | -7.572 | -11.454 | -11.454 | -4.920 | -4.919 | -14.940 | -15.088 |
| 131 | -7.681 | -7.681 | -11.460 | -11.460 | -4.881 | -4.880 | -14.989 | -15.157 |
| 132 | -7.759 | -7.759 | -11.460 | -11.460 | -4.850 | -4.850 | -15.014 | -15.205 |
| 133 | -3.256 | -6.122 | -3.256 | -6.122 | -13.075 | -9.682 | -13.146 | -9.682 |
| 134 | -3.230 | -6.176 | -3.230 | -6.176 | -13.104 | -9.682 | -13.191 | -9.682 |
| 135 | -3.208 | -6.216 | -3.208 | -6.216 | -13.123 | -9.681 | -13.228 | -9.681 |
| 136 | -3.192 | -6.246 | -3.192 | -6.246 | -13.132 | -9.682 | -13.259 | -9.677 |
| 137 | -3.178 | -6.265 | -3.178 | -6.265 | -13.130 | -9.680 | -13.283 | -9.668 |
| 138 | -3.163 | -6.275 | -3.163 | -6.275 | -13.115 | -9.673 | -13.302 | -9.654 |
| 139 | -3.154 | -6.283 | -3.154 | -6.283 | -13.098 | -9.670 | -13.318 | -9.640 |
| 140 | -3.149 | -6.285 | -3.149 | -6.286 | -13.083 | -9.667 | -13.326 | -9.630 |
| 141 | -3.145 | -6.285 | -3.145 | -6.286 | -13.070 | -9.664 | -13.331 | -9.622 |
| 142 | -3.135 | -6.282 | -3.135 | -6.286 | -13.038 | -9.659 | -13.344 | -9.602 |
| 143 | -3.129 | -6.279 | -3.129 | -6.287 | -13.003 | -9.657 | -13.359 | -9.583 |
| 144 | -3.122 | -6.273 | -3.122 | -6.287 | -12.964 | -9.656 | -13.376 | -9.561 |
| 145 | -3.118 | -6.266 | -3.117 | -6.287 | -12.921 | -9.658 | -13.397 | -9.538 |
| 146 | -3.113 | -6.255 | -3.109 | -6.285 | -12.871 | -9.660 | -13.423 | -9.510 |
| 147 | -3.109 | -6.242 | -3.103 | -6.284 | -12.815 | -9.664 | -13.452 | -9.477 |
| 148 | -3.106 | -6.224 | -3.094 | -6.282 | -12.752 | -9.670 | -13.489 | -9.438 |
| 149 | -3.102 | -6.203 | -3.085 | -6.280 | -12.685 | -9.677 | -13.531 | -9.391 |
| 150 | -3.099 | -6.176 | -3.073 | -6.278 | -12.618 | -9.687 | -13.582 | -9.338 |
| 151 | -3.096 | -6.143 | -3.058 | -6.278 | -12.552 | -9.703 | -13.645 | -9.277 |
| 152 | -3.095 | -6.103 | -3.040 | -6.280 | -12.490 | -9.726 | -13.724 | -9.209 |
| 153 | -3.094 | -6.054 | -3.016 | -6.284 | -12.433 | -9.759 | -13.815 | -9.132 |
| 154 | -3.096 | -5.995 | -2.986 | -6.293 | -12.389 | -9.805 | -13.919 | -9.050 |
| 155 | -3.103 | -5.925 | -2.947 | -6.310 | -12.359 | -9.868 | -14.026 | -8.968 |
| 156 | -3.119 | -5.848 | -2.899 | -6.346 | -12.357 | -9.959 | -14.140 | -8.897 |
| 157 | -3.146 | -5.767 | -2.841 | -6.400 | -12.374 | -10.067 | -14.245 | -8.842 |
| 158 | -3.148 | -5.764 | -2.839 | -6.402 | -12.375 | -10.071 | -14.248 | -8.841 |
| 159 | -3.206 | -5.686 | -2.765 | -6.502 | -12.429 | -10.216 | -14.364 | -8.819 |
| 160 | -3.322 | -5.636 | -2.677 | -6.667 | -12.520 | -10.390 | -14.488 | -8.853 |

Table 115

FIG. 139

| Design # | Label | | | | | | | |
|---|---|---|---|---|---|---|---|---|
| | 16 | 17 | 18 | 19 | 20 | 21 | 22 | 23 |
| 121 | 19.643 | 19.233 | 13.955 | 14.016 | 24.164 | 26.206 | 11.618 | 11.618 |
| 122 | 19.652 | 19.205 | 14.052 | 14.129 | 24.210 | 26.261 | 11.560 | 11.560 |
| 123 | 19.674 | 19.187 | 14.170 | 14.260 | 24.246 | 26.321 | 11.504 | 11.504 |
| 124 | 19.676 | 19.189 | 14.182 | 14.275 | 24.247 | 26.323 | 11.502 | 11.502 |
| 125 | 19.706 | 19.184 | 14.305 | 14.408 | 24.268 | 26.372 | 11.458 | 11.458 |
| 126 | 19.750 | 19.190 | 14.454 | 14.564 | 24.281 | 26.422 | 11.426 | 11.426 |
| 127 | 19.800 | 19.206 | 14.605 | 14.722 | 24.283 | 26.463 | 11.416 | 11.416 |
| 128 | 19.854 | 19.222 | 14.744 | 14.868 | 24.276 | 26.504 | 11.421 | 11.421 |
| 129 | 19.905 | 19.230 | 14.857 | 14.992 | 24.259 | 26.553 | 11.438 | 11.438 |
| 130 | 19.955 | 19.227 | 14.941 | 15.089 | 24.237 | 26.615 | 11.455 | 11.455 |
| 131 | 19.998 | 19.205 | 14.990 | 15.157 | 24.205 | 26.698 | 11.461 | 11.461 |
| 132 | 20.038 | 19.170 | 15.015 | 15.206 | 24.170 | 26.797 | 11.460 | 11.460 |
| 133 | 27.394 | 22.988 | 32.015 | 21.350 | 13.255 | 16.943 | 13.194 | 17.422 |
| 134 | 27.387 | 23.044 | 32.018 | 21.341 | 13.270 | 16.949 | 13.193 | 17.467 |
| 135 | 27.386 | 23.111 | 32.020 | 21.328 | 13.286 | 16.947 | 13.190 | 17.512 |
| 136 | 27.393 | 23.191 | 32.027 | 21.311 | 13.300 | 16.932 | 13.180 | 17.556 |
| 137 | 27.406 | 23.282 | 32.032 | 21.289 | 13.313 | 16.907 | 13.166 | 17.599 |
| 138 | 27.426 | 23.382 | 32.038 | 21.262 | 13.322 | 16.870 | 13.144 | 17.640 |
| 139 | 27.457 | 23.490 | 32.048 | 21.235 | 13.332 | 16.826 | 13.117 | 17.684 |
| 140 | 27.479 | 23.555 | 32.055 | 21.219 | 13.337 | 16.796 | 13.098 | 17.709 |
| 141 | 27.495 | 23.598 | 32.061 | 21.208 | 13.340 | 16.775 | 13.084 | 17.726 |
| 142 | 27.533 | 23.697 | 32.067 | 21.184 | 13.350 | 16.725 | 13.050 | 17.770 |
| 143 | 27.577 | 23.791 | 32.079 | 21.165 | 13.362 | 16.675 | 13.011 | 17.817 |
| 144 | 27.619 | 23.876 | 32.084 | 21.152 | 13.378 | 16.627 | 12.971 | 17.872 |
| 145 | 27.664 | 23.955 | 32.090 | 21.147 | 13.398 | 16.581 | 12.925 | 17.934 |
| 146 | 27.704 | 24.026 | 32.090 | 21.149 | 13.422 | 16.537 | 12.876 | 18.006 |
| 147 | 27.745 | 24.093 | 32.088 | 21.161 | 13.452 | 16.495 | 12.819 | 18.091 |
| 148 | 27.784 | 24.158 | 32.083 | 21.182 | 13.488 | 16.455 | 12.756 | 18.184 |
| 149 | 27.821 | 24.219 | 32.074 | 21.214 | 13.531 | 16.422 | 12.688 | 18.282 |
| 150 | 27.855 | 24.278 | 32.062 | 21.253 | 13.582 | 16.397 | 12.620 | 18.379 |
| 151 | 27.885 | 24.334 | 32.045 | 21.299 | 13.646 | 16.384 | 12.553 | 18.474 |
| 152 | 27.912 | 24.388 | 32.024 | 21.350 | 13.723 | 16.382 | 12.491 | 18.563 |
| 153 | 27.935 | 24.439 | 31.997 | 21.405 | 13.816 | 16.395 | 12.434 | 18.649 |
| 154 | 27.953 | 24.488 | 31.965 | 21.463 | 13.920 | 16.422 | 12.389 | 18.732 |
| 155 | 27.966 | 24.532 | 31.926 | 21.521 | 14.028 | 16.462 | 12.360 | 18.810 |
| 156 | 27.971 | 24.572 | 31.879 | 21.578 | 14.139 | 16.515 | 12.356 | 18.886 |
| 157 | 27.969 | 24.605 | 31.824 | 21.631 | 14.245 | 16.575 | 12.373 | 18.956 |
| 158 | 27.968 | 24.606 | 31.822 | 21.633 | 14.248 | 16.577 | 12.375 | 18.959 |
| 159 | 27.953 | 24.631 | 31.751 | 21.684 | 14.363 | 16.651 | 12.427 | 19.031 |
| 160 | 27.919 | 24.643 | 31.656 | 21.730 | 14.488 | 16.739 | 12.520 | 19.105 |

Table 116

FIG. 140

|  | Label | | | | | | | |
|---|---|---|---|---|---|---|---|---|
|  | 24 | 25 | 26 | 27 | 28 | 29 | 30 | 31 |
| Design # | | | | | | | | |
| 121 | 0.241 | 0.241 | 5.559 | 5.557 | -0.243 | -0.243 | 6.468 | 6.468 |
| 122 | 0.299 | 0.299 | 5.486 | 5.482 | -0.300 | -0.300 | 6.535 | 6.535 |
| 123 | 0.369 | 0.369 | 5.397 | 5.395 | -0.376 | -0.376 | 6.618 | 6.618 |
| 124 | 0.379 | 0.379 | 5.393 | 5.389 | -0.380 | -0.380 | 6.629 | 6.629 |
| 125 | 0.462 | 0.462 | 5.306 | 5.303 | -0.465 | -0.465 | 6.728 | 6.728 |
| 126 | 0.579 | 0.579 | 5.208 | 5.207 | -0.581 | -0.581 | 6.870 | 6.870 |
| 127 | 0.724 | 0.724 | 5.115 | 5.113 | -0.723 | -0.723 | 7.046 | 7.046 |
| 128 | 0.881 | 0.881 | 5.031 | 5.030 | -0.883 | -0.883 | 7.239 | 7.239 |
| 129 | 1.033 | 1.033 | 4.967 | 4.966 | -1.033 | -1.034 | 7.422 | 7.422 |
| 130 | 1.159 | 1.159 | 4.918 | 4.917 | -1.160 | -1.160 | 7.572 | 7.572 |
| 131 | 1.255 | 1.255 | 4.881 | 4.880 | -1.255 | -1.255 | 7.681 | 7.681 |
| 132 | 1.326 | 1.326 | 4.849 | 4.849 | -1.328 | -1.328 | 7.759 | 7.759 |
| 133 | 0.172 | 2.924 | 0.172 | 2.924 | 9.485 | 6.389 | 9.485 | 6.389 |
| 134 | 0.132 | 2.974 | 0.132 | 2.974 | 9.533 | 6.378 | 9.533 | 6.378 |
| 135 | 0.102 | 3.014 | 0.102 | 3.014 | 9.568 | 6.370 | 9.569 | 6.370 |
| 136 | 0.077 | 3.042 | 0.077 | 3.042 | 9.589 | 6.361 | 9.596 | 6.361 |
| 137 | 0.059 | 3.064 | 0.059 | 3.064 | 9.602 | 6.353 | 9.615 | 6.353 |
| 138 | 0.047 | 3.080 | 0.047 | 3.080 | 9.605 | 6.345 | 9.627 | 6.345 |
| 139 | 0.035 | 3.089 | 0.035 | 3.089 | 9.603 | 6.335 | 9.634 | 6.335 |
| 140 | 0.029 | 3.093 | 0.029 | 3.093 | 9.598 | 6.329 | 9.636 | 6.329 |
| 141 | 0.026 | 3.094 | 0.026 | 3.094 | 9.593 | 6.324 | 9.637 | 6.323 |
| 142 | 0.021 | 3.100 | 0.021 | 3.100 | 9.582 | 6.317 | 9.641 | 6.314 |
| 143 | 0.015 | 3.101 | 0.015 | 3.101 | 9.566 | 6.309 | 9.642 | 6.301 |
| 144 | 0.012 | 3.103 | 0.012 | 3.103 | 9.550 | 6.304 | 9.646 | 6.291 |
| 145 | 0.008 | 3.101 | 0.008 | 3.102 | 9.528 | 6.298 | 9.650 | 6.278 |
| 146 | 0.007 | 3.100 | 0.007 | 3.103 | 9.505 | 6.295 | 9.656 | 6.266 |
| 147 | 0.005 | 3.095 | 0.004 | 3.102 | 9.474 | 6.291 | 9.662 | 6.250 |
| 148 | 0.005 | 3.089 | 0.002 | 3.100 | 9.435 | 6.288 | 9.668 | 6.230 |
| 149 | 0.006 | 3.081 | -0.001 | 3.098 | 9.390 | 6.284 | 9.676 | 6.207 |
| 150 | 0.007 | 3.069 | -0.004 | 3.095 | 9.336 | 6.281 | 9.687 | 6.179 |
| 151 | 0.010 | 3.055 | -0.008 | 3.094 | 9.276 | 6.279 | 9.703 | 6.145 |
| 152 | 0.015 | 3.038 | -0.013 | 3.093 | 9.207 | 6.280 | 9.726 | 6.104 |
| 153 | 0.022 | 3.014 | -0.021 | 3.093 | 9.130 | 6.284 | 9.759 | 6.054 |
| 154 | 0.033 | 2.984 | -0.033 | 3.094 | 9.048 | 6.293 | 9.805 | 5.994 |
| 155 | 0.048 | 2.945 | -0.049 | 3.101 | 8.966 | 6.310 | 9.868 | 5.924 |
| 156 | 0.072 | 2.899 | -0.071 | 3.119 | 8.896 | 6.345 | 9.958 | 5.849 |
| 157 | 0.106 | 2.841 | -0.105 | 3.146 | 8.842 | 6.400 | 10.066 | 5.768 |
| 158 | 0.107 | 2.839 | -0.106 | 3.148 | 8.840 | 6.402 | 10.071 | 5.765 |
| 159 | 0.163 | 2.767 | -0.161 | 3.206 | 8.819 | 6.501 | 10.213 | 5.688 |
| 160 | 0.257 | 2.680 | -0.254 | 3.324 | 8.854 | 6.668 | 10.390 | 5.639 |

Table 117

FIG. 141

|  | Label | | | | | | | |
|---|---|---|---|---|---|---|---|---|
|  | 0 | 1 | 2 | 3 | 4 | 5 | 6 | 7 |
| Design # | | | | | | | | |
| 161 | -35.860 | -31.521 | 35.860 | -27.852 | -19.181 | -21.766 | -16.846 | -24.633 |
| 162 | -35.666 | -31.406 | 35.663 | -27.799 | -19.246 | -21.799 | -16.934 | -24.628 |
| 163 | -35.507 | -31.322 | 35.508 | -27.769 | -19.301 | -21.835 | -17.000 | -24.637 |
| 164 | -35.373 | -31.256 | 35.373 | -27.752 | -19.353 | -21.874 | -17.056 | -24.654 |
| 165 | -35.247 | -31.195 | 35.249 | -27.738 | -19.403 | -21.913 | -17.108 | -24.672 |
| 166 | -35.132 | -31.143 | 35.131 | -27.730 | -19.453 | -21.954 | -17.158 | -24.695 |
| 167 | -35.013 | -31.087 | 35.014 | -27.719 | -19.503 | -21.994 | -17.210 | -24.716 |
| 168 | -34.901 | -31.036 | 34.902 | -27.711 | -19.552 | -22.034 | -17.260 | -24.737 |
| 169 | -34.790 | -30.985 | 34.787 | -27.702 | -19.603 | -22.074 | -17.313 | -24.758 |
| 170 | -34.677 | -30.930 | 34.676 | -27.689 | -19.652 | -22.112 | -17.366 | -24.776 |
| 171 | -34.564 | -30.875 | 34.560 | -27.677 | -19.703 | -22.150 | -17.421 | -24.793 |
| 172 | -34.448 | -30.817 | 34.449 | -27.660 | -19.751 | -22.185 | -17.476 | -24.807 |
| 173 | -34.335 | -30.759 | 34.335 | -27.643 | -19.800 | -22.220 | -17.531 | -24.820 |
| 174 | -34.219 | -30.700 | 34.221 | -27.624 | -19.848 | -22.254 | -17.587 | -24.832 |
| 175 | -34.107 | -30.641 | -24.843 | -27.605 | 34.107 | 30.641 | -22.286 | -19.895 |
| 176 | -34.106 | -30.640 | -24.843 | -27.604 | 34.106 | 30.640 | -22.287 | -19.896 |
| 177 | -33.992 | -30.579 | -24.851 | -27.583 | 33.993 | 30.580 | -22.316 | -19.941 |
| 178 | -33.880 | -30.519 | -24.858 | -27.561 | 33.881 | 30.520 | -22.346 | -19.986 |
| 179 | -33.770 | -30.459 | -24.864 | -27.538 | 33.770 | 30.459 | -22.373 | -20.029 |
| 180 | -33.661 | -30.399 | -24.870 | -27.515 | 33.661 | 30.399 | -22.400 | -20.071 |
| 181 | -33.554 | -30.341 | -24.875 | -27.493 | 33.554 | 30.341 | -22.426 | -20.111 |
| 182 | -33.452 | -30.284 | -24.878 | -27.470 | 33.451 | 30.284 | -22.449 | -20.149 |
| 183 | -33.348 | -30.227 | -24.881 | -27.447 | 33.350 | 30.228 | -22.472 | -20.187 |
| 184 | -33.253 | -30.175 | -24.886 | -27.427 | 33.252 | 30.175 | -22.495 | -20.223 |
| 185 | -33.159 | -30.123 | -24.888 | -27.406 | 33.159 | 30.123 | -22.515 | -20.257 |

Table 118

FIG. 142

|  | Label | | | | | | | |
|---|---|---|---|---|---|---|---|---|
|  | 8 | 9 | 10 | 11 | 12 | 13 | 14 | 15 |
| Design # | | | | | | | | |
| 161 | -3.564 | -5.671 | -2.596 | -6.941 | -12.671 | -10.618 | -14.638 | -8.985 |
| 162 | -3.775 | -5.733 | -2.552 | -7.160 | -12.793 | -10.792 | -14.757 | -9.108 |
| 163 | -3.899 | -5.774 | -2.533 | -7.290 | -12.873 | -10.904 | -14.841 | -9.183 |
| 164 | -3.977 | -5.800 | -2.521 | -7.375 | -12.931 | -10.982 | -14.907 | -9.233 |
| 165 | -4.034 | -5.822 | -2.516 | -7.440 | -12.982 | -11.045 | -14.964 | -9.274 |
| 166 | -4.073 | -5.837 | -2.510 | -7.487 | -13.025 | -11.095 | -15.016 | -9.306 |
| 167 | -4.107 | -5.856 | -2.511 | -7.531 | -13.070 | -11.143 | -15.068 | -9.339 |
| 168 | -4.133 | -5.872 | -2.511 | -7.566 | -13.112 | -11.187 | -15.118 | -9.369 |
| 169 | -4.156 | -5.888 | -2.512 | -7.600 | -13.157 | -11.229 | -15.170 | -9.401 |
| 170 | -4.177 | -5.908 | -2.518 | -7.632 | -13.203 | -11.272 | -15.222 | -9.433 |
| 171 | -4.198 | -5.929 | -2.524 | -7.666 | -13.253 | -11.318 | -15.277 | -9.470 |
| 172 | -4.220 | -5.953 | -2.533 | -7.701 | -13.305 | -11.366 | -15.333 | -9.509 |
| 173 | -4.242 | -5.979 | -2.543 | -7.737 | -13.359 | -11.416 | -15.390 | -9.551 |
| 174 | -4.265 | -6.008 | -2.555 | -7.776 | -13.416 | -11.468 | -15.449 | -9.596 |
| 175 | -7.818 | -9.641 | -13.473 | -11.523 | -6.035 | -4.291 | -15.508 | -17.643 |
| 176 | -7.819 | -9.642 | -13.474 | -11.524 | -6.035 | -4.291 | -15.509 | -17.644 |
| 177 | -7.860 | -9.691 | -13.532 | -11.579 | -6.070 | -4.315 | -15.568 | -17.698 |
| 178 | -7.903 | -9.742 | -13.592 | -11.635 | -6.104 | -4.339 | -15.626 | -17.752 |
| 179 | -7.947 | -9.794 | -13.651 | -11.692 | -6.140 | -4.365 | -15.685 | -17.805 |
| 180 | -7.992 | -9.846 | -13.711 | -11.749 | -6.177 | -4.392 | -15.743 | -17.858 |
| 181 | -8.037 | -9.897 | -13.768 | -11.804 | -6.213 | -4.418 | -15.798 | -17.908 |
| 182 | -8.081 | -9.947 | -13.823 | -11.859 | -6.249 | -4.445 | -15.852 | -17.956 |
| 183 | -8.126 | -9.999 | -13.879 | -11.914 | -6.286 | -4.472 | -15.906 | -18.004 |
| 184 | -8.165 | -10.044 | -13.930 | -11.963 | -6.318 | -4.496 | -15.955 | -18.049 |
| 185 | -8.206 | -10.091 | -13.980 | -12.013 | -6.352 | -4.521 | -16.003 | -18.091 |

Table 119

FIG. 143

|        | Label  |        |        |        |        |        |        |        |
|--------|--------|--------|--------|--------|--------|--------|--------|--------|
|        | 16     | 17     | 18     | 19     | 20     | 21     | 22     | 23     |
| Design # |      |        |        |        |        |        |        |        |
| 161    | 27.855 | 24.636 | 31.523 | 21.769 | 14.639 | 16.849 | 12.670 | 19.184 |
| 162    | 27.798 | 24.627 | 31.405 | 21.799 | 14.757 | 16.934 | 12.794 | 19.246 |
| 163    | 27.769 | 24.637 | 31.322 | 21.836 | 14.841 | 17.000 | 12.873 | 19.302 |
| 164    | 27.751 | 24.654 | 31.255 | 21.874 | 14.906 | 17.056 | 12.931 | 19.353 |
| 165    | 27.740 | 24.675 | 31.197 | 21.914 | 14.964 | 17.108 | 12.981 | 19.404 |
| 166    | 27.729 | 24.694 | 31.142 | 21.953 | 15.016 | 17.157 | 13.025 | 19.452 |
| 167    | 27.721 | 24.717 | 31.089 | 21.995 | 15.068 | 17.209 | 13.069 | 19.503 |
| 168    | 27.711 | 24.737 | 31.037 | 22.034 | 15.118 | 17.260 | 13.112 | 19.553 |
| 169    | 27.699 | 24.755 | 30.982 | 22.072 | 15.170 | 17.312 | 13.158 | 19.601 |
| 170    | 27.689 | 24.775 | 30.930 | 22.111 | 15.221 | 17.365 | 13.203 | 19.652 |
| 171    | 27.673 | 24.791 | 30.872 | 22.148 | 15.277 | 17.421 | 13.254 | 19.702 |
| 172    | 27.660 | 24.808 | 30.818 | 22.186 | 15.333 | 17.476 | 13.305 | 19.752 |
| 173    | 27.644 | 24.822 | 30.760 | 22.221 | 15.390 | 17.531 | 13.359 | 19.800 |
| 174    | 27.625 | 24.833 | 30.701 | 22.254 | 15.449 | 17.587 | 13.415 | 19.848 |
| 175    | 22.286 | 19.895 | 15.508 | 17.643 | 24.843 | 27.605 | 13.473 | 11.523 |
| 176    | 22.286 | 19.895 | 15.508 | 17.643 | 24.843 | 27.604 | 13.473 | 11.523 |
| 177    | 22.317 | 19.942 | 15.568 | 17.698 | 24.852 | 27.584 | 13.532 | 11.578 |
| 178    | 22.346 | 19.986 | 15.627 | 17.753 | 24.859 | 27.562 | 13.592 | 11.635 |
| 179    | 22.374 | 20.029 | 15.685 | 17.806 | 24.864 | 27.539 | 13.652 | 11.692 |
| 180    | 22.400 | 20.071 | 15.742 | 17.858 | 24.869 | 27.515 | 13.710 | 11.749 |
| 181    | 22.425 | 20.111 | 15.798 | 17.908 | 24.874 | 27.493 | 13.768 | 11.805 |
| 182    | 22.450 | 20.150 | 15.852 | 17.957 | 24.879 | 27.471 | 13.824 | 11.859 |
| 183    | 22.473 | 20.188 | 15.906 | 18.004 | 24.882 | 27.448 | 13.879 | 11.913 |
| 184    | 22.495 | 20.223 | 15.955 | 18.048 | 24.885 | 27.427 | 13.930 | 11.964 |
| 185    | 22.516 | 20.257 | 16.004 | 18.092 | 24.889 | 27.407 | 13.981 | 12.013 |

Table 120

FIG. 144

|          | Label  |        |        |        |        |        |        |        |
|----------|--------|--------|--------|--------|--------|--------|--------|--------|
|          | 24     | 25     | 26     | 27     | 28     | 29     | 30     | 31     |
| Design # |        |        |        |        |        |        |        |        |
| 161      | 0.424  | 2.591  | -0.428 | 3.561  | 8.983  | 6.939  | 10.617 | 5.667  |
| 162      | 0.573  | 2.552  | -0.572 | 3.776  | 9.108  | 7.160  | 10.793 | 5.734  |
| 163      | 0.655  | 2.532  | -0.655 | 3.899  | 9.183  | 7.290  | 10.904 | 5.774  |
| 164      | 0.707  | 2.522  | -0.706 | 3.977  | 9.233  | 7.376  | 10.982 | 5.801  |
| 165      | 0.740  | 2.513  | -0.742 | 4.032  | 9.272  | 7.438  | 11.044 | 5.820  |
| 166      | 0.767  | 2.511  | -0.766 | 4.073  | 9.306  | 7.488  | 11.095 | 5.838  |
| 167      | 0.784  | 2.509  | -0.786 | 4.106  | 9.338  | 7.530  | 11.143 | 5.855  |
| 168      | 0.799  | 2.510  | -0.799 | 4.133  | 9.369  | 7.566  | 11.186 | 5.871  |
| 169      | 0.812  | 2.516  | -0.809 | 4.159  | 9.403  | 7.602  | 11.231 | 5.891  |
| 170      | 0.820  | 2.519  | -0.819 | 4.178  | 9.434  | 7.633  | 11.272 | 5.908  |
| 171      | 0.829  | 2.527  | -0.826 | 4.201  | 9.472  | 7.668  | 11.320 | 5.931  |
| 172      | 0.833  | 2.533  | -0.834 | 4.220  | 9.509  | 7.701  | 11.366 | 5.953  |
| 173      | 0.839  | 2.542  | -0.841 | 4.241  | 9.550  | 7.737  | 11.416 | 5.979  |
| 174      | 0.845  | 2.554  | -0.846 | 4.264  | 9.595  | 7.776  | 11.468 | 6.007  |
| 175      | 0.855  | 2.563  | 6.035  | 4.291  | -0.856 | -2.563 | 7.818  | 9.641  |
| 176      | 0.856  | 2.564  | 6.036  | 4.292  | -0.855 | -2.562 | 7.819  | 9.641  |
| 177      | 0.859  | 2.577  | 6.069  | 4.314  | -0.860 | -2.578 | 7.859  | 9.691  |
| 178      | 0.864  | 2.593  | 6.104  | 4.339  | -0.865 | -2.594 | 7.902  | 9.742  |
| 179      | 0.869  | 2.610  | 6.140  | 4.365  | -0.870 | -2.610 | 7.947  | 9.794  |
| 180      | 0.875  | 2.627  | 6.177  | 4.392  | -0.874 | -2.626 | 7.993  | 9.846  |
| 181      | 0.880  | 2.643  | 6.213  | 4.419  | -0.880 | -2.642 | 8.037  | 9.898  |
| 182      | 0.885  | 2.658  | 6.248  | 4.444  | -0.886 | -2.660 | 8.080  | 9.947  |
| 183      | 0.890  | 2.675  | 6.285  | 4.471  | -0.891 | -2.676 | 8.125  | 9.998  |
| 184      | 0.896  | 2.691  | 6.319  | 4.496  | -0.896 | -2.691 | 8.166  | 10.045 |
| 185      | 0.900  | 2.705  | 6.352  | 4.520  | -0.902 | -2.707 | 8.206  | 10.091 |

Table 121

FIG. 145

| Design # | SNRs | 5.00% | 40.00% | 50.00% | 60.00% | 70.00% | 100.00% |
|---|---|---|---|---|---|---|---|
| 63 | 7 | 2.79 | 2.51 | 2.26 | 2.03 | 1.48 | 0 |
| 64 | 7.2 | 2.88 | 2.59 | 2.33 | 2.1 | 1.38 | 0 |
| 65 | 7.4 | 2.75 | 2.47 | 2.23 | 2 | 1.31 | 0 |
| 66 | 7.6 | 2.74 | 2.47 | 2.22 | 2 | 1.31 | 0 |
| 67 | 7.8 | 2.74 | 2.47 | 2.22 | 2 | 1.31 | 0 |
| 68 | 8 | 2.72 | 2.45 | 2.2 | 1.98 | 1.3 | 0 |
| 69 | 8.2 | 2.7 | 2.43 | 2.18 | 1.96 | 1.29 | 0 |
| 70 | 8.4 | 2.66 | 2.39 | 2.15 | 1.94 | 1.27 | 0 |
| 71 | 8.6 | 2.62 | 2.36 | 2.12 | 1.91 | 1.25 | 0 |
| 72 | 8.8 | 2.56 | 2.3 | 2.07 | 1.87 | 1.22 | 0 |
| 73 | 8.99 | 2.59 | 1.28 | 1.15 | 1.04 | 0.93 | 0 |
| 74 | 9 | 2.59 | 1.28 | 1.15 | 1.04 | 0.93 | 0 |
| 75 | 9.2 | 2.57 | 1.25 | 1.13 | 1.02 | 0.91 | 0 |
| 76 | 9.4 | 2.54 | 1.23 | 1.1 | 0.99 | 0.89 | 0 |
| 77 | 9.6 | 2.51 | 1.2 | 1.08 | 0.97 | 0.87 | 0 |
| 78 | 9.8 | 2.48 | 1.18 | 1.06 | 0.95 | 0.86 | 0 |
| 79 | 10 | 2.39 | 2.15 | 1.93 | 1.74 | 1.14 | 0 |
| 80 | 10.2 | 2.13 | 1.92 | 1.73 | 1.56 | 1.13 | 0 |
| 81 | 10.4 | 2.31 | 2.08 | 1.87 | 1.69 | 1.11 | 0 |
| 82 | 10.6 | 2.26 | 2.03 | 1.83 | 1.64 | 1.08 | 0 |
| 83 | 10.8 | 2.2 | 1.98 | 1.78 | 1.6 | 1.17 | 0 |
| 84 | 11 | 2.19 | 1.97 | 1.77 | 1.59 | 1.05 | 0 |
| 85 | 11.2 | 2.15 | 1.93 | 1.74 | 1.56 | 1.03 | 0 |
| 86 | 11.4 | 2.1 | 1.89 | 1.7 | 1.53 | 1.12 | 0 |
| 87 | 11.6 | 2.05 | 1.84 | 1.66 | 1.49 | 1.09 | 0 |
| 88 | 11.8 | 2.2 | 1.98 | 1.78 | 1.61 | 1.05 | 0 |
| 89 | 12 | 2.13 | 1.91 | 1.72 | 1.55 | 1.02 | 0 |
| 90 | 12.2 | 2.04 | 1.84 | 1.65 | 1.49 | 1.09 | 0 |
| 91 | 12.21 | 2.04 | 1.83 | 1.65 | 1.49 | 1.08 | 0 |
| 92 | 12.4 | 2.17 | 1.96 | 1.76 | 1.58 | 1.04 | 0 |
| 93 | 12.6 | 2.12 | 1.91 | 1.72 | 1.39 | 1.02 | 0 |
| 94 | 12.8 | 2.07 | 1.87 | 1.68 | 1.51 | 0.99 | 0 |
| 95 | 13 | 2.02 | 1.82 | 1.64 | 1.47 | 0.97 | 0 |
| 96 | 13.2 | 1.96 | 1.76 | 1.59 | 1.43 | 1.04 | 0 |
| 97 | 13.4 | 1.89 | 1.7 | 1.53 | 1.38 | 1.01 | 0 |
| 98 | 13.6 | 1.83 | 1.65 | 1.48 | 1.33 | 0.97 | 0 |
| 99 | 13.8 | 1.76 | 1.58 | 1.42 | 1.28 | 0.93 | 0 |
| 100 | 14 | 1.89 | 1.7 | 1.53 | 1.38 | 1 | 0 |
| 101 | 14.2 | 1.85 | 1.66 | 1.5 | 1.35 | 0.88 | 0 |
| 102 | 14.4 | 1.81 | 1.63 | 1.47 | 1.32 | 0.96 | 0 |

Table 122

FIG. 146

| Design # | SNRs | 5.00% | 40.00% | 50.00% | 60.00% | 70.00% | 100.00% |
|---|---|---|---|---|---|---|---|
| 103 | 14.6 | 1.77 | 1.59 | 1.43 | 1.29 | 0.94 | 0 |
| 104 | 14.8 | 1.72 | 1.55 | 1.39 | 1.25 | 0.91 | 0 |
| 105 | 15 | 1.86 | 1.67 | 1.5 | 1.35 | 0.89 | 0 |
| 106 | 15.2 | 1.81 | 1.63 | 1.47 | 1.32 | 0.87 | 0 |
| 107 | 15.27 | 1.8 | 1.62 | 1.46 | 1.32 | 0.86 | 0 |
| 108 | 15.4 | 1.79 | 1.61 | 1.45 | 1.17 | 0.86 | 0 |
| 109 | 15.6 | 1.58 | 1.43 | 1.28 | 1.15 | 0.84 | 0 |
| 110 | 15.8 | 1.72 | 1.55 | 1.4 | 1.26 | 0.82 | 0 |
| 111 | 16 | 1.54 | 1.38 | 1.25 | 1.12 | 0.82 | 0 |
| 112 | 16.2 | 1.53 | 1.37 | 1.24 | 1.11 | 0.81 | 0 |
| 113 | 16.4 | 1.51 | 1.36 | 1.22 | 1.1 | 0.8 | 0 |
| 114 | 16.6 | 1.65 | 1.49 | 1.34 | 1.08 | 0.79 | 0 |
| 115 | 16.8 | 1.62 | 1.46 | 1.31 | 1.18 | 0.77 | 0 |
| 116 | 17 | 1.57 | 1.41 | 1.27 | 1.14 | 0.75 | 0 |
| 117 | 17.2 | 1.55 | 1.39 | 1.25 | 1.02 | 0.74 | 0 |
| 118 | 17.4 | 1.52 | 1.37 | 1.23 | 1 | 0.73 | 0 |
| 119 | 17.6 | 1.34 | 1.21 | 1.09 | 0.98 | 0.71 | 0 |
| 120 | 17.8 | 1.46 | 1.31 | 1.18 | 1.06 | 0.7 | 0 |
| 121 | 18 | 1.27 | 1.14 | 1.03 | 0.92 | 0.67 | 0 |
| 122 | 18.2 | 1.36 | 1.22 | 1.1 | 0.99 | 0.65 | 0 |
| 123 | 18.4 | 1.31 | 1.18 | 1.06 | 0.95 | 0.63 | 0 |
| 124 | 18.42 | 1.3 | 1.17 | 1.05 | 0.95 | 0.62 | 0 |
| 125 | 18.6 | 1.25 | 1.12 | 1.01 | 0.91 | 0.66 | 0 |
| 126 | 18.8 | 1.3 | 1.17 | 1.05 | 0.95 | 0.56 | 0 |
| 127 | 19 | 1.2 | 1.08 | 0.97 | 0.88 | 0.57 | 0 |
| 128 | 19.2 | 1.18 | 1.06 | 0.96 | 0.86 | 0.57 | 0 |
| 129 | 19.4 | 1.1 | 0.99 | 0.89 | 0.81 | 0.59 | 0 |
| 130 | 19.6 | 1.14 | 1.02 | 0.92 | 0.83 | 0.54 | 0 |
| 131 | 19.8 | 1.15 | 1.04 | 0.93 | 0.84 | 0.55 | 0 |
| 132 | 20 | 1.04 | 0.94 | 0.84 | 0.76 | 0.55 | 0 |
| 133 | 20.2 | 1.03 | 0.93 | 0.84 | 0.75 | 0.49 | 0 |
| 134 | 20.4 | 1.05 | 0.94 | 0.85 | 0.69 | 0.5 | 0 |
| 135 | 20.6 | 1.05 | 0.95 | 0.85 | 0.69 | 0.5 | 0 |
| 136 | 20.8 | 0.95 | 0.86 | 0.77 | 0.69 | 0.51 | 0 |
| 137 | 21 | 0.95 | 0.86 | 0.77 | 0.7 | 0.46 | 0 |
| 138 | 21.2 | 0.95 | 0.86 | 0.77 | 0.63 | 0.46 | 0 |
| 139 | 21.4 | 0.95 | 0.86 | 0.77 | 0.62 | 0.45 | 0 |
| 140 | 21.52 | 0.85 | 0.77 | 0.69 | 0.62 | 0.45 | 0 |
| 141 | 21.6 | 0.85 | 0.77 | 0.69 | 0.62 | 0.45 | 0 |
| 142 | 21.8 | 0.85 | 0.76 | 0.68 | 0.62 | 0.45 | 0 |
| 143 | 22 | 0.78 | 0.71 | 0.64 | 0.57 | 0.42 | 0 |

Table 123

FIG. 147

| Design # | SNRs | 5.00% | 40.00% | 50.00% | 60.00% | 70.00% | 100.00% |
|---|---|---|---|---|---|---|---|
| 144 | 22.2 | 0.81 | 0.73 | 0.66 | 0.53 | 0.39 | 0 |
| 145 | 22.4 | 0.75 | 0.68 | 0.61 | 0.55 | 0.36 | 0 |
| 146 | 22.6 | 0.78 | 0.7 | 0.63 | 0.57 | 0.37 | 0 |
| 147 | 22.8 | 0.72 | 0.65 | 0.59 | 0.53 | 0.35 | 0 |
| 148 | 23 | 0.67 | 0.6 | 0.54 | 0.49 | 0.36 | 0 |
| 149 | 23.2 | 0.69 | 0.62 | 0.56 | 0.5 | 0.33 | 0 |
| 150 | 23.4 | 0.64 | 0.57 | 0.52 | 0.47 | 0.34 | 0 |
| 151 | 23.6 | 0.66 | 0.59 | 0.53 | 0.43 | 0.31 | 0 |
| 152 | 23.8 | 0.61 | 0.55 | 0.49 | 0.44 | 0.29 | 0 |
| 153 | 24 | 0.56 | 0.5 | 0.45 | 0.41 | 0.3 | 0 |
| 154 | 24.2 | 0.57 | 0.52 | 0.46 | 0.42 | 0.27 | 0 |
| 155 | 24.4 | 0.53 | 0.48 | 0.43 | 0.39 | 0.28 | 0 |
| 156 | 24.6 | 0.54 | 0.49 | 0.44 | 0.39 | 0.26 | 0 |
| 157 | 24.79 | 0.5 | 0.45 | 0.4 | 0.36 | 0.27 | 0 |
| 158 | 24.8 | 0.5 | 0.45 | 0.41 | 0.36 | 0.24 | 0 |
| 159 | 25 | 0.46 | 0.42 | 0.38 | 0.34 | 0.25 | 0 |
| 160 | 25.2 | 0.48 | 0.43 | 0.39 | 0.35 | 0.25 | 0 |
| 161 | 25.4 | 0.44 | 0.4 | 0.36 | 0.32 | 0.23 | 0 |
| 162 | 25.6 | 0.45 | 0.41 | 0.37 | 0.33 | 0.22 | 0 |
| 163 | 25.8 | 0.42 | 0.38 | 0.34 | 0.3 | 0.22 | 0 |
| 164 | 26 | 0.38 | 0.34 | 0.31 | 0.28 | 0.2 | 0 |
| 165 | 26.2 | 0.38 | 0.34 | 0.31 | 0.28 | 0.2 | 0 |
| 166 | 26.4 | 0.37 | 0.33 | 0.3 | 0.27 | 0.2 | 0 |
| 167 | 26.6 | 0.36 | 0.32 | 0.29 | 0.26 | 0.19 | 0 |
| 168 | 26.8 | 0.35 | 0.32 | 0.28 | 0.26 | 0.19 | 0 |
| 169 | 27 | 0.34 | 0.31 | 0.28 | 0.25 | 0.16 | 0 |
| 170 | 27.2 | 0.3 | 0.27 | 0.24 | 0.22 | 0.16 | 0 |
| 171 | 27.4 | 0.29 | 0.26 | 0.23 | 0.21 | 0.15 | 0 |
| 172 | 27.6 | 0.28 | 0.25 | 0.23 | 0.2 | 0.15 | 0 |
| 173 | 27.8 | 0.27 | 0.24 | 0.22 | 0.2 | 0.14 | 0 |
| 174 | 28 | 0.26 | 0.23 | 0.21 | 0.19 | 0.14 | 0 |
| 175 | 28.2 | 0.25 | 0.23 | 0.2 | 0.18 | 0.13 | 0 |
| 176 | 28.2 | 0.25 | 0.23 | 0.2 | 0.18 | 0.13 | 0 |
| 177 | 28.4 | 0.24 | 0.22 | 0.2 | 0.18 | 0.13 | 0 |
| 178 | 28.6 | 0.21 | 0.19 | 0.17 | 0.15 | 0.11 | 0 |
| 179 | 28.8 | 0.22 | 0.2 | 0.18 | 0.16 | 0.12 | 0 |
| 180 | 29 | 0.19 | 0.17 | 0.16 | 0.14 | 0.1 | 0 |
| 181 | 29.2 | 0.18 | 0.17 | 0.15 | 0.13 | 0.1 | 0 |
| 182 | 29.4 | 0.2 | 0.18 | 0.16 | 0.13 | 0.09 | 0 |
| 183 | 29.6 | 0.17 | 0.15 | 0.14 | 0.12 | 0.09 | 0 |
| 184 | 29.8 | 0.16 | 0.15 | 0.13 | 0.12 | 0.09 | 0 |
| 185 | 30 | 0.15 | 0.14 | 0.12 | 0.11 | 0.08 | 0 |

Table 124

METHODS AND APPARATUSES FOR SIGNALING WITH GEOMETRIC CONSTELLATIONS

CROSS-REFERENCE TO RELATED APPLICATIONS

The present invention is a continuation application of U.S. patent application Ser. No. 13/608,838 filed Sep. 10, 2012 entitled "Methods and Apparatuses for Signaling with Geometric Constellations", which application is a continuation application of U.S. patent application Ser. No. 12/650,532 filed Dec. 30, 2009 entitled "Methods and Apparatuses for Signaling with Geometric Constellations" and issued as U.S. Pat. No. 8,265,175 on Sep. 11, 2012, which application claims priority as a Continuation-In-Part to U.S. patent application Ser. No. 12/156,989 filed Jun. 5, 2008 entitled "Design Methodology and Method and Apparatus for Signaling with Capacity Optimized Constellation" and issued as U.S. Pat. No. 7,978,777 on Jul. 12, 2011, which claims priority to U.S. Provisional Application Ser. No. 60/933,319 filed Jun. 5, 2007 entitled "New Constellations for Communications Signaling: Design Methodology and Method and Apparatus for the New Signaling Scheme" to Barsoum et al. U.S. patent application Ser. No. 12/650,532 also claims priority to U.S. Provisional Application Ser. No. 61/141,662 filed Dec. 30, 2008 and U.S. Provisional Application Ser. No. 61/141,935 filed Dec. 31, 2008, both of which are entitled "PAM-8, 16, 32 Constellations Optimized for Joint and PD Capacity" and are to Barsoum et al. The disclosure of U.S. patent application Ser. Nos. 13/608,838, 12/650,532, 12/156,989 and U.S. Provisional Application Nos. 60/933,319, 61/141,662 and 61/141,935 are expressly incorporated by reference herein in its entirety.

STATEMENT OF FEDERALLY SPONSORED RESEARCH

This invention was made with Government support under contract NAS7-03001 awarded by NASA. The Government has certain rights in this invention.

BACKGROUND

The present invention generally relates to bandwidth and/or power efficient digital transmission systems and more specifically to the use of unequally spaced constellations having increased capacity.

The term "constellation" is used to describe the possible symbols that can be transmitted by a typical digital communication system. A receiver attempts to detect the symbols that were transmitted by mapping a received signal to the constellation. The minimum distance ($d_{min}$) between constellation points is indicative of the capacity of a constellation at high signal-to-noise ratios (SNRs). Therefore, constellations used in many communication systems are designed to maximize $d_{min}$. Increasing the dimensionality of a constellation allows larger minimum distance for constant constellation energy per dimension. Therefore, a number of multi-dimensional constellations with good minimum distance properties have been designed.

Communication systems have a theoretical maximum capacity, which is known as the Shannon limit. Many communication systems attempt to use codes to increase the capacity of a communication channel. Significant coding gains have been achieved using coding techniques such as turbo codes and LDPC codes. The coding gains achievable using any coding technique are limited by the constellation of the communication system. The Shannon limit can be thought of as being based upon a theoretical constellation known as a Gaussian distribution, which is an infinite constellation where symbols at the center of the constellation are transmitted more frequently than symbols at the edge of the constellation. Practical constellations are finite and transmit symbols with equal likelihoods, and therefore have capacities that are less than the Gaussian capacity. The capacity of a constellation is thought to represent a limit on the gains that can be achieved using coding when using that constellation.

Prior attempts have been made to develop unequally spaced constellations. For example, a system has been proposed that uses unequally spaced constellations that are optimized to minimize the error rate of an uncoded system. Another proposed system uses a constellation with equiprobable but unequally spaced symbols in an attempt to mimic a Gaussian distribution.

Other approaches increase the dimensionality of a constellation or select a new symbol to be transmitted taking into consideration previously transmitted symbols. However, these constellation were still designed based on a minimum distance criteria.

SUMMARY OF THE INVENTION

Systems and methods are described for constructing a modulation such that the constrained capacity between a transmitter and a receiver approaches the Gaussian channel capacity limit first described by Shannon [ref Shannon 1948]. Traditional communications systems employ modulations that leave a significant gap to Shannon Gaussian capacity. The modulations of the present invention reduce, and in some cases, nearly eliminate this gap. The invention does not require specially designed coding mechanisms that tend to transmit some points of a modulation more frequently than others but rather provides a method for locating points (in a one or multiple dimensional space) in order to maximize capacity between the input and output of a bit or symbol mapper and demapper respectively. Practical application of the method allows systems to transmit data at a given rate for less power or to transmit data at a higher rate for the same amount of power.

One embodiment of the invention includes a transmitter configured to transmit signals to a receiver via a communication channel, where the transmitter, includes a coder configured to receive user bits and output encoded bits at an expanded output encoded bit rate, a mapper configured to map encoded bits to symbols in a symbol constellation, a modulator configured to generate a signal for transmission via the communication channel using symbols generated by the mapper, where the receiver, includes a demodulator configured to demodulate the received signal via the communication channel, a demapper configured to estimate likelihoods from the demodulated signal, and a decoder that is configured to estimate decoded bits from the likelihoods generated by the demapper. In addition, the symbol constellation is a PAM-8 symbol constellation having constellation points within at least one of the ranges specified in FIGS. 25-46.

In a further embodiment, the code is a Turbo code. In another embodiment, the code is a LDPC code.

In a still further embodiment, the constellation provides an increase in capacity at a predetermined SNR that is at least 5% of the gain in capacity achieved by a constellation optimized for joint capacity at the predetermined SNR.

In still another embodiment, the constellation provides an increase in capacity at a predetermined SNR that is at least 15% of the gain in capacity achieved by a constellation optimized for joint capacity at the predetermined SNR.

In a yet further embodiment, the constellation provides an increase in capacity at a predetermined SNR that is at least 30% of the gain in capacity achieved by a constellation optimized for joint capacity at the predetermined SNR.

In yet another embodiment, the constellation provides an increase in capacity at a predetermined SNR that is at least 45% of the gain in capacity achieved by a constellation optimized for joint capacity at the predetermined SNR.

A further embodiment again, the constellation provides an increase in capacity at a predetermined SNR that is at least 60% of the gain in capacity achieved by a constellation optimized for joint capacity at the predetermined SNR.

In another embodiment again, the constellation provides an increase in capacity at a predetermined SNR that is at least 100% of the gain in capacity achieved by a constellation optimized for joint capacity at the predetermined SNR.

In a further additional embodiment, the constellation provides an increase in capacity at a predetermined SNR that is at least 5% of the gain in capacity achieved by a constellation optimized for PD capacity at the predetermined SNR.

In another additional embodiment, the constellation provides an increase in capacity at a predetermined SNR that is at least 40% of the gain in capacity achieved by a constellation optimized for PD capacity at the predetermined SNR.

In a still yet further embodiment, the constellation provides an increase in capacity at a predetermined SNR that is at least 50% of the gain in capacity achieved by a constellation optimized for PD capacity at the predetermined SNR.

In still yet another embodiment, the constellation provides an increase in capacity at a predetermined SNR that is at least 60% of the gain in capacity achieved by a constellation optimized for PD capacity at the predetermined SNR.

In a still further embodiment again, the constellation provides an increase in capacity at a predetermined SNR that is at least 70% of the gain in capacity achieved by a constellation optimized for PD capacity at the predetermined SNR.

In still another embodiment again, the constellation provides an increase in capacity at a predetermined SNR that is at least 100% of the gain in capacity achieved by a constellation optimized for PD capacity at the predetermined SNR.

A still further additional embodiment includes a transmitter configured to transmit signals to a receiver via a communication channel, where the transmitter, includes a coder configured to receive user bits and output encoded bits at an expanded output encoded bit rate, a mapper configured to map encoded bits to symbols in a symbol constellation, a modulator configured to generate a signal for transmission via the communication channel using symbols generated by the mapper, where the receiver, includes a demodulator configured to demodulate the received signal via the communication channel, a demapper configured to estimate likelihoods from the demodulated signal, and a decoder that is configured to estimate decoded bits from the likelihoods generated by the demapper. In addition, the symbol constellation is a PAM-16 symbol constellation having constellation points within at least one of the ranges specified in FIGS. 47-84.

Still another additional embodiment includes a transmitter configured to transmit signals to a receiver via a communication channel, where the transmitter, includes a coder configured to receive user bits and output encoded bits at an expanded output encoded bit rate, a mapper configured to map encoded bits to symbols in a symbol constellation, a modulator configured to generate a signal for transmission via the communication channel using symbols generated by the mapper, where the receiver, includes a demodulator configured to demodulate the received signal via the communication channel, a demapper configured to estimate likelihoods from the demodulated signal, and a decoder that is configured to estimate decoded bits from the likelihoods generated by the demapper. In addition, the symbol constellation is a PAM-32 symbol constellation having constellation points within at least one of the ranges specified in FIGS. 85-148.

Another further embodiment includes a transmitter configured to transmit signals to a receiver via a communication channel, where the transmitter, includes a coder configured to receive user bits and output encoded bits at an expanded output encoded bit rate, a mapper configured to map encoded bits to symbols in a symbol constellation, a modulator configured to generate a signal for transmission via the communication channel using symbols generated by the mapper, where the receiver, includes a demodulator configured to demodulate the received signal via the communication channel, a demapper configured to estimate likelihoods from the demodulated signal, and a decoder that is configured to estimate decoded bits from the likelihoods generated by the demapper. In addition, the symbol constellation is a N-Dimensional symbol constellation, where the constellation points in at least one dimension are within at least one of the ranges specified in FIGS. 25-167.

BRIEF DESCRIPTION OF DRAWINGS

FIG. 2 is a conceptual illustration of a transmitter in accordance with an embodiment of the invention.

FIG. 3 is a conceptual illustration of a receiver in accordance with an embodiment of the invention.

FIGS. 11a and 11b are design tables of PD capacity and joint capacity optimized PAM-4 constellations in accordance with embodiments of the invention.

FIGS. 13a and 13b are design tables of PD capacity and joint capacity optimized PAM-8 constellations in accordance with embodiments of the invention.

FIGS. 15a and 15b are design tables of PD capacity and joint capacity optimized PAM-16 constellations in accordance with embodiments of the invention.

FIGS. 17a and 17b are design tables of PD capacity and joint capacity optimized PAM-32 constellations in accordance with embodiments of the invention.

FIGS. 25-28 are tables showing the performance of geometric PAM-8 constellations optimized for Joint Capacity at specific SNRs in accordance with embodiments of the invention.

FIGS. 29-32 are tables listing the constellation points corresponding to the geometric PAM-8 constellation designs optimized for Joint Capacity at specific SNRs listed in FIGS. 25-28.

FIGS. 33-36 are tables showing maximum ranges for the geometric PAM-8 constellation designs optimized for Joint Capacity at specific SNRs lised in FIGS. 25-28.

FIGS. 37-40 are tables showing the performance of geometric PAM-8 constellations optimized for PD Capacity at specific SNRs in accordance with embodiments of the invention.

FIGS. 41-44 are tables listing the constellation points corresponding to the geometric PAM-8 constellation designs optimized for PD Capacity at specific SNRs listed in FIGS. 37-40.

FIGS. 45-46 are tables showing maximum ranges for the geometric PAM-8 constellation designs optimized for PD Capacity at specific SNRs lised in FIGS. 37-40.

FIGS. 47-51 are tables showing the performance of geometric PAM-16 constellations optimized for Joint Capacity at specific SNRs in accordance with embodiments of the invention.

FIGS. 52-61 are tables listing the constellation points corresponding to the geometric PAM-16 constellation designs optimized for Joint Capacity at specific SNRs listed in FIGS. 47-51.

FIGS. 62-66 are tables showing maximum ranges for the geometric PAM-16 constellation designs optimized for Joint Capacity at specific SNRs listed in FIGS. 47-51.

FIGS. 67-71 are tables showing the performance of geometric PAM-16 constellations optimized for PD Capacity at specific SNRs in accordance with embodiments of the invention.

FIGS. 72-81 are tables listing the constellation points corresponding to the geometric PAM-16 constellation designs optimized for PD Capacity at specific SNRs listed in FIGS. 67-71.

FIGS. 82-84 are tables showing maximum ranges for the geometric PAM-16 constellation designs optimized for PD Capacity at specific SNRs listed in FIGS. 67-71.

FIGS. 85-90 are tables showing the performance of geometric PAM-32 constellations optimized for Joint Capacity at specific SNRs in accordance with embodiments of the invention.

FIGS. 91-114 are tables listing the constellation points corresponding to the geometric PAM-32 constellation designs optimized for Joint Capacity at specific SNRs listed in FIGS. 85-90.

FIGS. 115-120 are tables showing maximum ranges for the geometric PAM-32 constellation designs optimized for Joint Capacity at specific SNRs listed in FIGS. 85-90.

FIGS. 121-125 are tables showing the performance of geometric PAM-32 constellations optimized for PD Capacity at specific SNRs in accordance with embodiments of the invention.

FIGS. 126-145 are tables listing the constellation points corresponding to the geometric PAM-32 constellation designs optimized for PD Capacity at specific SNRs listed in FIGS. 121-125.

FIGS. 146-148 are tables showing maximum ranges for the geometric PAM-32 constellation designs optimized for Joint Capacity at specific SNRs listed in FIGS. 121-125.

DETAILED DESCRIPTION OF THE INVENTION

Figure 1:
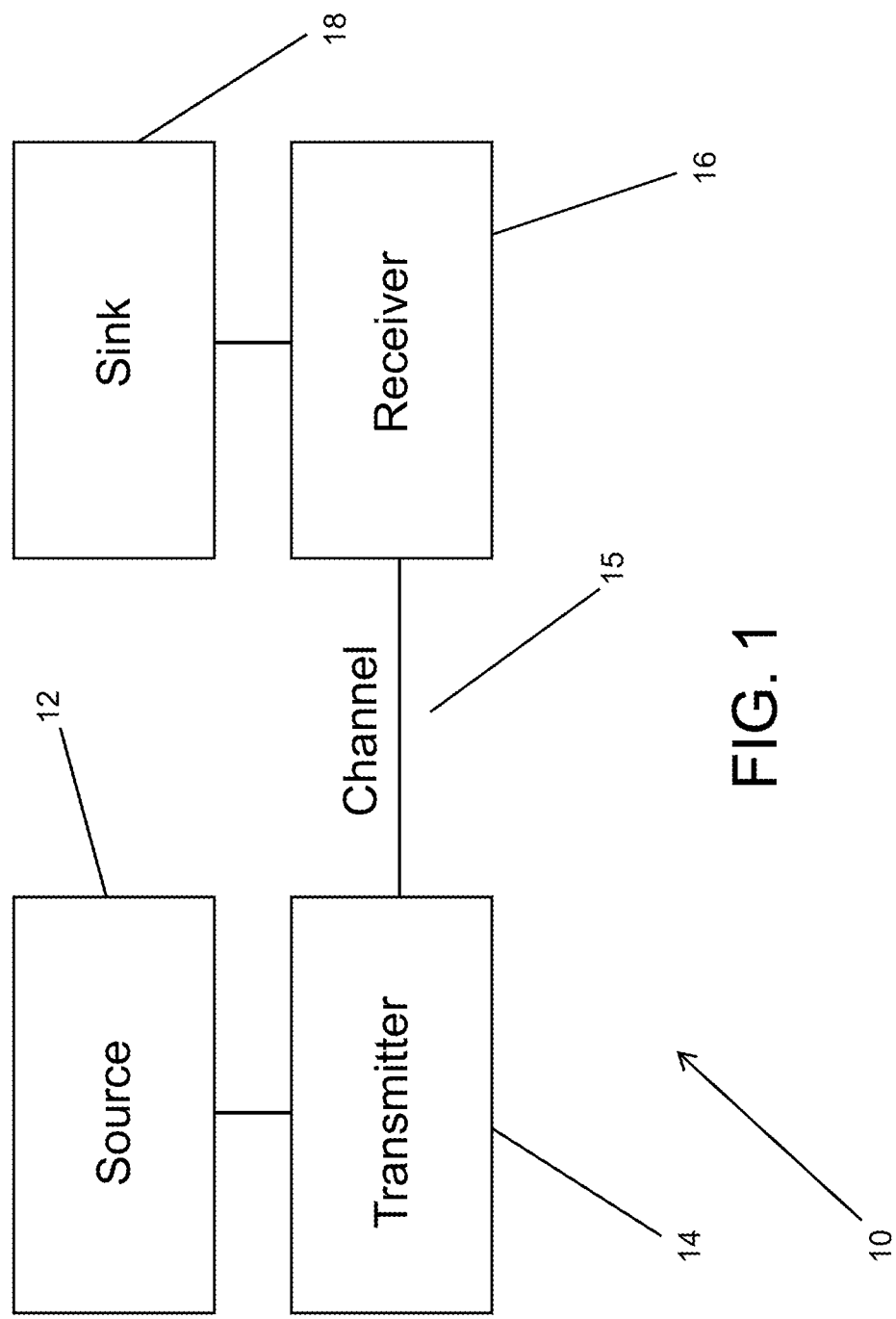
FIG. 1 is a conceptual illustration of a communication system in accordance with an embodiment of the invention.

Turning now to the detailed description of the invention, communication systems in accordance with embodiments of the invention are described that use signal constellations, which have unequally spaced (i.e. 'geometrically' shaped) points. In many embodiments, the communication systems use specific geometric constellations that are capacity optimized at a specific SNR. In addition, ranges within which the constellation points of a capacity optimized constellation can be perturbed and are still likely to achieve a given percentage of the optimal capacity increase compared to a constellation that maximizes $d_{min}$, are also described. Capacity measures that are used in the selection of the location of constellation points include, but are not limited to, parallel decode (PD) capacity and joint capacity.

In many embodiments, the communication systems utilize capacity approaching codes including, but not limited to, LDPC and Turbo codes. As is discussed further below, direct optimization of the constellation points of a communication system utilizing a capacity approaching channel code, can yield different constellations depending on the SNR for which they are optimized. Therefore, the same constellation is unlikely to achieve the same coding gains applied across all code rates; that is, the same constellation will not enable the best possible performance across all rates. In many instances, a constellation at one code rate can achieve gains that cannot be achieved at another code rate. Processes for selecting capacity optimized constellations to achieve increased coding gains based upon a specific coding rate in accordance with embodiments of the invention are described below. Constellations points for geometric PAM-8, PAM-16, and PAM-32 constellations that are optimized for joint capacity or PD capacity at specific SNRs are also provided. Additional geometric PAM-8, PAM-16, and PAM-32 constellations that are probabilistically likely to provide performance gains compared to constellations that maximize $d_{min}$, which were identified by perturbing the constellation points of geometric PAM-8, PAM-16, and PAM-32 constellations optimized for joint capacity or PD capacity, are also described. The constellations are described as being probabilistically likely to provide performance gains, because all possible constellations within the ranges have not been exhaustively searched. Within each disclosed range, a large number of constellations were selected at random, and it was verified that all the selected constellations provided a gain that exceeds the given percentage of the optimal capacity increase achieved by the optimized constellations relative to a constellation that maximizes $d_{min}$ (i.e. a PAM equally spaced constellation). In this way, ranges that are probabilistically likely to provide a performance gain that is at least a predetermined percentage of the optimal increase in capacity can be identified and a specific geometric constellation can be compared against the ranges as a guide to the increase in capacity that is likely to be achieved. In a number of embodiments, the communication systems can adapt the location of points in a constellation in response to channel conditions, changes in code rate and/or to change the target user data rate.

Communication Systems

A communication system in accordance with an embodiment of the invention is shown in FIG. 1. The communication system 10 includes a source 12 that provides user bits to a transmitter 14. The transmitter transmits symbols over a channel to a receiver 16 using a predetermined modulation scheme. The receiver uses knowledge of the modulation scheme, to decode the signal received from the transmitter. The decoded bits are provided to a sink device that is connected to the receiver.

A transmitter in accordance with an embodiment of the invention is shown in FIG. 2. The transmitter 14 includes a coder 20 that receives user bits from a source and encodes the bits in accordance with a predetermined coding scheme. In a number of embodiments, a capacity approaching code such as a turbo code or a LDPC code is used. In other embodiments, other coding schemes can be used to providing a coding gain within the communication system. A mapper 22 is connected to the coder. The mapper maps the bits output by the coder to a symbol within a geometrically distributed signal constellation stored within the mapper. The mapper provides the symbols to a modulator 24, which modulates the symbols for transmission via the channel.

A receiver in accordance with an embodiment of the invention is illustrated in FIG. 3. The receiver 16 includes a demodulator 30 that demodulates a signal received via the channel to obtain symbol or bit likelihoods. The demapper uses knowledge of the geometrically shaped symbol constellation used by the transmitter to determine these likelihoods. The demapper 32 provides the likelihoods to a decoder 34 that decodes the encoded bit stream to provide a sequence of received bits to a sink.

Geometrically Shaped Constellations

Transmitters and receivers in accordance with embodiments of the invention utilize geometrically shaped symbol constellations. In several embodiments, a geometrically shaped symbol constellation is used that optimizes the capacity of the constellation. In many embodiments, geometrically shaped symbol constellations, which include constellation points within predetermined ranges of the constellation points of a capacity optimized constellation, and that provide improved capacity compared to constellations that maximize $d_{min}$ are used. Various geometrically shaped symbol constellations that can be used in accordance with embodiments of the invention, techniques for deriving geometrically shaped symbol constellations are described below.

Selection of a Geometrically Shaped Constellations

Selection of a geometrically shaped constellation for use in a communication system in accordance with an embodiment of the invention can depend upon a variety of factors including whether the code rate is fixed. In many embodiments, a geometrically shaped constellation is used to replace a conventional constellation (i.e. a constellation maximized for $d_{min}$) in the mapper of transmitters and the demapper of receivers within a communication system. Upgrading a communication system involves selection of a constellation and in many instances the upgrade can be achieved via a simple firmware upgrade. In other embodiments, a geometrically shaped constellation is selected in conjunction with a code rate to meet specific performance requirements, which can for example include such factors as a specified bit rate, a maximum transmit power. Processes for selecting a geometric constellation when upgrading existing communication systems and when designing new communication systems are discussed further below.

Upgrading Existing Communication Systems

A geometrically shaped constellation that provides a capacity, which is greater than the capacity of a constellation maximized for $d_{min}$, can be used in place of a conventional constellation in a communication system in accordance with embodiments of the invention. In many instances, the substitution of the geometrically shaped constellation can be achieved by a firmware or software upgrade of the transmitters and receivers within the communication system. Not all geometrically shaped constellations have greater capacity than that of a constellation maximized for $d_{min}$. One approach to selecting a geometrically shaped constellation having a greater capacity than that of a constellation maximized for $d_{min}$ is to optimize the shape of the constellation with respect to a measure of the capacity of the constellation for a given SNR. Another approach is to select a constellation from a range that is probabilistically likely to yield a constellation having at least a predetermined percentage of the optimal capacity increase. Such an approach can prove useful in circumstances, for example, where an optimized constellation is unable to be implemented. Capacity measures that can be used in the optimization process can include, but are not limited to, joint capacity or parallel decoding capacity.

Joint Capacity and Parallel Decoding Capacity

Figure 4A:
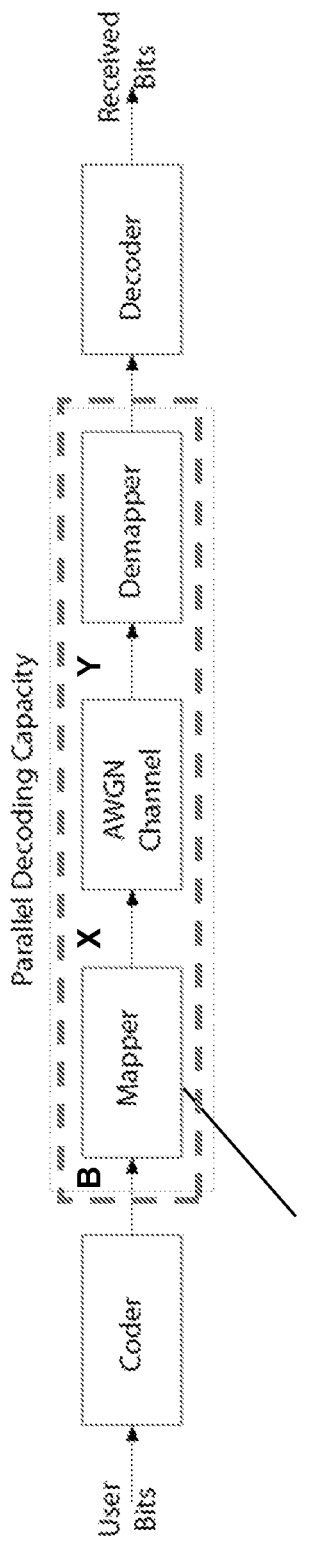
FIG. 4a is a conceptual illustration of the joint capacity of a channel.

A constellation can be parameterized by the total number of constellation points, M, and the number of real dimensions, $N_{dim}$. In systems where there are no belief propagation iterations between the decoder and the constellation demapper, the constellation demapper can be thought of as part of the channel. A diagram conceptually illustrating the portions of a communication system that can be considered part of the channel for the purpose of determining PD capacity is shown in FIG. 4a. The portions of the communication system that are considered part of the channel are indicated by the ghost line 40. The capacity of the channel defined as such is the parallel decoding (PD) capacity, given by:

$$C_{PD} = \sum_{i=0}^{l-1} I(X_i; Y)$$

where $X_i$ is the ith bit of the l-bits transmitted symbol, and Y is the received symbol, and l(A;B) denotes the mutual information between random variables A and B.

Expressed another way, the PD capacity of a channel can be viewed in terms of the mutual information between the output bits of the encoder (such as an LDPC encoder) at the transmitter and the likelihoods computed by the demapper at the receiver. The PD capacity is influenced by both the placement of points within the constellation and by the labeling assignments.

Figure 4B:
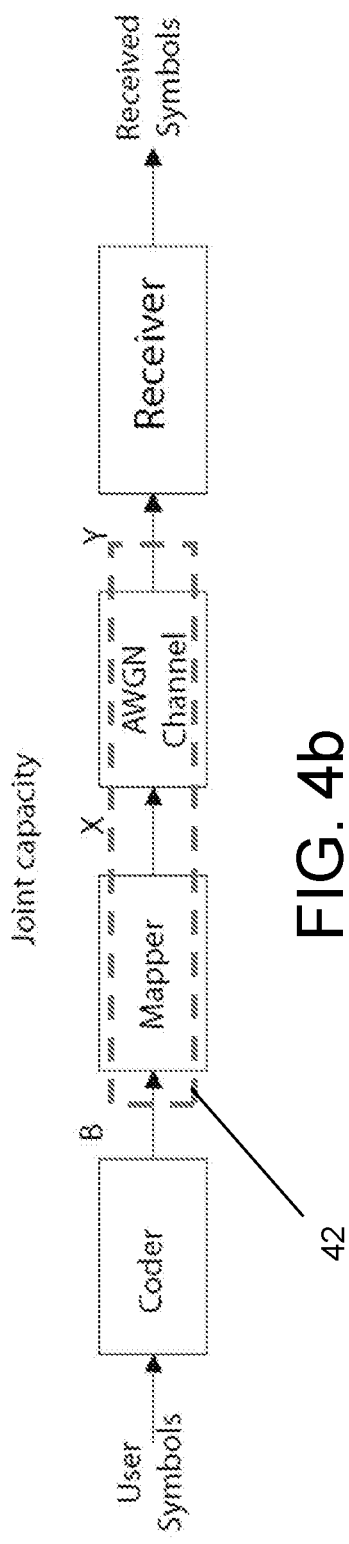
FIG. 4b is a conceptual illustration of the parallel decoding capacity of a channel.

With belief propagation iterations between the demapper and the decoder, the demapper can no longer be viewed as part of the channel, and the joint capacity of the constellation becomes the tightest known bound on the system performance. A diagram conceptually illustrating the portions of a communication system that are considered part of the channel for the purpose of determining the joint capacity of a constellation is shown in FIG. 4b. The portions of the communication system that are considered part of the channel are indicated by the ghost line 42. The joint capacity of the channel is given by:

$$C_{JOINT} = I(X;Y)$$

Joint capacity is a description of the achievable capacity between the input of the mapper on the transmit side of the link and the output of the channel (including for example AWGN and Fading channels). Practical systems must often 'demap' channel observations prior to decoding. In general, the step causes some loss of capacity. In fact it can be proven that $C_G \geq C_{JOINT} \geq C_{PD}$. That is, $C_{JOINT}$ upper bounds the capacity achievable by $C_{PD}$. The methods of the present invention are motivated by considering the fact that practical limits to a given communication system capacity are limited by $C_{JOINT}$ and $C_{PD}$. In several embodiments of the invention, geometrically shaped constellations are selected that maximize these measures.

Selecting a Constellation Having an Optimal Capacity

Figure 5:
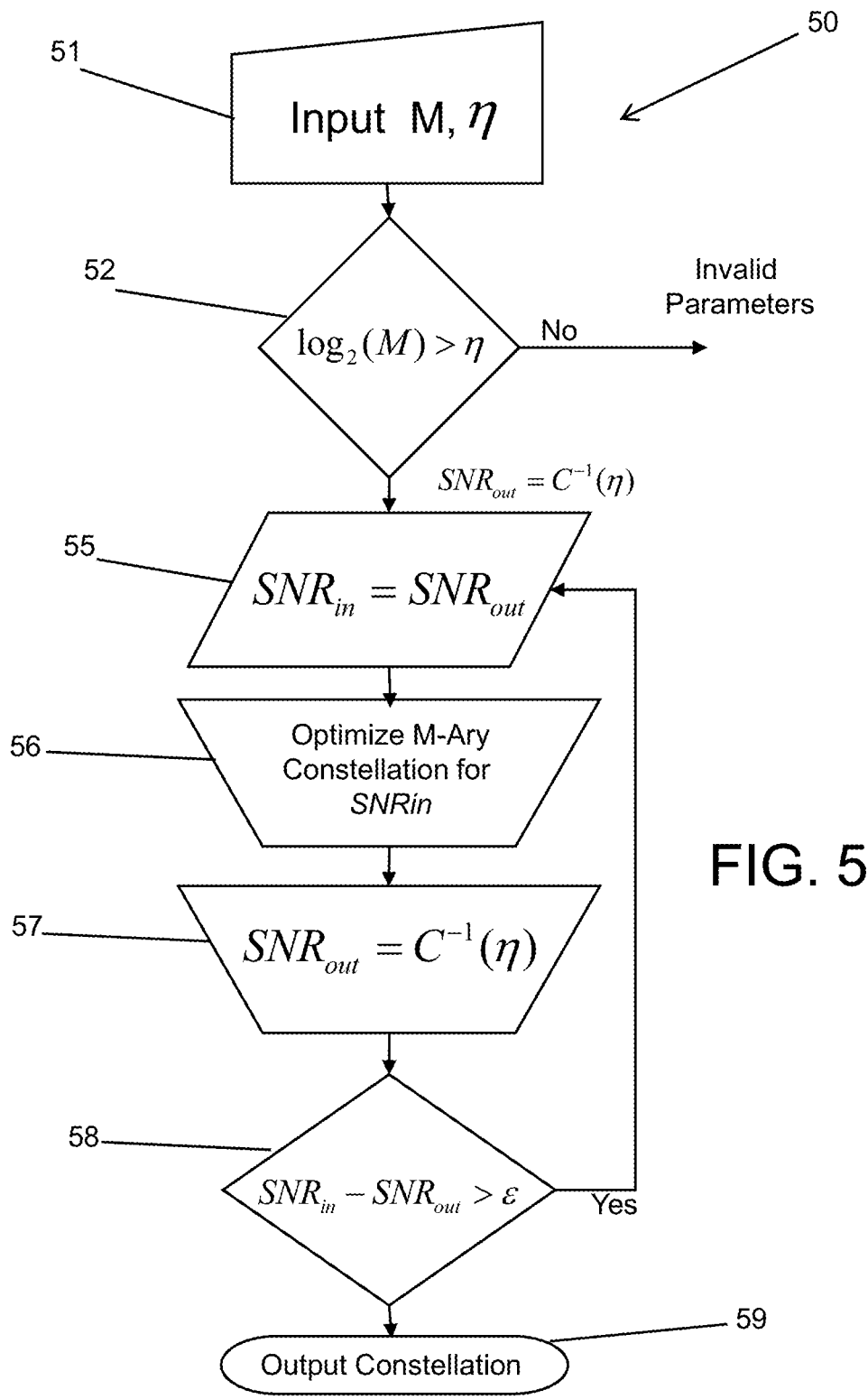
FIG. 5 is a flow chart showing a process for obtaining a constellation optimized for capacity for use in a communication system having a fixed code rate and modulation scheme in accordance with an embodiment of the invention.

Geometrically shaped constellations in accordance with embodiments of the invention can be designed to optimize capacity measures including, but not limited to PD capacity or joint capacity. A process for selecting the points, and potentially the labeling, of a geometrically shaped constellation for use in a communication system having a fixed code rate in accordance with an embodiment of the invention is shown in FIG. 5. The process 50 commences with the selection (52) of an appropriate constellation size M and a desired capacity per dimension η. In the illustrated embodiment, the process involves a check (52) to ensure that the constellation size can support the desired capacity. In the event that the constellation size could support the desired capacity, then the process iteratively optimizes the M-ary constellation for the specified capacity. Optimizing a constellation for a specified capacity often involves an iterative process, because the optimal constellation depends upon the SNR at which the communication system operates. The SNR for the optimal constellation to give a required capacity is not known a priori. Throughout the description of the present invention SNR is defined as the ratio of the average constellation energy per dimension to the average noise energy per dimension. In most cases the capacity can be set to equal the target user bit rate per symbol per dimension. In some cases adding some implementation margin on top of the target user bit rate could result in a practical system that can provide the required user rate at a lower rate. The margin is code dependent. The following procedure could be used to determine the target capacity that includes some margin on top of the user rate. First, the code (e.g. LDPC or Turbo) can be simulated in conjunction with a conventional equally spaced constellation. Second, from the simulation results the actual SNR of operation at the required error rate can be found. Third, the capacity of the conventional constellation at that SNR can be computed. Finally, a geometrically shaped constellation can be optimized for that capacity.

In the illustrated embodiment, the iterative optimization loop involves selecting an initial estimate of the SNR at which the system is likely to operate (i.e. $SNR_{in}$). In several embodiments the initial estimate is the SNR required using a conventional constellation. In other embodiments, other techniques can be used for selecting the initial SNR. An M-ary constellation is then obtained by optimizing (56) the constellation to maximize a selected capacity measure at the initial $SNR_{in}$ estimate. Various techniques for obtaining an optimized constellation for a given SNR estimate are discussed below.

The SNR at which the optimized M-ary constellation provides the desired capacity per dimension η ($SNR_{out}$) is determined (57). A determination (58) is made as to whether the $SNR_{out}$ and $SNR_{in}$ have converged. In the illustrated embodiment convergence is indicated by $SNR_{out}$ equaling $SNR_{in}$. In a number of embodiments, convergence can be determined based upon the difference between $SNR_{out}$ and $SNR_{in}$ being less than a predetermined threshold. When $SNR_{out}$ and $SNR_{in}$ have not converged, the process performs another iteration selecting $SNR_{out}$ as the new $SNR_{in}$ (55). When $SNR_{out}$ and $SNR_{in}$ have converged, the capacity measure of the constellation has been optimized. As is explained in more detail below, capacity optimized constellations at low SNRs are geometrically shaped constellations that can achieve significantly higher performance gains (measured as reduction in minimum required SNR) than constellations that maximize $d_{min}$.

The process illustrated in FIG. 5 can maximize PD capacity or joint capacity of an M-ary constellation for a given SNR. Although the process illustrated in FIG. 5 shows selecting an M-ary constellation optimized for capacity, a similar process could be used that terminates upon generation of an M-ary constellation where the SNR gap to Gaussian capacity at a given capacity is a predetermined margin lower than the SNR gap of a conventional constellation, for example 0.5 db. Alternatively, other processes that identify M-ary constellations having capacity greater than the capacity of a conventional constellation can be used in accordance with embodiments of the invention. For example, the effect of perturbations on the constellation points of optimized constellations can be used to identify ranges in which predetermined performance improvements are probabilistically likely to be obtained. The ranges can then be used to select geometrically shaped constellations for use in a communication system. A geometrically shaped constellation in accordance with embodiments of the invention can achieve greater capacity than the capacity of a constellation that maximizes $d_{min}$ without having the optimal capacity for the SNR range within which the communication system operates.

We note that constellations designed to maximize joint capacity may also be particularly well suited to codes with symbols over GF(q), or with multi-stage decoding. Conversely constellations optimized for PD capacity could be better suited to the more common case of codes with symbols over GF(2)

Optimizing the Capacity of an M-Ary Constellation at a Given SNR

Processes for obtaining a capacity optimized constellation often involve determining the optimum location for the points of an M-ary constellation at a given SNR. An optimization process, such as the optimization process 56 shown in FIG. 5, typically involves unconstrained or constrained non-linear optimization. Possible objective functions to be maximized are the Joint or PD capacity functions. These functions may be targeted to channels including but not limited to Additive White Gaussian Noise (AWGN) or Rayleigh fading channels. The optimization process gives the location of each constellation point identified by its symbol labeling. In the case where the objective is joint capacity, point bit labelings are irrelevant meaning that changing the bit labelings doesn't change the joint capacity as long as the set of point locations remains unchanged.

The optimization process typically finds the constellation that gives the largest PD capacity or joint capacity at a given SNR. The optimization process itself often involves an iterative numerical process that among other things considers several constellations and selects the constellation that gives the highest capacity at a given SNR. In other embodiments, the constellation that requires the least SNR to give a required PD capacity or joint capacity can also be found. This requires running the optimization process iteratively as shown in FIG. 5.

Optimization constraints on the constellation point locations may include, but are not limited to, lower and upper bounds on point location, peak to average power of the resulting constellation, and zero mean in the resulting constellation. It can be easily shown that a globally optimal constellation will have zero mean (no DC component). Explicit inclusion of a zero mean constraint helps the optimization routine to converge more rapidly. Except for cases where exhaustive search of all combinations of point locations and labelings is possible it will not necessarily always be the case that solutions are provably globally optimal. In cases where exhaustive search is possible, the solution provided by the non-linear optimizer is in fact globally optimal.

The processes described above provide examples of the manner in which a geometrically shaped constellation having an increased capacity relative to a conventional capacity can be obtained for use in a communication system having a fixed code rate and modulation scheme. The actual gains achievable using constellations that are optimized for capacity compared to conventional constellations that maximize $d_{min}$ are considered below.

Gains Achieved by Optimized Geometrically Spaced Constellations

The ultimate theoretical capacity achievable by any communication method is thought to be the Gaussian capacity, $C_G$ which is defined as:

$$C_G = \tfrac{1}{2} \log_2(1+\text{SNR})$$

Where signal-to-noise (SNR) is the ratio of expected signal power to expected noise power. The gap that remains between the capacity of a constellation and $C_G$ can be considered a measure of the quality of a given constellation design.

Figure 6A:
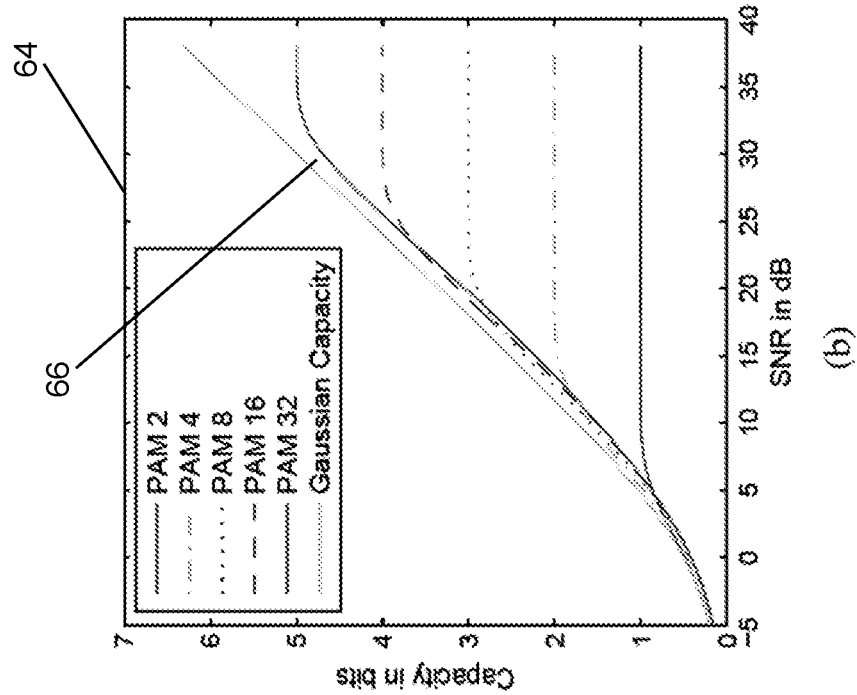
FIG. 6a is a chart showing a comparison of Gaussian capacity and PD capacity for traditional PAM-2, 4, 8, 16, 32.
Figure 6B:
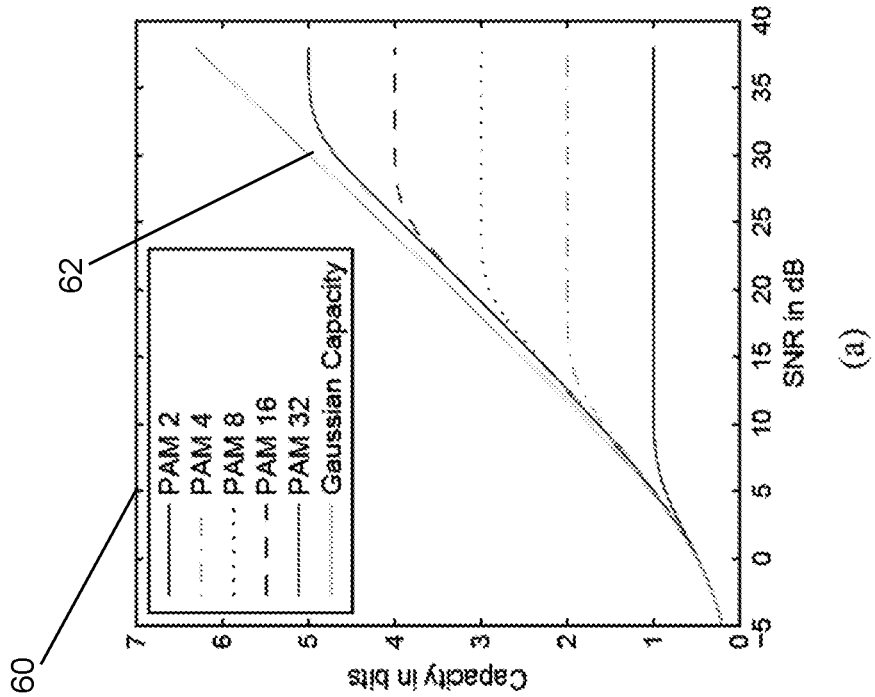
FIG. 6b is a chart showing a comparison between Gaussian capacity and joint capacity for traditional PAM-2, 4, 8, 16, 32.

The gap in capacity between a conventional modulation scheme in combination with a theoretically optimal coder can be observed with reference to FIGS. 6a and 6b. FIG. 6a includes a chart 60 showing a comparison between Gaussian capacity and the PD capacity of conventional PAM-2, 4, 8, 16, and 32 constellations that maximize $d_{min}$. Gaps 62 exist between the plot of Gaussian capacity and the PD capacity of the various PAM constellations. FIG. 6b includes a chart 64 showing a comparison between Gaussian capacity and the joint capacity of conventional PAM-2, 4, 8, 16, and 32 constellations that maximize $d_{min}$, Gaps 66 exist between the plot of Gaussian capacity and the joint capacity of the various PAM constellations. These gaps in capacity represent the extent to which conventional PAM constellations fall short of obtaining the ultimate theoretical capacity i.e. the Gaussian capacity.

Figure 7:
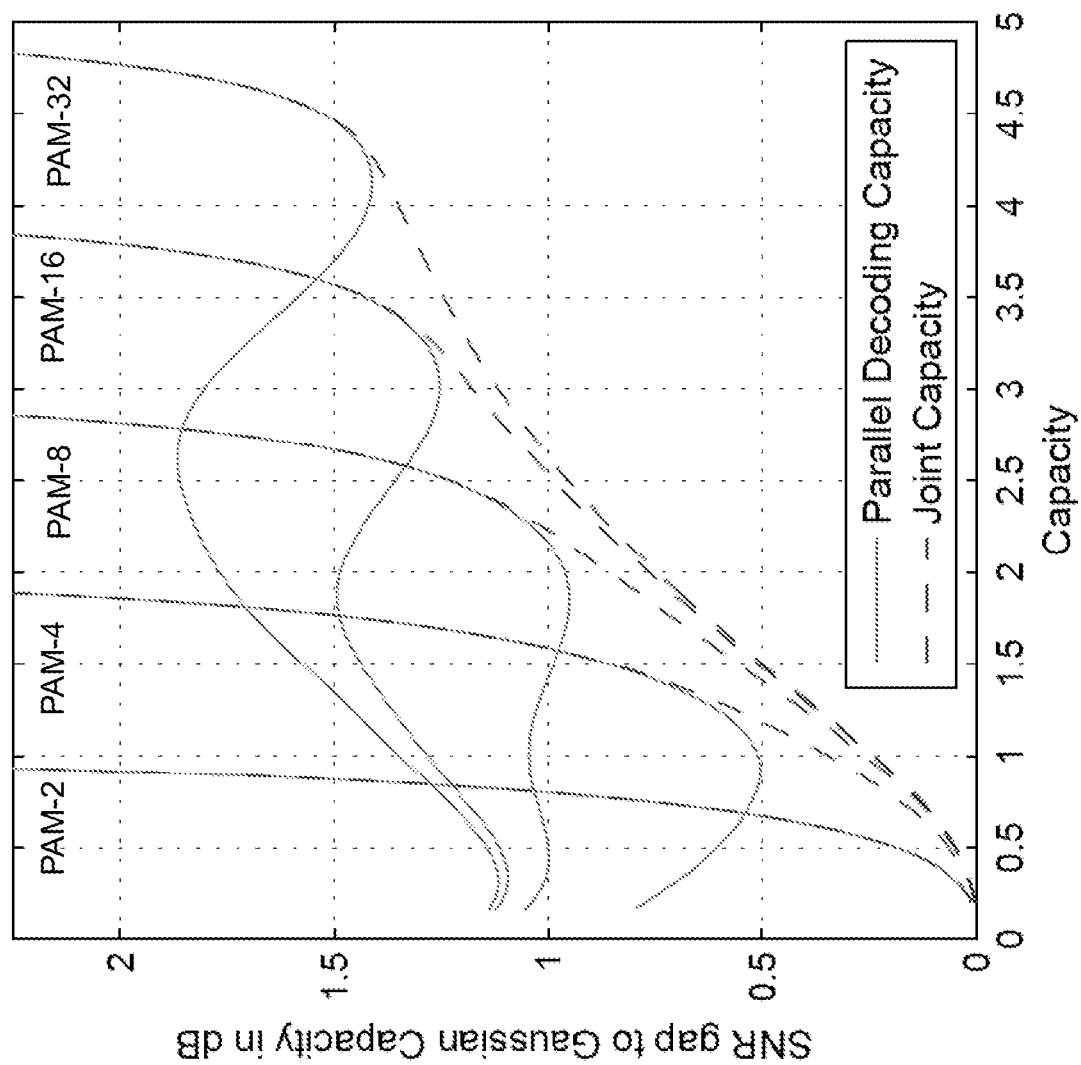
FIG. 7 is a chart showing the SNR gap to Gaussian capacity for the PD capacity and joint capacity of traditional PAM-2, 4, 8, 16, 32 constellations.

In order to gain a better view of the differences between the curves shown in FIGS. 6a and 6b at points close to the Gaussian capacity, the SNR gap to Gaussian capacity for different values of capacity for each constellation are plotted in FIG. 7. It is interesting to note from the chart 70 in FIG. 7 that (unlike the joint capacity) at the same SNR, the PD capacity does not necessarily increase with the number of constellation points. As is discussed further below, this is not the case with PAM constellations optimized for PD capacity.

Figure 8A:
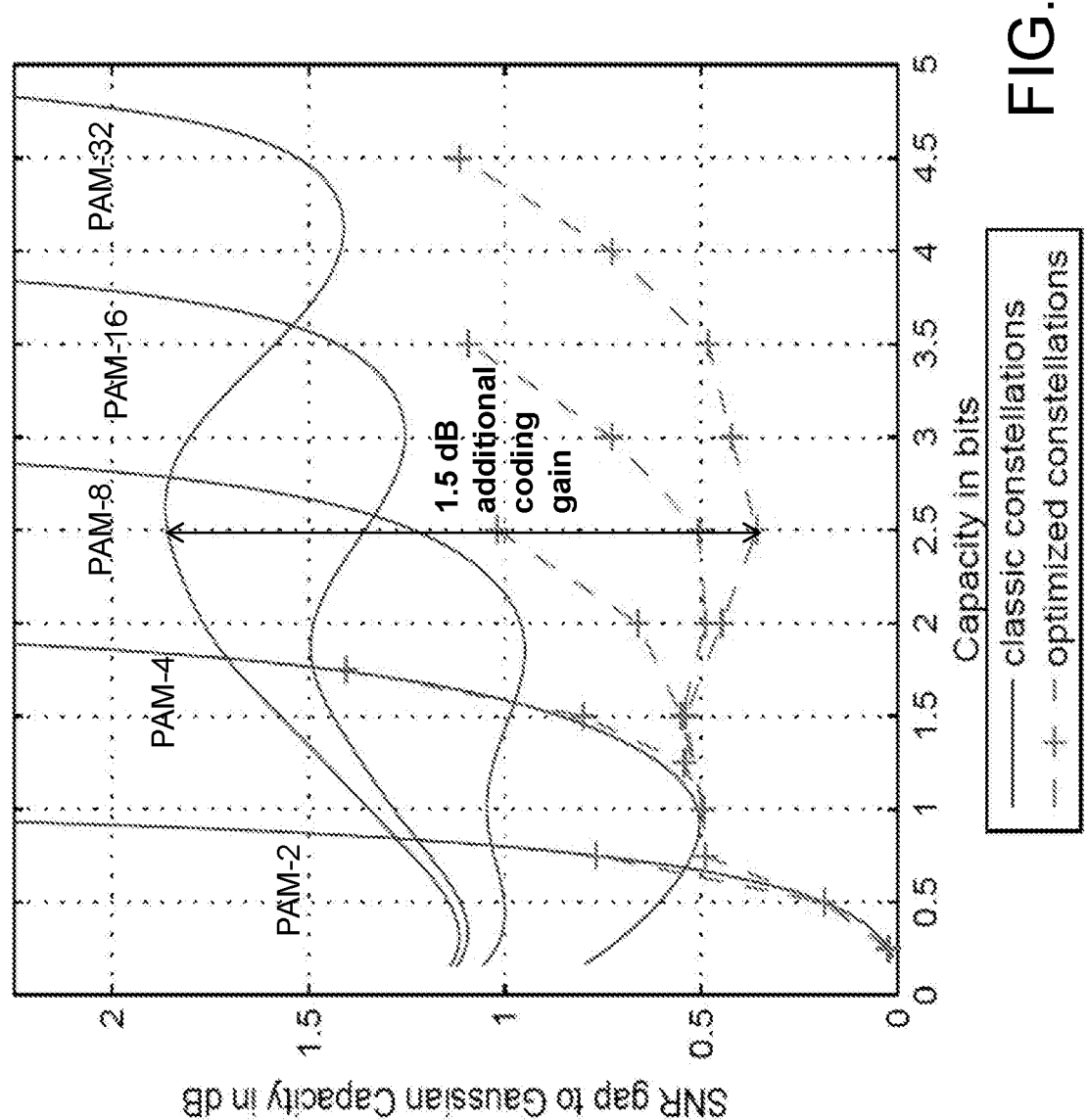
FIG. 8a is a chart comparing the SNR gap to Gaussian capacity of the PD capacity for traditional and optimized PAM-2, 4, 8, 16, 32 constellations.
Figure 8B:
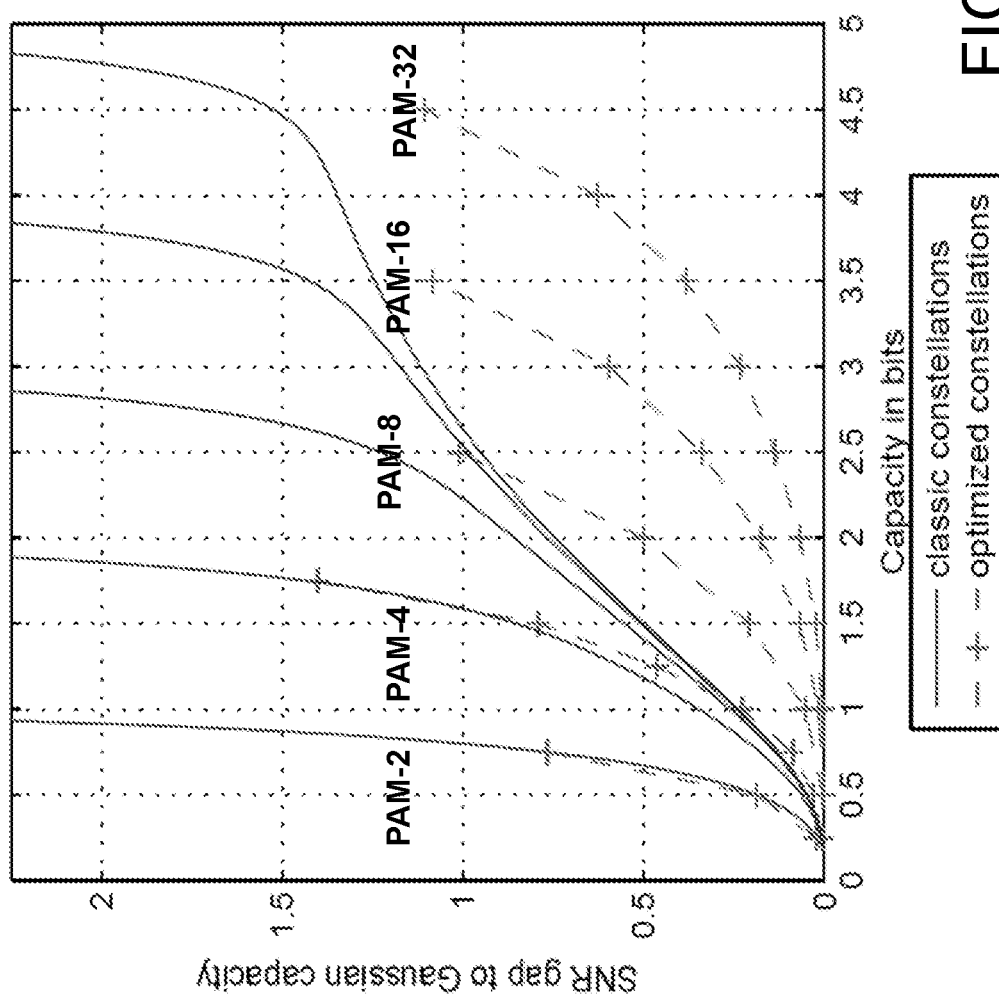
FIG. 8b is a chart comparing the SNR gap to Gaussian capacity of the joint capacity for traditional and optimized PAM-2, 4, 8, 16, 32 constellations.

FIGS. 8a and 8b summarize performance of constellations for PAM-4, 8, 16, and 32 optimized for PD capacity and joint capacity (it should be noted that BPSK is the optimal PAM-2 constellation at all code rates). The constellations are optimized for PD capacity and joint capacity for different target user bits per dimension (i.e. code rates). The optimized constellations are different depending on the target user bits per dimension, and also depending on whether they have been designed to maximize the PD capacity or the joint capacity. All the PD optimized PAM constellations are labeled using a gray labeling which is not always the binary reflective gray labeling. It should be noted that not all gray labels achieve the maximum possible PD capacity even given the freedom to place the constellation points anywhere on the real line. FIG. 8a shows the SNR gap for each constellation optimized for PD capacity. FIG. 8b shows the SNR gap to Gaussian capacity for each constellation optimized for joint capacity. Again, it should be emphasized that each '+' on the plot represents a different constellation.

Referring to FIG. 8a, the coding gain achieved using a constellation optimized for PD capacity can be appreciated by comparing the SNR gap at a user bit rate per dimension of 2.5 bits for PAM-32. A user bit rate per dimension of 2.5 bits for a system transmitting 5 bits per symbol constitutes a code rate of ½. At that code rate the constellation optimized for PD capacity provides an additional coding gain of approximately 1.5 dB when compared to the conventional PAM-32 constellation.

Figure 9:
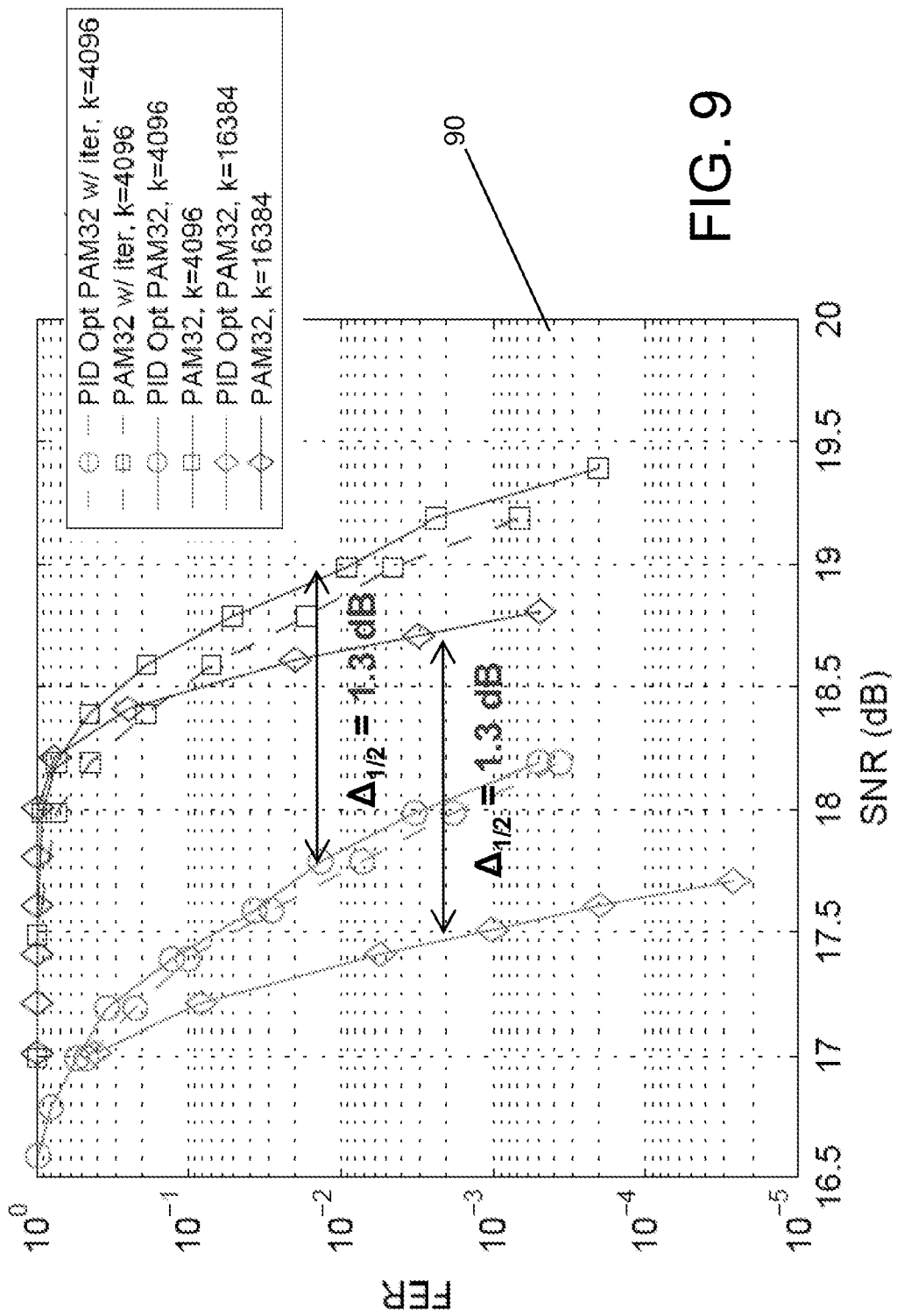
FIG. 9 is a chart showing Frame Error Rate performance of traditional and PD capacity optimized PAM-32 constellations in simulations involving several different length LDPC codes.

The SNR gains that can be achieved using constellations that are optimized for PD capacity can be verified through simulation. The results of a simulation conducted using a rate 1/2 LDPC code in conjunction with a conventional PAM-32 constellation and in conjunction with a PAM-32 constellation optimized for PD capacity are illustrated in FIG. 9. A chart 90 includes plots of Frame Error Rate performance of the different constellations with respect to SNR and using different length codes (i.e. k=4,096 and k=16,384). Irrespective of the code that is used, the constellation optimized for PD capacity achieves a gain of approximately 1.3 dB, which closely approaches the gain predicted from FIG. 8a.

Capacity Optimized Pam Constellations

Using the processes outlined above, locus plots of PAM constellations optimized for capacity can be generated that show the location of points within PAM constellations versus SNR. Locus plots of PAM-4, 8, 16, and 32 constellations optimized for PD capacity and joint capacity and corresponding design tables at various typical user bit rates per dimension are illustrated in FIGS. 10a-17b. The locus plots and design tables show PAM-4, 8, 16, and 32 constellation point locations and labelings from low to high SNR corresponding to a range of low to high spectral efficiency.

Figure 10A:
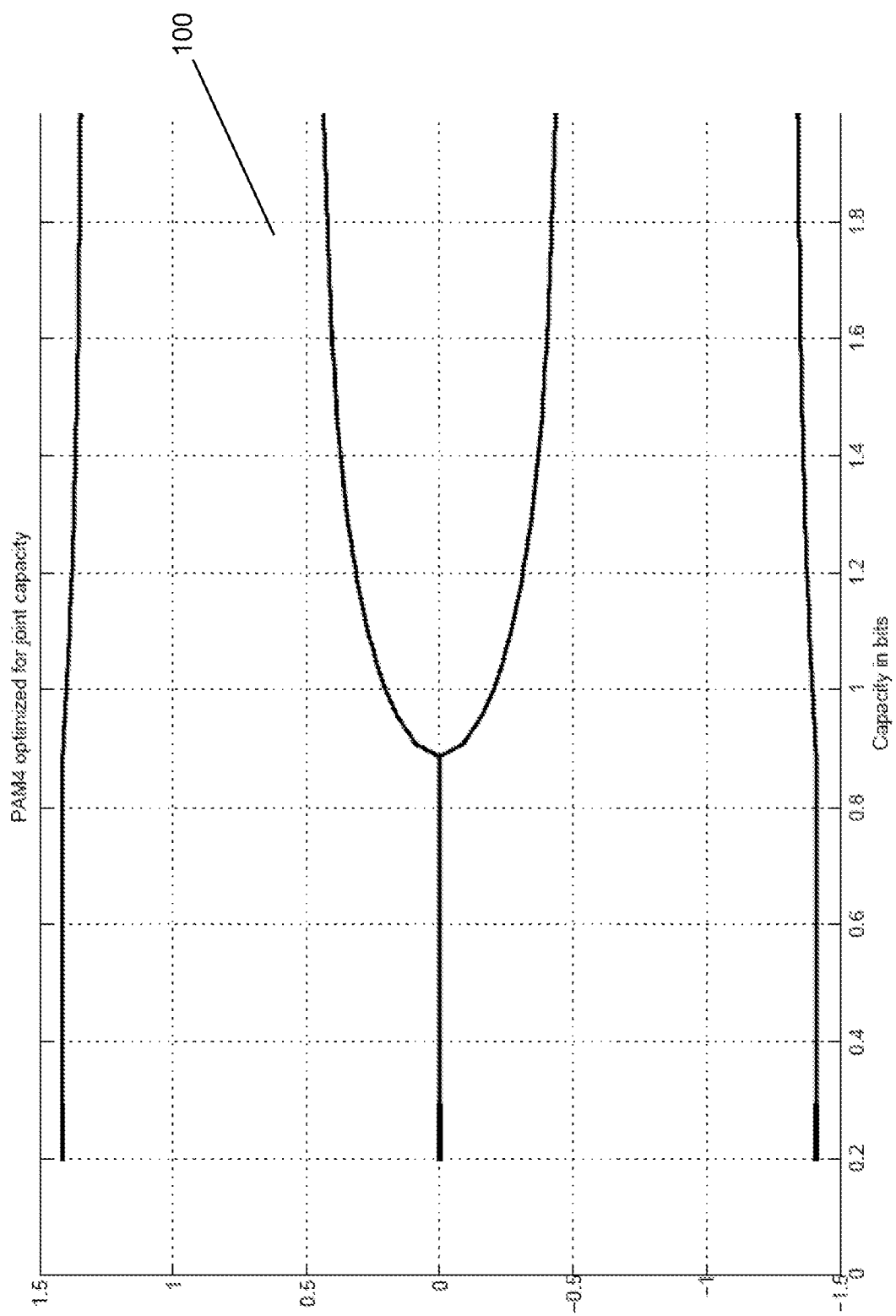
FIGS. 10a-10d are locus plots showing the location of constellation points of a PAM-4 constellation optimized for PD capacity and joint capacity versus user bit rate per dimension and versus SNR.
Figure 10B:
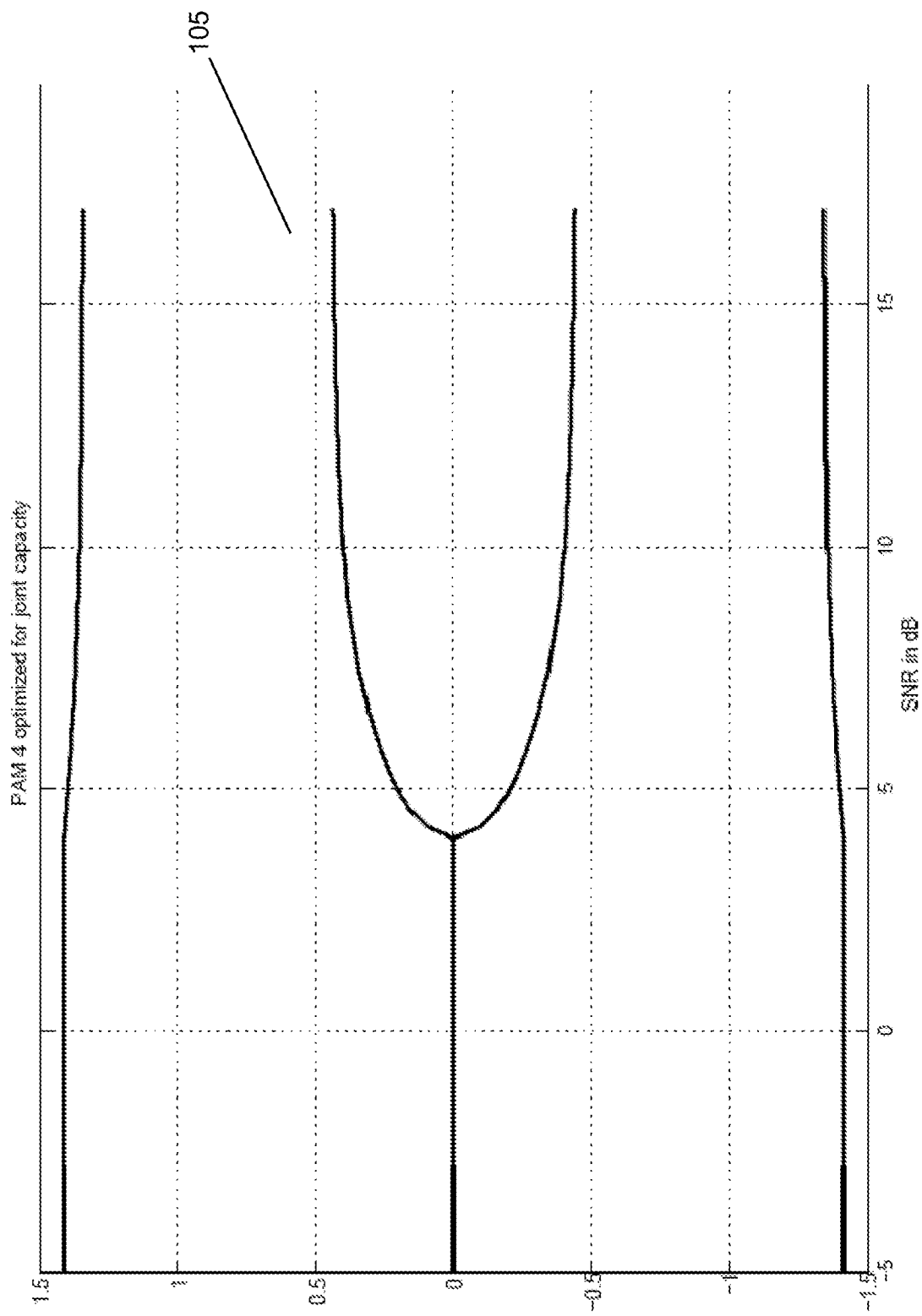
Figure 10C:
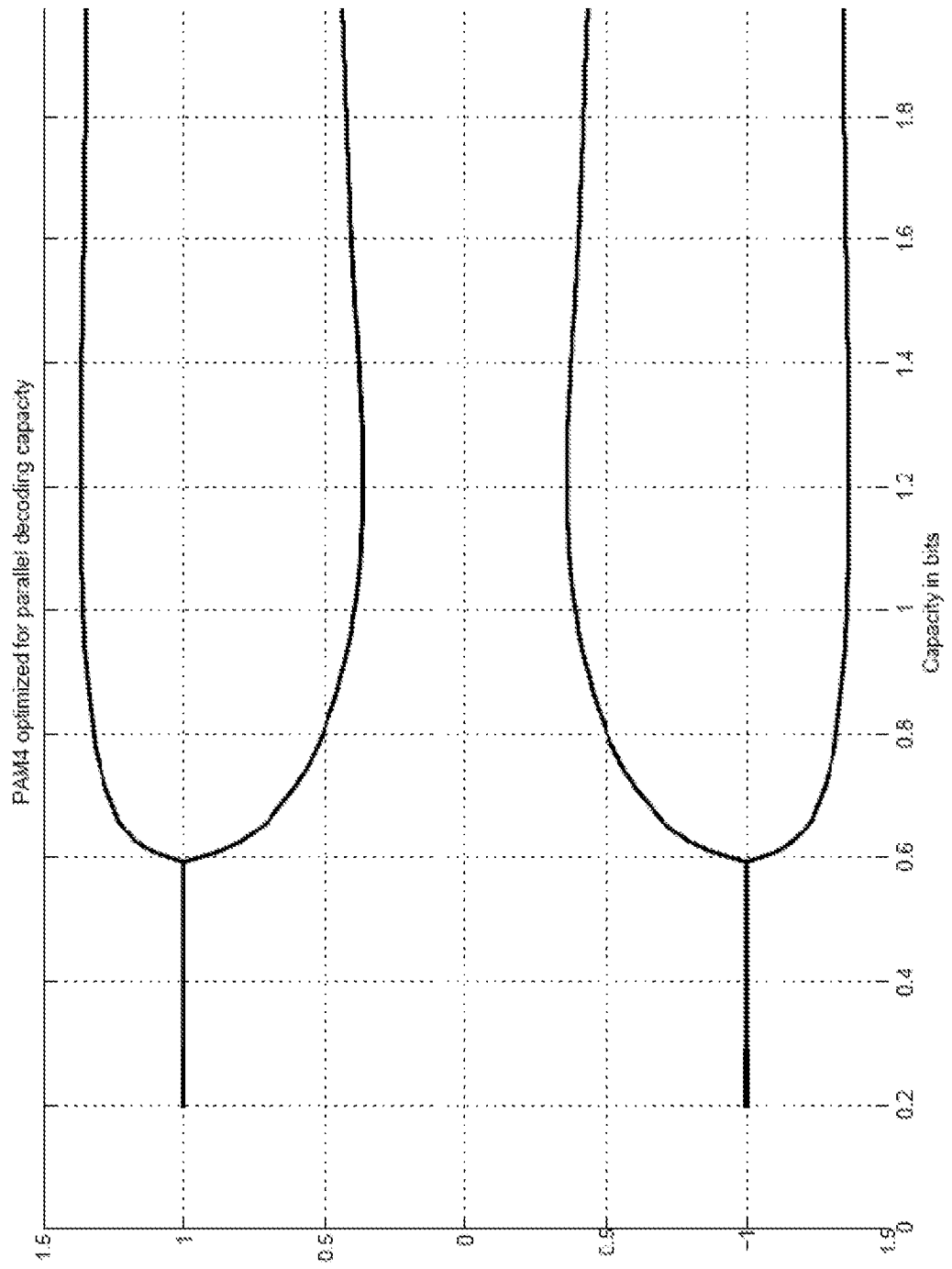
Figure 10D:
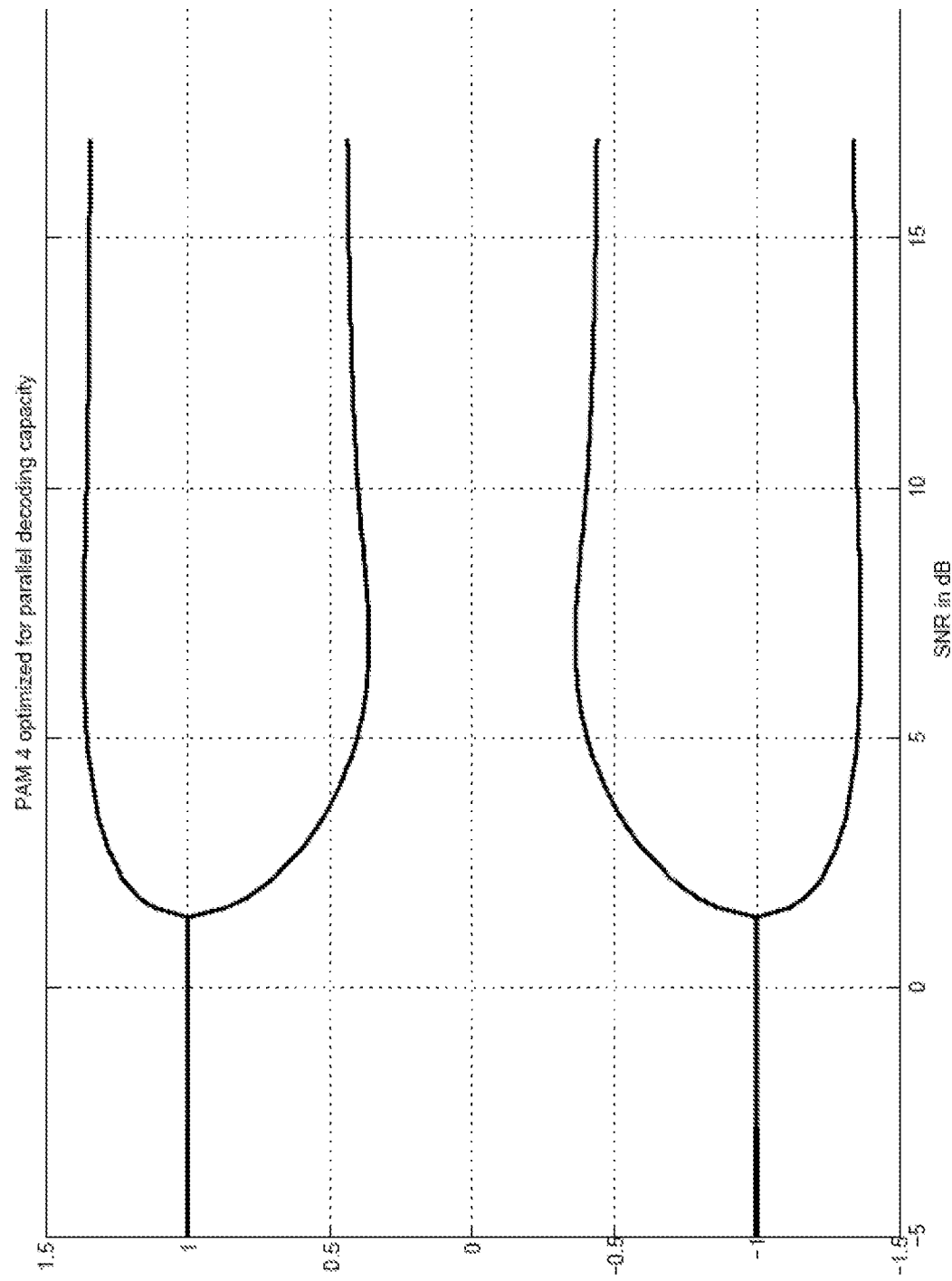

In FIG. 10a, a locus plot 100 shows the location of the points of PAM-4 constellations optimized for joint capacity plotted against achieved capacity. A similar locus plot 105 showing the location of the points of joint capacity optimized PAM-4 constellations plotted against SNR is included in FIG. 10b. In FIG. 10c, the location of points for PAM-4 optimized for PD capacity is plotted against achievable capacity and in FIG. 10d the location of points for PAM-4 for PD capacity is plotted against SNR. At low SNRs, the PD capacity optimized PAM-4 constellations have only 2 unique points, while the joint capacity optimized constellations have 3. As SNR is increased, each optimization eventually provides 4 unique points. This phenomenon is explicitly described in FIG. 11a and FIG. 11b where vertical slices of FIGS. 10ab and 10cd are captured in tables describing some PAM-4 constellations designs of interest. The SNR slices selected represent designs that achieve capacities={0.5, 0.75, 1.0, 1.25, 1.5} bits per symbol (bps). Given that PAM-4 can provide at most $\log_2(4)=2$ bps, these design points represent systems with information code rates R={¼, ⅜, ½, ⅝, ¾} respectively.

Figure 12A:
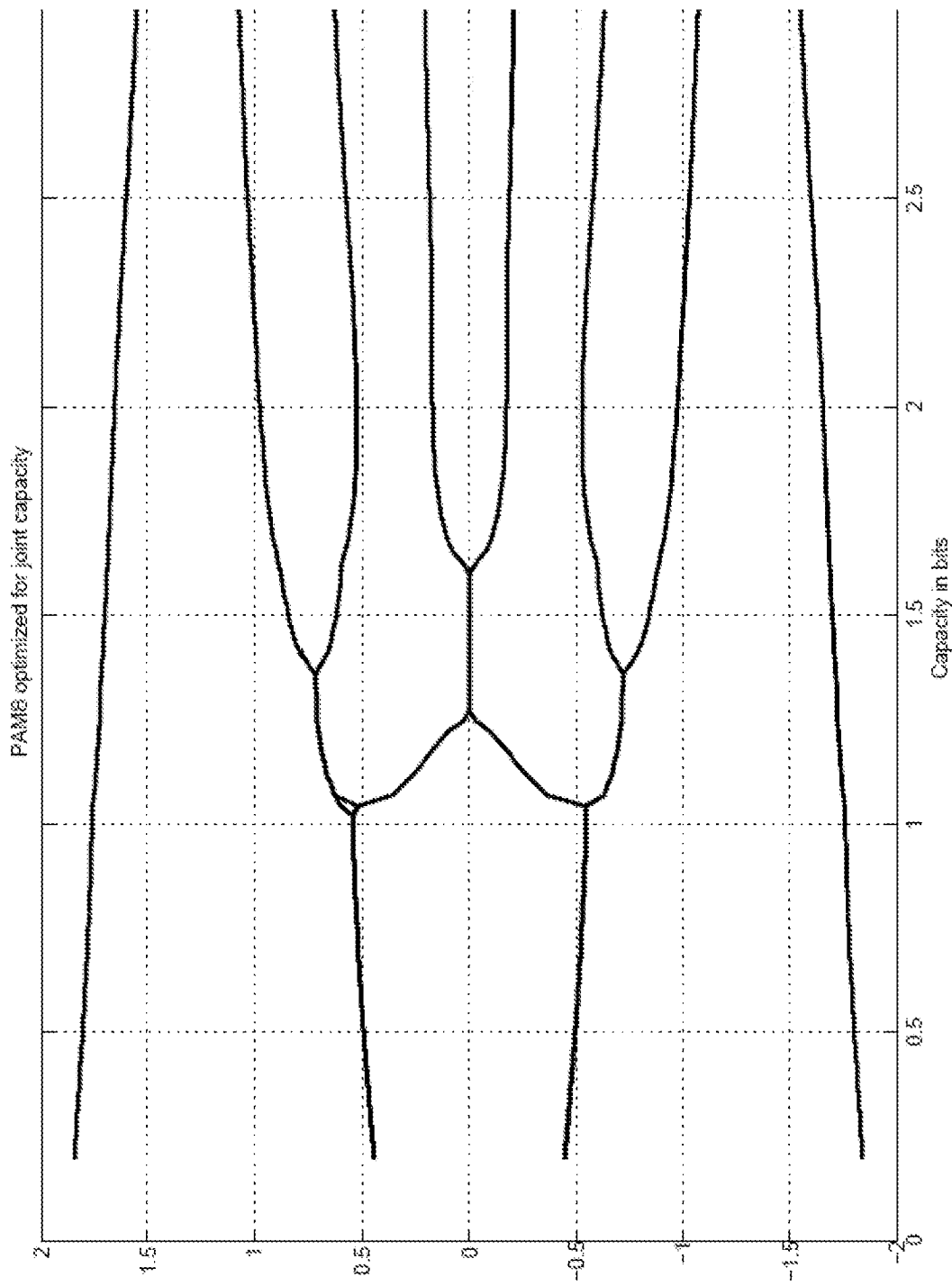
FIGS. 12a-12d are locus plots showing the location of constellation points of a PAM-8 constellation optimized for PD capacity and joint capacity versus user bit rate per dimension and versus SNR.
Figure 12B:
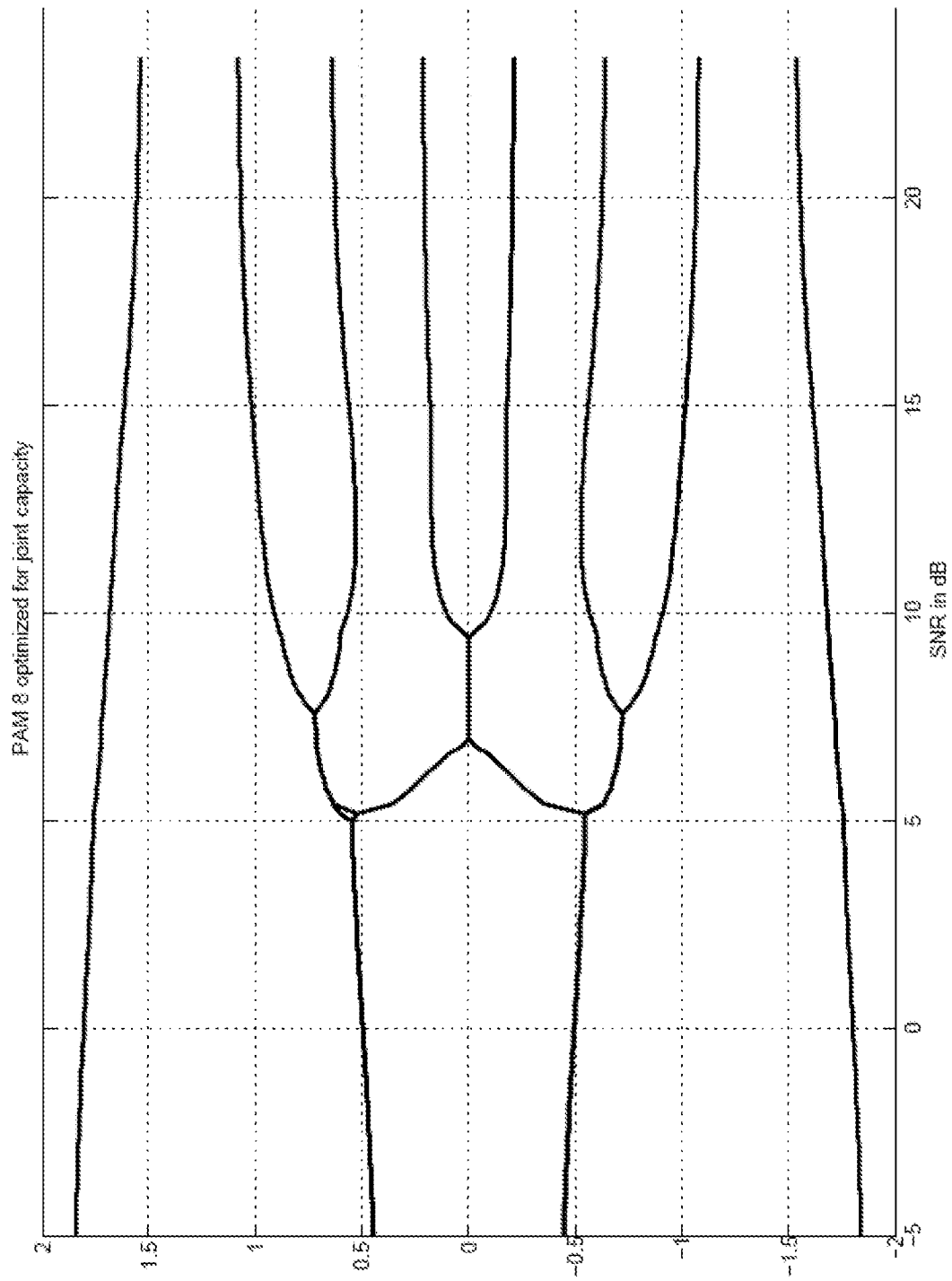
Figure 12C:
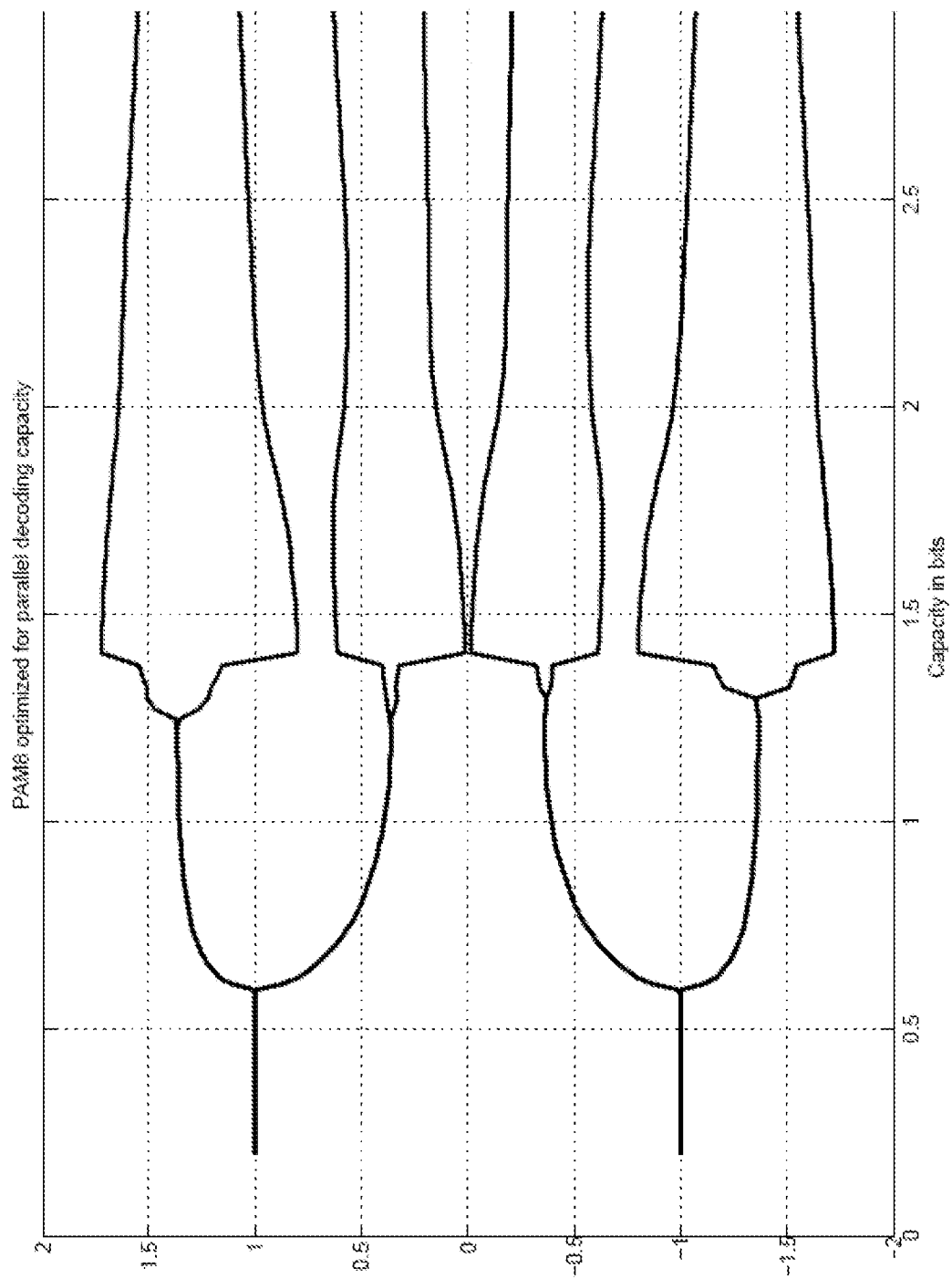
Figure 12D:
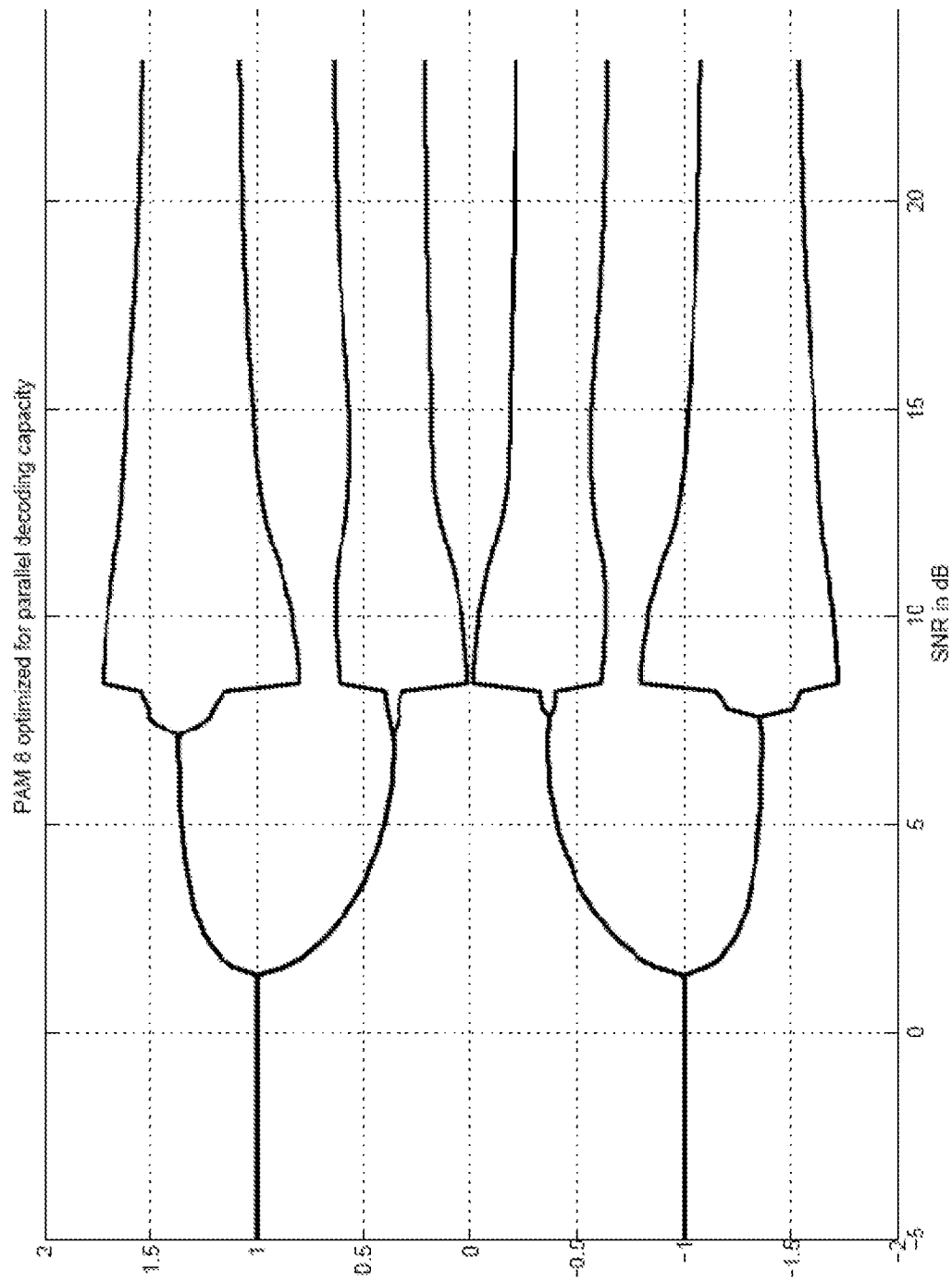
Figure 14A:
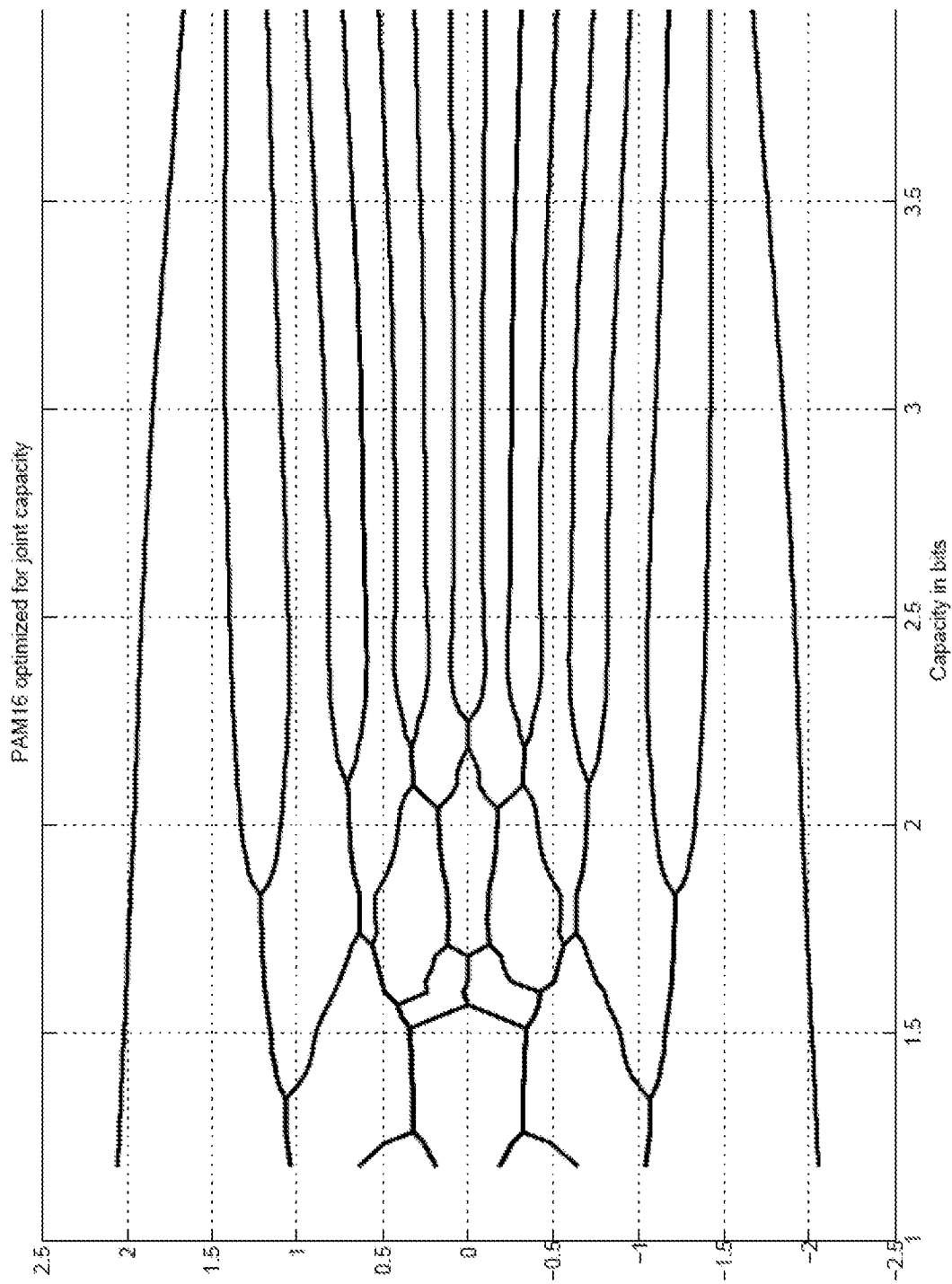
FIGS. 14a-14d are locus plots showing the location of constellation points of a PAM-16 constellation optimized for PD capacity and joint capacity versus user bit rate per dimension and versus SNR.
Figure 14B:
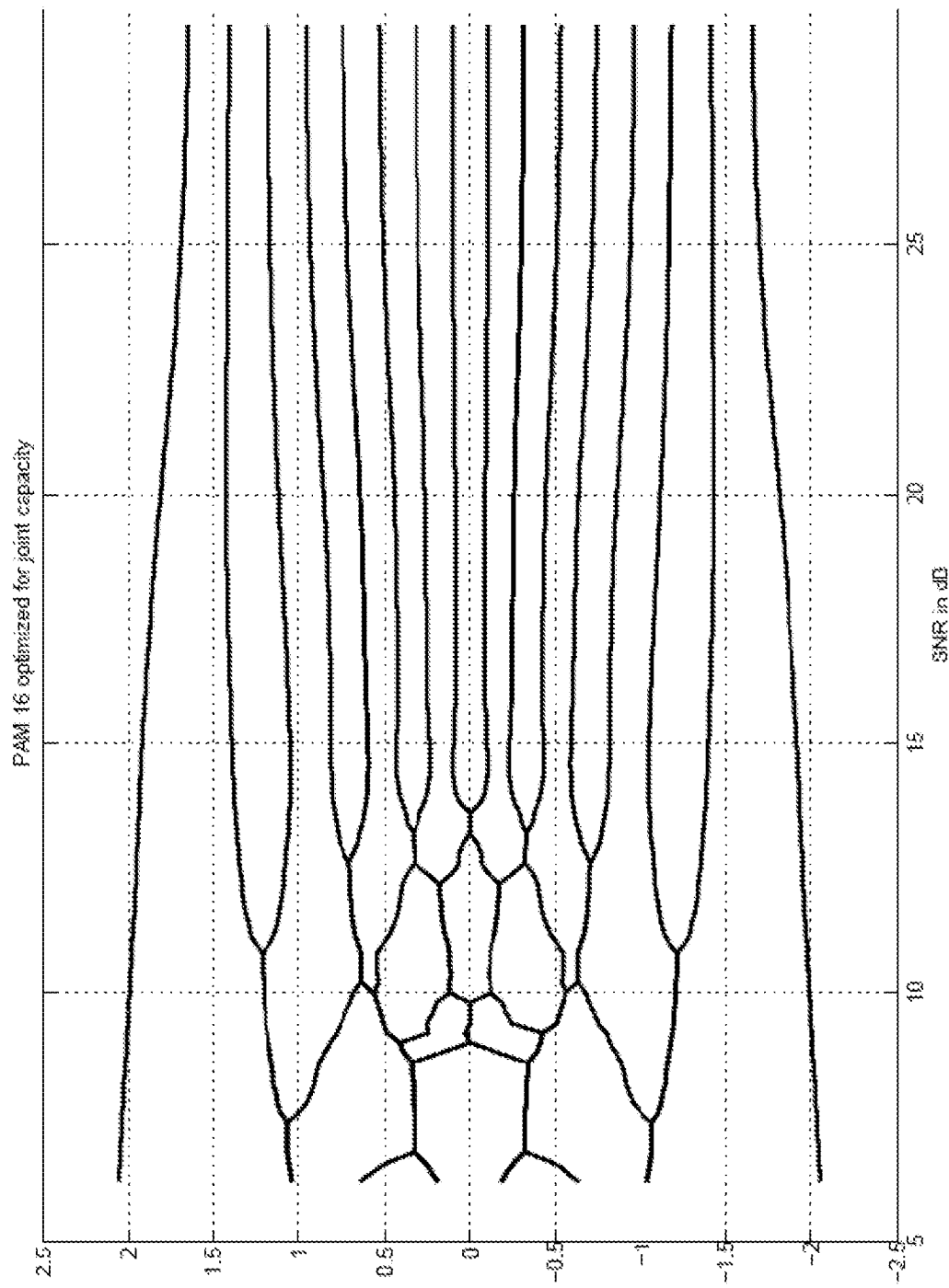
Figure 14C:
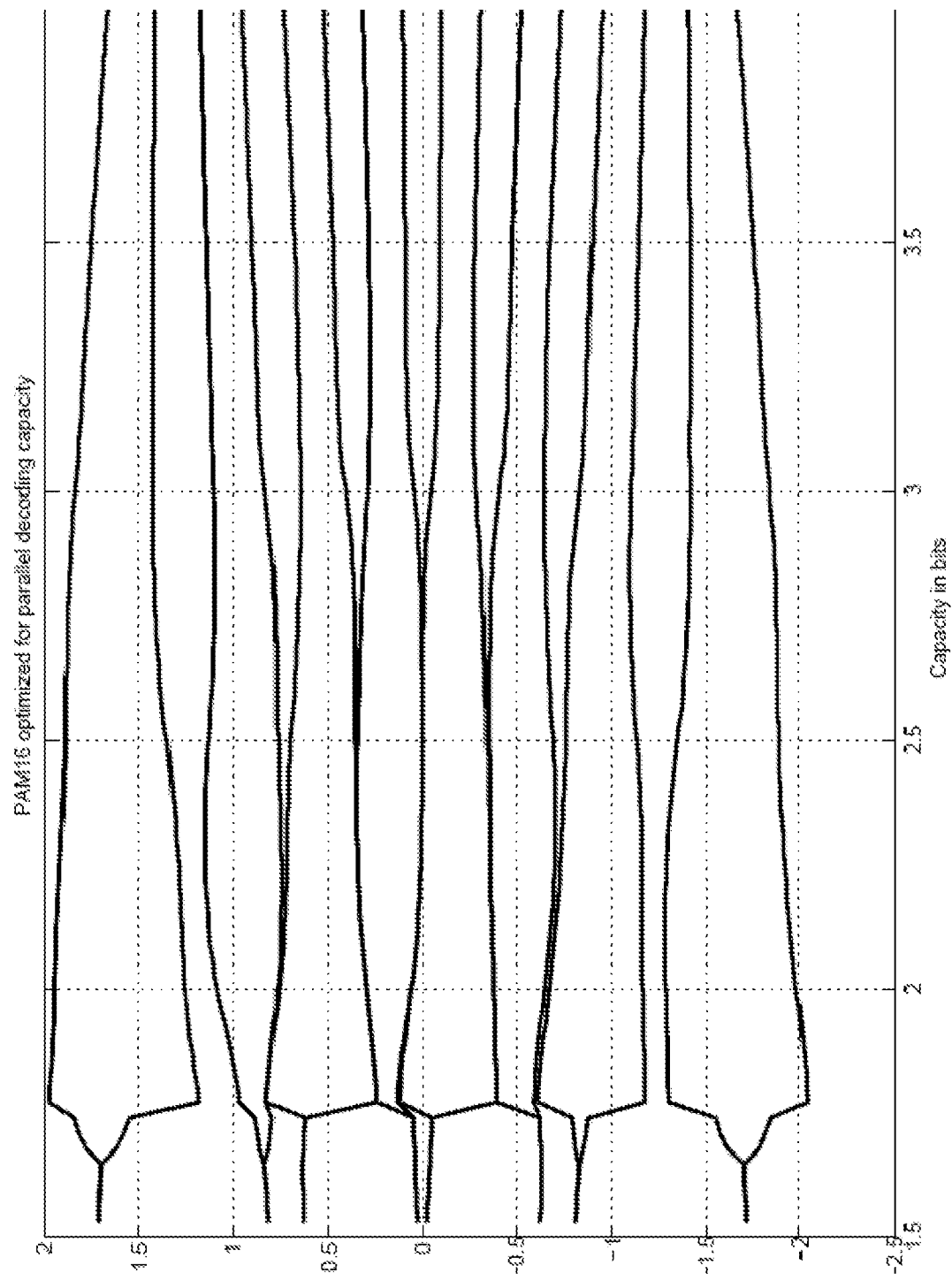
Figure 14D:
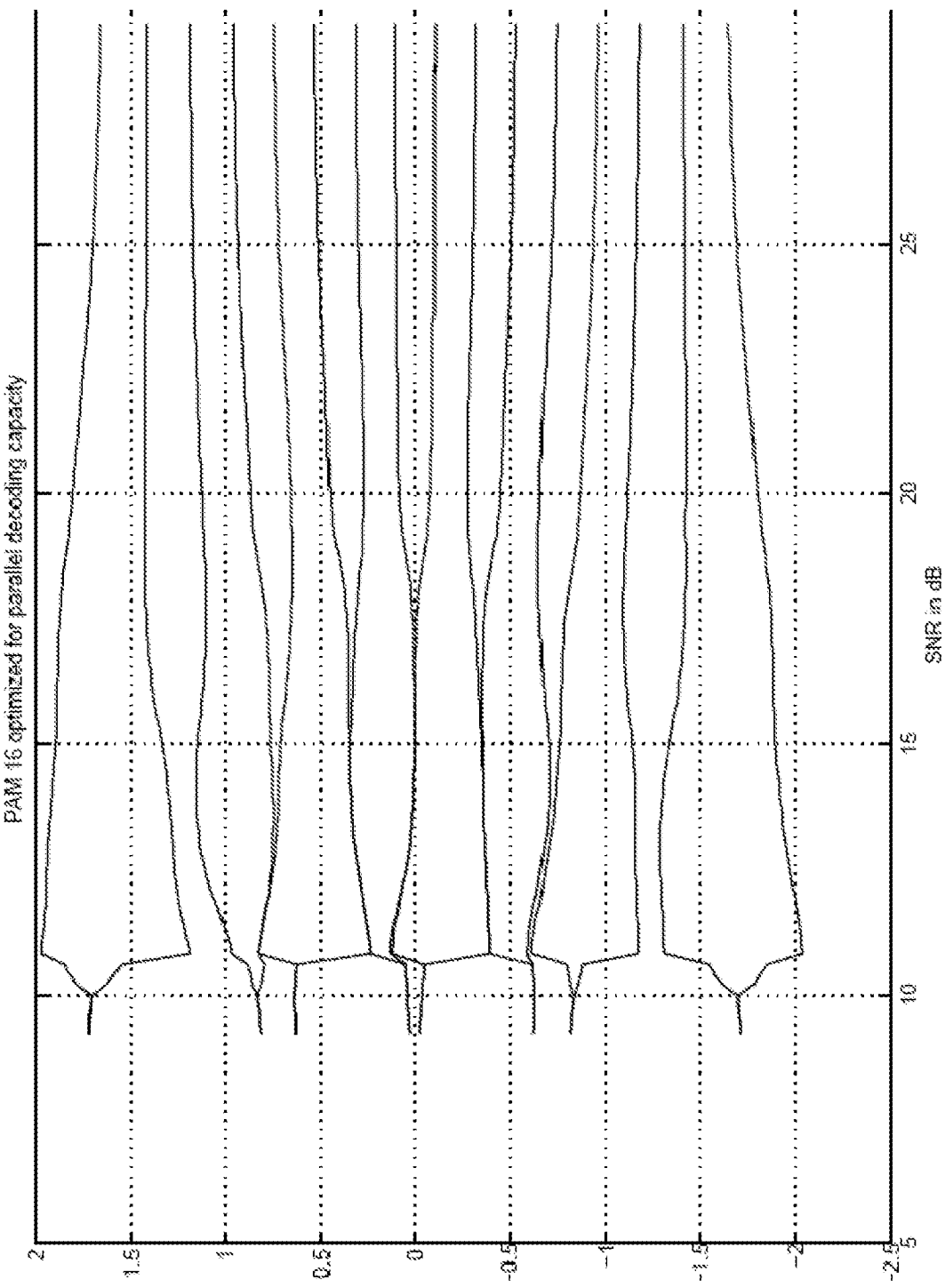
Figure 16A:
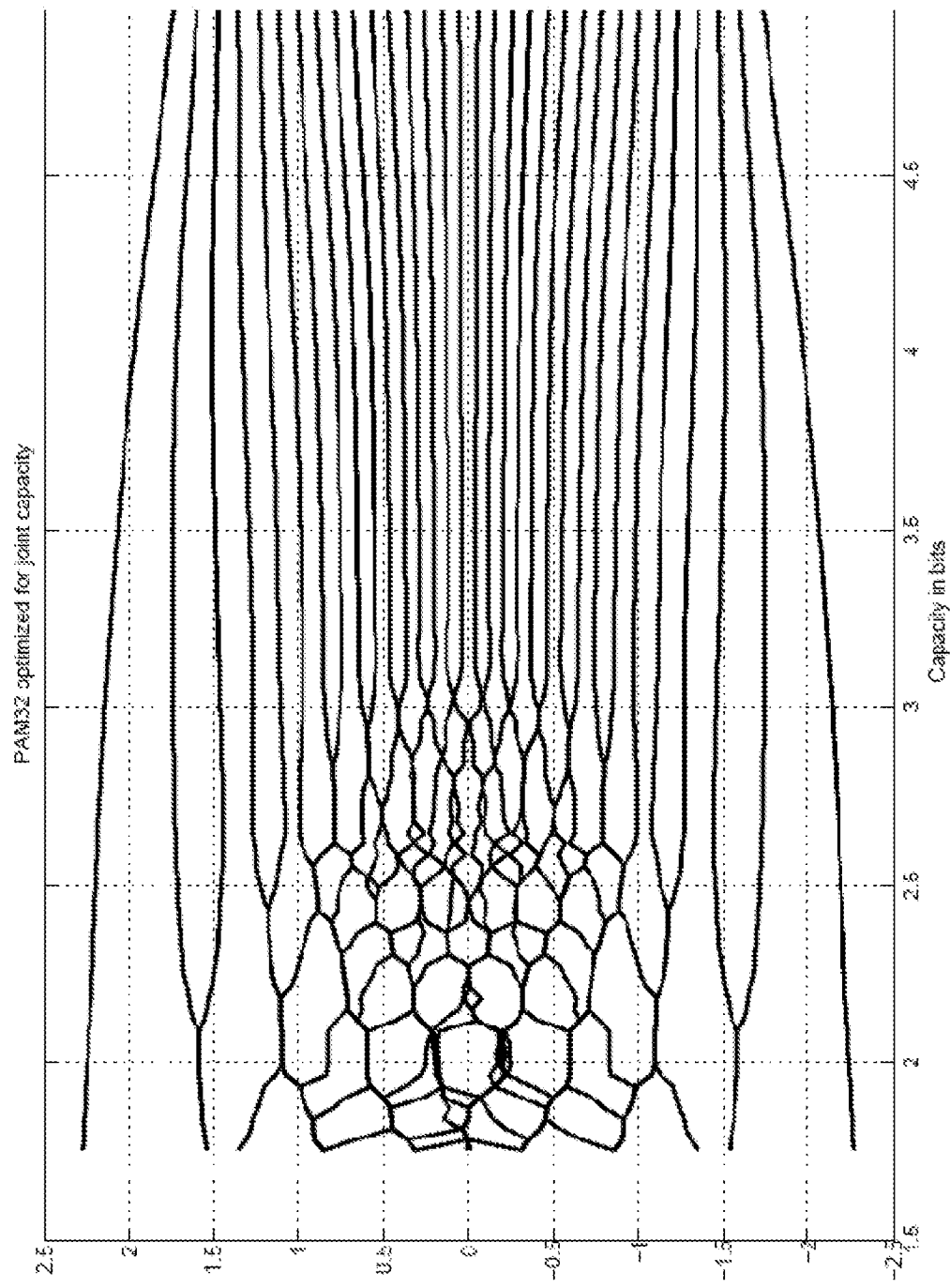
FIGS. 16a-16d are locus plots showing the location of constellation points of a PAM-32 constellation optimized for PD capacity and joint capacity versus user bit rate per dimension and versus SNR.
Figure 16B:
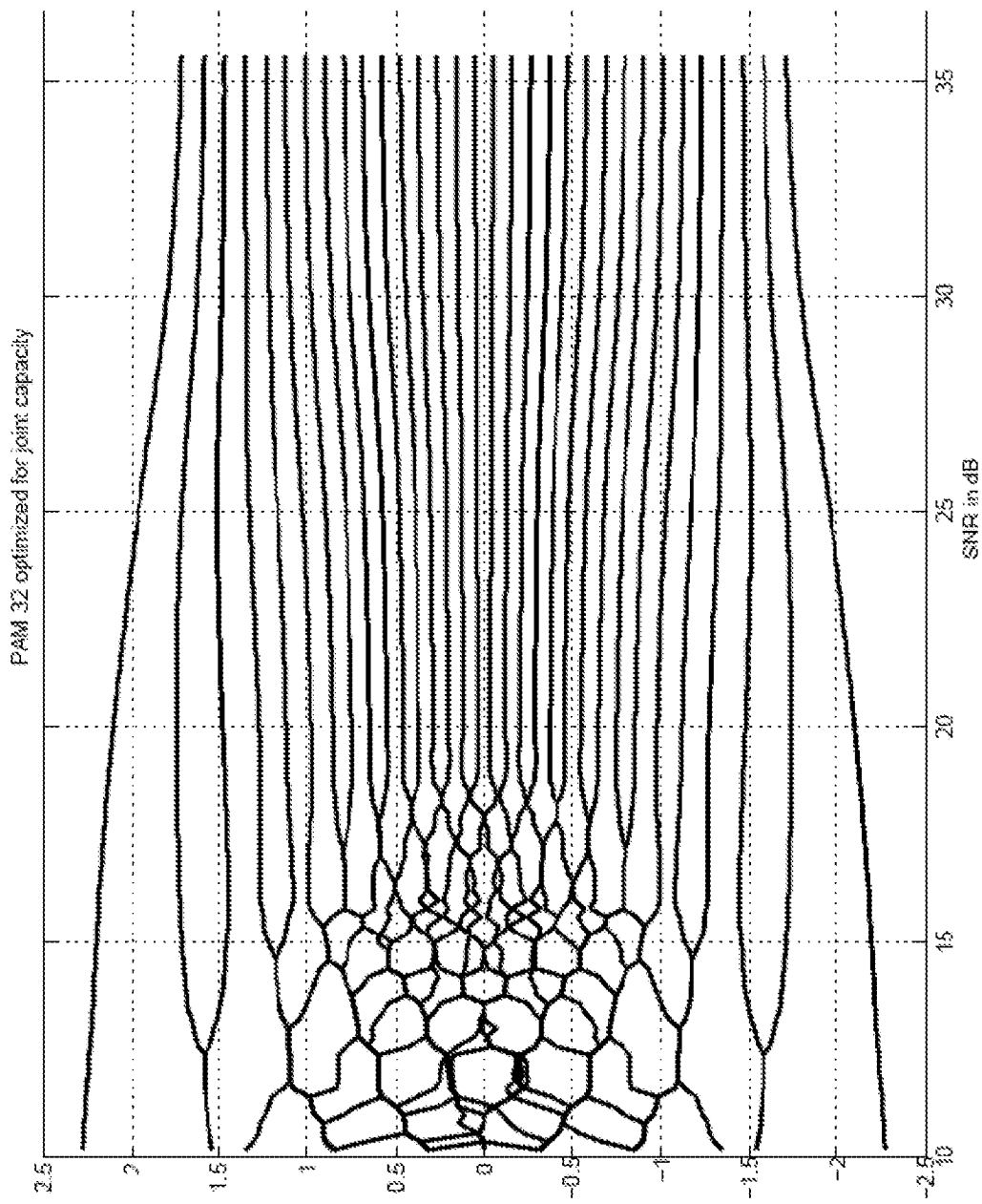
Figure 16C:
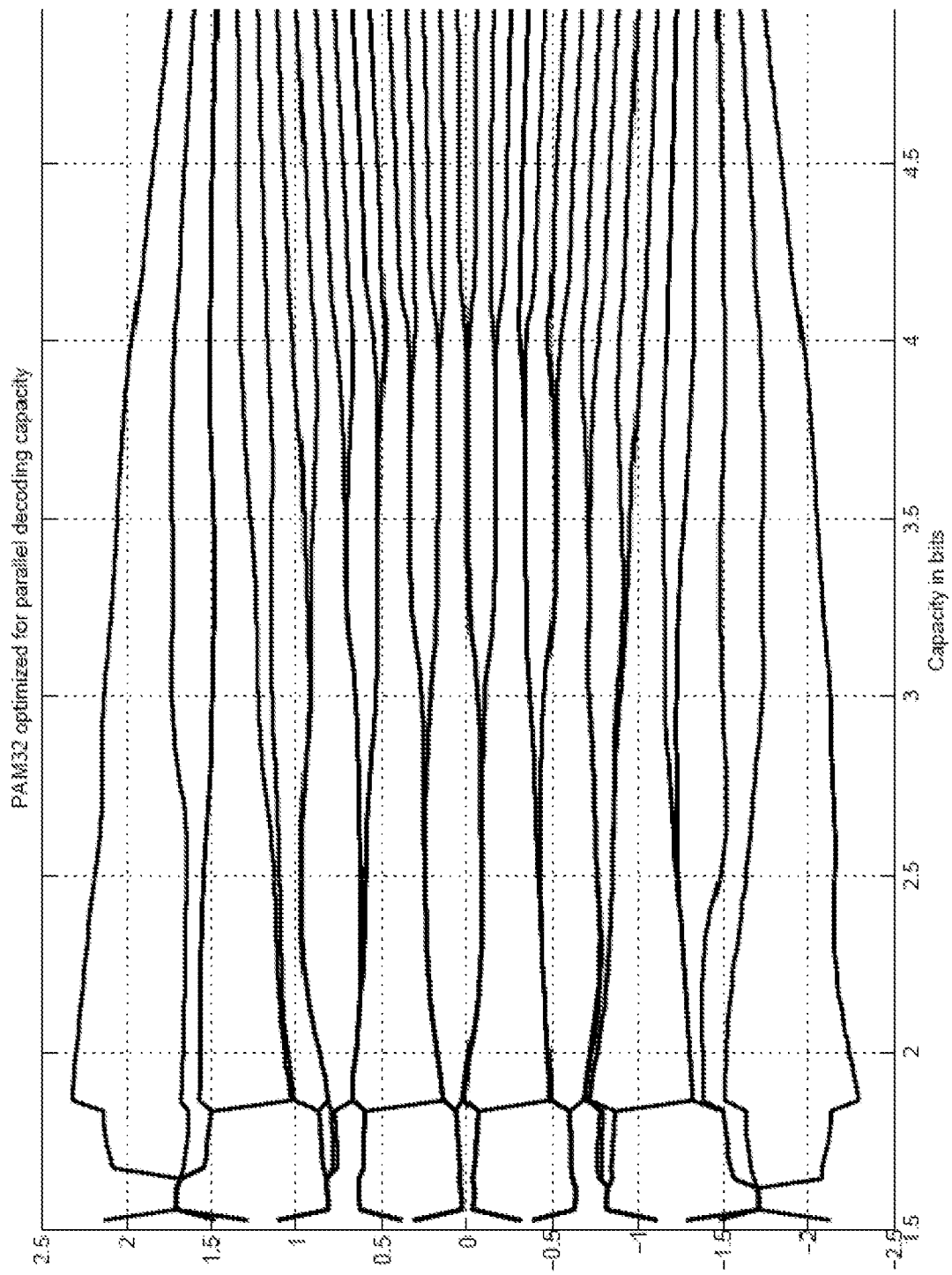
Figure 16D:
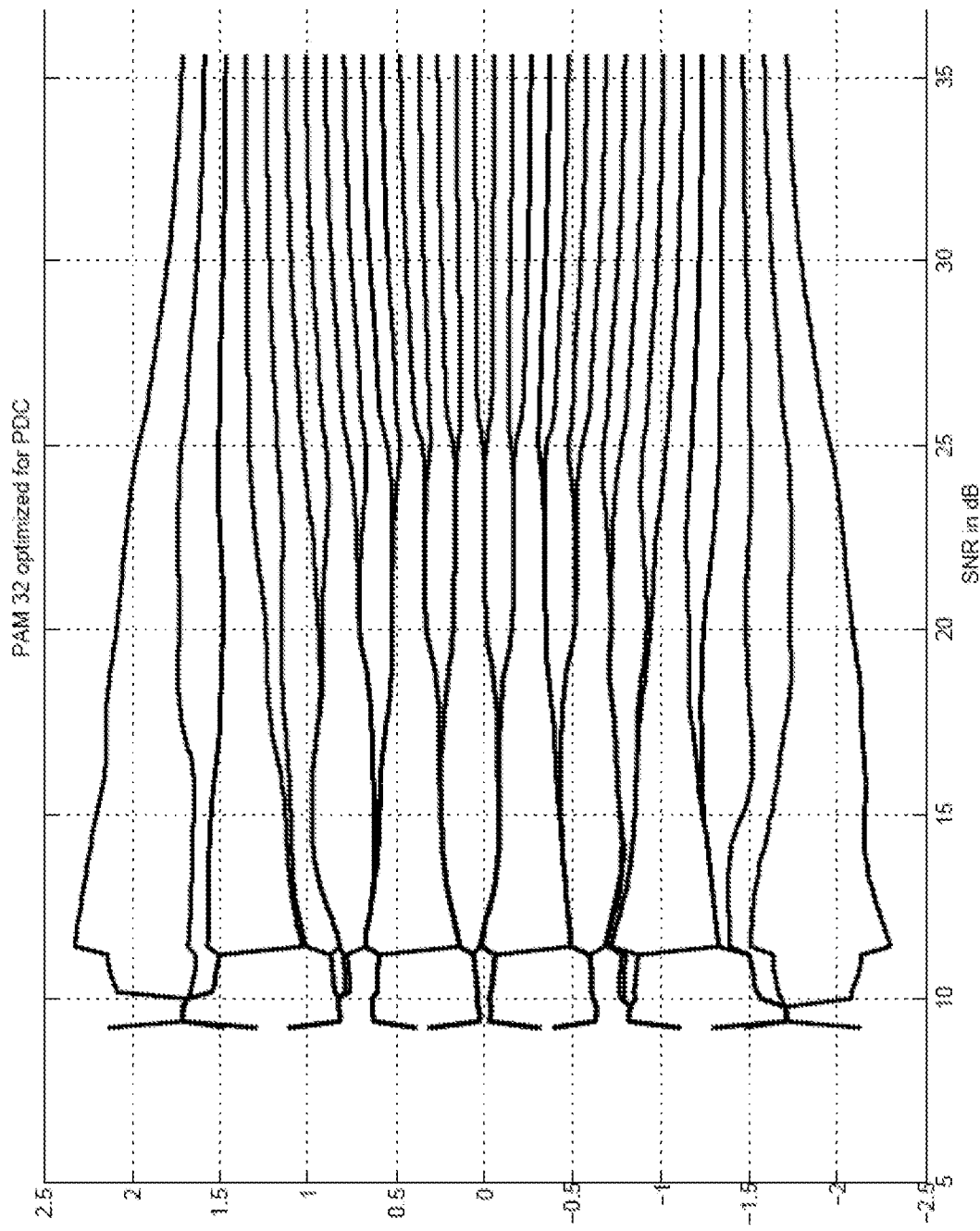

FIGS. 12ab and 12cd present locus plots of PD capacity and joint capacity optimized PAM-8 constellation points versus achievable capacity and SNR. FIGS. 13a and 13b provide slices from these plots at SNRs corresponding to achievable capacities $\eta$={0.5, 1.0, 1.5, 2.0, 2.5} bps. Each of these slices correspond to systems with code rate R=$\eta$ bps/$\log_2(8)$, resulting in R={⅙, ⅓, ½, ⅔, ⅚}. As an example of the relative performance of the constellations in these tables, consider FIG. 13b which shows a PD capacity optimized PAM-8 constellation optimized for SNR=9.00 dB, or 1.5 bps. We next examine the plot provided in FIG. 8a and see that the gap of the optimized constellation to the ultimate, Gaussian, capacity (CG) is approximately 0.5 dB. At the same spectral efficiency, the gap of the traditional PAM-8 constellation is approximately 1.0 dB. The advantage of the optimized constellation is 0.5 dB for the same rate (in this case R=½). This gain can be obtained by only changing the mapper and demapper in the communication system and leaving all other blocks the same.

Similar information is presented in FIGS. 14a-14d, and 15a-15b which provide loci plots and design tables for PAM-16 PD capacity and joint capacity optimized constellations. Likewise FIGS. 16a-16d, 17a and 17b provide loci plots and design tables for PAM-32 PD capacity and joint capacity optimized constellations.

Capacity Optimized PSK Constellations

Traditional phase shift keyed (PSK) constellations are already quite optimal. This can be seen in the chart 180 comparing the SNR gaps of tradition PSK with capacity optimized PSK constellations shown in FIG. 18 where the gap between PD capacity and Gaussian capacity is plotted for traditional PSK-4, 8, 16, and 32 and for PD capacity optimized PSK-4, 8, 16, and 32.

Figure 19:
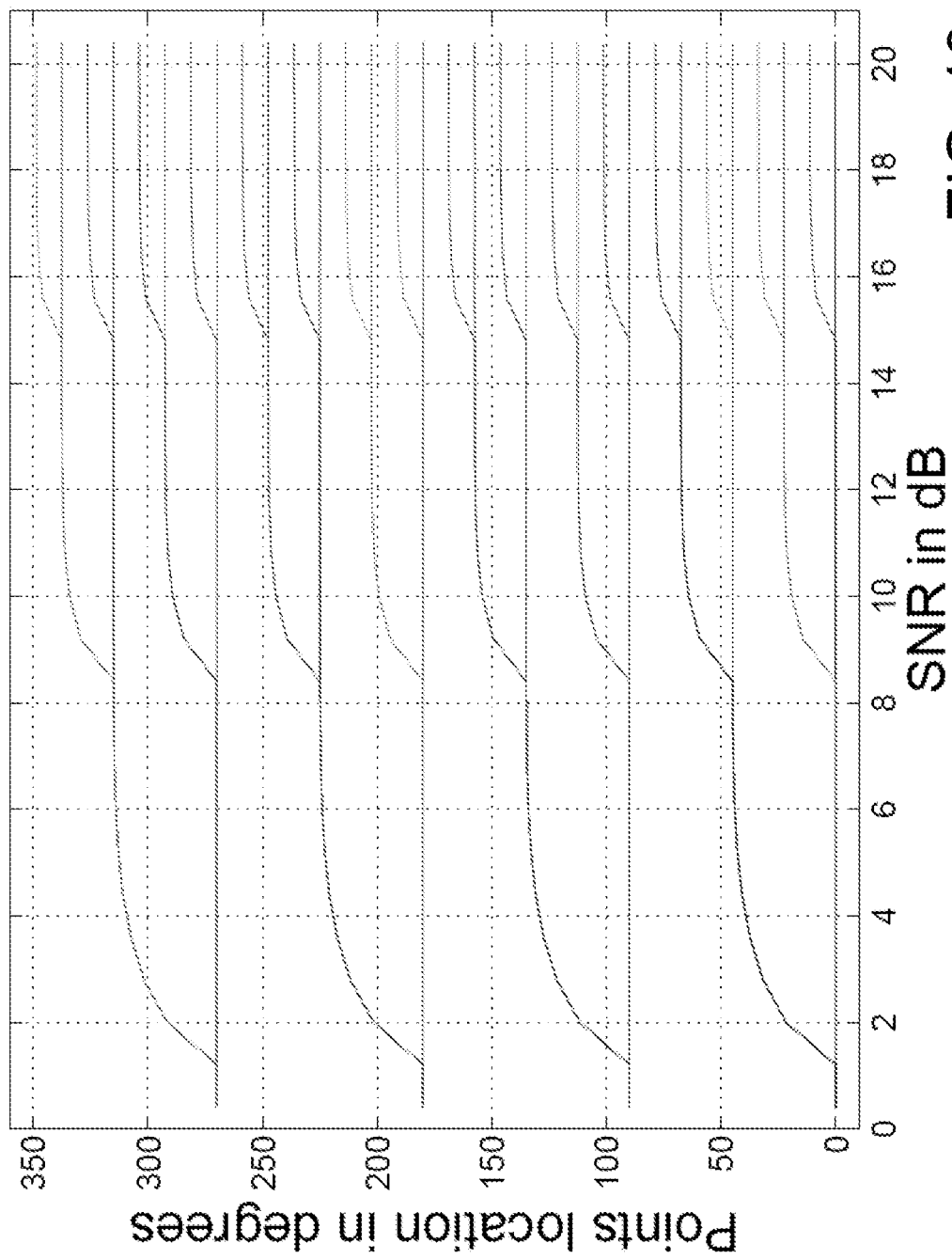
FIG. 19 is a chart showing the location of constellation points of PD capacity optimized PSK-32 constellations.
Figure 20:
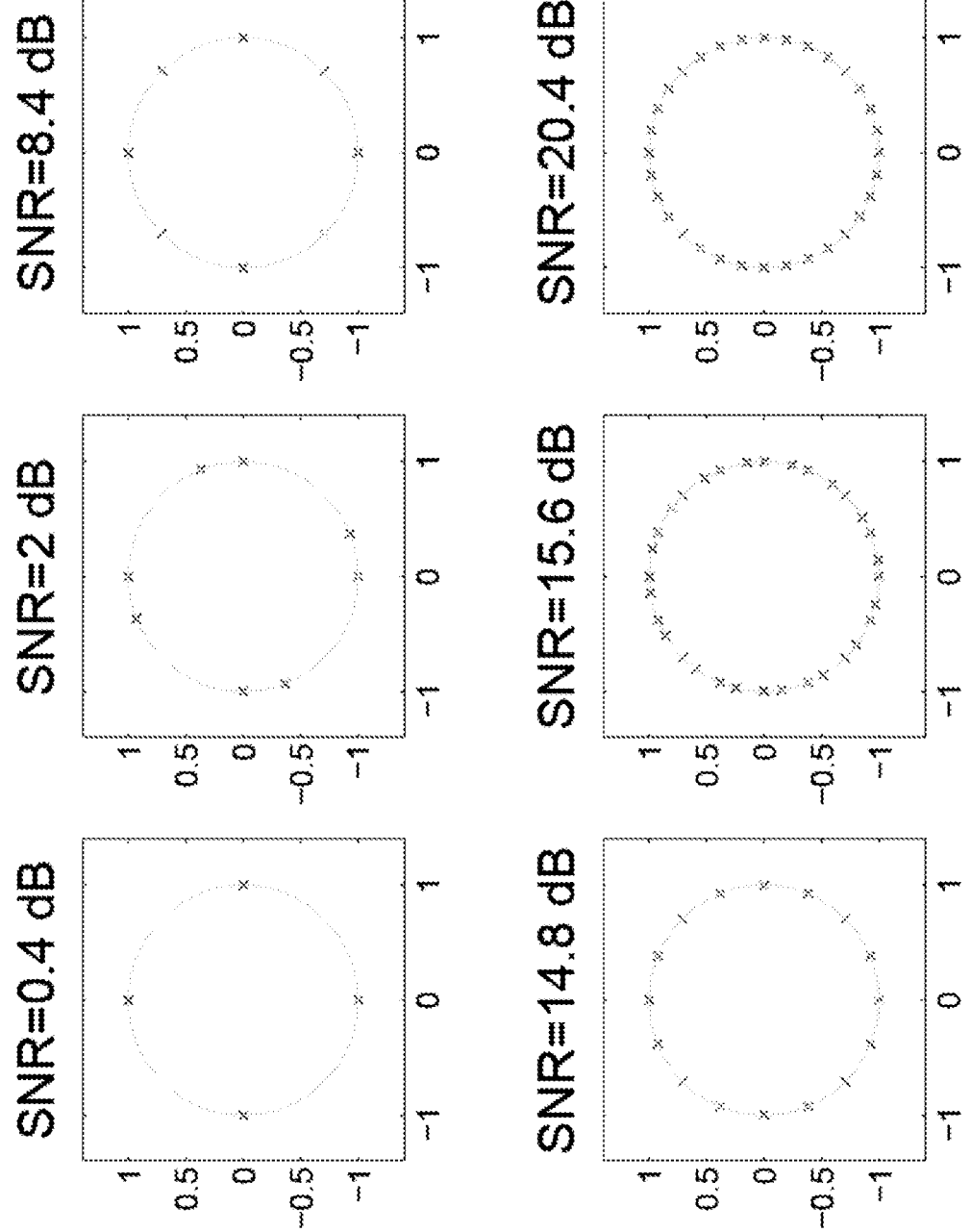
FIG. 20 is a series of PSK-32 constellations optimized for PD capacity at different SNRs in accordance with embodiments of the invention.

The locus plot of PD optimized PSK-32 points across SNR is shown in FIG. 19, which actually characterizes all PSKs with spectral efficiency $\eta \leq 5$. This can be seen in FIG. 20. Note that at low SNR (0.4 dB) the optimal PSK-32 design is the same as traditional PSK-4, at SNR=8.4 dB optimal PSK-32 is the same as traditional PSK-8, at SNR=14.8 dB optimal PSK-32 is the same as traditional PSK-16, and finally at SNRs greater than 20.4 dB optimized PSK-32 is the same as traditional PSK-32. There are SNRs between these discrete points (for instance SNR=2 and 15 dB) for which optimized PSK-32 provides superior PD capacity when compared to traditional PSK constellations.

Figure 18:
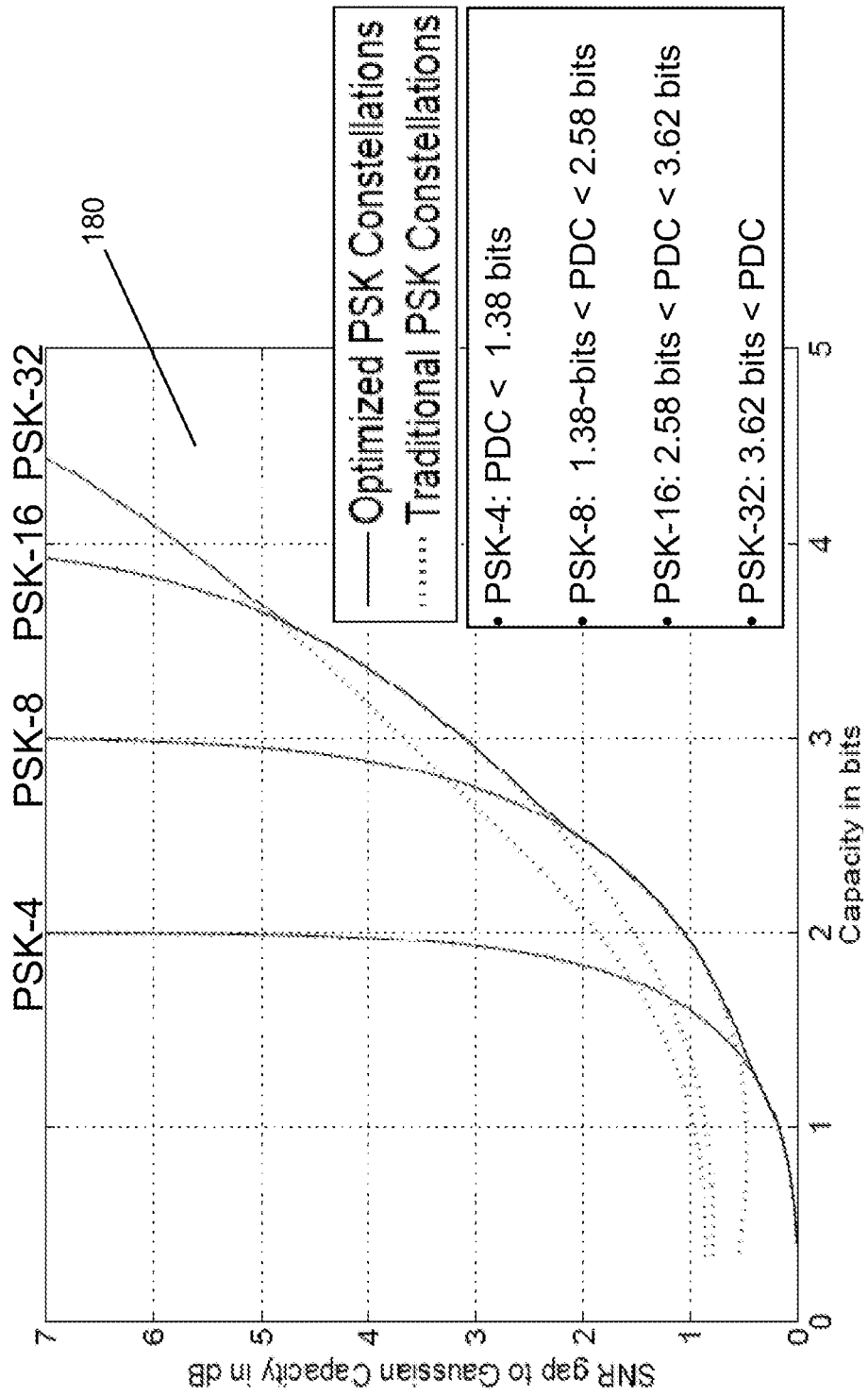
FIG. 18 is a chart showing the SNR gap to Gaussian capacity for traditional and capacity optimized PSK constellations.

We note now that the locus of points for PD optimized PSK-32 in FIG. 19 in conjunction with the gap to Gaussian capacity curve for optimized PSK-32 in FIG. 18 implies a potential design methodology. Specifically, the designer could achieve performance equivalent or better than that enabled by traditional PSK-4,8, and 16 by using only the optimized PSK-32 in conjunction with a single tuning parameter that controlled where the constellation points should be selected from on the locus of FIG. 19. Such an approach would couple a highly rate adaptive channel code that could vary its rate, for instance, rate 4/5 to achieve and overall (code plus optimized PSK-32 modulation) spectral efficiency of 4 bits per symbol, down to ⅕ to achieve an overall spectral efficiency of 1 bit per symbol. Such an adaptive modulation and coding system could essentially perform on the optimal continuum represented by the rightmost contour of FIG. 18.

Adaptive Rate Design

In the previous example spectrally adaptive use of PSK-32 was described. Techniques similar to this can be applied for other capacity optimized constellations across the link between a transmitter and receiver. For instance, in the case where a system implements quality of service it is possible to instruct a transmitter to increase or decrease spectral efficiency on demand. In the context of the current invention a capacity optimized constellation designed precisely for the target spectral efficiency can be loaded into the transmit mapper in conjunction with a code rate selection that meets the end user rate goal. When such a modulation/code rate change occurred a message could propagated to the receiver so that the receiver, in anticipation of the change, could select a demapper/decoder configuration in order to match the new transmit-side configuration.

Conversely, the receiver could implement a quality of performance based optimized constellation/code rate pair control mechanism. Such an approach would include some form of receiver quality measure. This could be the receiver's estimate of SNR or bit error rate. Take for example the case where bit error rate was above some acceptable threshold. In this case, via a backchannel, the receiver could request that the transmitter lower the spectral efficiency of the link by swapping to an alternate capacity optimized constellation/code rate pair in the coder and mapper modules and then signaling the receiver to swap in the complementary pairing in the demapper/decoder modules.

Geometrically Shaped QAM Constellations

Quadrature amplitude modulation (QAM) constellations can be constructed by orthogonalizing PAM constellations into QAM in phase and quadrature components. Constellations constructed in this way can be attractive in many applications because they have low-complexity demappers.

Figure 21:
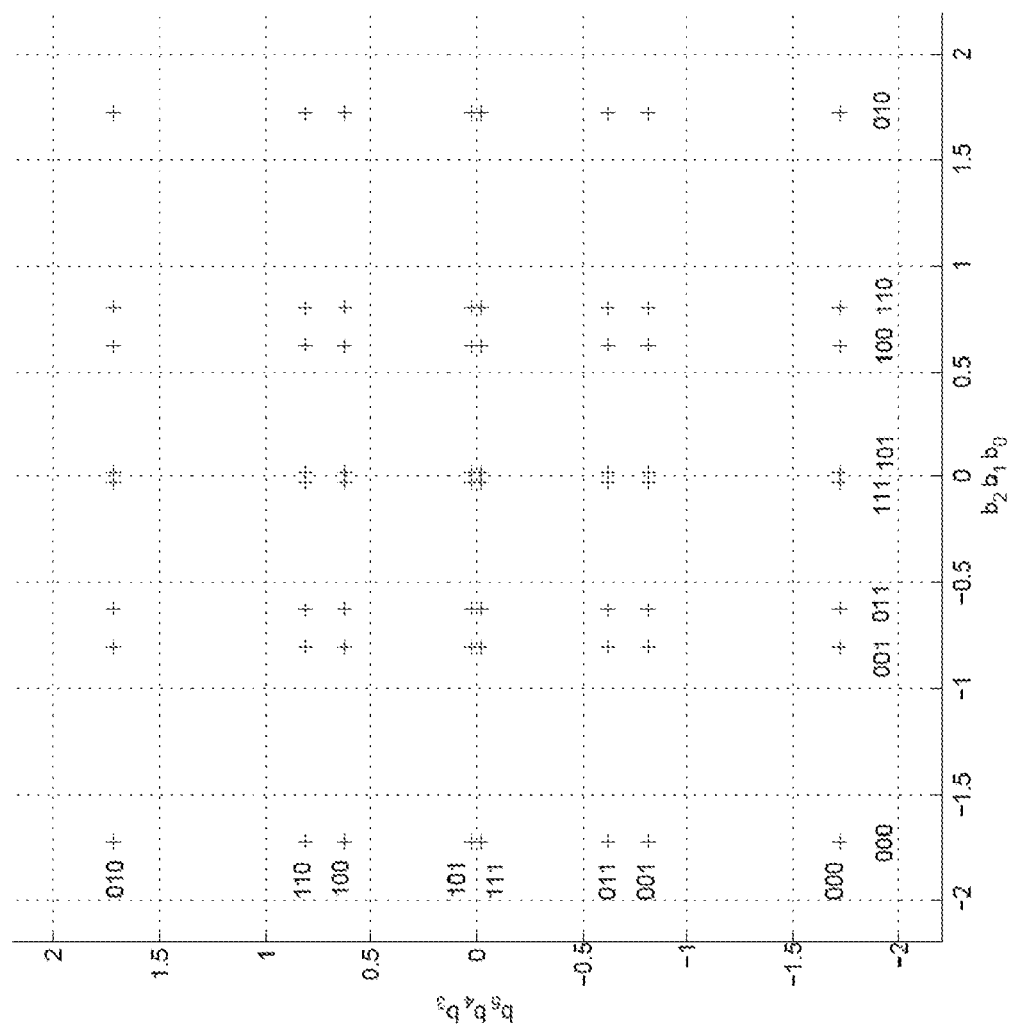
FIG. 21 illustrates a QAM-64 constructed from orthogonal Cartesian product of two PD optimized PAM-8 constellations in accordance with an embodiment of the invention.
Figure 22A:
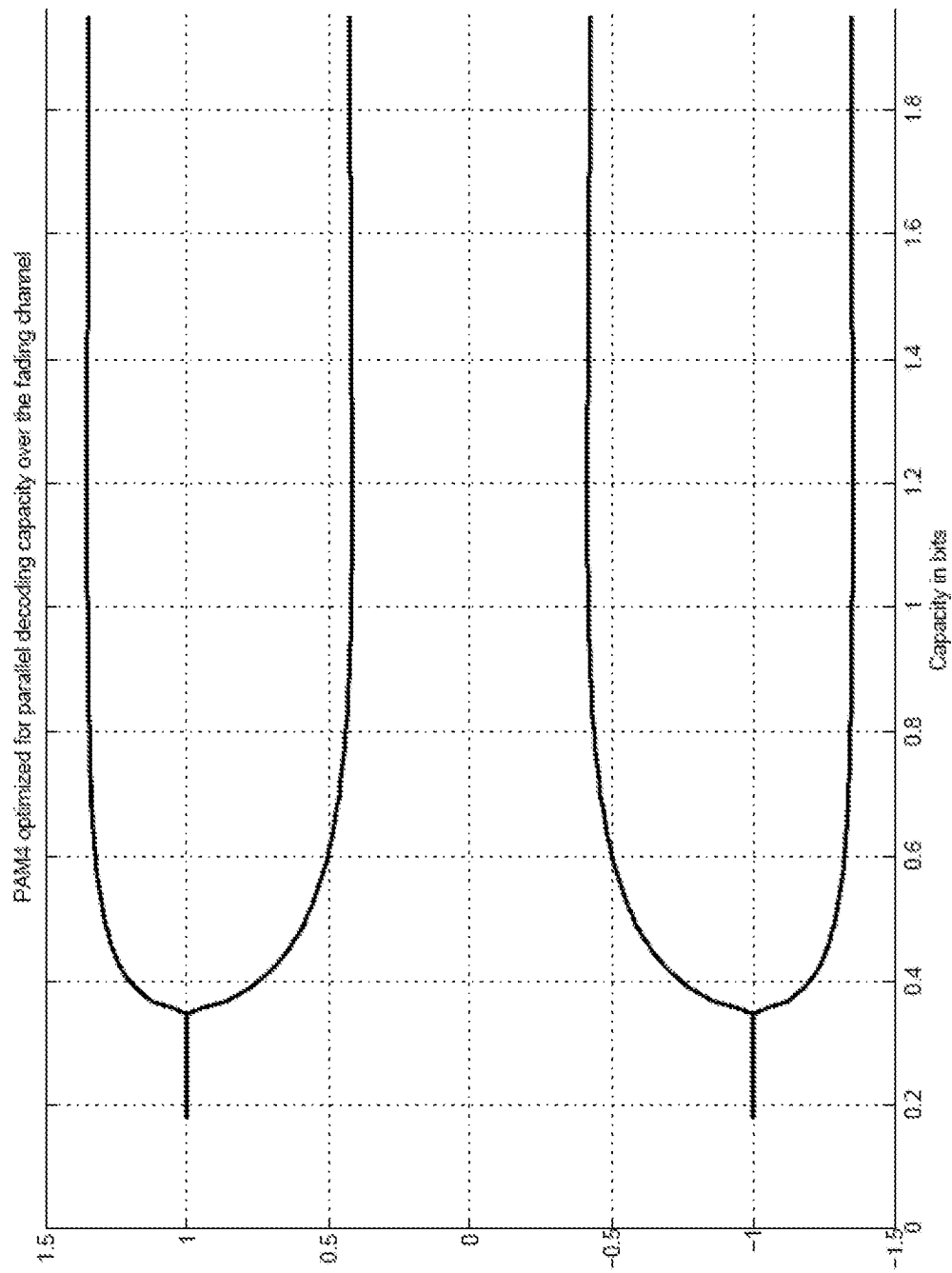
FIGS. 22a and 22b are locus plots showing the location of constellation points of a PAM-4 constellation optimized for PD capacity over a fading channel versus user bit rate per dimension and versus SNR.
Figure 22B:
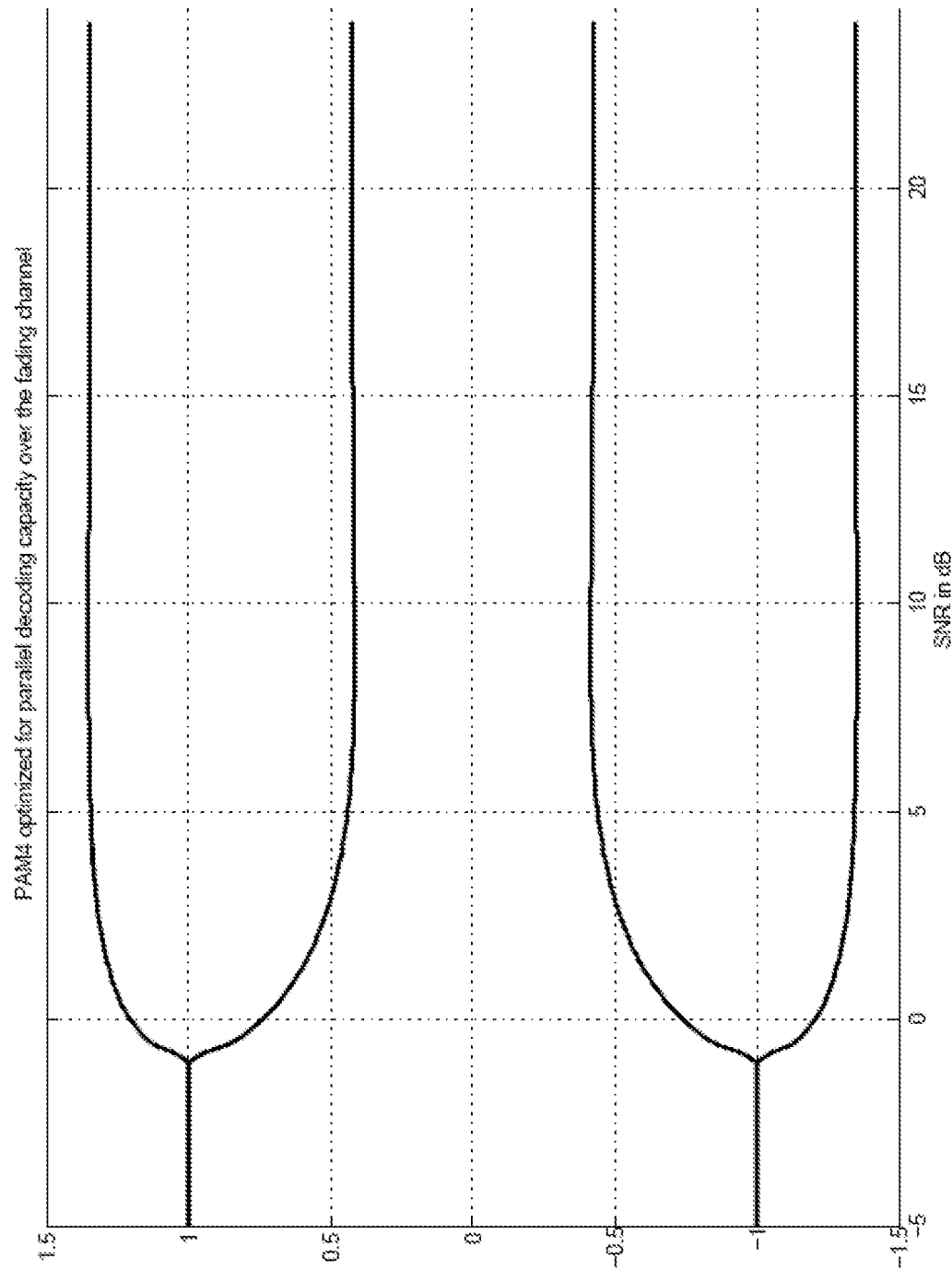
Figure 23A:
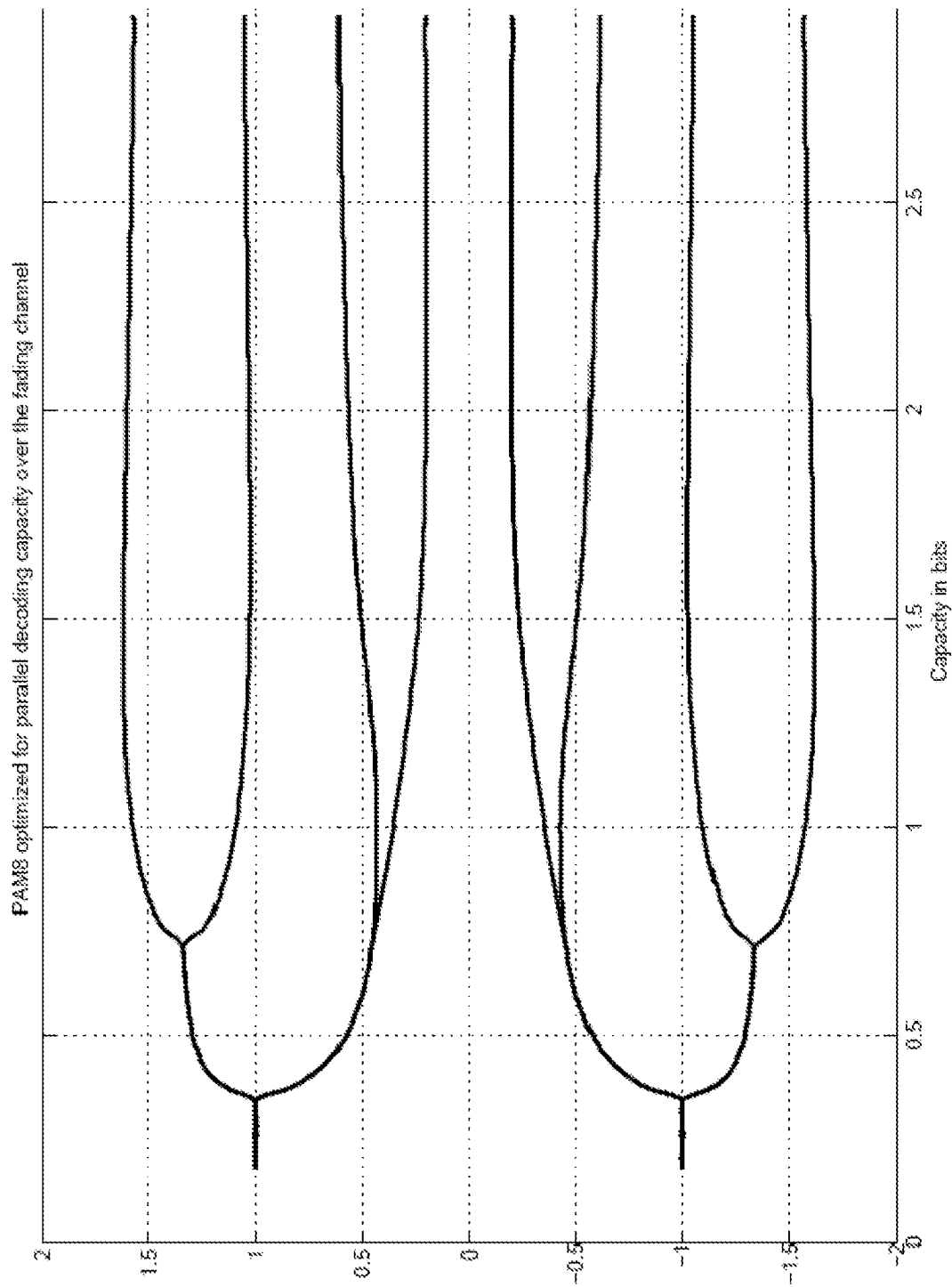
FIGS. 23a and 23b are locus plots showing the location of constellation points of a PAM-8 constellation optimized for PD capacity over a fading channel versus user bit rate per dimension and versus SNR.
Figure 23B:
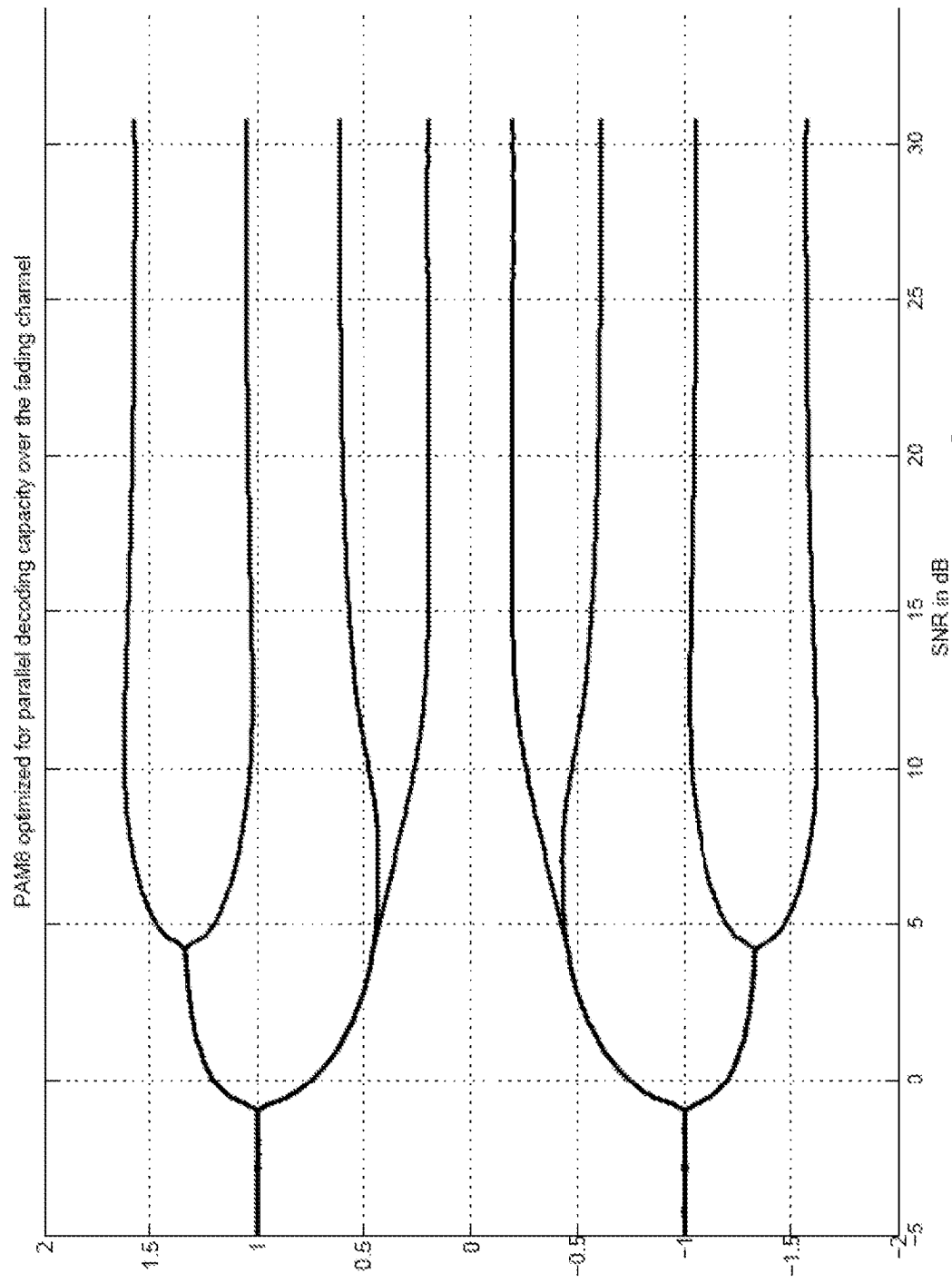
Figure 24A:
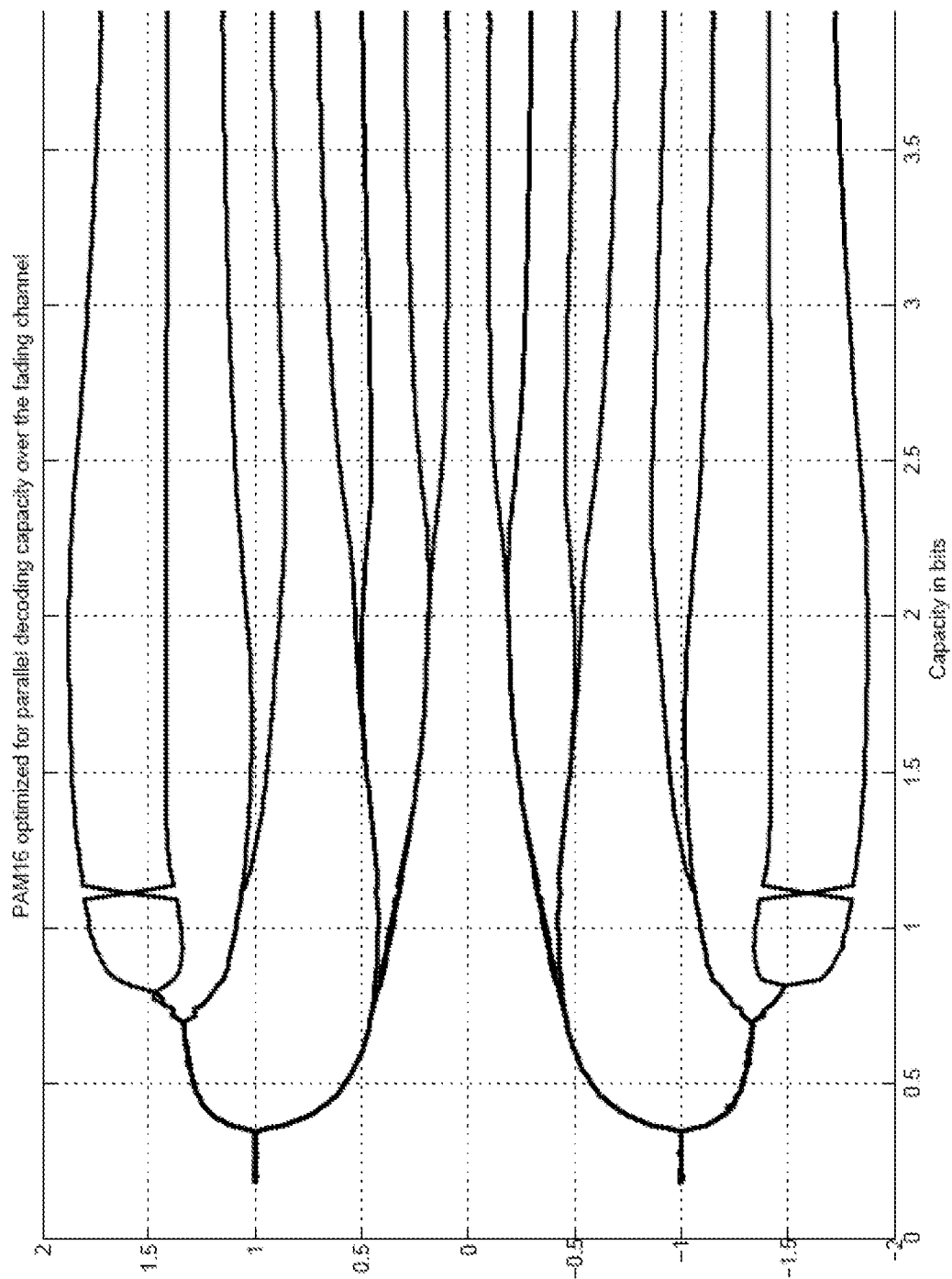
FIGS. 24a and 24b are locus plots showing the location of constellation points of a PAM-16 constellation optimized for PD capacity over a fading channel versus user bit rate per dimension and versus SNR.
Figure 24B:
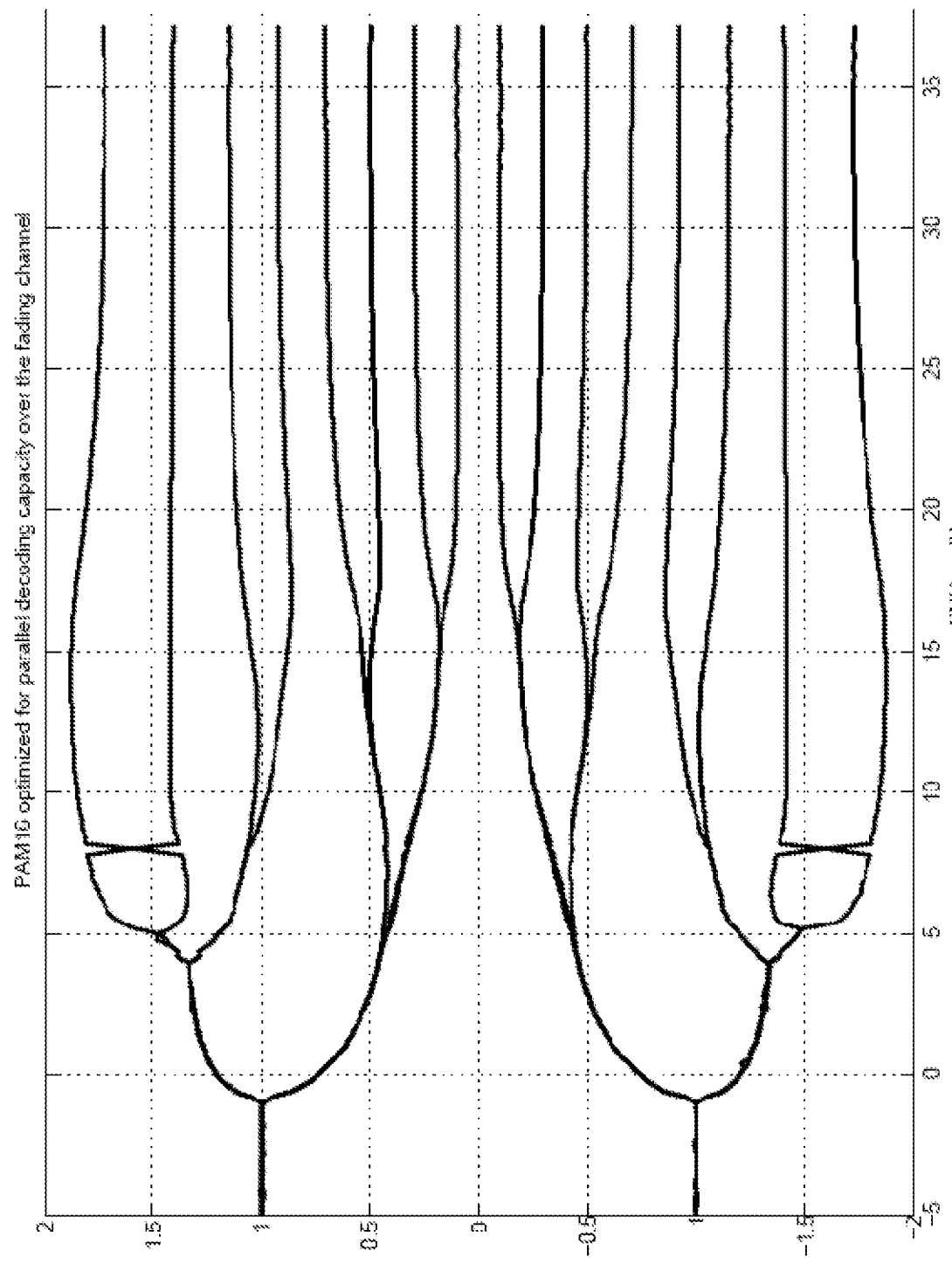

In FIG. 21 we provide an example of a Quadrature Amplitude Modulation constellation constructed from a Pulse Amplitude Modulation constellation. The illustrated embodiment was constructed using a PAM-8 constellation optimized for PD capacity at user bit rate per dimension of 1.5 bits (corresponds to an SNR of 9.0 dB) (see FIG. 13b). The label-point pairs in this PAM-8 constellation are {(000, −1.72), (001, −0.81), (010, 1.72), (011, −0.62), (100, 0.62), (101, 0.02), (110, 0.81), (111, −0.02)}. Examination of FIG. 21 shows that the QAM constellation construction is achieved by replicating a complete set of PAM-8 points in the quadrature dimension for each of the 8 PAM-8 points in the in-phase dimension. Labeling is achieved by assigning the PAM-8 labels to the LSB range on the in-phase dimension and to the MSB range on the quadrature dimension. The resulting 8×8 outer product forms a highly structured QAM-64 for which very low-complexity de-mappers can be constructed. Due to the orthogonality of the in-phase and quadrature components the capacity characteristics of the resulting QAM-64 constellation are identical to that of the PAM-8 constellation on a per-dimension basis.

N-Dimensional Constellation Optimization

Rather than designing constellations in 1-D (PAM for instance) and then extending to 2-D (QAM), it is possible to take direct advantage in the optimization step of the additional degree of freedom presented by an extra spatial dimension. In general it is possible to design N-dimensional constellations and associated labelings. The complexity of the optimization step grows exponentially in the number of dimensions as does the complexity of the resulting receiver de-mapper. Such constructions constitute embodiments of the invention and simply require more 'run-time' to produce.

Capacity Optimized Constellations for Fading Channels

Similar processes to those outlined above can be used to design capacity optimized constellations for fading channels in accordance with embodiments of the invention. The processes are essentially the same with the exception that the manner in which capacity is calculated is modified to account for the fading channel. A fading channel can be described using the following equation:

$$Y=a(t) \cdot X+N$$

where X is the transmitted signal, N is an additive white Gaussian noise signal and a(t) is the fading distribution, which is a function of time.

In the case of a fading channel, the instantaneous SNR at the receiver changes according to a fading distribution. The fading distribution is Rayleigh and has the property that the average SNR of the system remains the same as in the case of the AWGN channel, $E[X^2]/E[N^2]$. Therefore, the capacity of the fading channel can be computed by taking the expectation of AWGN capacity, at a given average SNR, over the Rayleigh fading distribution of a that drives the distribution of the instantaneous SNR.

Many fading channels follow a Rayleigh distribution. FIGS. 22a-24b are locus plots of PAM-4, 8, and 16 constellations that have been optimized for PD capacity on a Rayleigh fading channel. Locus plots versus user bit rate per dimension and versus SNR are provided. Similar processes can be used to obtain capacity optimized constellations that are optimized using other capacity measures, such as joint capacity, and/or using different modulation schemes.

Geometric PAM-8, PAM-16, and PAM-32 Constellations

As described above, geometric constellations can be obtained that are optimized for joint or PD capacity at specific SNRs. In addition, ranges can be specified for the constellation points of a geometric constellation that are probabilistically likely to result in geometric constellations that provide at least a predetermined performance improvement relative to a constellation that maximizes $d_{min}$. Turning now to FIGS. 25-167, geometric PAM-8, PAM-16, and PAM-32 constellations optimized for joint and PD capacity over the Additive White Gaussian Noise (AWGN) channel at specific SNRs are listed. The performances of the optimal constellations are compared to the performances of traditional constellations that maximize $d_{min}$. Ranges for the constellation points are also defined at specific SNRs, where constellations having constellation points selected from within the ranges are probabilistically likely (with probability close to one) to result in at least a predetermined performance improvement at the specified SNR relative to a traditional constellation that maximizes $d_{min}$.

The geometric constellations disclosed in FIGS. 25-167 are defined by points y(i) such that y(i)=k(x(i)+r(i))+c. Values for x(i) and bounds on r(i) are provided in FIGS. 25-167 for PAM-8, PAM-16, and PAM-32 optimized for joint and PD capacity. For PAM-8 0≤i≤7, PAM-16 0≤i≤15, and for PAM-32 0≤i≤31. To achieve optimal power efficiency, c should be set to zero. In addition to optimized constellations, FIGS. 25-167 specify ranges for the points of a geometric constellation, where selecting the points of a constellation from within the ranges is probabilistically likely to provide a geometric constellation having at least a predetermined performance improvement relative to a constellation that maximizes $d_{min}$. The ranges are expressed as a maximum value for the constellation range parameter, r(i), which specifies the amount by which the point x(i) in the constellation is perturbed relative to the location of the corresponding point in the optimal constellation. A communication system using a constellation formed from constellations points selected from within the ranges specified by the maximum value (i.e. $-r_{max} \le r(i) \le r_{max}$) is probabilistically likely to achieve a predetermined performance improvement relative to a constellation that maximizes $d_{min}$. The predetermined performance improvements associated with the ranges specified in FIGS. 25-167 are expressed in terms of a percentage of the increase in capacity achieved by the optimized constellation relative to a constellation that maximizes $d_{min}$. Constellations formed from constellation points selected from within the ranges are probabilistically likely to achieve an increase in capacity at least as great as the indicated percentage.

With regard to the specific tables shown in FIGS. 25-167, each table is one of three different types of table. A first set of tables shows the performance of specific geometric constellations optimized for joint capacity or PD capacity. These tables include 6 columns. The first column enumerates a design number. The second column provides the SNR at which the constellation was optimized for the design defined by the entry in the first column. The third column provides the capacity achieved by the optimized constellation (Opt. Cap) at the SNR given in the second column. The fourth column provides the capacity achieved (Std. Cap) by a traditional uniformly spaced constellation i.e. a PAM constellation that maximizes $d_{min}$ (with the same number of points as the optimized constellation and where binary reflective gray labeling is assumed) at the SNR given in the second column. The fifth column shows the gain in bits per transmission provided by the optimized constellation over a constellation that maximizes $d_{min}$. The sixth column shows the percentage gain in capacity provided by the optimized constellation over the capacity provided by the traditional uniformly spaced constellation.

A second set of tables lists the constellation points of the designs indicated in the first set of tables. These tables contain 9 columns. The first column enumerates a design number. The remaining 8 columns describe a constellation point x(i) enumerated by label in the second row of the table. Labels are given in decimal number format. With PAM 8 as an example, a label of 011 is given as the decimal number 3.

The third set of tables specifies maximum perturbation ranges for the capacity optimized constellations indicated in the first set of tables, where the maximum ranges correspond to a high probabilistic likelihood of at least a predetermined performance improvement relative to a constellation that maximizes $d_{min}$. These tables contain 8 columns. The first enumerates a design number (corresponding to a design from one of the aforementioned tables). The second column provides the SNR for the design defined by the entry in the first column. The remaining 5 columns describe parameter $r_{max}$ which is the maximum amount any point in the designed constellation may be perturbed (in either the positive or negative direction) and still retain, with probability close to unity, at least the gain noted by each column header of the joint or PD capacity as a percentage of the gain provided by the corresponding optimized point design over a traditional constellation that maximizes $d_{min}$ (all at the given SNR). Each table has a last column showing that if 100% of the gain afforded by the optimized constellation is desired, then parameter r(i) must be equal to zero (no deviation from designed points described in the point specification tables).

Example of Performance Achieved by Constellation within Predetermined Ranges

By way of example, a constellation can be selected using the ranges specified with respect to the constellation points of a geometric PAM-8 constellation optimized with respect to PD capacity at SNR=9 dB. The optimized constellation points are as follows:

−7.8780 −3.7100 7.8780 −2.8590 2.8590 0.0990 3.7100 −0.0990

The PD capacity of the above constellation at 9 dB=1.4999 bits. FIGS. 26-167 define a range around each constellation $r_{max}$ of 0.47 that is probabilistically likely to result in a constellation that can be used by a communication system to achieve at least 5% of the gain of the optimized constellation (compared to an equally spaced constellation).

An example of a PAM-8 constellation formed using constellation points selected from within the specified ranges is as follows:

−7.8462 −3.9552 7.7361 −3.2614 2.9395 0.5152 3.3867 0.0829

The distance between each of the constellation points and the constellation points of the optimized constellation are as follows:

0.0318 −0.2452 −0.1419 −0.4024 0.0805 0.4162 −0.3233 0.1819

The magnitude of each of the distances is less than $r_{max}$ at 9 dB (i.e. 0.47). The capacity of the selected constellation=1.4884. The capacity of a constellation that maximizes $d_{min}$ at 9 dB=1.435 bits. Therefore, the selected constellation achieves 82% of the gain made possible by the optimal constellation (i.e. at least 5%).

Labelling of Constellations Using Cyclically Rotated Binary Reflective Gray Labels In performing optimization with respect to PD capacity, a conjecture can be made that constraining the optimization process to the subsequently described class of labelings results in no or negligible loss in PD capacity (the maximum observed loss is 0.005 bits, but in many cases there is no loss at all). Use of this labeling constraint speeds the optimization process considerably. We note that joint capacity optimization is invariant to choice of labeling. Specifically, joint capacity depends only on point locations whereas PD capacity depends on point locations and respective labelings.

The class of cyclically rotated binary reflective gray labels can be used. The following example, using constellations with cardinality 8, describes the class of cyclically rotated binary reflective gray labels. Given for example the standard gray labeling scheme for PAM-8:

000, 001, 011, 010, 110, 111, 101, 100

Application of a cyclic rotation, one step left, yields:

001, 011, 010, 110, 111, 101, 100, 000

Application of a cyclic rotation, two steps left, yields:

011, 010, 110, 111, 101, 100, 000, 001

For a constellation with cardinality 8, cyclic rotations of 0 to 7 steps can be applied. It should be noted that within this class of labelings, some labelings perform better than others. It should also be noted that different rotations may yield labelings that are equivalent (through trivial column swapping and negation operations). In general, labelings can be expressed in different but equivalent forms through trivial operations such as column swapping and negation operations. For example the binary reflective gray labels with one step rotation:

001, 011, 010, 110, 111, 101, 100, 000

Can be shown to be equivalent to:

000, 001, 011, 111, 101, 100, 110, 010

The above equivalence can be shown by the following steps of trivial operations:

1) Negate the third column. This gives 000, 010, 011, 111, 110, 100, 101, 001

2) Swap the second and third columns. This gives 000, 001, 011, 111, 101, 100, 110, 010

The two labelings are considered equivalent because they yield the same PD Capacity as long as the constellation points locations are the same.

In the constellation point specifications shown in FIGS. 25-167, a labeling can be interchanged by any equivalent labeling without affecting the performance parameters. A labeling used in the specifications may not directly appear to be a cyclically rotated binary reflective gray labeling, but it can be shown to be equivalent to one or more cyclically rotated binary reflective gray labelings.

Prior Art Geometric Constellations

Geometric constellations have been specified in the prior art in attempts to achieve performance gains relative to constellations that maximize $d_{min}$. Examples of such constellations are disclosed in Sommer and Fettweis, "Signal Shaping by Non-Uniform QAM for AWGN Channerls and Applications Using Turbo Coding" *ITG Conference Source and Channel Coding*, p. 81-86, 2000. The specific constellations disclosed by Sommer and Fettweis for PAM-8, PAM-16, and PAM-32 are as follows:

PAM-8:

−1.6630 −0.9617 −0.5298 −0.1705 0.1705 0.5298 0.9617 1.6630

PAM-16:

−1.9382 −1.3714 −1.0509 −0.8079 −0.6026 −0.4185 −0.2468 −0.0816 0.0816
0.2468 0.4185 0.6026 0.8079 1.0509 1.3714 1.9382

PAM-32:

−2.1970 −1.7095 −1.4462 −1.2545 −1.0991 −0.9657 −0.8471 −0.7390 −0.6386
−0.5441 −0.4540 −0.3673 −0.2832 −0.2010 −0.1201 −0.0400 0.0400 0.1201
0.2010 0.2832 0.3673 0.4540 0.5441 0.6386 0.7390 0.8471 0.9657
1.0991 1.2545 1.4462 1.7095 2.1970

Another class of geometric constellations is disclosed in Long et al., "Approaching the AWGN Channel Capacity without Active Shaping" *Proceedings of International Symposium on Information Theory*, p. 374, 1997. The specific PAM-8, PAM-16, and PAM-32 constellations disclosed by Long et al. are as follows:

PAM-8:

−3 −1 −1 −1 1 1 1 3

PAM-16:

−4 −2 −2 −2 −2 0 0 0 0 0 0 2 2 2 2 4

PAM-32:

−5 −3 −3 −3 −3 −3 −1 −1 −1 −1 −1 −1 −1 −1 −1 −1
1 1 1 1 1 1 1 1 1 1 3 3 3 3 3 5

The above prior art constellations are geometric and can provide performance improvements at some SNRs relative to constellations that maximize $d_{min}$. The performance of the constellations varies with SNR and at certain SNRs the constellations are proximate to capacity optimized constellations. Therefore, the ranges specified in FIGS. 25-167 are defined so that prior art constellations are excluded at the specific SNRs at which these constellations are proximate to a capacity optimized constellation.

Constructing Multidimensional Constellations

The tables shown in FIGS. 25-167 can be used to identify optimal N-dimensional constellations. The optimized multidimensional constellation can be determined by finding the Cartesian power $X^n$ and the resulting labeling constructed by finding the corresponding Cartesian power of $L^n$. Ranges within which the multi-dimensional constellation points can be selected (i.e. perturbed), can then be defined with respect to each constellation point of the constructed multi-dimensional constellation, using an n-dimensional perturbation vector, such that each component of the perturbation vector has a magnitude that is less than $r_{max}$ defined by the range tables.

Example of a QAM Constellation

The optimized constellation points for a PAM-8 constellation optimized for PD capacity at SNR=9 dB are as follows:

−7.8780 −3.7100 7.8780 −2.8590 2.8590 0.0990 3.7100 −0.0990

The labelings corresponding to the above PAM-8 constellation points are:

000 001 010 011 100 101 110 111

Using this PAM-8 constellation, it is possible to construct a QAM-64 constellation. While PAM-8 maps 3 bits to one dimension, QAM-64 maps 6 bits to two dimensions. The first three bits will determine the location in the X-dimension and the second three bits will determine the location in the Y-dimension. The resulting QAM-64 constellation for example will map the bits 000 010 to the two dimensional constellation point (−7.878, 7.878), and 111 110 to the two dimensional constellation point (−0.099, 3.71). The points corresponding to the remaining labels can be derived in a similar manner.

The ranges shown in FIGS. 25-167 can be utilized to select QAM constellations in a similar manner to that outlined above with respect to the selection of a PAM-8 constellation based upon ranges specified with respect to a PAM-8 constellation optimized for PD capacity at 9 dB. A range of 0.47 can be applied to every component of each two dimensional constellation point. For example, the two points two points (−7.787, 8.078) and (0.201, 3.31) are within the ranges as they are spaced distances (−0.1, 0.2) and (0.3, −0.4) respectively from the optimized constellation points. In this way, the ranges can be used to identify constellations that are probabilistically likely to result in a performance improvement relative to a constellation that maximizes $d_{min}$.

The same procedure can apply to a constellation optimized for joint capacity. However, the choice of labeling does not affect joint capacity. The above procedure can similarly be applied to an N-dimensional constellation constructed from a PAM constellation.

Although the present invention has been described in certain specific embodiments, many additional modifications and variations would be apparent to those skilled in the art. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A digital communication system, comprising:
a transmitter configured to transmit signals to a receiver via a communication channel;
wherein the transmitter comprises:
 a coder configured to receive user bits and output encoded bits at an expanded output encoded bit rate;
 a mapper configured to map encoded bits to symbols in a non-uniform quadrature amplitude modulation 1024-point symbol constellation (NU-QAM 1024); and
 a modulator configured to generate a signal for transmission via the communication channel using symbols generated by the mapper;
wherein the receiver comprises:
 a demodulator configured to demodulate a signal received via the communication channel;

a demapper configured to estimate likelihoods from a demodulated signal based upon the NU-QAM 1024; and a decoder configured to estimate decoded bits from likelihoods generated by the demapper and output a sequence of received bits;

wherein the NU-QAM 1024 comprises an in-phase component and a quadrature component, where each component comprises 32 levels of amplitude such that the amplitudes scaled by a scaling factor are within 1.18 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

2. The digital communication system of claim 1, where each component comprises 32 levels of amplitude such that the amplitudes scaled by a scaling factor are within 1.06 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

3. The digital communication system of claim 1, where each component comprises 32 levels of amplitude such that the amplitudes scaled by a scaling factor are within 0.7 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

4. The digital communication system of claim 1, where each component comprises 32 levels of amplitude such that the amplitudes scaled by a scaling factor are:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

5. The digital communication system of claim 1, wherein the receiver is configured to select the NU-QAM 1024 constellation from a plurality of constellations including a plurality of different NU-QAM 1024 constellations.

6. The digital communication system of claim 5, wherein the receiver is configured to select a code rate and the NU-QAM 1024 constellation from a plurality of different combinations of code rates and NU-QAM 1024 constellations.

7. The digital communication system of claim 1, wherein:
the coder is configured to encode bits using a low-density parity check (LDPC) code; and
the decoder is configured to decode bits using the LDPC code.

8. The digital communication system of claim 1, wherein the symbols in the non-uniform quadrature amplitude modulation 1024-point symbol constellation (NU-QAM 1024) are labelled using gray labels.

9. The digital communication system of claim 1, wherein the symbols in the non-uniform quadrature amplitude modulation 1024-point symbol constellation (NU-QAM 1024) are labelled using binary reflective gray labels.

10. A digital communication system, comprising:
a transmitter capable of transmitting signals via a communication channel;

wherein the transmitter comprises:
a coder capable of receiving user bits and output encoded bits at an expanded output encoded bit rate;
a mapper capable of mapping encoded bits to symbols in a non-uniform quadrature amplitude modulation 1024-point symbol constellation (NU-QAM 1024); and
a modulator capable of generating a signal for transmission via the communication channel using symbols generated by the mapper;

wherein the NU-QAM 1024 comprises an in-phase component and a quadrature component, where each component comprises 32 levels of amplitude such that the amplitudes scaled by a scaling factor are within 1.18 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

11. The digital communication system of claim 10, where each component comprises 32 levels of amplitude such that the amplitudes scaled by a scaling factor are within 1.06 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

12. The digital communication system of claim 10, where each component comprises 32 levels of amplitude such that the amplitudes scaled by a scaling factor are within 0.7 from the following set of amplitudes:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

13. The digital communication system of claim 10, where each component comprises 32 levels of amplitude such that the amplitudes scaled by a scaling factor are:

−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

14. The digital communication system of claim 10, wherein the transmitter is capable of selecting the NU-QAM 1024 constellation from a plurality of constellations including a plurality of different NU-QAM 1024 constellations.

15. The digital communication system of claim 14, wherein the transmitter is capable of selecting a code rate and the NU-QAM 1024 constellation from a plurality of different combinations of code rates and NU-QAM 1024 constellations.

16. The digital communication system of claim 10, wherein the coder is capable of encoding bits using a low-density parity check (LDPC) code.

17. The digital communication system of claim 10, wherein the symbols in the non-uniform quadrature amplitude modulation 1024-point symbol constellation (NU-QAM 1024) are labelled using gray labels.

18. The digital communication system of claim 10, wherein the symbols in the non-uniform quadrature amplitude modulation 1024-point symbol constellation (NU-QAM 1024) are labelled using binary reflective gray labels.

19. A digital communication system, comprising:
a receiver capable of receiving signals via a communication channel;
wherein the receiver comprises:
- a demodulator capable of demodulating a signal received via the communication channel;
- a demapper capable of estimating likelihoods from a demodulated signal based upon a non-uniform quadrature amplitude modulation 1024-point symbol constellation (NU-QAM 1024); and
- a decoder capable of estimating decoded bits from likelihoods generated by the demapper and outputting a sequence of received bits;

wherein the NU-QAM 1024 comprises an in-phase component and a quadrature component, where each component comprises 32 levels of amplitude such that the amplitudes scaled by a scaling factor are within 1.18 from the following set of amplitudes:
−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

20. The digital communication system of claim 19, where each component comprises 32 levels of amplitude such that the amplitudes scaled by a scaling factor are within 1.06 from the following set of amplitudes:
−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

21. The digital communication system of claim 19, where each component comprises 32 levels of amplitude such that the amplitudes scaled by a scaling factor are within 0.7 from the following set of amplitudes:
−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

22. The digital communication system of claim 19, where each component comprises 32 levels of amplitude such that the amplitudes scaled by a scaling factor are from:
−39.866, −32.361, −24.251, −26.129, −15.266, −15.266, −19.035, −18.407, 39,865, 32.360, 24.250, 26.128, −9.954, −9.954, −8.580, −8.596, 9.954, 9.954, 8.581, 8.596, 2.735, 2.735, 3.234, 3.232, 15.266, 15.266, 19.034, 18.406, −2.735, −2.735, −3.233, and −3.232.

23. The digital communication system of claim 19, wherein the receiver is capable of selecting the NU-QAM 1024 constellation from a plurality of constellations including a plurality of different NU-QAM 1024 constellations.

24. The digital communication system of claim 23, wherein the receiver is capable of selecting a code rate and the NU-QAM 1024 constellation from a plurality of different combinations of code rates and NU-QAM 1024 constellations.

25. The digital communication system of claim 19, wherein the decoder is capable of decoding bits using a low-density parity check (LDPC) code.

26. The digital communication system of claim 19, wherein the symbols in the non-uniform quadrature amplitude modulation 1024-point symbol constellation (NU-QAM 1024) are labelled using gray labels.

27. The digital communication system of claim 19, wherein the symbols in the non-uniform quadrature amplitude modulation 1024-point symbol constellation (NU-QAM 1024) are labelled using binary reflective gray labels.

* * * * *